(12) United States Patent
Thaker et al.

(10) Patent No.: US 11,521,709 B2
(45) Date of Patent: Dec. 6, 2022

(54) SYSTEMS AND METHODS FOR ANALYSES OF BIOLOGICAL SAMPLES

(71) Applicant: BERKELEY LIGHTS, INC., Emeryville, CA (US)

(72) Inventors: Darshan Thaker, Emeryville, CA (US); Keith J. Breinlinger, Emeryville, CA (US); Vincent Haw Tien Pai, Emeryville, CA (US); Christoph Andreas Neyer, Emeryville, CA (US); Thomas M. Vetterli, Berkeley, CA (US); Hayley M. Bennett, Emeryville, CA (US); Elisabeth Marie Walczak, Emeryville, CA (US); Alexander Gerald Olson, Emeryville, CA (US); Wesley Arthur Zink, Emeryville, CA (US); John A. Tenney, Emeryville, CA (US); Oleksandr Tokmakov, Khmelnytskyi (UA); Igor Fastnacht, Lviv (UA); Yuriy Nicheporuk, Khmelnytskyi (UA); Andriy Koval, Khmelnytskyi (UA); Khrystyna Andres, Lviv (UA); Alona Kostenko, Lviv (UA)

(73) Assignee: Berkeley Lights Inc., Emeryville, CA (US)

(*) Notice: Subject to any disclaimer, the term of this patent is extended or adjusted under 35 U.S.C. 154(b) by 0 days.

(21) Appl. No.: 17/325,196

(22) Filed: May 19, 2021

(65) Prior Publication Data

US 2021/0272654 A1 Sep. 2, 2021

Related U.S. Application Data

(63) Continuation of application No. PCT/US2020/060784, filed on Nov. 16, 2020.
(Continued)

(51) Int. Cl.
*G01N 33/48* (2006.01)
*G01N 33/50* (2006.01)
(Continued)

(52) U.S. Cl.
CPC ........ *G16B 40/20* (2019.02); *B01L 3/502784* (2013.01); *G16B 30/20* (2019.02); *G16B 45/00* (2019.02); *B01L 2200/027* (2013.01)

(58) Field of Classification Search
CPC ........ G16B 40/20; G16B 30/20; G16B 45/00; B01L 3/502784; B01L 2200/027;
(Continued)

(56) References Cited

U.S. PATENT DOCUMENTS

2011/0053151 A1 3/2011 Hansen et al.
2012/0009671 A1 1/2012 Hansen et al.
(Continued)

FOREIGN PATENT DOCUMENTS

WO WO 2019/075476 4/2019
WO WO 2019/232473 5/2019

OTHER PUBLICATIONS

Extended European Search Report and Written Opinion of the EPO for Application No. 20887548.4, dated Aug. 2, 2022, pp. 1-9.*
(Continued)

*Primary Examiner* — Russell S Negin
(74) *Attorney, Agent, or Firm* — InventIQ LLP; Anna Ison; Daniel J. Kennedy

(57) ABSTRACT

Disclosed are methods, systems, and articles of manufacture for performing a process on biological samples. An analysis of biological samples in multiple regions of interest in a microfluidic device and a timeline correlated with the analysis may be identified. One or more region-of-interest types for the multiple regions of interest may be determined; and multiple characteristics may be determined for the biological
(Continued)

samples based at least in part upon the one or more region-of-interest types. Associated data that respectively correspond to the multiple regions of interest in a user interface for at least a portion of the biological samples in the user interface based at least in part upon the multiple identifiers and the timeline. A count of the biological samples in a region of interest may be determined based at least in part upon a class or type of data using a convolutional neural network (CNN).

21 Claims, 103 Drawing Sheets

Related U.S. Application Data

(60) Provisional application No. 62/936,550, filed on Nov. 17, 2019, provisional application No. 62/950,573, filed on Dec. 19, 2019, provisional application No. 63/035,726, filed on Jun. 6, 2020, provisional application No. 63/060,647, filed on Aug. 3, 2020.

(51) Int. Cl.
*G16B 40/20* (2019.01)
*G16B 45/00* (2019.01)
*G16B 30/20* (2019.01)
*B01L 3/00* (2006.01)

(58) Field of Classification Search
CPC ..... B01L 2200/0668; B01L 2300/0645; B01L 2300/0883; B01L 2300/165; B01L 2400/0427; B01L 2400/086; B01L 3/502761; B01L 3/502792; G06T 2207/10056; G06T 2207/20081; G06T 2207/20084; G06T 2207/30024; G06T 2207/30242; G06T 7/0016; G01N 35/00871; G01N 2015/1006; G01N 2015/1486; G01N 2015/1493; G01N 2015/1497; G01N 2035/0091; G01N 15/1463; G01N 15/1475; G01N 15/1484; G01N 21/6458; G01N 2021/6439; G16H 30/40; G16H 10/40

See application file for complete search history.

(56) References Cited

U.S. PATENT DOCUMENTS

| | | |
|---|---|---|
| 2012/0219029 A1 | 8/2012 | Scott et al. |
| 2013/0115606 A1 | 5/2013 | Hansen et al. |
| 2016/0160259 A1 | 6/2016 | Du |
| 2016/0171686 A1 | 6/2016 | Du et al. |
| 2017/0095818 A1 | 4/2017 | Liu et al. |
| 2017/0205981 A1* | 7/2017 | Lee .................. G06F 11/3017 |
| 2018/0064377 A1 | 3/2018 | Rorgers et al. |
| 2018/0078146 A1* | 3/2018 | Shadforth ............. G16H 50/30 |
| 2018/0211380 A1 | 7/2018 | Tandon et al. |
| 2019/0091684 A1 | 3/2019 | Liou et al. |
| 2019/0240665 A1 | 8/2019 | Lionberger et al. |
| 2019/0276874 A1 | 9/2019 | Deciu et al. |
| 2019/0345488 A1 | 11/2019 | Soumillon et al. |
| 2019/0384963 A1 | 12/2019 | Kim et al. |
| 2020/0139362 A1 | 5/2020 | Beemiller et al. |
| 2020/0371126 A1 | 11/2020 | Thaker et al. |
| 2021/0349075 A1 | 11/2021 | Bronevetsky et al. |

OTHER PUBLICATIONS

PCT Notification of Transmittal of the International Search Report and Written Opinion for PCT/US2020/060784, dated Feb. 17, 2021, 8 pages.

Sorkin et al., "Rapid Generation of Production Cell Lines with Superior Titers and >99% Monoclonality for Complex Antibody Molecules," entire poster, 2020, Berkeley Lights Inc., Emeryville, California, USA.

Berkeley Lights Inc., "Opto CLD 2.0 Workflow," entire datasheet, 2020, Berkeley Lights Inc., Emeryville, California, USA.

Berkeley Lights Inc., "Screening Challenging Clones at Light Speed," entire poster, PEGS Summit, Apr. 30, 2018, Boston, Massachusetts, USA.

* cited by examiner

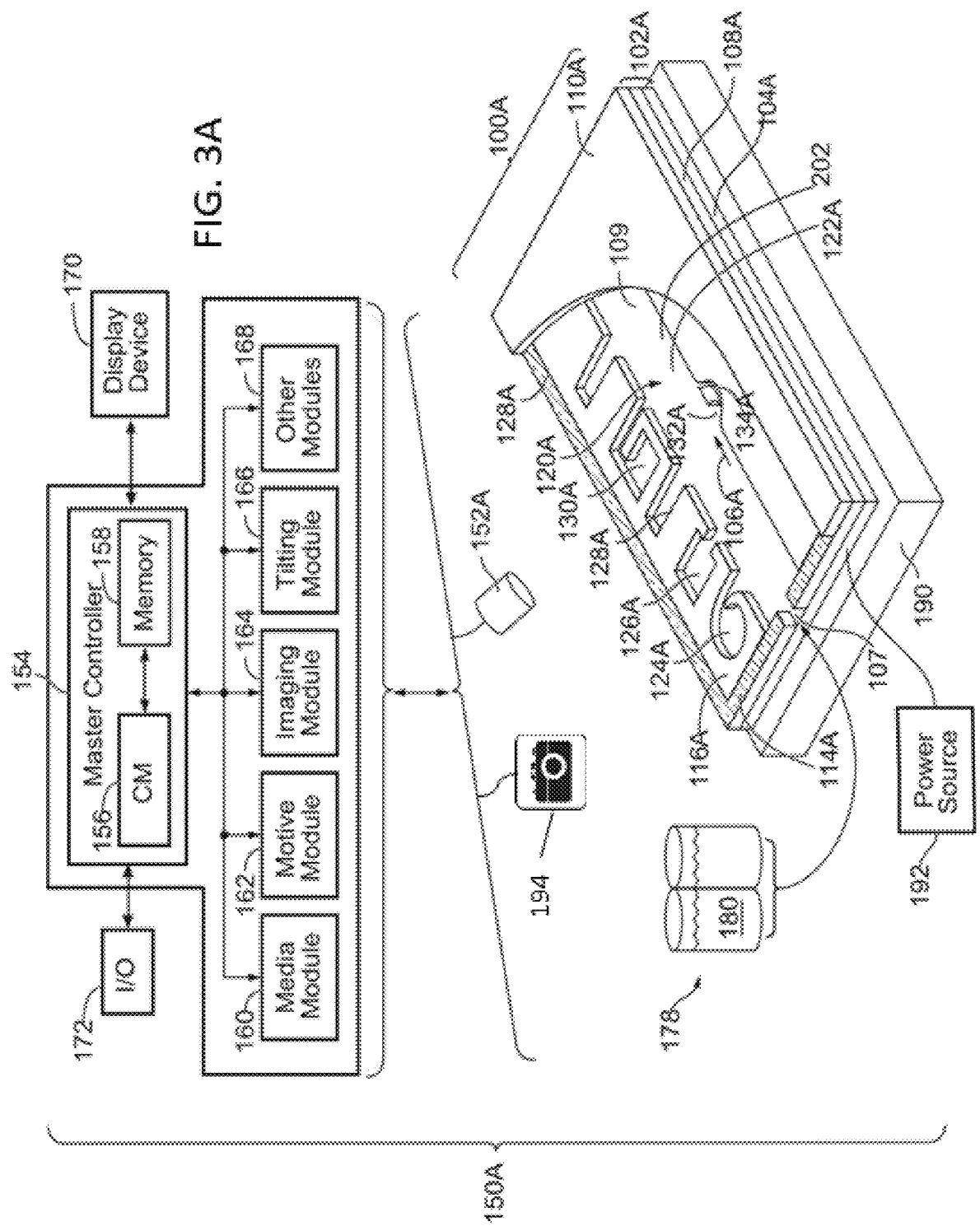

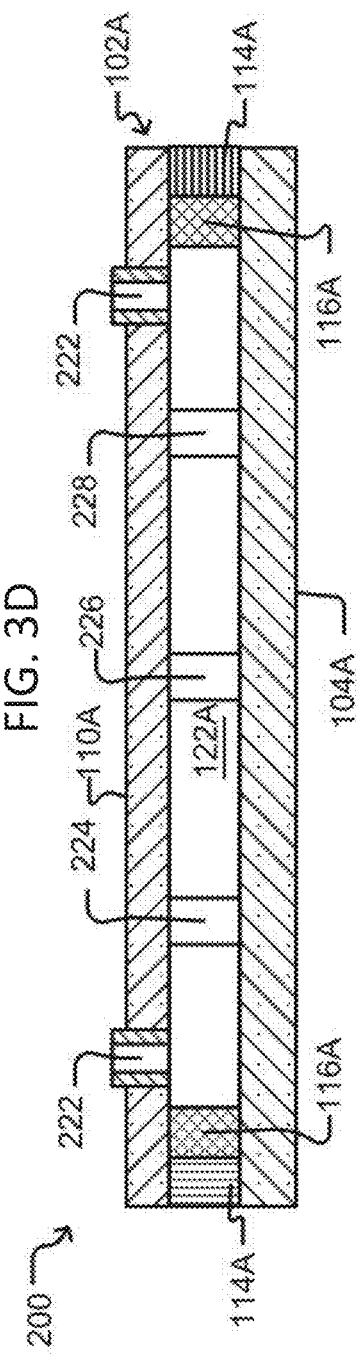
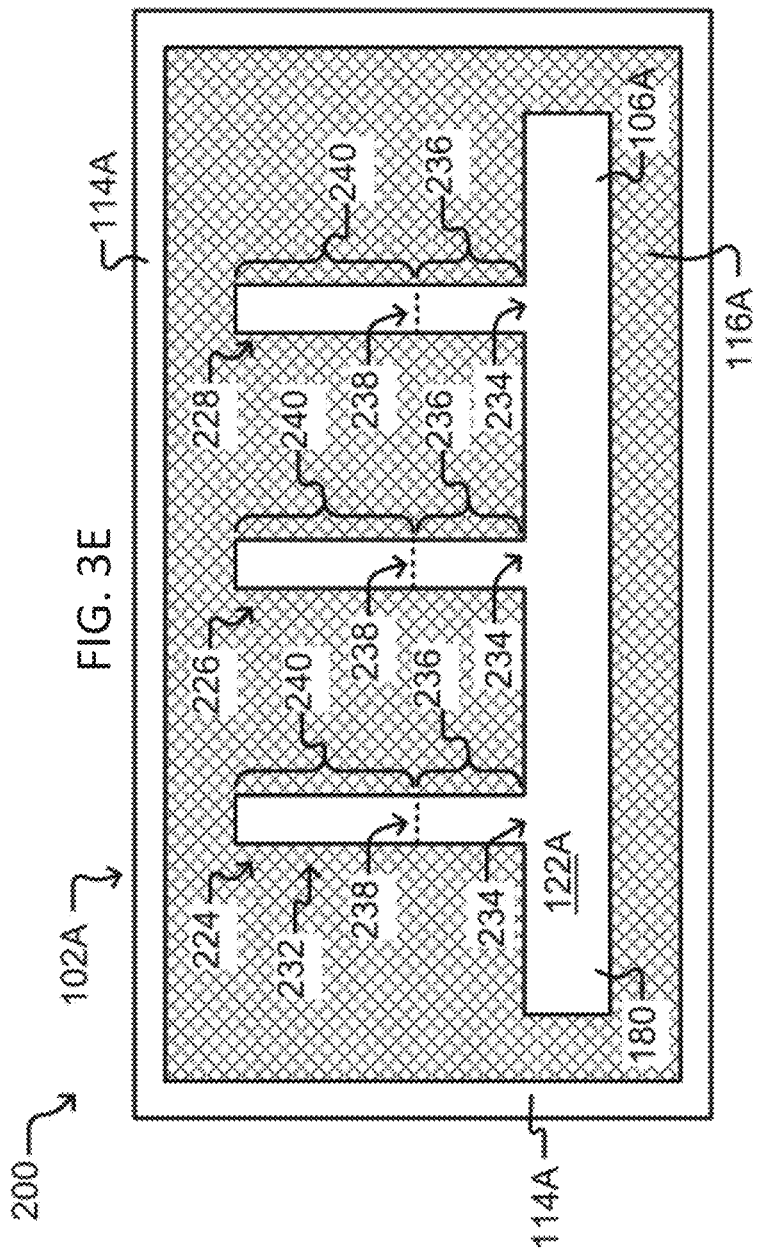

FIG. 4D

| 502H | 504H | 506H | 508H | 510H | 512H | 514H | 516H | 518H | 520H | 522H | 524H |
|---|---|---|---|---|---|---|---|---|---|---|---|
| ChipId | PenId | AssayHuFc: DeviceId | AssayHuFc: PenId | AssayHuFc: rQP | AssayHuFc: Score | AssayHuFc: Timestamp | AssayHuFc_2: DeviceId | AssayHuFc_2: PenId | AssayHuFc_2: rQP | AssayHuFc_2: Score | AssayHu |
| D48204 | 1 | D48204 | 1 | 0 | 0.013540862 | 4/20/2020 102:00 PM | D48204 | 1 | 0 | 0.016016642 | 4/21/20 |
| D48204 | 2 | D48204 | 2 | 0.014234002 | 0.014234002 | 4/20/2020 102:00 PM | D48204 | 1 | 0 | 0.016016642 | 4/21/20 |
| D48204 | 2 | D48204 | 3 | 0 | 0.013043168 | 4/20/2020 102:00 PM | D48204 | 3 | 0 | 0.015205976 | 4/21/20 |
| D48204 | 4 | D48204 | 4 | 0 | 0.013020785 | 4/20/2020 102:00 PM | D48204 | 4 | 0 | 0.015032397 | 4/21/20 |
| D48204 | 5 | D48204 | 5 | 0.006492302 | 0.012984604 | 4/20/2020 102:00 PM | D48204 | 5 | 0.007839473 | 0.015678946 | 4/21/20 |
| D48204 | 5 | D48204 | 6 | 0.012493583 | 0.012493583 | 4/20/2020 102:00 PM | D48204 | 6 | 0.015101718 | 0.015101718 | 4/21/20 |
| D48204 | 5 | D48204 | 7 | 0.004149343 | 0.016597372 | 4/20/2020 102:00 PM | D48204 | 7 | 0.003991447 | 0.02394868 | 4/21/20 |
| D48204 | 8 | D48204 | 8 | 0.0009645676 | 0.013929135 | 4/20/2020 102:00 PM | D48204 | 8 | 0.0051052715 | 0.015315815 | 4/21/20 |
| D48204 | 9 | D48204 | 9 | 0.005866896 | 0.017600687 | 4/20/2020 102:00 PM | D48204 | 9 | 0.004217647 | 0.025305882 | 4/21/20 |
| D48204 | 10 | D48204 | 10 | 0.01296334 | 0.01296334 | 4/20/2020 102:00 PM | D48204 | 10 | 0.011608631 | 0.023217283 | 4/21/20 |
| D48204 | 11 | D48204 | 11 | 0.0040484746 | 0.016193898 | 4/20/2020 102:00 PM | D48204 | 11 | 0.0045440285 | 0.022720143 | 4/21/20 |
| D48204 | 12 | D48204 | 12 | 0.0020172514 | 0.01412076 | 4/20/2020 102:00 PM | D48204 | 12 | 0.0015535691 | 0.01708926 | 4/21/20 |
| D48204 | 13 | D48204 | 13 | 0.004586486 | 0.018335945 | 4/20/2020 102:00 PM | D48204 | 13 | 0.004544967 | 0.027269801 | 4/21/20 |
| D48204 | 14 | D48204 | 14 | 0.006549675 | 0.01309935 | 4/20/2020 102:00 PM | D48204 | 14 | 0.005216803 | 0.015650408 | 4/21/20 |
| D48204 | 15 | D48204 | 15 | 0.0126591325 | 0.0126591325 | 4/20/2020 102:00 PM | D48204 | 15 | 0.007929702 | 0.015859495 | 4/21/20 |
| D48204 | 16 | D48204 | 16 | 0.004073021 | 0.016292084 | 4/20/2020 102:00 PM | D48204 | 16 | 0.002675402 | 0.024078619 | 4/21/20 |
| D48204 | 17 | D48204 | 17 | 0.0066682135 | 0.01336427 | 4/20/2020 102:00 PM | D48204 | 17 | 0.0074778143 | 0.014955529 | 4/21/20 |
| D48204 | 18 | D48204 | 18 | 0.0023243534 | 0.018594828 | 4/20/2020 102:00 PM | D48204 | 18 | 0.0020379932 | 0.030369896 | 4/21/20 |
| D48204 | 19 | D48204 | 19 | 0.0010808604 | 0.021613209 | 4/20/2020 102:00 PM | D48204 | 19 | 0.0034473576 | 0.027578862 | 4/21/20 |

| Loaded Dataset | |
|---|---|
| Genes | Cells |
| 15994 | 552 |

| Filtered Dataset | | |
|---|---|---|
| | N Cells Kept | % Cells Kept |
| HVSR Filter | 366 | 66.3 |
| Genes Filter | 526 | 95.29 |
| % Mito Filter | 476 | 86.23 |
| All Filters | 308 | 55.8 |

714C

| Summary for consumable | D66660 |
|---|---|
| Number of pens recovered / chip | 552 |
| Avg. PF % / chip | 79.01 |
| Avg. Q30 % / export | 85.05 |
| Avg. percent debarcoded / export | 97.22 |
| Avg. raw reads / export | 9853928 |
| Avg. input reads / export | 9367940 |
| Avg. % mapped / bead | 62.12 |
| Median HVSRs captured / bead | 6848 |
| Median genes captured / bead | 2152 |
| Avg. mitochondrial % / bead | 2.95 |

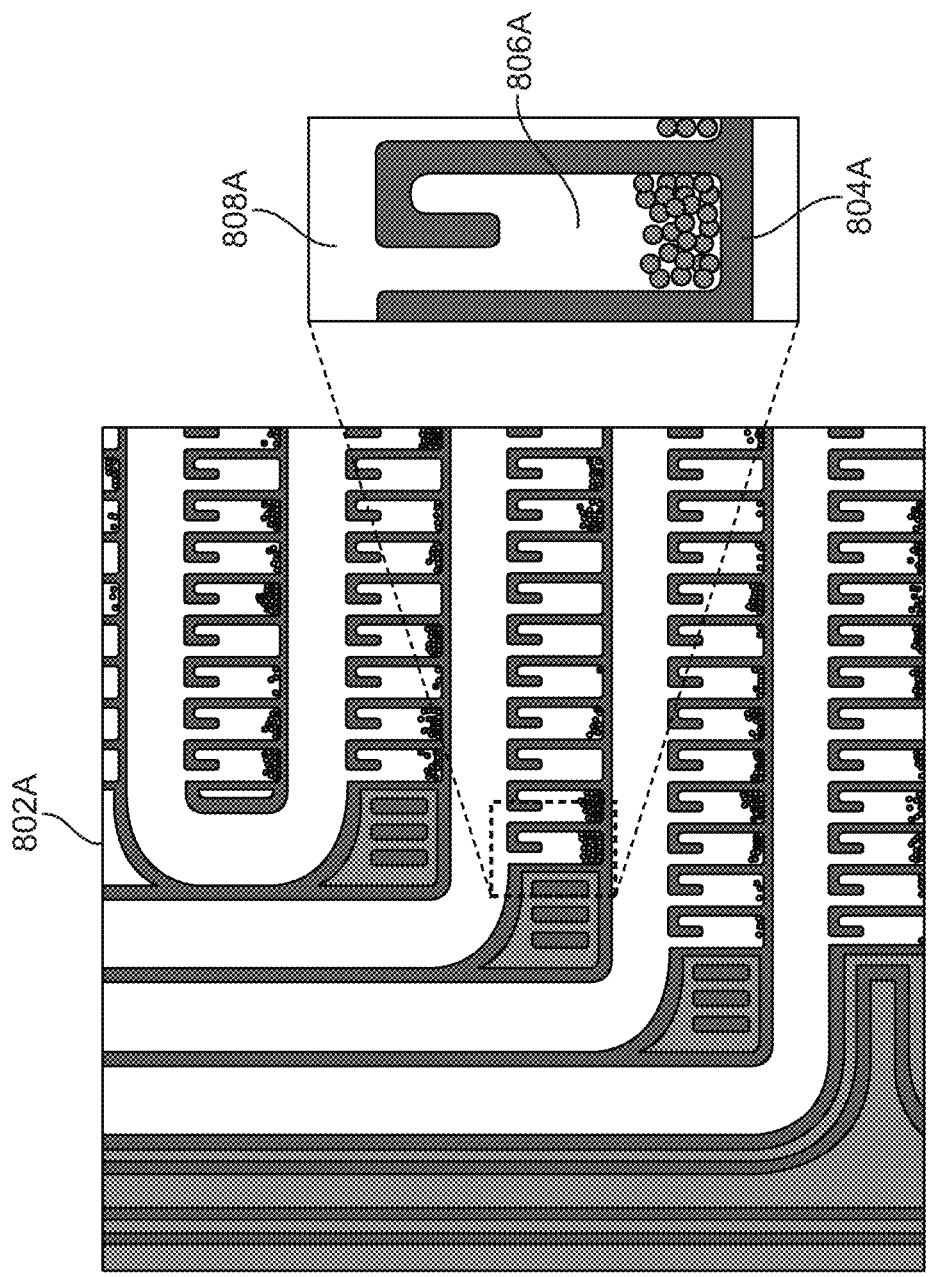

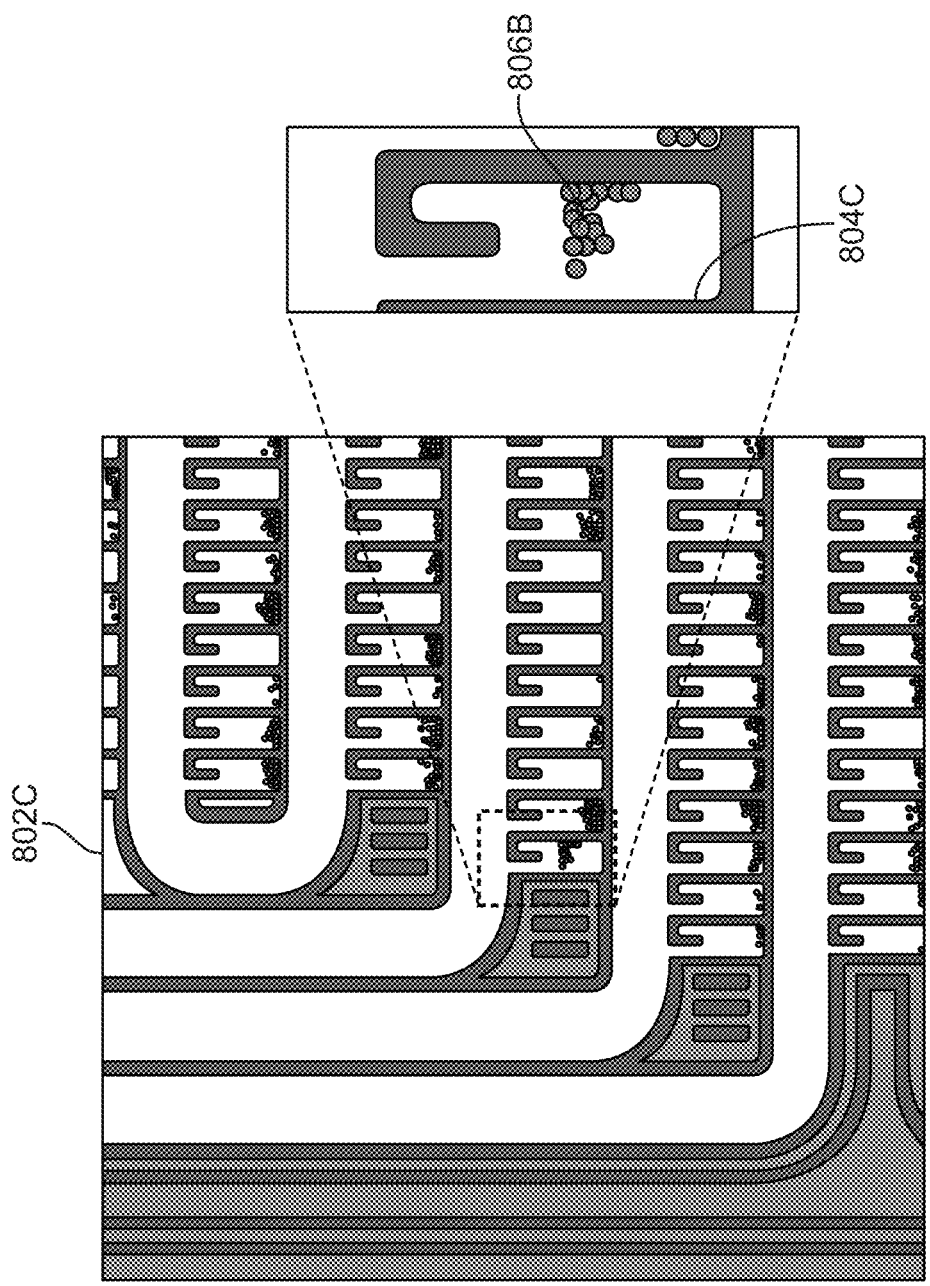

SYSTEMS AND METHODS FOR ANALYSES OF BIOLOGICAL SAMPLES

CROSS REFERENCE TO RELATED APPLICATIONS

This application is a continuation of international application number PCT/US2020/060784, filed on Nov. 16, 2020, which claims the benefit of U.S. Prov. Pat. App. Ser. No. 62/936,550 filed on Nov. 17, 2019 and entitled "ASSAY DATA GRAPHICAL USER INTERFACE SYSTEMS AND METHODS", U.S. Prov. Pat. App. Ser. No. 63/035,726 filed on Jun. 6, 2020 and entitled "ASSAY DATA GRAPHICAL USER INTERFACE SYSTEMS AND METHODS", U.S. Prov. Pat. App. Ser. No. 63/060,647 filed on Aug. 3, 2020 and entitled "ASSAY DATA GRAPHICAL USER INTERFACE SYSTEMS AND METHODS", and U.S. Prov. Pat. App. Ser. No. 62/950,573 filed on Dec. 19, 2019 and entitled "AUTOMATED COUNTING OF MICRO-OBJECTS IN MICROFLUIDIC DEVICES". The contents of the aforementioned U.S. provisional patent applications are hereby expressly incorporated by reference in their entireties for all purposes.

COPYRIGHT NOTICE

A portion of the disclosure of this patent document includes material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF ENDEAVOR

The present invention relates to devices, systems, and processes which may be useful in, for example, generating and displaying analysis results of micro-objects in a graphical user interfaces (GUI), and more specifically to such methods, systems, and GUIs used with data generated by analysis of micro-objects.

BACKGROUND

Biological assays on a microfluidic device, also called "lab-on-a-chip", have become important research tools because of the high throughput they are capable of producing, which may in turn vastly reduce both the time and expense of running large, statistically relevant numbers of tests. Understandably, improvements in this area may have great impacts on the evaluation of therapeutics.

Digital cell biology technologies available from Berkeley Lights (Emeryville, Calif.), including the Beacon and Lightning platforms, include significant new tools for researchers to manipulate micro-objects, including biological cells, beads, and other objects used in biological assays. The following documents, the entireties of which are incorporated by reference herein, describe some aspects of these technologies:

For microfluidic devices with chambers (or pens): U.S. Pat. No. 9,857,333, issued Jan. 2, 2018 (see also WO 2014/070873, published May 8, 2014); and U.S. Pat. No. 10,010,882, issued Jul. 3, 2018 (see also WO 2015/061497, published Apr. 30, 2015).

For microfluidic devices capable of generating a dielectrophoretic (DEP) force and other means of moving micro-objects within a microfluidic device: U.S. Pat. No. RE44,711, issued Jan. 21, 2014; U.S. Pat. No. 7,956,339, issued Jun. 7, 2011; U.S. Pat. No. 9,227,200, issued Jan. 5, 2016; U.S. Pat. No. 9,908,115, issued Mar. 6, 2018 (see also, WO 2016/094308, published Jun. 16, 2016); U.S. Pat. No. 9,403,172, issued Aug. 2, 2016, and U.S. Pat. No. 9,895,699, issued Feb. 20, 2018 (see also WO 2014/074367, published Mary 15, 2014); U.S. Pat. No. 9,815,056, issued Nov. 14, 2017 (see also WO 2016/090295, published Jun. 9, 2016); U.S. Pat. No. 10,058,865, issued Aug. 28, 2018 (see also WO 2016/094333, published Jun. 16, 2016); and WO 2017/117408, published Jun. 28, 2018.

For methods for assaying biological cells in microfluidic chips: WO 2015/061497, published Apr. 30, 2015; U.S. Pat. No. 9,889,445, issued Feb. 13, 2018, and U.S. Pat. No. 10,376,886, issued Aug. 13, 2019 (see also WO 2015/061506, published Apr. 30, 2015); WO 2017100347, published Jun. 15, 2017; WO 2017091601, published Jun. 1, 2017; WO 2017/181135, published Oct. 19, 2017; WO 2017/161210, published Sep. 21, 2017; WO 2018018017, published Jan. 25, 2018; WO 2018064640, published Apr. 5, 2018; WO 2018/076024, published Jul. 26, 2018; WO 2019075476, published Apr. 19, 2019; WO 2019191459, published Oct. 3, 2019; WO 2020092975, published May 7, 2020; WO 20200056339, published Mar. 19, 2020; WO 2020077274, published Apr. 16, 2020; U.S. Pat. No. 10,751,715 issued Aug. 25, 2020; and WO2020223555, published Nov. 5, 2020.

For instruments and software suitable for operating such microfluidic devices and performing all or part of such methods: U.S. Pat. No. RE44,711, issued Jan. 21, 2014; U.S. Pat. No. 10,384,204, issued Aug. 20, 2019 (see also WO 2016/094308, published Jun. 16, 2016); WO 2018/102747, published Jun. 7, 2018; WO 2018/102748, published Jun. 7, 2018; U.S. Pat. No. 9,996,920, issued Jun. 12, 2018 (see also WO 2016/094459, published Jun. 16, 2016); WO 2016/094522, published Jun. 16, 2016; and PCT/US2019/035046, filed Mary 31, 2019.

Other types of microfluidic devices having chambers, methods for assaying biological cells, and instruments for operating such devices and performing such methods include: U.S. Pat. No. 6,294,063 (Becker, et al.), U.S. Pat. No. 6,408,878 (Unger et al.), U.S. Pat. No. 6,942,776 (Medoro), U.S. Pat. No. 10,421,936 (Hansen et al.), and U.S. Pat. No. 10,466,241 (Hansen et al.)

In these technologies, a couple or a few to tens to hundreds of chambers are present on a single device; a chamber may be a microwell in a substrate, or large chambers that may be hundreds to thousands of times larger. In certain embodiments, after assays are run on the micro-objects (e.g., beads, proteins, and/or biological cells, etc.) in the chambers, the data outputs of these systems include very large datasets which include, for example, data nodes including high-resolution image data of the individual chambers themselves (or many discrete regions of large chambers), including any micro-objects that are included therein. The data nodes may also include time stamps for each image, as well as other operating conditions at the time the image was taken, and qualitative and/or quantitative results of the assays performed on the micro-objects.

Because the resulting datasets from even a single systems or a single analysis are extremely large and often include both image and alphanumeric elements, it is difficult, if not entirely impossible, for a human researcher to capture or visualize what processes may be occurring in any one or more chambers of interest, particularly over a long period of time during which an assay is run, and to analyze (e.g., visually compare) data from multiple micro-objects at the same time, let alone to derive any useful information therefrom.

To further exacerbate the problems caused by the extremely large datasets from even a single analysis, a dataset including, for example, the analysis results, the input data for the analysis, the metadata correlated with the biological samples and to the apparatus for the analysis, etc. often includes a large number of data elements that are often unstructured or uncorrelated with one another.

Sifting through such a large dataset having various types of data or information scattered in such an unstructured manner to decipher what the dataset is intended to convey presents insurmountable, impracticable obstacles for researchers to quickly and efficiently perform multiple analyses on biological samples and to extract the most impactful and meaningful synthesis of the analysis results. In one example, therapeutic antibody discovery is a laborious, expensive process with high uncertainty during the discovery process. In another nonlimiting example, detection and high-throughput drug screening, especially in a pandemic situation such as the Covid-19 pandemic requires rapid multifactorial evaluation of potential leads and candidate therapeutics. Thus, there is a dire need for improvements in correlating various data and information (e.g., analysis results, inputs, metadata, etc.), analyzing the biological samples of interest, presenting pertinent results of interest for visualization, and allowing researchers to efficiently and rapidly manipulate the datasets to identify data of interest to address at least the aforementioned problems and shortcomings of conventional detection or drug screening approaches.

SUMMARY

Disclosed are method(s), system(s), and article(s) of manufacture for performing a process on biological samples in one or more embodiments. Some embodiments are directed at a method for performing an assay analysis or sequencing analysis for biological samples. In these embodiments, a user interface is identified and coupled to a processor of a system (e.g., an assay analyzer, a general-purpose computer, a specific-purpose computer, etc.) for processing one or more attributes of inputs captured from a plurality of biological samples. Some embodiments are directed to a method for performing an automated count of biological samples in a region of interest in a microfluidic device having a plurality of chambers.

A system for performing any of the aforementioned methods in any of the embodiments is also described herein. A non-transitory computer readable medium for storing thereupon a sequence of instructions which, when executed by a processor or a processor core, causes the processor or processor core to perform any of the aforementioned methods in any of the embodiments is also described.

Summary Recitation of Some Embodiments of the Disclosure

1. A method for analyzing biological samples, comprising: identifying an analysis of biological samples in multiple regions of interest in a microfluidic device and a timeline correlated with the analysis, wherein the timeline comprises information that is temporally aligned with a workflow or pipeline of the analysis of the biological samples; determining one or more region-of-interest types for the multiple regions of interest, wherein the one or more region-of-interest types comprise a target-based type correlated with at least one biological sample of the biological samples or a structure-based type correlated with the microfluidic device; determining multiple characteristics for the biological samples based at least in part upon the one or more region-of-interest types, wherein the multiple characteristics respectively correspond to an attribute, a property, or a quantifiable metric for the biological samples or the analysis; and arranging and rendering associated data that respectively correspond to the multiple regions of interest in a user interface for at least a portion of the biological samples in the user interface based at least in part upon the multiple characteristics and the timeline.

2. The method of embodiment 1, wherein arranging and rendering the associated data comprises: determining a gallery structure having a plurality of gallery sub-structures for the associated data based at least in part upon an allocable space in the user interface for rendering the associated data.

3. The method of any of embodiments 1-2, wherein a gallery sub-structure of the plurality of gallery sub-structures corresponds to a characteristic correlated with the analysis of the biological samples or the biological samples, the gallery sub-structure comprises one or more gallery fields, and the characteristic comprises at least one target-based characteristic, at least one structure-based characteristic, or a combination of the at least one target-based characteristic and the at least one structure-based characteristic.

4. The method of any of embodiments 1-3, wherein arranging and rendering the associated data comprises: populating the associated data into the plurality of gallery sub-structures in the gallery structure based at least in part upon the characteristic.

5. The method of any of embodiments 1-4, wherein a gallery field of the gallery sub-structure corresponds to an image of an image sequence captured for a structured-based region of interest or a target-based region of interest of at least one of the biological samples, and the image or the image sequence is determined from one or more base images.

6. The method of any of embodiments 1-5, wherein the plurality of graphic representations in the timeline portion respectively corresponds to the plurality of gallery sub-structures.

7. The method of any of embodiments 1-4, determining the gallery structure comprising: determining a first sequence of data correlated with captured at a set of time points or time periods for at least a first portion of the biological samples obtained from at least a first portion of the multiple regions of interest from the gallery structure stored in an addressable space in the non-transitory computer accessible storage medium, wherein the first sequence of data corresponds to at least a first characteristic of the multiple characteristics.

8. The method of any of embodiments 1-7, determining the gallery structure comprising: determining a second sequence of data correlated with captured at the set of time points or time periods for at least a second portion of the biological samples obtained from at least a second portion of the multiple regions of interest from the gallery structure, wherein the second sequence of data corresponds to at least a second characteristic of the multiple characteristics.

9. The method of any of embodiments 1-8, arranging and rendering associated data comprising: rendering, in a first window portion of the user interface and with a graphics processing unit, the first and the second sequences of data in a gallery view.

10. The method of any of embodiments 1-9, rendering the first and the second sequences of data in the first view comprising: in response to a selection of at least the first characteristic from the multiple characteristics with a first selection widget in the user interface, extracting a first value of the first characteristic from a plurality of values for at least the first portion of the biological samples or for the analysis; and extracting a second value of the second characteristic from the plurality of values for at least the second portion of the biological samples or for the analysis.

11. The method of any of embodiments 1-10, arranging and rendering associated data comprising: rendering a first interactive object and a second interactive object respectively corresponding to the first and the second sequences of data into the gallery view.

12. The method of any of embodiments 1-11, wherein the first interactive object is representative of the first value for at least the first portion of the biological samples or for the analysis, and the second interactive object is representative of the second value for at least the second portion of the biological samples or for the analysis.

13. The method of any of embodiments 1-12, wherein the user interface is coupled to a processor for processing data for one or more attributes of inputs and comprises a set of images captured from at least the first and the second portions of the biological samples and obtained at the set of time points or time periods.

14. The method of any of embodiments 1-13, wherein an image in the set of images is obtained from a respective biological sample disposed within a region of interest of the multiple regions of interest correlated with the microfluidic device comprising a plurality of chambers.

15. The method of any of embodiments 1-14, arranging and rendering associated data comprising: rendering the first selection widget for selecting the first characteristic for the biological samples.

16. The method of any of embodiments 1-15, wherein a first set of data for a first set of images captured for the first region of interest in the microfluidic device is represented in a first gallery substructure of the gallery structure; and a second set of data for a second set of images captured for the second region of interest in the microfluidic device is represented in a second gallery substructure of the gallery structure.

17. The method of any of embodiments 1-16, wherein the first interactive object is associated with a first rank at a first time point or time period of a set of time points or time periods, the first rank indicating a first place of the first region of interest pertaining to the plurality of chambers in the microfluidic device based at least in part upon the first value of the first characteristic for the first region of interest.

18. The method of any of embodiments 1-17, wherein the second interactive object is associated with a second rank at the first time point or time period of the set of time points or time periods, the second rank indicating a second place of the second region of interest correlated with the plurality of chambers in the microfluidic device based at least in part upon the first value of the first characteristic for the second region of interest.

19. The method of any of embodiments 1-18, wherein the first and second ranks are respectively displayed together with the first and the second interactive objects in the first view to respective indicate a first status of the first biological sample in the first region of interest and a second status of the second biological sample in the second region of interest at the first time point or time period.

20. The method of any of embodiments 1-19, wherein first gallery substructure of data and the second gallery substructure of data are arranged to comprise a third gallery substructure having an interactive identifier that corresponds to the first identifier.

21. The method of any of embodiments 1-20, wherein the interactive identifier of the third gallery substructure, when invoked in the user interface, triggers a ranking operation that arranges the first gallery substructure and the second gallery substructure based at least in part upon the first rank and the second rank.

22. The method of any of embodiments 1-21, wherein a height or a width of a gallery sub-structure of the plurality of gallery sub-structures is configurable into a modified height or a modified width, or a width of a field in the third linear structure is configurable into a modified width in the first view.

23. The method of any of embodiments 1-16, wherein the gallery structure includes a column structure and a row structure, the column structure comprises multiple columns, the row structure comprises multiple rows, and biological sample data that is specific to the analysis performed on one or more biological samples in a single chamber of the microfluidic device.

24. The method of any of embodiments 1-23, wherein a column in the column structure corresponds to the biological sample data that is specific to the analysis performed on the single chamber, and each row corresponding to the column respectively corresponds to the biological sample data that is captured or generated for the single chamber at a specific time point or for a specific time period.

25. The method of any of embodiments 1-23, wherein a row in the row structure corresponds to the biological sample data that is specific to the analysis performed on a chamber in the microfluidic device, and each column corresponding to the row respectively corresponds to the biological sample data that is captured or generated for the chamber at a specific time point or for a specific time period.

26. The method of any of embodiments 1-25, wherein an identifier of the multiple characteristics pertains to at least one aspect of an assay analysis or a result of the assay analysis that is performed on the at least one biological sample of the biological samples in the microfluidic device.

27. The method of any of embodiments 1-23, wherein the set of images, the first sequence of data, or the second sequence of data is time stamped with a unique time stamp at the time the set of images, the first sequence of data, or the second sequence of data is captured or generated.

28. The method of any of embodiments 1-22, wherein the multiple characteristics comprise at least one of an identifier of a chamber in the microfluidic device, a size attribute of the biological samples, a maximum brightness attribute for the biological samples, a minimum brightness attribute for the biological samples, a first pixel count attribute in a first direction for a centroid of a biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of chambers or the multiple regions of interest, a gate path index, an area pixel attribute, a background pixel attribute, or a median brightness attribute for the biological samples.

29. The method of any of embodiments 1-28, rendering the first interactive object and the second interactive object comprising: determining, by the processor, a dynamic width or length for a first gallery sub-structure of the gallery structure in the user interface based at least in part upon a first rank that is to be represented in the user interface.

30. The method of any of embodiments 1-29, rendering the first interactive object and the second interactive object further comprising: rendering at least a portion of the first sequence of data comprising a first sequence of images into the first gallery sub-structure based at least in part upon the dynamic width or length for the first gallery sub-structure.

31. The method of any of embodiments 1-30, wherein a gallery field in a first plurality of gallery fields of the first gallery sub-structure corresponds to a region of interest of the multiple regions of interest, wherein the region of interest corresponds to a first unique identifier.

32. The method of any of embodiments 1-31, wherein the gallery field further corresponds to the region of interest correlated with the plurality of chambers and is further arranged to correspond to a plurality of gallery sub-structures.

33. The method of any of embodiments 1-32, wherein a gallery sub-structure of the plurality of gallery sub-structures corresponds to an identifier of the multiple characteristics.

34. The method of any of embodiments 1-33, further comprising: in response to an invocation of a timeline view through a timeline view activation interactive widget in the user interface based at least in part upon the timeline, rendering the timeline view and a matching grid portion in the user interface.

35. The method of any of embodiments 1-34, wherein the timeline view comprises respective progress of multiple workflow tasks in the analysis of the biological samples.

36. The method of any of embodiments 1-35, wherein the timeline view is rendered based at least in part upon a first sequence of data and a second sequence of data correlated with the analysis or to the biological samples.

37. The method of any of embodiments 1-36, wherein the respective progress graphically indicates respective temporal durations of the multiple workflow tasks.

38. The method of any of embodiments 1-37, wherein the respective progress is represented with an interactive progress widget which, when interacted upon in the timeline view, causes the processor at least to populate the matching grid portion with at least a portion of the first sequence of data or at least a portion of the first analysis result.

39. The method of any of embodiments 1-37, further comprising: determining whether the gallery structure exists for the microfluidic device in response to an identification of the microfluidic device, the first sequence of data, or the second sequence of data represented in the user interface, wherein the data comprises the first sequence of data correlated with the first biological sample from a first region of interest of the multiple regions of interest, or the second sequence of data correlated with the second biological sample from the second region of interest of the multiple regions of interest represented in the user interface.

40. The method of any of embodiments 1-39, further comprising: when it is determined that the gallery structure exists for the microfluidic device, populating the matching grid portion with at least a portion of the first sequence of data or at least a portion of the associated data; and rendering an identifier widget which, when receiving an identifier change input from the user interface, triggers an instruction that changes a first identifier of the first sequence of data.

41. The method of any of embodiments 1-40, further comprising: rendering a delete widget which, when invoked in the user interface, causes at least the processor to remove the microfluidic device and data correlated with the microfluidic device from the timeline view.

42. The method of any of embodiments 1-41, wherein the timeline view comprises a first adjustable size or shape in the user interface.

43 The method of any of embodiments 1-42, wherein the matching grid portion comprises a second adjustable size or shape in the user interface.

44. The method of any of embodiments 1-43, wherein the timeline portion comprises multiple graphical representations respectively identifying corresponding experiment types of the multiple biological experiments.

45. The method of any of embodiments 1-44, further comprising: associating a first region of interest of the multiple regions of interest with one or more graphical elements illustrated in a timeline view.

46. The method of any of embodiments 1-36, wherein associating the first region of interest with the one or more graphical elements comprises rendering a first interactive object, which corresponds to a first sequence of data captured at a first time point or a first temporal period, for a first graphical element of the one or more graphical elements in a first column in a portion of the user interface.

47. The method of any of embodiments 1-46, wherein associating the first region of interest with the one or more graphical elements comprises: rendering a second interactive object, which corresponds to a first sequence of data captured at a second time point or a second temporal period, for a second graphical element of the one or more graphical elements, the second interactive object corresponding to a second column in the portion of the user interface.

48. The method of any of embodiments 1-46, wherein a size of a graphical element of the one or more graphical elements corresponds to a temporal duration of a time period during which data is captured for the biological samples, and a larger graphical element indicates a longer temporal period.

49. The method of any of embodiments 1-36, wherein arranging and rendering the associated data comprises: determining the timeline based at least in part upon a pipeline or a workflow for the analysis of the biological samples.

50. The method of any of embodiments 1-49, wherein arranging and rendering the associated data comprises: determining a plurality of stages for the analysis based at least in part upon the timeline, wherein the plurality of stages respectively corresponds to a plurality of timepoints or time periods for the analysis of the biological samples.

51. The method of any of embodiments 1-50, wherein arranging and rendering the associated data comprises: respectively determining a plurality of graphic representations for the plurality of stages based at least in part upon the plurality of timepoints or time periods.

52. The method of any of embodiments 1-51, wherein arranging and rendering the associated data comprises: arranging and rendering the plurality of graphic representations in the timeline view in the user interface according to a temporal order correlated with the plurality of timepoints or time periods.

53. The method of any of embodiments 1-52, further comprising rendering a data control view in the user interface, rendering the data control view comprising: generating a microfluidic device data structure having a plurality of fields for the microfluidic device having a plurality of chambers.

54. The method of any of embodiments 1-53, rendering the data control view comprising: populating first data of the microfluidic device into a first field in the microfluidic device data structure, wherein the first data comprises a first identifier of the microfluidic device.

55. The method of any of embodiments 1-54, rendering the data control view comprising: rendering a first interactive data control widget for the first field in the microfluidic device data structure, wherein the first interactive data control widget, when interacted upon, invokes one of multiple first candidate actions that are correlated to a timeline view or a gallery view, depending upon a first input received in the data control view for configuring a chamber list correlated with at least the first data and the gallery view.

56. The method of any of embodiments 1-55, rendering the data control view further comprising: populating second data of the microfluidic device into a second field in the microfluidic device data structure, wherein the second data comprises a tag correlated with a first biological processing on the biological samples in the microfluidic device.

57. The method of any of embodiments 1-56, rendering the data control view further comprising: rendering a second interactive data control widget for the second field, wherein the second interactive data control widget invokes at least one of multiple second candidate actions in response to a second user input in the data control view for configuring one or more visualization options of the associated data.

58. The method of any of embodiments 1-55, rendering the data control view further comprising: populating third data of the microfluidic device into one or more third fields in the microfluidic device data structure, wherein the third data comprises a time stamp for the microfluidic device.

59. The method of any of embodiments 1-58, rendering the data control view further comprising: rendering a third interactive data control widget for the one or more third fields, wherein the third interactive data control widget, when interacted upon, invokes at least one of multiple third candidate actions in response to a third user input in the data control view for configuring dimensionality reduction or clustering for the analysis.

60. The method of any of embodiments 1-59, further comprising rendering a filter view, wherein rendering the filter view comprises: determining a first filter type for a first filter based at least in part upon an execution of one or more instructions triggered by an interaction with a first filter selector switch in a filter generation module.

61. The method of any of embodiments 1-60, rendering the filter view comprises: in response to a determination of the first filter type, rendering the first filter selector switch for the first filter type of one or more first filters in the filter view in the user interface, wherein the first filter selector switch, when invoked, triggers a first presentation of a list of one or more first interactive filter attributes for the first filter type.

62. The method of any of embodiments 1-61, rendering the filter view further comprising: in response to invocation of a first interactive filter attribute in the list of one or more first interactive filter attributes, rendering a first filter configurator for filtering the plurality of chambers or the multiple regions of interest in the microfluidic device according to the first filter.

63. The method of any of embodiments 1-62, wherein the first filter configurator imposes a first dynamic constraint on the plurality of chambers or the multiple regions of interest in response to a first interactive filter input for the first interactive filter attribute.

64. The method of any of embodiments 1-63, wherein the first dynamic constraint constrains the plurality of chambers or the multiple regions of interest to generate a first set of filtered regions of interest from the plurality of chambers or the multiple regions of interest to be displayed in the user interface.

65. The method of any of embodiments 1-64, wherein the first filter configurator comprises a first configuration slider widget which, when manipulated with a dynamic manipulation in the filter view, confines a number of dynamically constrained regions of interest in the microfluidic device and further triggers a graphical representation of the number of dynamically constrained regions of interest in the filter view based at least in part upon the dynamic manipulation.

66. The method of any of embodiments 1-64, rendering the filter view further comprising: dynamically determining and displaying, in the filter view for the microfluidic device, a first total number of regions of interest for the first set of filtered regions of interest that satisfies the first dynamic constraint.

67. The method of any of embodiments 1-66, rendering the filter view further comprising: rendering a first histogram that dynamically varies in response to a first dynamic change in the first dynamic constraint for the first filter.

68. The method of any of embodiments 1-67, wherein the first histogram comprises a de-emphasized histogram of the plurality of chambers or a region of interest that is overlaid on top of the first histogram that dynamically varies in response to the first dynamic change in the first dynamic constraint.

69. The method of any of embodiments 1-68, wherein the filter view further comprises information about a filtered region of interest of the first set of filtered regions of interest, the information comprising one or more region of interest identifiers, the first total number of regions of interest satisfying the first dynamic constraint, a histogram illustrating a first distribution of the plurality of chambers or the multiple regions of interest over the first interactive filter attribute, a highlighted portion of the histogram illustrating a second distribution of the first set of filtered regions of interest over the first interactive filter attribute, or any combination thereof.

70. The method of any of embodiments 1-61, rendering the filter view further comprising: generating, at the filter generation module, a logical combination of at least a second filter of a second filter type and a third filter of a third filter type.

71. The method of any of embodiments 1-70, rendering the filter view further comprising rendering the first filter switch for the second filter type.

72. The method of any of embodiments 1-71, wherein the first filter selector switch, when invoked, is used to determine the second filter type, a second attribute selector for the second filter, or a third attribute selector for the third filter.

73. The method of any of embodiments 1-72, rendering the filter view further comprising: in response to a determination of a second filter attribute, rendering a second filter configurator for filtering the plurality of chambers or the multiple regions of interest according to the second filter, wherein the second filter configurator imposes a second dynamic constraint in response to a second filter input, the second dynamic constraint constrains a second number of filtered regions of interest from the multiple regions of interest to be displayed in the user interface.

74. The method of any of embodiments 1-73, rendering the filter view further comprising: dynamically determining and displaying, in the filter view for the microfluidic device, a second total number of filtered regions of interest that satisfies the second dynamic constraint.

75. The method of any of embodiments 1-74, rendering the filter view further comprising: rendering a second histogram that dynamically varies in response to a second dynamic change in the second dynamic constraint from the second filter input.

76. The method of any of embodiments 1-75, rendering the filter view further comprising: rendering the first filter selector switch for the second filter type, wherein the first filter selector switch, when invoked, is used to determine the second filter type and the second attribute selector corresponding to the second filter type.

77. The method of any of embodiments 1-76, rendering the filter view further comprising: in response to an invocation of the second filter type, rendering the second attribute selector switch for the second filter type of one or more second filters in the filter view in the user interface.

78. The method of any of embodiments 1-77, wherein the second attribute selector, when invoked, triggers a second presentation of a list of one or more second interactive filter attributes for the second filter type.

79. The method of any of embodiments 1-78, rendering the filter view further comprising: rendering the first filter selector switch in the filter generation module for the third filter type, wherein the first filter selector switch, when invoked, is used to determine the third filter type and the third attribute selector corresponding to the third filter type.

80. The method of any of embodiments 1-79, rendering the filter view further comprising: in response to an invocation of the third filter type, rendering the third attribute selector for the third filter type of one or more third filters in the filter view in the user interface, wherein the third attribute selector, when invoked, triggers a third presentation of a list of one or more third interactive filter attributes for the third filter type.

81. The method of any of embodiments 1-80, rendering the filter view further comprising: in response to selection of a second interactive filter attribute, rendering the second filter configurator for filtering the plurality of chambers or the multiple regions of interest in the microfluidic device according to the second filter.

82. The method of any of embodiments 1-81, wherein the second filter configurator is used to impose the second dynamic constraint in response to a second interactive filter input.

83. The method of any of embodiments 1-82, wherein the second dynamic constraint constrains the plurality of chambers or the multiple regions of interest from the first filter into a second set of filtered regions of interest to be displayed in the user interface.

84. The method of any of embodiments 1-83, wherein the second filter configurator comprises a second configuration slider widget which, when manipulated with a second dynamic manipulation, confines the plurality of chambers or the multiple regions of interest into a separate number of dynamically constrained regions of interest for the microfluidic device and further triggers rendering a graphical representation of the separate number of dynamically constrained regions of interest in the filter view based at least in part upon the second dynamic manipulation.

85. The method of any of embodiments 1-82, rendering the filter view further comprising: in response to selection or determination of a third interactive filter attribute, rendering a third filter configurator for filtering the second set of filtered regions of interest in the microfluidic device according to the third filter.

86. The method of any of embodiments 1-85, wherein the third filter configurator imposes a third dynamic constraint in response to a third interactive filter input, and the third dynamic constraint constrains the second set of filtered regions of interest from the second filter into a third set of filtered regions of interest to be displayed in the user interface.

87. The method of any of embodiments 1-86, rendering the filter view further comprising: dynamically determining and displaying, in the filter view for the microfluidic device, a second total number of regions of interest for the second set of filtered regions of interest that satisfies the second dynamic constraint.

88. The method of any of embodiments 1-87, rendering the filter view further comprising: dynamically determining and displaying, in the filter view for the microfluidic device, a third total number of regions of interest for the third set of filtered regions of interest that satisfies the third dynamic constraint.

89. The method of any of embodiments 1-88, wherein the filter view further comprises second information about a filtered region of interest of the second or the third set of filtered regions of interest, the second information comprising one or more region of interest identifiers, the second or the third total number of regions of interest respectively satisfying the second or the third dynamic constraint, a separate histogram illustrating a separate distribution of the plurality of regions of interest over the second and the third interactive filter attributes, a separate highlighted portion of the separate histogram illustrating a third distribution of the second or the third set of filtered regions of interest over the first interactive filter attribute, or any combination thereof.

90. The method of any of embodiments 1-89, rendering the filter view further comprising: rendering a third histogram or scatter plot that dynamically varies in response to the second dynamic change in the second dynamic constraint from the second interactive filter input.

91. The method of any of embodiments 1-90, rendering the filter view further comprising: rendering a fourth histogram or scatter plot that dynamically varies in response to a third dynamic change in the third dynamic constraint from the third interactive filter input.

92. The method of any of embodiments 1-91, rendering the filter view further comprising: generating, at a list generation module, a first region of interest list.

93. The method of any of embodiments 1-92, generating the first region of interest list comprising at least one of: receiving a first instruction from the user interface for generating the first region of interest list based at least in part upon a first interaction with the user interface, wherein the first interaction corresponds to toggling a multi-state selector in the user interface to set a selected state for a selected region of interest in a set of filtered regions of interest or in the plurality of chambers or the multiple regions of interest in the filter view; rendering a list generation switch in the filter view, wherein the list generation switch, when invoked, is used to generate the first region of interest list to include one or more first selected regions of interest that are selected by at least the first interaction from the set of filtered regions of interest or the plurality of chambers or the multiple regions of interest; or generating the first region of interest list for the one or more first selected regions of interest in response to an interaction with the list generation switch.

94. The method of any of embodiments 1-93, rendering the filter view further comprising: generating, at the list generation module, a second region of interest list; and presenting a number of presented regions of interest in a graphical plot in the filter view based at least in part upon one or more filters, wherein the graphical plot illustrates how one or more properties of the number of presented regions of interest distribute with respect to the one or more filters.

95. The method of any of embodiments 1-94, rendering the filter view further comprising: receiving a second instruction based at least in part upon a second interaction from the user interface, wherein the second interaction comprises a selection of a subset of regions of interest from the number of presented regions of interest with a user-defined curvilinear or rectilinear boundary that encloses one or more display areas displaying data correlated with the associated data in the user interface.

96. The method of any of embodiments 1-95, rendering the filter view further comprising: generating the second region of interest list for the one or more display areas in response to activation of the list generation switch.

97. The method of any of embodiments 1-96, wherein the user-defined curvilinear or rectilinear boundary in the filter view is determined based at least in part upon one or more selection criteria that comprise one or more characteristics of one or more regions of interest in the number of presented regions of interest, and the number of presented regions of interest is displayed in the filter view with a heat map having multiple colors or a uniform color scheme based at least in part upon a first property of the number of presented regions of interest.

98. The method of any of embodiments 1-97, rendering the filter view further comprising: in response to a cursor of a pointing device hovering at or around the region of interest in the filter view, triggering a generation of a pop-up display region to display information about the region of interest, wherein the information is configurable by a user based at least in part upon a selection of the one or more characteristics of the region of interest.

99. The method of any of embodiments 1-98, rendering the filter view further comprising: modifying the use-defined curvilinear or rectilinear boundary at least by adding one or more nodes to the use-defined curvilinear or a rectilinear bound and by modifying the use-defined curvilinear or a rectilinear bound based at least in part upon the one or more nodes.

100. The method of any of embodiments 1-99, further comprising generating a bioinformatics pipeline view, generating the bioinformatics pipeline view comprising: determining a sequencing dataset for the biological samples in the plurality of chambers or the multiple regions of interest of the microfluidic device, wherein a biological sample comprises a sequence of nucleotides or amino acids.

101. The method of any of embodiments 1-100, generating the bioinformatics pipeline view further comprising: receiving the sequencing dataset in the user interface; and identifying, in the user interface, a characteristic correlated with a sequence of nucleotides or amino acids.

102. The method of any of embodiments 1-101, generating the bioinformatics pipeline view further comprising: in response to a first interaction with a first sequencing view widget in the user interface, rendering a first sequencing view in the bioinformatics pipeline view that illustrates a distribution of an attribute of the sequence of first biological samples including at least one of a sequence of nucleotides, a sequence of amino acids, or a sequence of macromolecules in the plurality of chambers or the multiple regions of interest of the microfluidic device.

103. The method of any of embodiments 1-102, generating the bioinformatics pipeline view further comprising: overlaying the first sequencing view with first information that comprises one or more statistical measures of the distribution of the characteristic of the sequences of first biological samples, wherein the user interface comprises a total number of multiple sequences of first biological samples, a total number of regions of interest having the sequences of first biological samples, and a respective total number of one or more sequences of first biological samples in a respective region of interest of the array of regions of interest.

104. The method of any of embodiments 1-103, generating the bioinformatics pipeline view further comprising: in response to a second interaction on a portion of the distribution in the first sequencing view, overlaying the first sequencing view with second information that comprises one or more quantifiable measures correlated with one or more sequences of multiple sequences of first biological samples with respect to the portion of the distribution in the first sequencing view.

105. The method of any of embodiments 1-104, further comprising: receiving the second interaction with a first curvilinear or rectilinear selection widget in the bioinformatics pipeline view of the user interface, the second interaction triggers a first instruction to eliminate a portion of the first sequencing view in the bioinformatics pipeline view based at least in part upon an extent of the second interaction.

106. The method of any of embodiments 1-105, further comprising: in response to a third interaction with a second sequencing view widget in the user interface, rendering a second sequencing view in the bioinformatics pipeline view that illustrates a second distribution of the characteristic of the sequence of nucleotides or amino acids in the plurality of chambers or the multiple regions of interest.

107. The method of any of embodiments 1-106, wherein the second distribution comprises respective intensities of the plurality of biological samples in the plurality of chambers or the multiple regions of interest in response to a fluorescent dye, and the respective intensities are associated with respective coloring tones that are customizable by users.

108. The method of any of embodiments 1-107, further comprising: receiving a fourth interaction with the curvilinear or rectilinear selection widget or a different curvilinear or rectilinear selection widget in the bioinformatics pipeline view, the third interaction causes execution of a second instruction to select one or more regions of interest from the second sequencing view in the bioinformatics pipeline view based at least in part upon an extent of the fourth interaction.

109. The method of any of embodiments 1-108, further comprising: receiving a fifth instruction from the user interface for generating a first region of interest list.

110. The method of any of embodiments 1-109, receiving the fifth instruction for generating the first region of interest list comprising: generating the first region of interest list for the one or more regions of interest selected from the second sequencing view based at least in part upon the curvilinear or rectilinear selection widget or the different curvilinear or rectilinear selection widget in the bioinformatics pipeline view.

111. The method of any of embodiments 1-110, receiving the fifth instruction for generating the first region of interest list comprising: in response to generation of the first region of interest list comprising the one or more regions of interest selected from the second sequencing view, triggering a sixth instruction that invokes an operation for rendering a second sequence of data into multiple gallery fields in the gallery structure or a separate gallery structure.

112. The method of any of embodiments 1-111, receiving the fifth instruction for generating the first region of interest list further comprising: determining the dynamic width or a different dynamic width for a respective gallery field of the multiple gallery fields for display in the user interface.

113. The method of any of embodiments 1-112, receiving the fifth instruction for generating the first region of interest list further comprising: rendering a respective interactive object with a corresponding display property for a respective region of interest of the one or more regions of interest selected from the second sequencing view.

114. The method of any of embodiments 1-113, the set of acts further comprising: rendering a multi-directional placement widget in the user interface that includes at least one view; and identifying an addition instruction for adding a separate object into the user interface based at least in part upon a first input from a user.

115. The method of any of embodiments 1-114, the set of acts further comprising: determining a candidate placement position from multiple candidate placement positions for the separate object based at least in part upon the first input.

116. The method of any of embodiments 1-115, the set of acts further comprising: rendering a ghosting object at the candidate position in the user interface to graphically present where the separate object is to be placed in relation to the at least one view prior to placement of the separate object in the user interface.

117. The method of any of embodiments 1-116, further comprising: snapping the separate object to the candidate placement position upon a separate input from the user input device.

118. The method of any of embodiments 1-118, wherein the multi-directional placement widget provides multiple candidate placement positions in at least two orthogonal directions for placing the separate object in the user interface, and one or more boundaries of the separate object are individually adjustable after the placement of the separate object in the user interface.

119. The method of any of embodiments 1-118, wherein the first input comprises information correlated with a relative position of the cursor of the user input device in relation to the multi-directional placement widget rendered in the user interface, or the at least one view and the separate object are both presented in a non-overlapping manner in the user interface at least by resizing the at least one view to accommodate the placement of the separate object at the candidate placement position in the user interface.

120. The method of any of embodiments 1-119, wherein each chamber of the plurality of chambers in the microfluidic device comprises a unique identifier.

121. The method of any of embodiments 1-120, wherein the multiple characteristics correspond to one or more attributes that further comprise at least one of an identifier of a region of interest in the microfluidic device, a size attribute of the plurality of biological samples, a maximum brightness attribute for the plurality of biological samples, a minimum brightness attribute for the plurality of biological samples, a first pixel count attribute in a first direction for a centroid of a biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of regions of interest, a gate path index, an area pixel attribute, a background pixel attribute, or a median brightness attribute for the plurality of biological samples.

122. The method of any of embodiments 1-121, further comprising determining a first count of the biological samples at a first time point in a region of interest in the microfluidic device.

123. The method of any of embodiments 1-122, determining the first count of the biological samples at the first time point comprising: receiving first image data captured at a first time point for a region of interest in the microfluidic device.

124. The method of any of embodiments 1-123, further comprising: pre-processing the first image data into first pre-processed image data at least by arranging the first image data into an array of first pixel information by second pixel information by a pixel depth information.

125. The method of any of embodiments 1-124, further comprising: determining a first count of the biological samples in the region of interest at least by recognizing the biological samples with the convolutional neural network (CNN) having multiple processing blocks.

126. The method of any of embodiments 1-125, further comprising: determining a first class or type of the first image data at least by classifying the first image data or the first pre-processed image data into the first class or type with at least a machine learning model.

127. The method of any of embodiments 1-126, further comprising: determining the first count of the biological samples in the region of interest based at least in part upon the first class or type using the convolutional neural network (CNN).

128. The method of any of embodiments 1-127, further comprising: displaying textual or graphical information correlated with the first count for the region of interest in a gallery view of a graphical user interface (GUI).

129. The method of any of embodiments 1-128, wherein the multiple processing blocks comprise: a first processing block, a second processing block, and a third processing block, the first processing block comprising a first down-sampling block that down-samples a first input to the second down-sampling block into first down-sampled image data.

130. The method of any of embodiments 1-129, the first processing block further comprising: a first residual network, wherein the first residual network follows the first down-sampling block, wherein each of the first down-sampling block and the first residual network in the first processing block comprises at least one first convolutional layer.

131. The method of any of embodiments 1-130, wherein the first residual network comprises a first parallel path and a second parallel path, both of which receive a first down-sampling block output from the first down-sampling block, the first parallel path comprises a first filter size, and the second parallel path comprises a second filter size that is smaller than the first filter size of the first parallel path.

132. The method of any of embodiments 1-130, wherein the multiple processing blocks further comprise a fourth processing block that further comprises: a number of transpose convolutional layers each of which is followed by a respective normalization layer.

133. The method of any of embodiments 1-132, wherein a transpose convolutional layer of the number of transpose convolutional layers has a same stride number as the at least one first convolutional layer in the first processing block or the at least one second convolutional layer in the second processing block.

134. The method of any of embodiments 1-133, wherein convolutional layers in the convolutional neural network have filter sizes greater than one-by-one so that no convolutional layers in the convolutional neural network have a one-by-one filter.

135. The method of any of embodiments 1-134, wherein the convolutional neural network comprises no pooling layers.

136. The method of any of embodiments 1-135, further comprising: receiving, at a differential gene expression module, a first dataset correlated with the biological samples in the multiple regions of interest in the microfluidic device at a first time point or time period.

137. The method of any of embodiments 1-136, further comprising: receiving, at the differential gene expression module, a second dataset correlated with the biological samples in the multiple regions of interest at a second time point or time period.

138. The method of any of embodiments 1-137, further comprising: determining a first list of regions of interest for first dataset of the biological samples; and determining a second list of regions for the second dataset of the biological samples.

139. The method of any of embodiments 1-138, further comprising: determining at least one statistic measure correlated with a change in a first quantifiable metric between the first and the second time points or time periods.

140. The method of any of embodiments 1-139, wherein the at least one statistic measure comprises a fold change, and the change comprises a first ratio between the first quantifiable metric at the first time point or time period and the first quantifiable metric at the second time point or time period.

141. The method of any of embodiments 1-140, wherein the at least one statistic measure comprises a logarithm of a second ratio between the first quantifiable metric at the first time point or time period and the first quantifiable metric at the second time point or time period.

142. The method of any of embodiments 1-141, further comprising: receiving a first configurable constraint value from a first user interaction with a fold change slider widget, wherein the first configurable constraint value suppresses first data correlated with the biological samples that exhibits the change in the first quantifiable metric below the first configurable constraint value.

143. The method of any of embodiments 1-142, further comprising: dynamically filtering at least a portion of the first and the second datasets based at least in part upon the first user interaction.

144. The method of any of embodiments 1-143, further comprising: displaying first differential gene expression data in a differential gene expression view from the first dataset and the second dataset based at least in part upon the first configurable constraint value, wherein the first data correlated with the first and the second datasets that exhibit the change below the first configurable constraint value is suppressed in the differential gene expression view.

145. The method of any of embodiments 1-144, further comprising configuring a bioinformatics pipeline view for a first dataset correlated with the biological samples in the microfluidic device with a set of configuration widgets.

146. The method of any of embodiments 1-145, wherein the plurality of configuration widgets comprises at least one of a dimensionality reduction widget, a clustering widget, a coordinate configuration widget, a color scale configuration widget, a number of color scales configuration widget, a scatter plot configuration widget, a list of regions of interest manipulation module, or a dynamic filtering slider widget.

147. The method of any of embodiments 1-146, configuring the bioinformatics pipeline view comprising: receiving, from a first interaction with the dimensional reduction widget, a number of principal component analysis (PCA) components for the first dataset of the biological samples.

148. The method of any of embodiments 1-147, configuring the bioinformatics pipeline view comprising: reducing dimensionality of the first dataset correlated with the biological samples based at least in part upon the number of principal component analysis components.

149. The method of any of embodiments 1-148, configuring the bioinformatics pipeline view comprising: receiving, from a second interaction with the clustering widget, a Louvain clustering parameter value for the first dataset of the biological samples.

150. The method of any of embodiments 1-149, configuring the bioinformatics pipeline view comprising: clustering at least a portion of the biological samples into one or more clusters at least by processing the first dataset based at least in part upon the Louvain clustering parameter value.

151. The method of any of embodiments 1-150, configuring the bioinformatics pipeline view comprising: determining, from a third interaction with the coordinate configuration widget, a coordinate system for presenting at least a portion of the first dataset in the bioinformatics pipeline view, wherein the third interaction selects the coordinate system from a plurality of options that comprises Uniform Manifold Approximation and Projection (UMAP) or a principal component analysis (PCA).

152. The method of any of embodiments 1-151, configuring the bioinformatics pipeline view comprising: determining, from a fourth interaction with the color scale configuration widget, a color scale for presenting at least a portion of the first dataset in the bioinformatics pipeline view, wherein the fourth interaction selects the color scale from a plurality of options that comprises a linear color scale or a logarithmic color scale.

153. The method of any of embodiments 1-152, configuring the bioinformatics pipeline view comprising: determining, from a fifth interaction with the number of color scales configuration widget, a number color scales for presenting at least a portion of the first dataset in the bioinformatics pipeline view, wherein the fifth interaction selects the number of color scales from a plurality of options that comprises a single color-bar or multiple color-bars.

154. The method of any of embodiments 1-153, configuring the bioinformatics pipeline view comprising: determining, from a sixth interaction with the scatter plot configuration widget, one or more scatter plot options for presenting at least a portion of the first dataset in the bioinformatics pipeline view, wherein the six interaction selects the one or more scatter plot options from a plurality of scatter plot options.

155. The method of any of embodiments 1-154, configuring the bioinformatics pipeline view comprising: determining, from a seventh interaction with the list of regions of interest manipulation module, one or more options for one or more lists of regions of interest for the first dataset, wherein the seventh interaction selects the one or more options from a plurality of options that comprises a first list selection mode option, a second list selection mode option, or a identifier option for the one or more lists of regions of interest.

156. The method of any of embodiments 1-155, configuring the bioinformatics pipeline view comprising: identifying a graphic representation for at least a portion of the first dataset for the biological samples in the bioinformatics pipeline view.

157. The method of any of embodiments 1-156, configuring the bioinformatics pipeline view comprising: dynamically generating the dynamic filtering slider widget associated with a dynamically generated range for the graphic representation of for the at least a portion of the first data set for the biological samples.

158. The method of any of embodiments 1-157, configuring the bioinformatics pipeline view comprising: determining, from an eighth interaction with the dynamic filtering slider widget, a dynamic value based at least in part upon the eighth interaction with the dynamically generated range of the dynamic filtering slider widget.

159. The method of any of embodiments 1-158, configuring the bioinformatics pipeline view comprising: dynamically refreshing the graphic representation for the at least a portion of the first dataset for the biological samples in response to the dynamic value that is determined based at least in part upon the eighth interaction with the dynamically generated range.

160. A method for analyzing an image of biological samples, comprising: receiving first image data captured at a first time point or time period for a region of interest in a microfluidic device; pre-processing the first image data into first pre-processed image data at least by arranging the first image data into an array of first pixel information by second pixel information by pixel depth information; determining a first class or type of the first image data at least by classifying the first image data into the first class or type with at least a machine learning model; determining a first count of the biological samples in the region of interest based at least in part upon the first class or type at least by recognizing the biological samples with a convolutional neural network (CNN) having multiple processing blocks; and displaying textual or graphical information correlated with the first count for the region of interest in a gallery view of a graphical user interface (GUI).

161. The method of embodiment 160, wherein the multiple processing blocks comprise a first processing block that further comprises: a first down-sampling block that down-samples a first input to the second down-sampling block into first down-sampled image data; and a first residual network, wherein the first residual network follows the first down-sampling block, wherein each of the first down-sampling block and the first residual network in the first processing block comprises at least one first convolutional layer.

162. The method of any of embodiments 160-161, wherein the first down-sampling block comprises a first convolution kernel having a first dimension and a first stride for a first depth, the first dimension is greater than one-by-one, and the first stride is greater than one.

163. The method of any of embodiments 161-162, wherein the first convolution kernel is followed by a first batch normalization layer that is further followed by a first activation layer in the first down-sampling block.

164. The method of any of embodiments 161-163, wherein the first residual network comprises a first parallel path and a second parallel path, both of which receive a first down-sampling block output from the first down-sampling block, the first parallel path comprises a first filter size, and the second parallel path comprises a second filter size that is smaller than the first filter size of the first parallel path.

165. The method of any of embodiments 161-164, wherein the first parallel path comprises a plurality of second convolution kernels having at least a second dimension and a second stride for a second depth, the second dimension is lower than the first dimension and greater than one-by-one, and the second stride is smaller than the first stride.

166. The method of any of embodiments 161-165, further comprising: reducing first loss of spatial information in processing the first image data at least by processing a first down-sampling block output with a third convolution kernel having a third dimension with a third stride along the second parallel path, wherein the third dimension is smaller than the first dimension and the second dimension, and the third stride is smaller than the first stride.

167. The method of any of embodiments 161-166, the first processing block further comprising a first recombination layer that is followed by a second activation layer, wherein the first recombination layer is operatively coupled to both the first parallel path and the second parallel path.

168. The method of any of embodiments 161-167, wherein the multiple blocks further comprise a second processing block that further comprises: a second down-sampling block that down-samples a second input to the second down-sampling block into second down-sampled image data; and a second residual network that follows the second down-sampling block, wherein each of the second down-sampling block and the second residual network in the second processing block comprises at least one second convolutional layer.

169. The method of any of embodiments 161-168, wherein the second down-sampling block comprises a fourth convolution kernel having a fourth dimension and a fourth stride for a fourth depth, and the fourth dimension is greater than one-by-one, and the fourth stride is greater than one.

170. The method of any of embodiments 161-169, wherein the second convolution kernel is followed by a second batch normalization layer that is further followed by a third activation layer in the second down-sampling block.

171. The method of any of embodiments 161-170, wherein the second residual network comprises a third parallel path and a fourth parallel path, both of which receiving a second down-sampling block output from the second down-sampling layer, and the fourth parallel path comprises a second smaller filter size that is smaller than a second larger filter size of the third parallel path.

172. The method of any of embodiments 161-171, wherein the third parallel path comprises a plurality of second convolution kernels having at least a fifth dimension and a fifth stride for a fifth depth, the fifth dimension is lower than the fourth dimension and greater than one-by-one, and the fifth stride is smaller than the fourth stride.

173. The method of any of embodiments 161-172, further comprising: reducing second loss of the spatial information at least by processing the second down-sampling block output with a sixth convolution kernel having a sixth dimension with a sixth stride along the fourth parallel path, wherein the sixth dimension is smaller than the fourth dimension and the fifth dimension, and the sixth stride is smaller than the fourth stride.

174. The method of any of embodiments 161-173, the second processing block further comprising a second recombination layer that is followed by a fourth activation layer, wherein the second recombination layer is operatively coupled to both the third parallel path and the fourth parallel path.

175. The method of any of embodiments 161-174, wherein the multiple blocks further comprise a third processing block that further comprises: a third down-sampling block that down-samples a third input to the third down-sampling block into third down-sampled image data; and a third residual network that follows the third down-sampling block, wherein each of the third down-sampling block and the second residual network in the third processing block comprises at least one third convolutional layer.

176. The method of any of embodiments 161-175, wherein the third down-sampling block comprises a seventh convolution kernel having a seventh dimension and a seventh stride for a seventh depth, and the seventh dimension is greater than one-by-one, and the seventh stride is greater than one.

177. The method of any of embodiments 161-176, wherein the seventh convolution kernel is followed by a third batch normalization layer that is further followed by a fifth activation layer in the third down-sampling block.

178. The method of any of embodiments 161-177, wherein the third residual network comprises a fifth parallel path and a sixth parallel path, both of which receiving a third down-sampling block output from the third down-sampling layer, and the sixth parallel comprises a third smaller filter size that is smaller than a third larger filter size of the fifth parallel path.

179. The method of any of embodiments 161-178, wherein the fifth parallel path comprises a plurality of eighth convolution kernels having at least an eighth dimension and an eighth stride for a depth value, the eighth dimension is lower than the seventh dimension and greater than one-by-one, and the eighth stride is smaller than the seventh stride.

180. The method of any of embodiments 161-179, further comprising: reducing third loss of the spatial information at least by processing the third down-sampling block output with a ninth convolution kernel having a ninth dimension with a ninth stride along the sixth parallel path, wherein the ninth dimension is smaller than the seventh dimension and the eighth dimension, and the ninth stride is smaller than the seventh stride.

181. The method of any of embodiments 161-180, the third processing block further comprising a third recombination layer that is followed by a sixth activation layer, wherein the third recombination layer is operatively coupled to both the fifth parallel path and the sixth parallel path.

182. The method of any of embodiments 161-181, wherein the multiple blocks further comprise a fourth processing block that further comprises: a number of transpose convolutional layers each of which is followed by a respective normalization layer, wherein a transpose convolutional layer of the number of transpose convolutional layers has a same stride number as the at least one first convolutional layer in the first processing block or the at least one second convolutional layer in the second processing block.

183. The method of any of embodiments 161-182, wherein the number of transpose convolutional layers corresponds to a value that is at least one less than a total number of convolutional layers in the first and the second processing blocks.

184. The method of embodiments 161-183, wherein convolutional layers in the convolutional neural network have filter sizes greater than one-by-one so that no convolutional layers in the convolutional neural network have a one-by-one filter.

185. The method of any of embodiments 161-184, wherein the convolutional neural network comprises no pooling layers.

186. The method of any of embodiments 161-185, wherein pre-processing the first image data into the first pre-processed image data comprises at least reducing the first image data into the first pre-processed image data based at least in part upon the region of interest or a type of the first image data, wherein a type of the first image data corresponds an operation during which the first image data is captured for analyzing the biological samples, and the operation comprises an export operation or an import operation.

187. The method of any of embodiments 161-186, further comprising: determining a pixel size for the first image data based at least in part upon a first geometric characteristic of the biological samples and a second geometric characteristic of the region of interest.

188. The method of any of embodiments 161-187, wherein the first geometric characteristic of the biological sample comprises a diameter, a major diameter, a minor diameter, or an area of the biological samples, and the second geometric characteristic of the region of interest comprises a width or a length of the region of interest or a portion thereof.

189. The method of any of embodiments 161-188, determining the first class or type of the first image data comprising: processing a plurality of low-level features by using at least the first processing block of the convolutional neural network.

190. The method of any of embodiments 161-189, determining the first class or type of the first image data further comprising: processing a plurality of abstract features by using at least the third processing block of the convolutional neural network.

191. The method of any of embodiments 161-190, determining the first class or type of the first image data further comprising: determining the first class or type or a first statistic corresponding to the first class or type, wherein the first statistic comprises a first probability that one or more pixels in the first image data represent a corresponding biological sample characteristic.

192. The method of any of embodiments 1-191, further comprising: determining a second count of the biological samples from second image data captured at a second time point or time period for the region of interest using at least the convolutional neural network (CNN) having the multiple processing blocks.

193. The method of any of embodiments 1-192, further comprising: replaying a video or image sequence of the region of interest at least by sequentially rendering a portion of the first image data and a portion of the second image data in the gallery view of the graphical user interface (GUI).

194. The method of any of embodiments 1-192, determining the second count of the biological samples comprising: receiving the second image data captured at the first time point for the region of interest in the microfluidic device; and pre-processing the second image data into second pre-processed image data at least by arranging the second image data into the array of the first pixel information by the second pixel information by the pixel depth information.

195. The method of any of embodiments 1-194, wherein pre-processing the second image data into the second pre-processed image data comprises at least reducing the second image data into the second pre-processed image data based at least in part upon the region of interest or the type of the second image data, wherein the type of the second image data corresponds a separate operation during which the second image data is captured for analyzing the biological samples, and the separate operation comprises the export operation, the import operation, a separate export operation, or a separate import operation.

196. The method of any of embodiments 1-195, determining the second count of the biological samples further comprising: classifying the second image data into the first class or type with at least a machine learning model; and determining the second count of the biological samples at the second time point in the region of interest based at least in part upon the first class or type at least by recognizing the biological samples with a convolutional neural network having the multiple processing blocks.

197. The method of any of embodiments 1-196, further comprising: determining one or more first images from the first images data, the one or more first images comprising first information correlated with the first count and temporally corresponding to the first time point or time period; determining one or more second images from the second images data, the one or more second images comprising second information correlated with the second count and temporally corresponding to the second time point or time period; and presenting a temporal progression of at least a portion of the biological samples at least by dynamically rendering the one or more first images and the one or more second images in a temporal sequence in the graphical user interface.

198. An article of manufacture comprising a non-transitory machine accessible storage medium storing thereupon a sequence of instructions which, when executed by a processor, causes the process to perform any of the methods of embodiments 1-198.

199. A system, comprising: a processor; a user interface coupled to the processor for processing a plurality of molecular-biological samples that comprise a first molecular-biological sample and a second molecular-biological sample in a first molecular-biological device; a non-transitory computer accessible storage medium storing thereupon a sequence of instructions which, when executed by a processor, causes the processor to perform any of the methods of embodiments 1-198.

BRIEF DESCRIPTION OF THE DRAWING FIGURES

The invention of the present application will now be described in more detail with reference to example embodiments of the apparatus and method, given only by way of example, and with reference to the accompanying drawings, in which:

FIG. 5H illustrates more details about a portion of the example display of the example data structure illustrated in FIG. 5G in one or more embodiments.

FIG. 5J illustrates an example grouping of an example data structure that stores raw data in one or more embodiments.

FIG. 6C illustrates more details of the gallery view illustrated for a loaded bioinformatics pipeline dataset in some embodiments.

FIG. 7D illustrates more details about an example bioinformatics pipeline user interface illustrated in FIGS. 7A-7C in one or more embodiments.

FIG. 7O illustrates an example differential gene expression results from FIG. 7L in some embodiments.

FIG. 8A illustrates an example image captured for a plurality of chambers in a microfluidic device in some embodiments.

FIG. 8C illustrates another example image captured at a next timepoint for the same multiple chambers as those captured at previous timepoints in FIGS. 8A-8B in some embodiments.

Figure 10A:
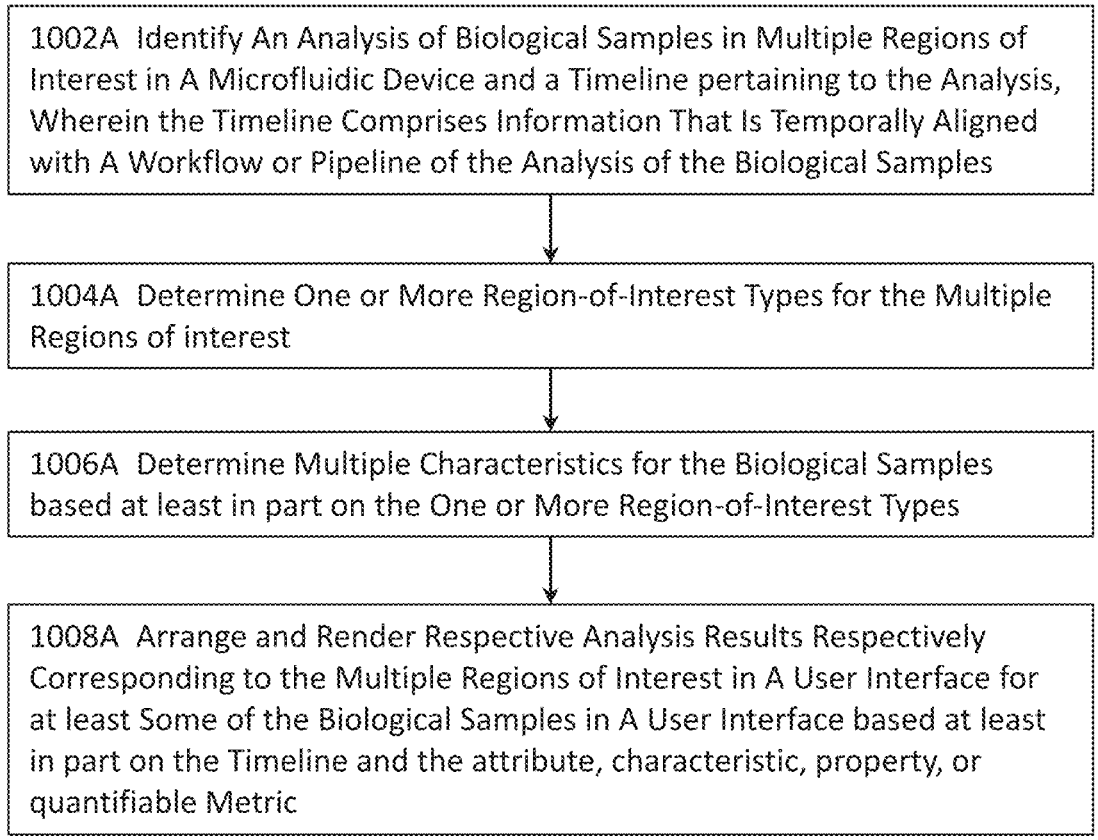
FIG. 10A illustrates a simplified example of a block diagram of a process and/or system for analyzing biological samples with an enhanced user interface in one or more embodiments.

FIGS. 10G-1, 10G-2, 10G-3, and 10G-4 illustrate more details about a portion of the simplified example of a block diagram illustrated in FIG. 10A in one or more embodiments.

Figure 1:
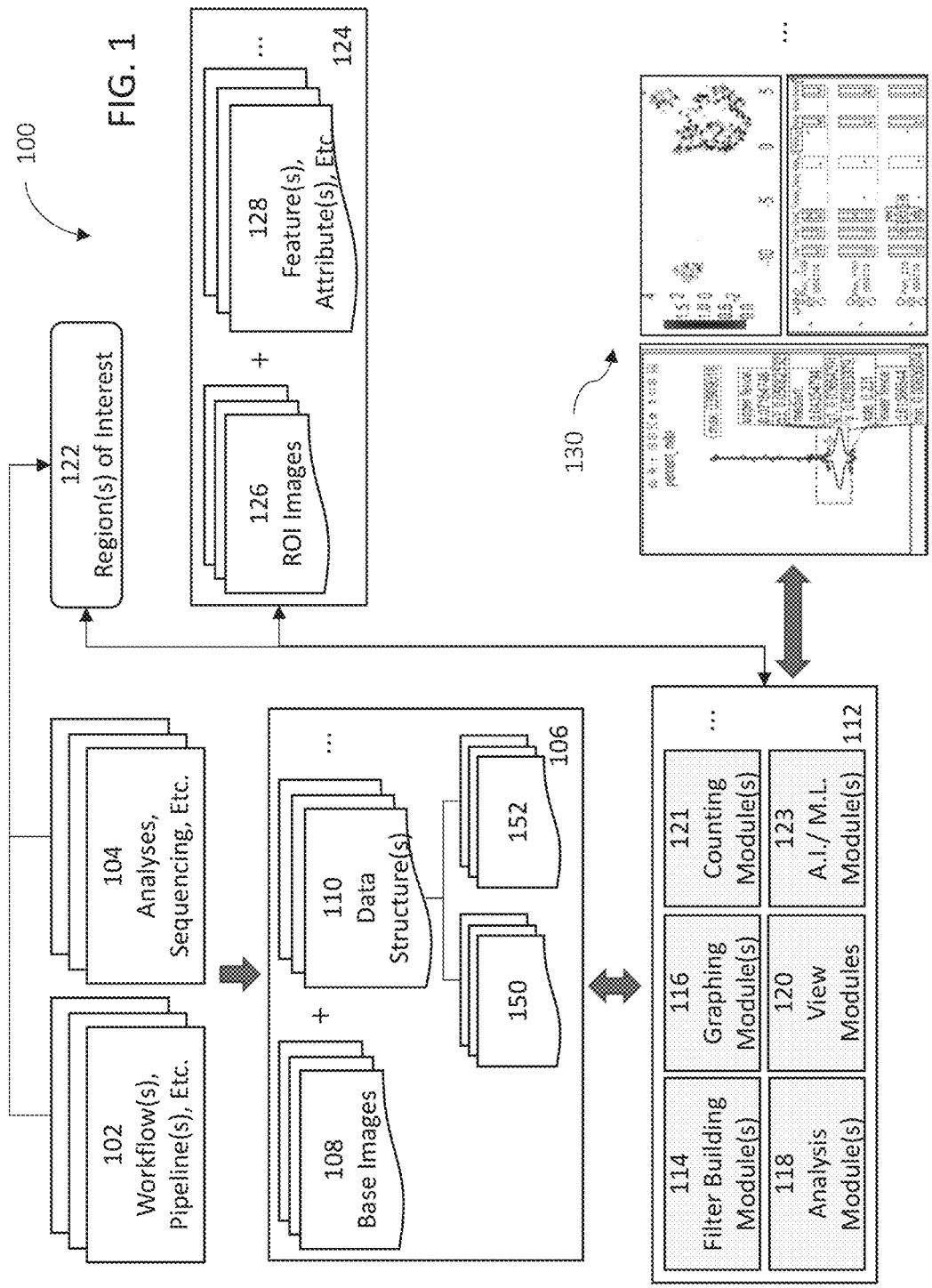
FIG. 1 illustrates a simplified example of a block diagram of a process and/or system for analyzing biological samples with an enhanced user interface in one or more embodiments.
Figure 10B:
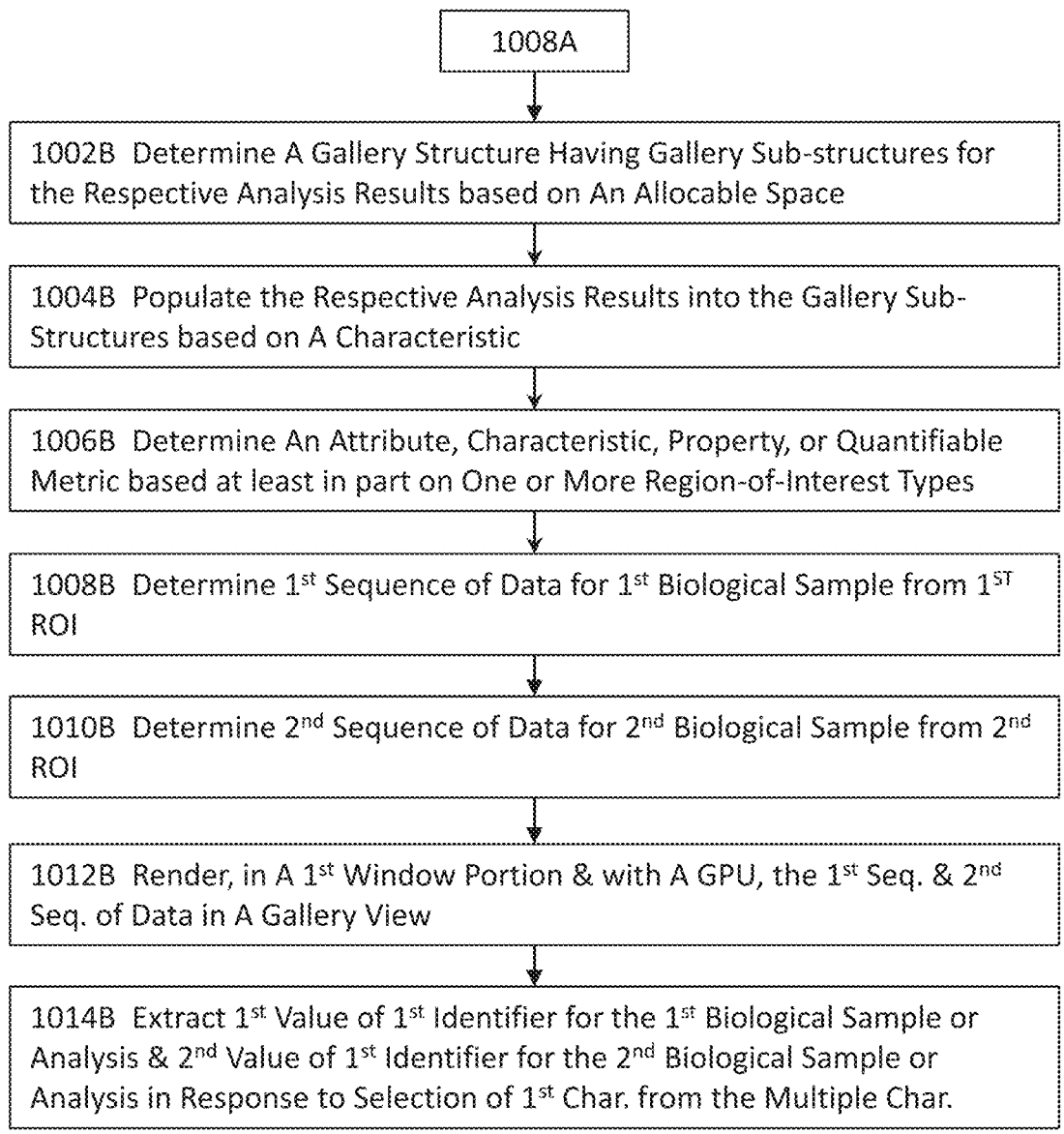
FIGS. 10B-10C illustrate more details about a portion of the simplified example of a block diagram illustrated in FIG. 10A in one or more embodiments.
Figure 10C:
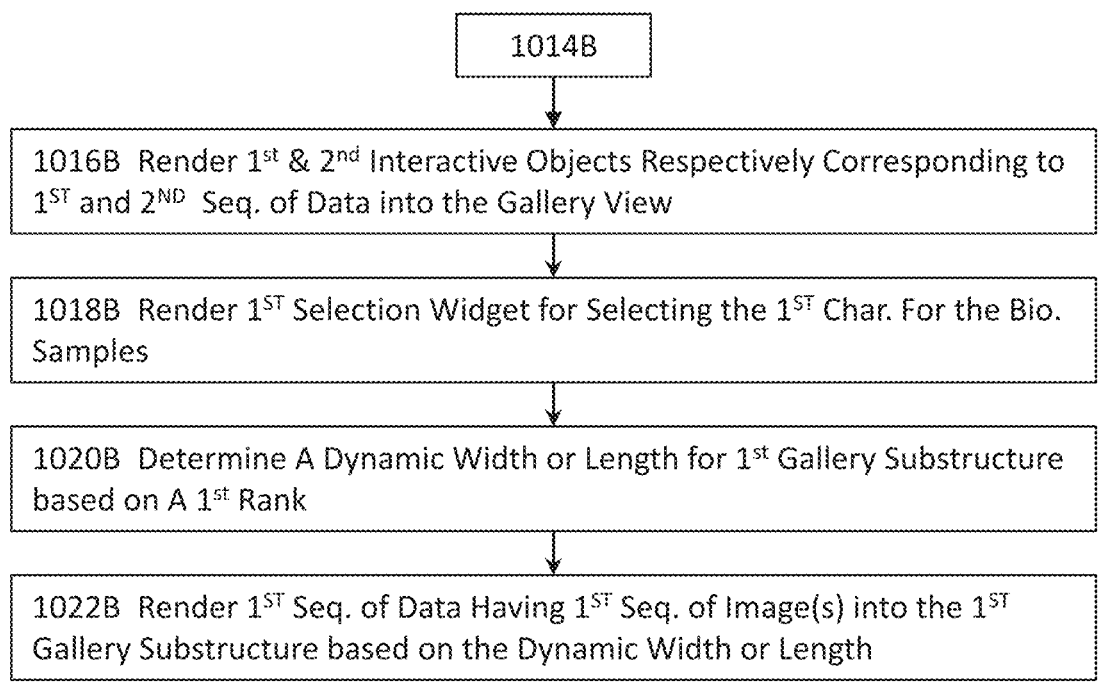
Figure 10D:
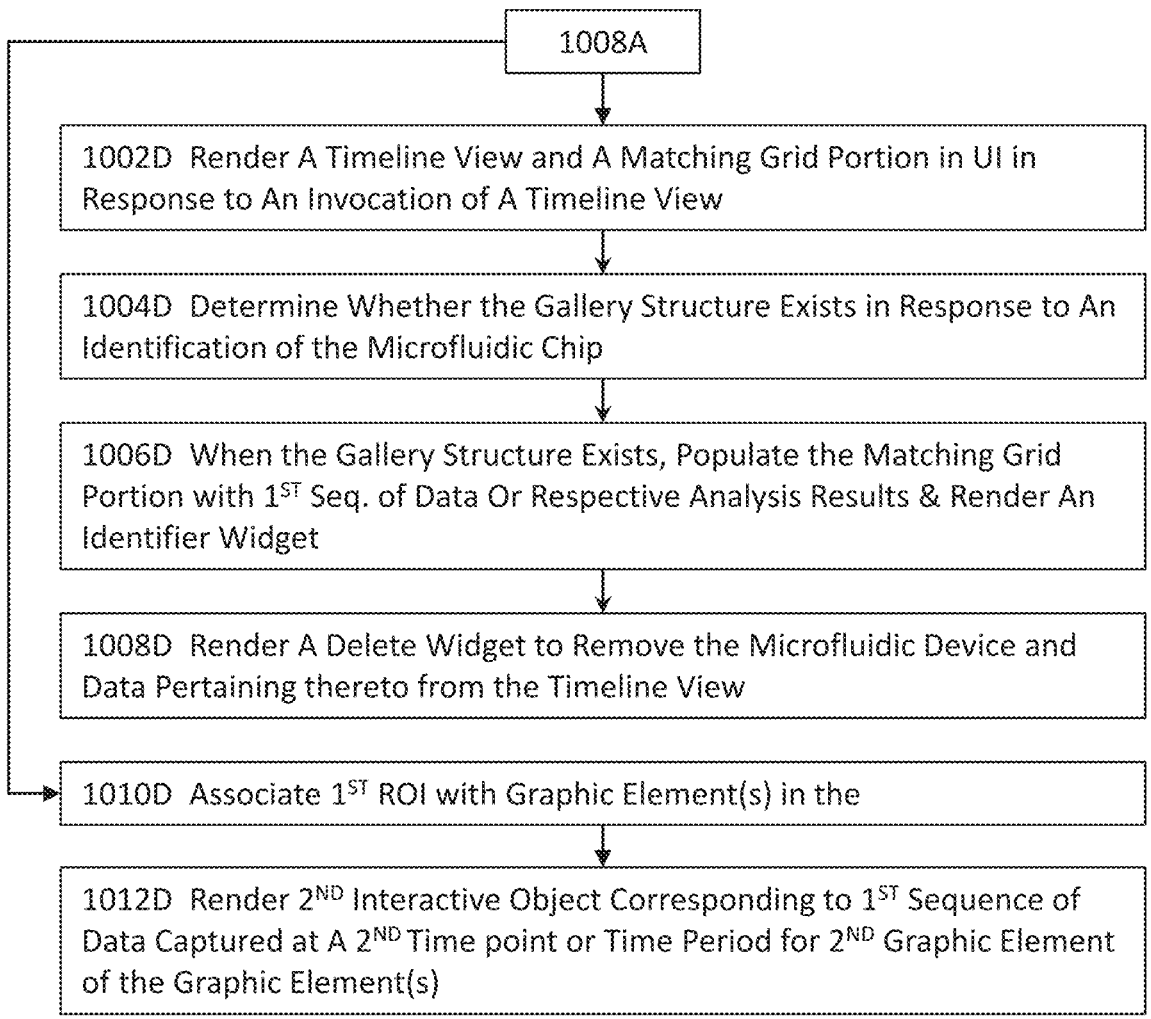
FIGS. 10D-10E illustrate more details about a portion of the simplified example of a block diagram illustrated in FIG. 10A in one or more embodiments.
Figure 10E:
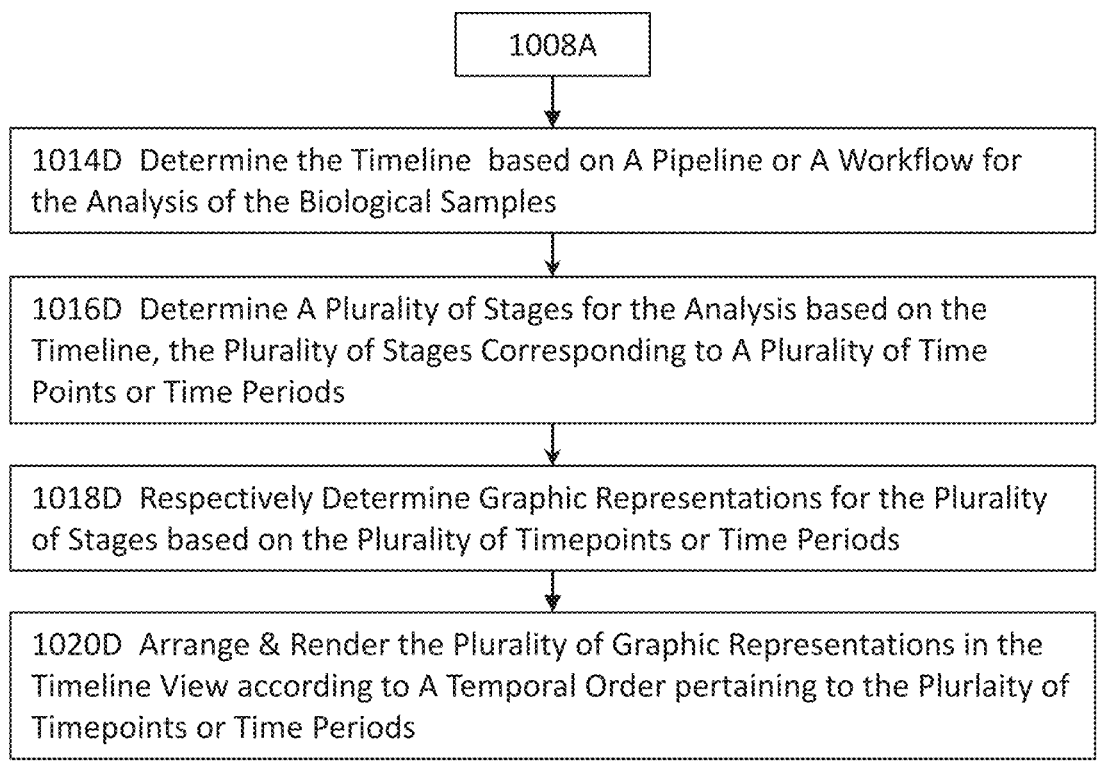
Figure 10F:
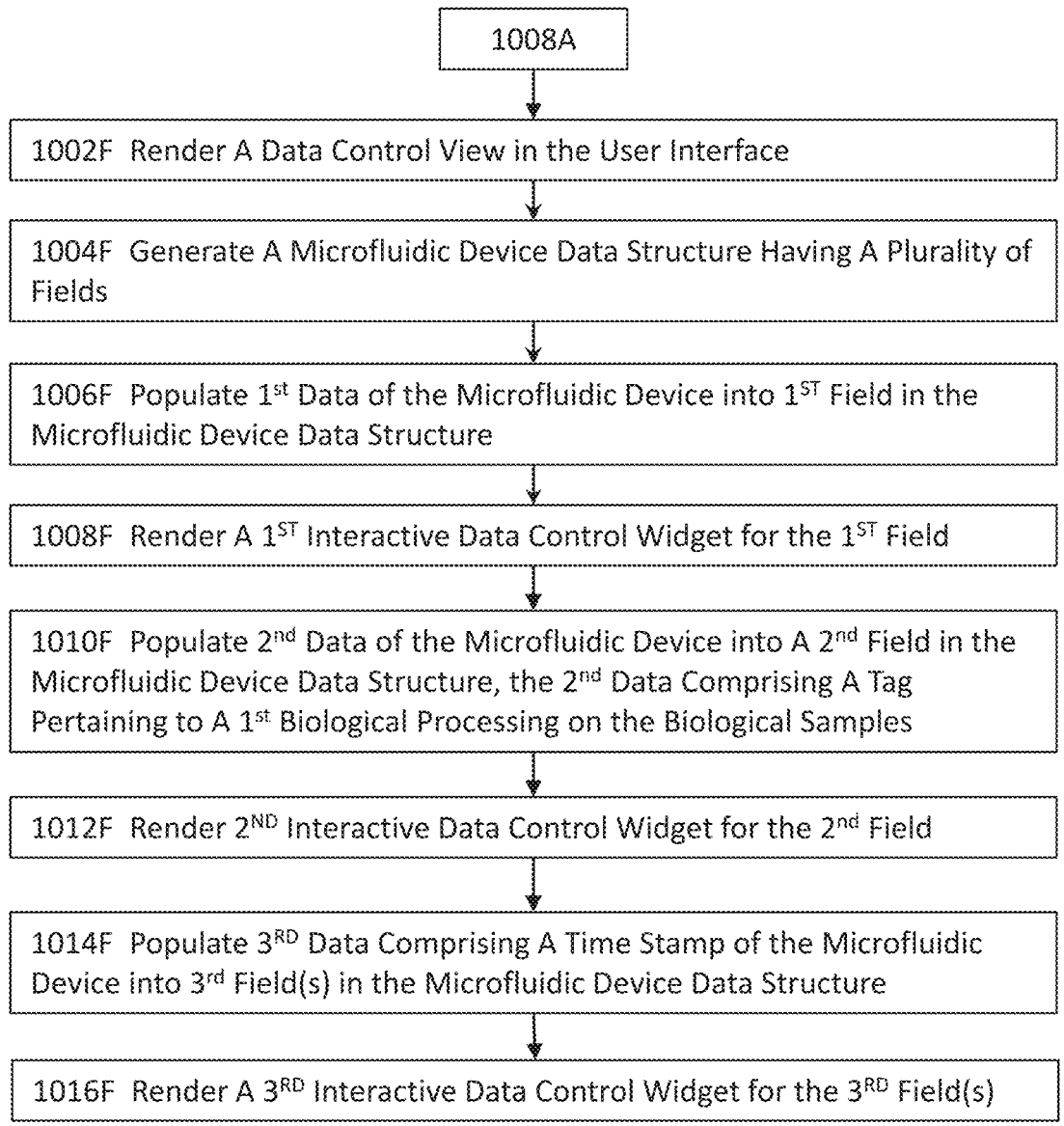
FIG. 10F illustrates more details about a portion of the simplified example of a block diagram illustrated in FIG. 10A in one or more embodiments.
Figures 1, 10G:
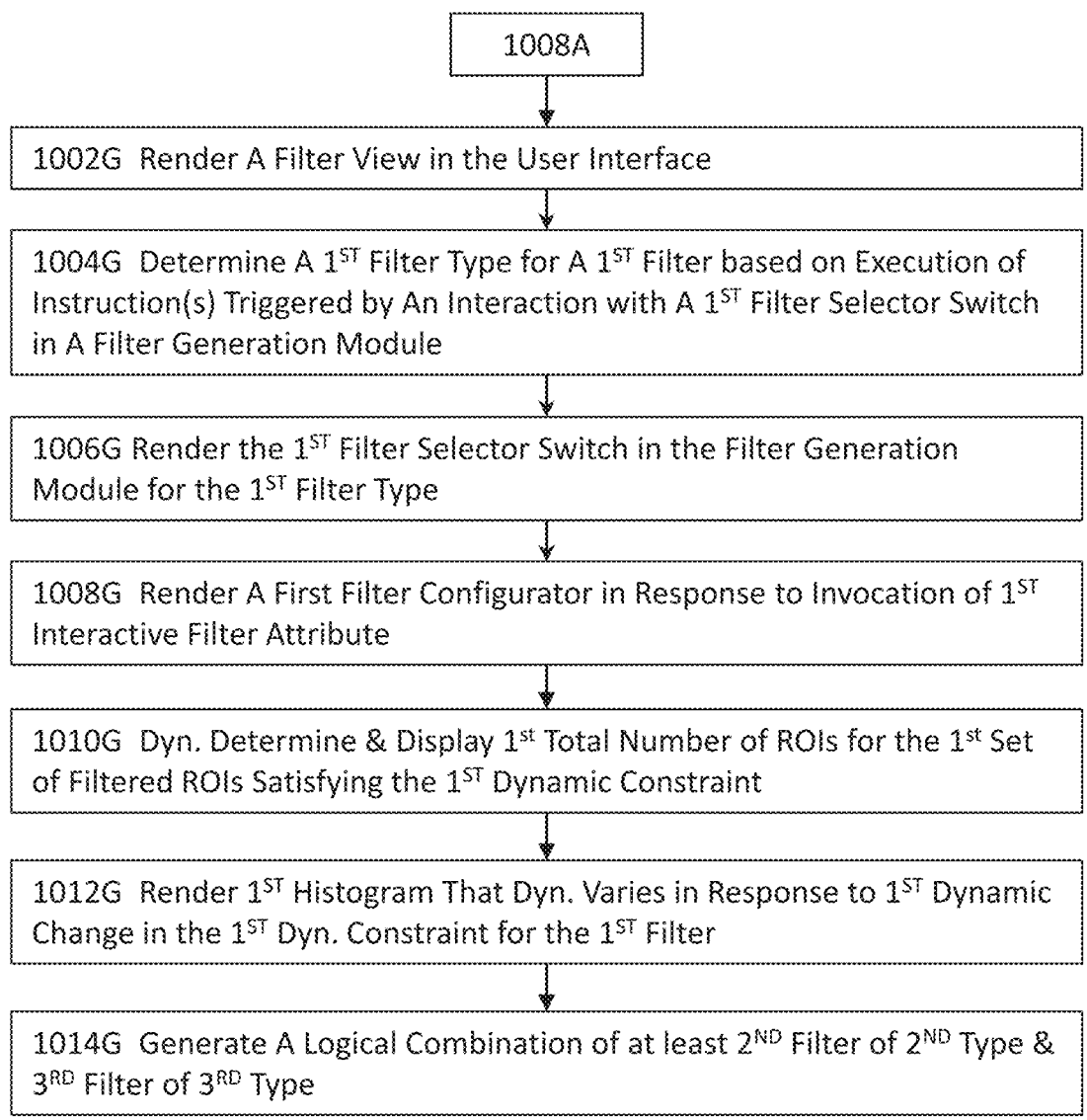
Figures 2, 10G:
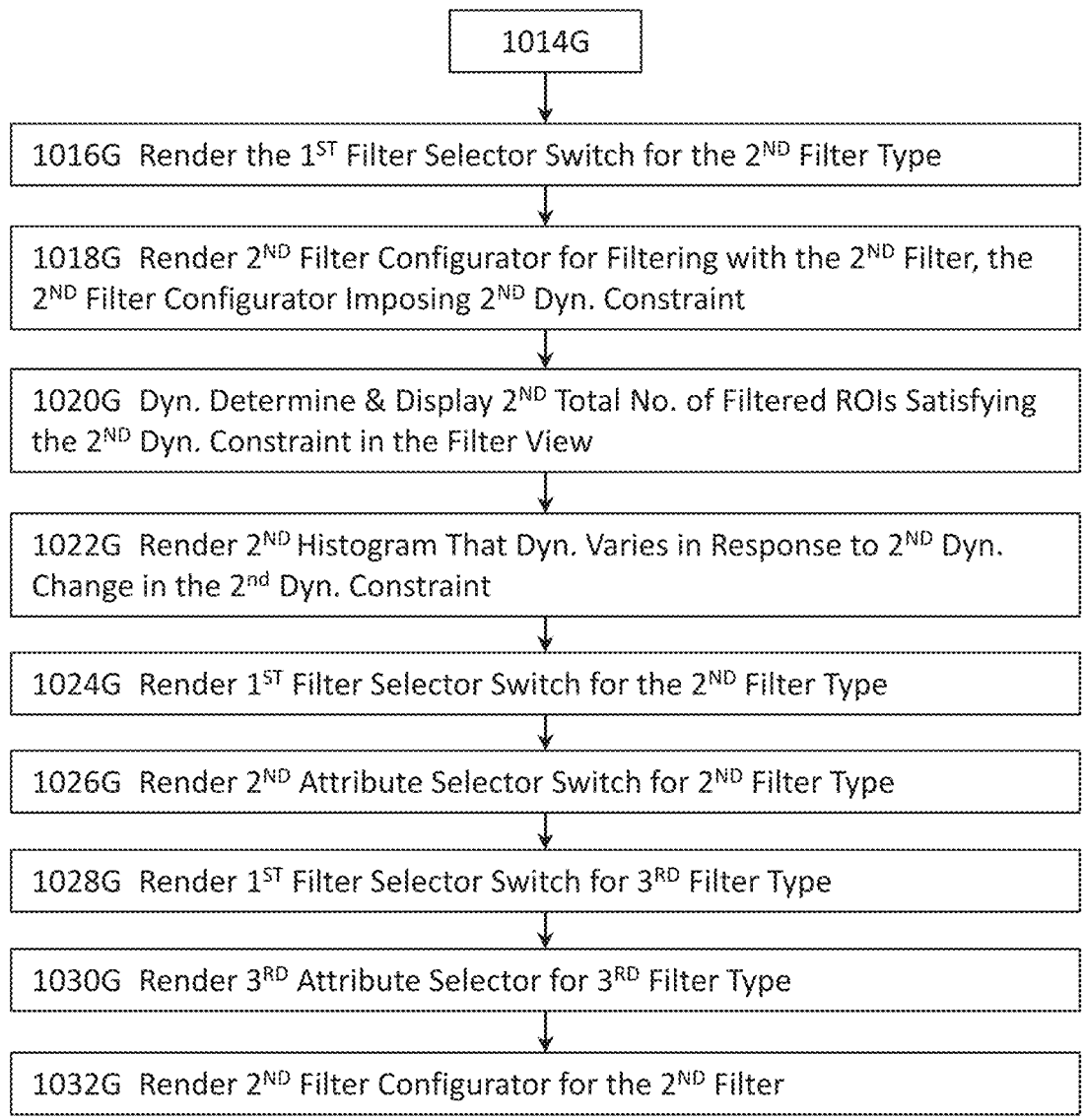
Figures 3, 10G:
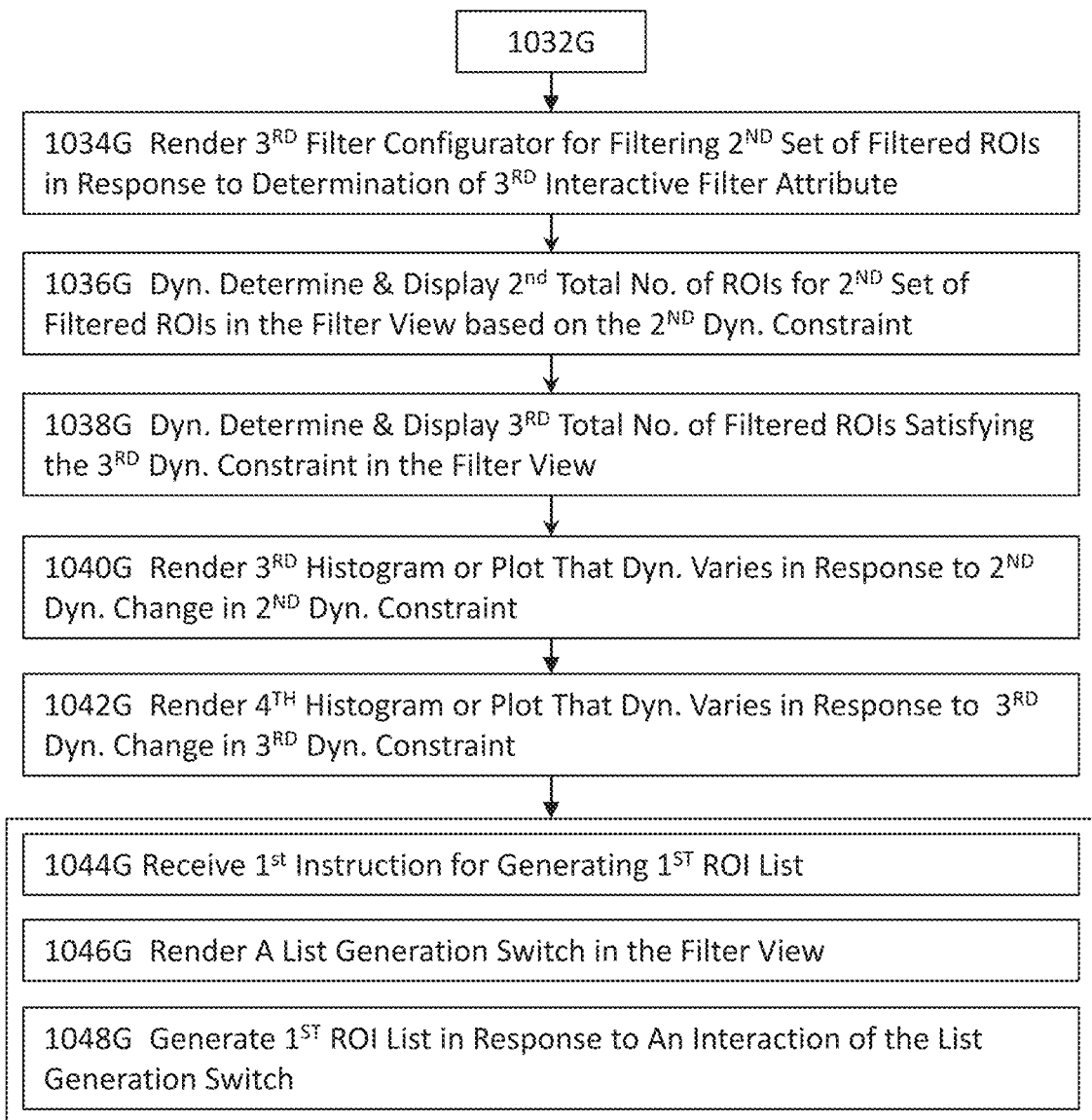
Figures 4, 10G:
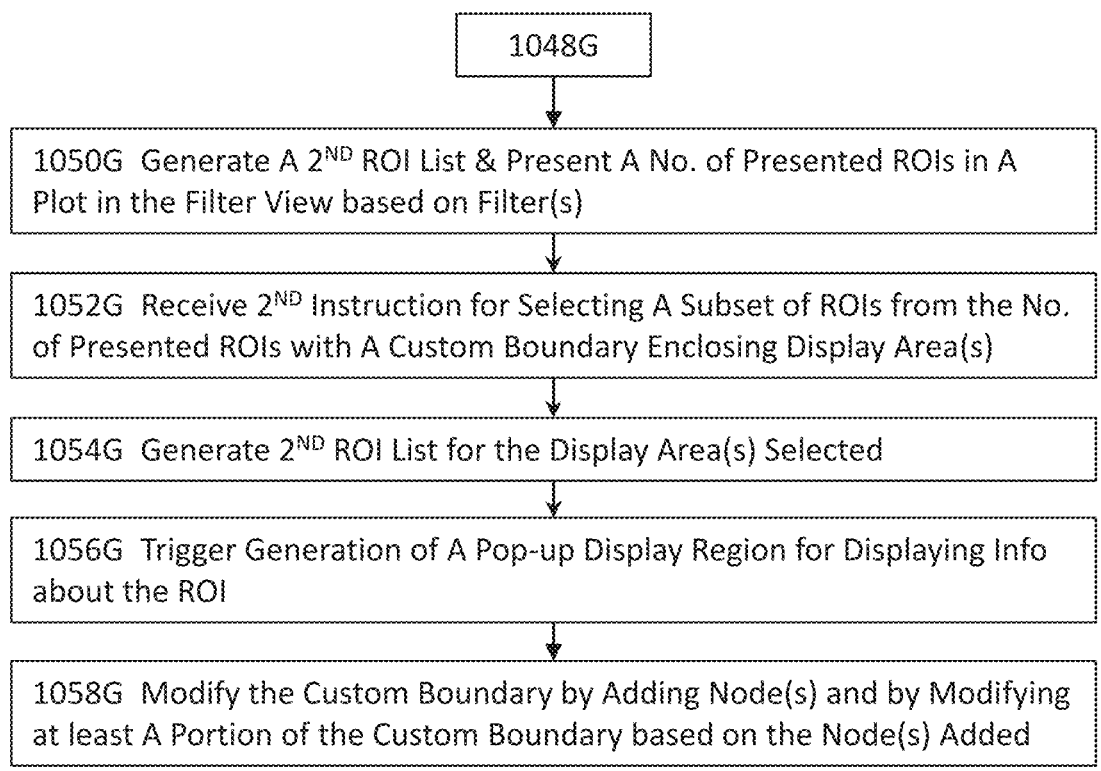
FIG. 4D illustrates another example of a chip timeline view in one or more embodiments.
Figures 1, 10H:
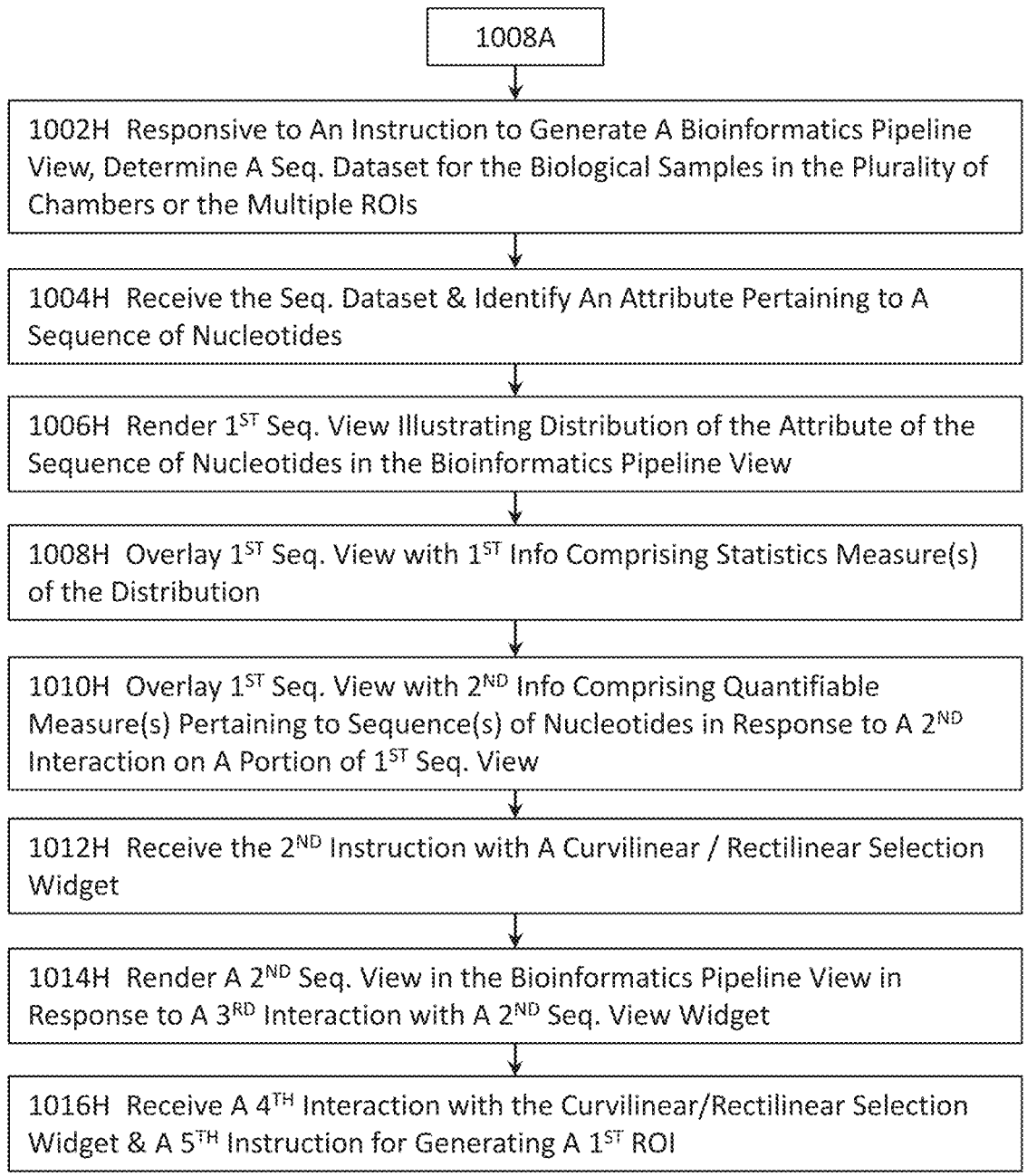
Figures 2, 10H:
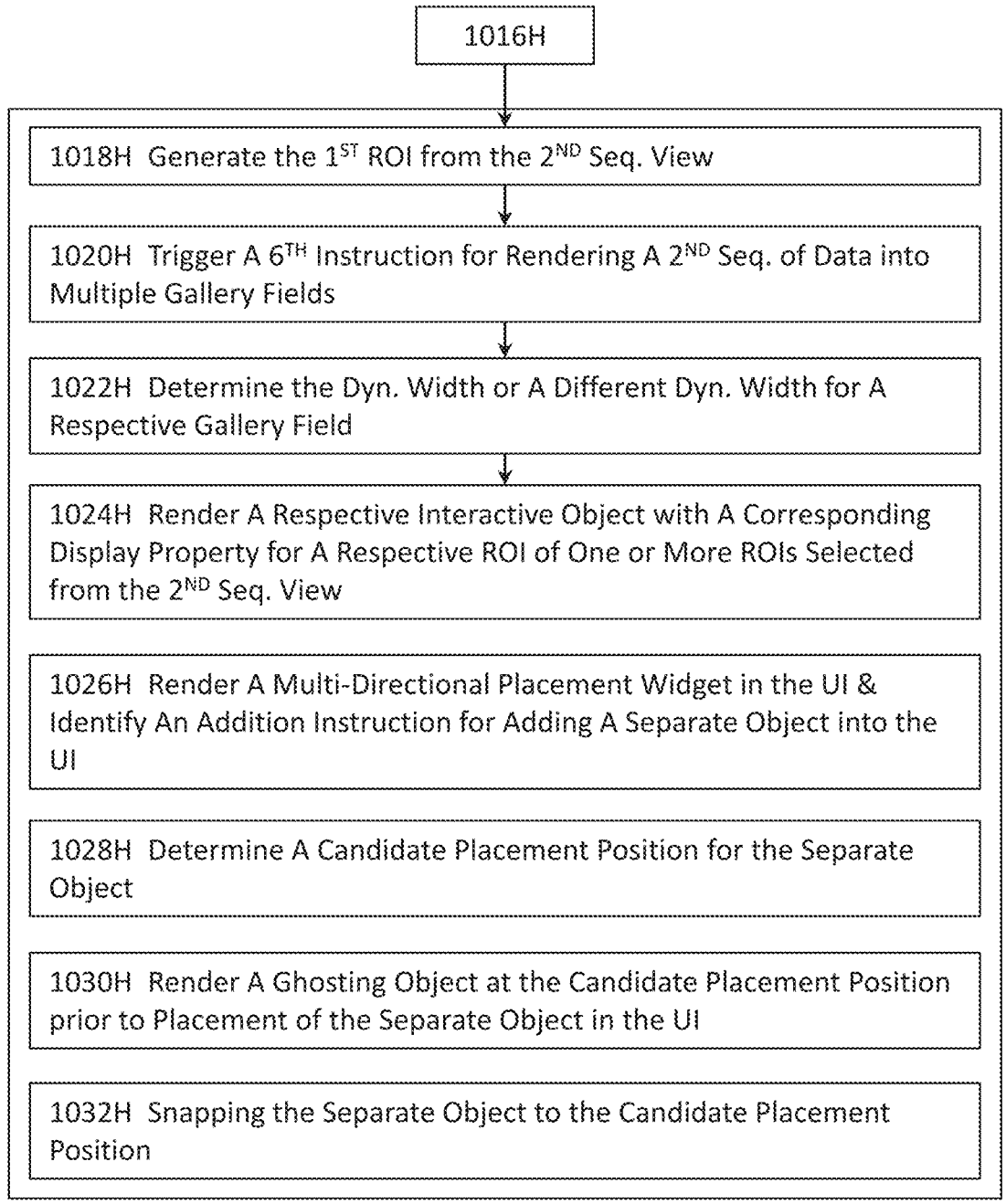
Figures 3, 10H:
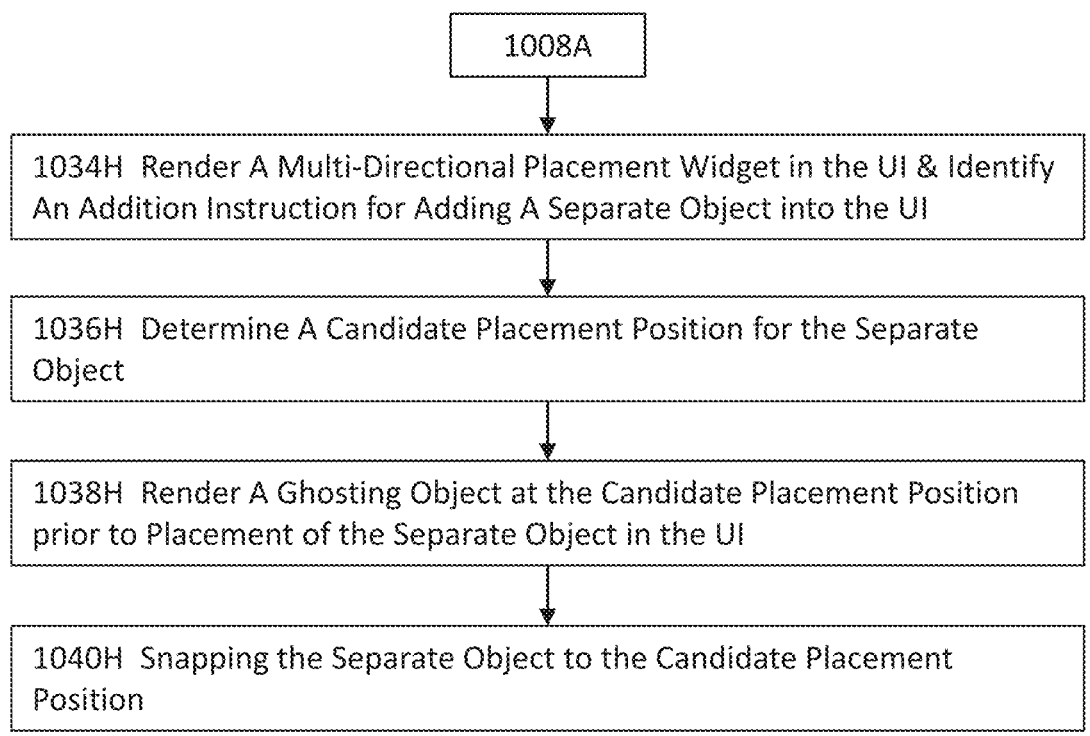

FIGS. 10H-1 and 10H-2 illustrate more details about a portion of the simplified example of a block diagram illustrated in FIG. 10A in one or more embodiments.

FIG. 10H-3 illustrates more details about a portion of the simplified example of a block diagram illustrated in FIG. 10A in one or more embodiments.

Figure 10I:
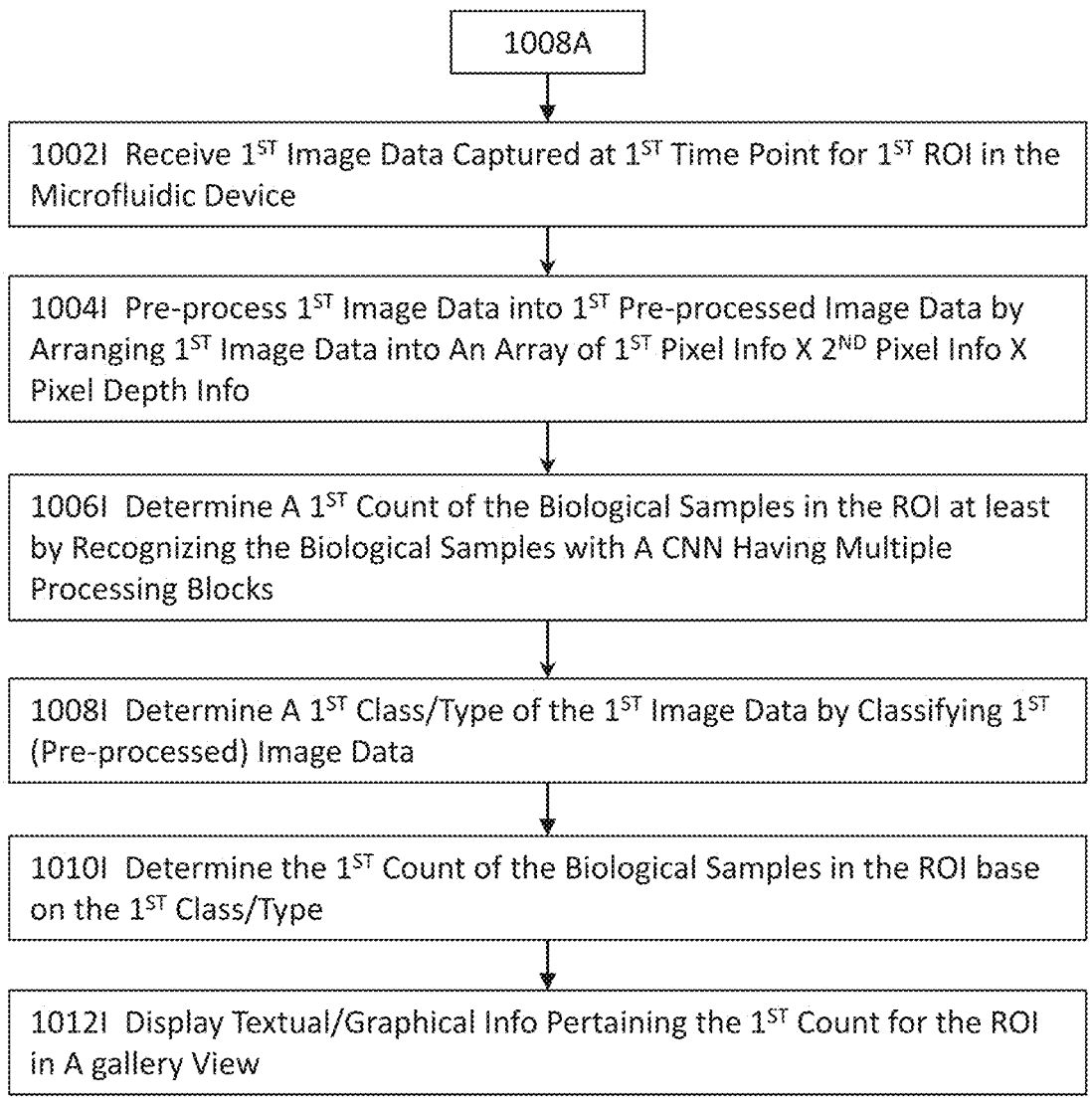

FIG. 10I illustrates more details about a portion of the simplified example of a block diagram illustrated in FIG. 10A in one or more embodiments.

Figure 10J:
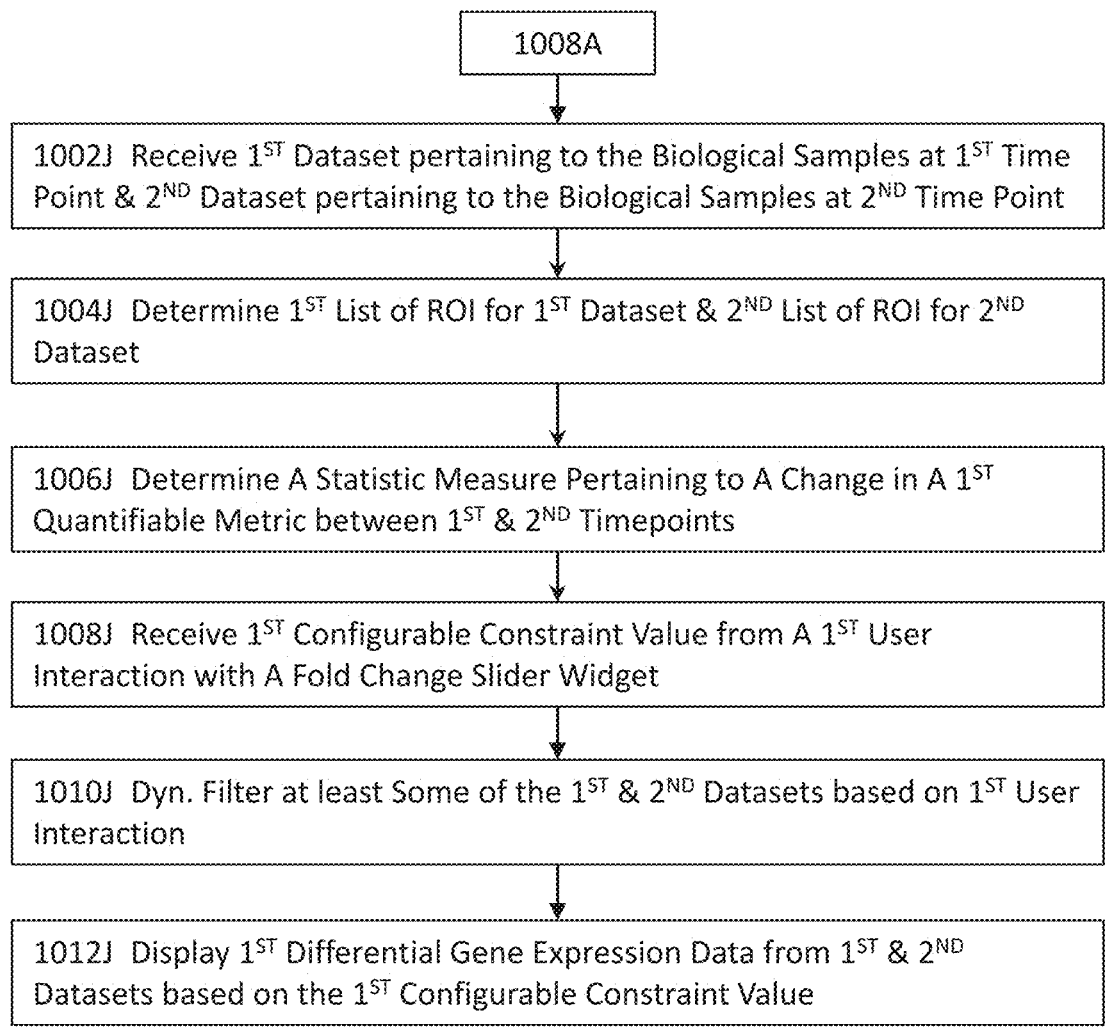

FIG. 10J illustrates more details about a portion of the simplified example of a block diagram illustrated in FIG. 10A in one or more embodiments.

Figures 1, 10K:
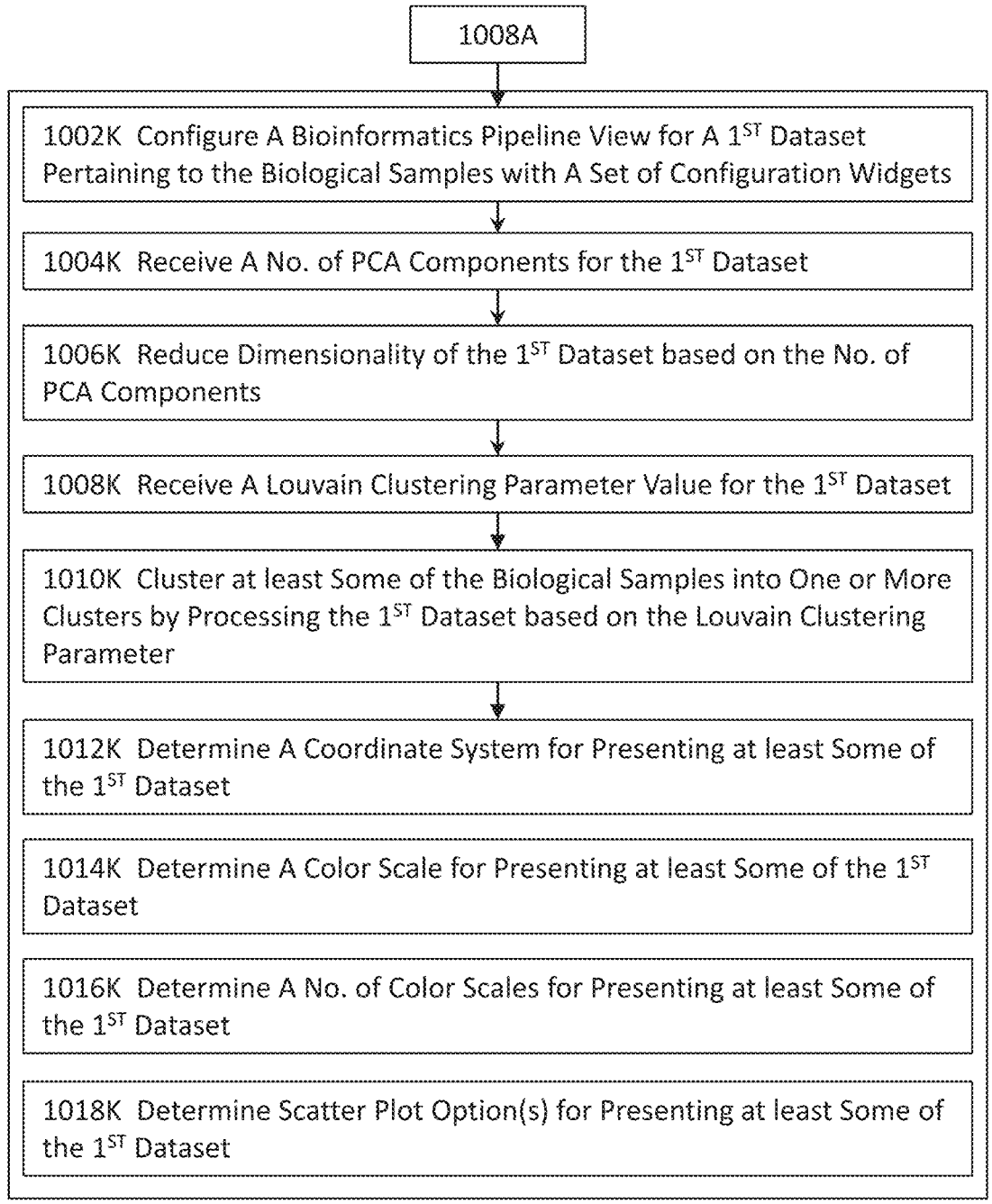
Figures 2, 10K:
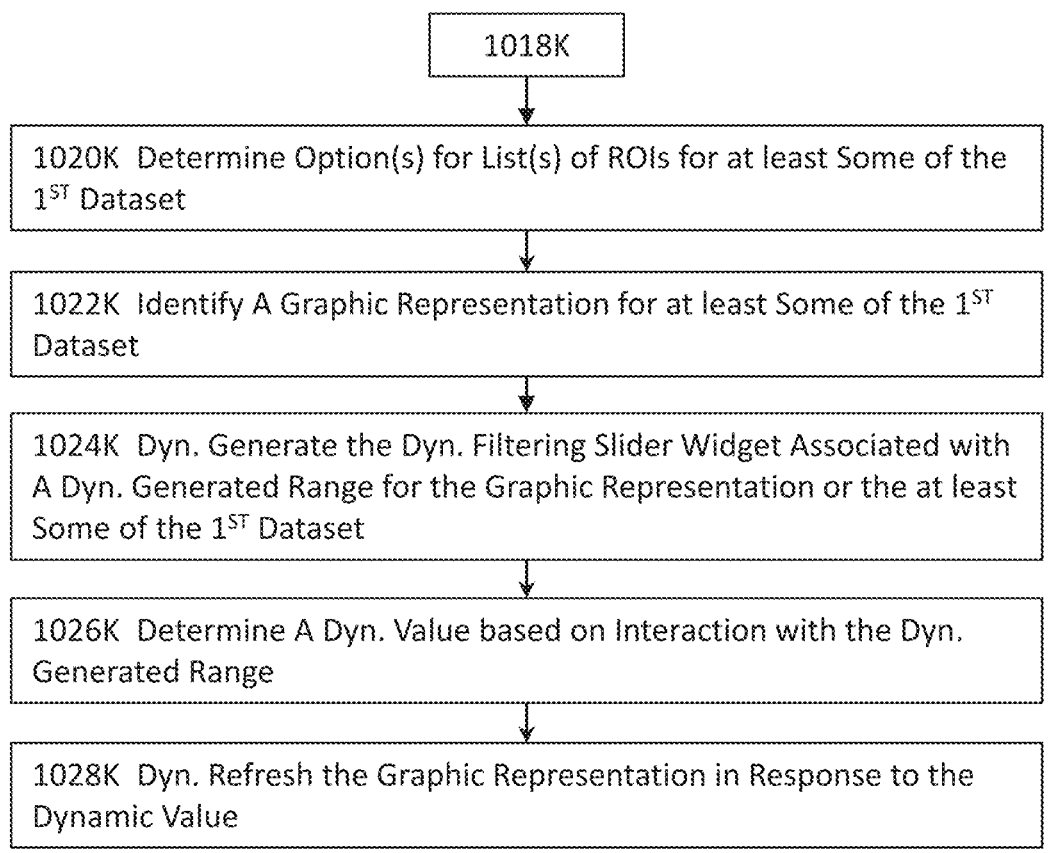

FIGS. 10K-1 and 10K-2 illustrate more details about a portion of the simplified example of a block diagram illustrated in FIG. 10A in one or more embodiments.

Figures 1, 11A:
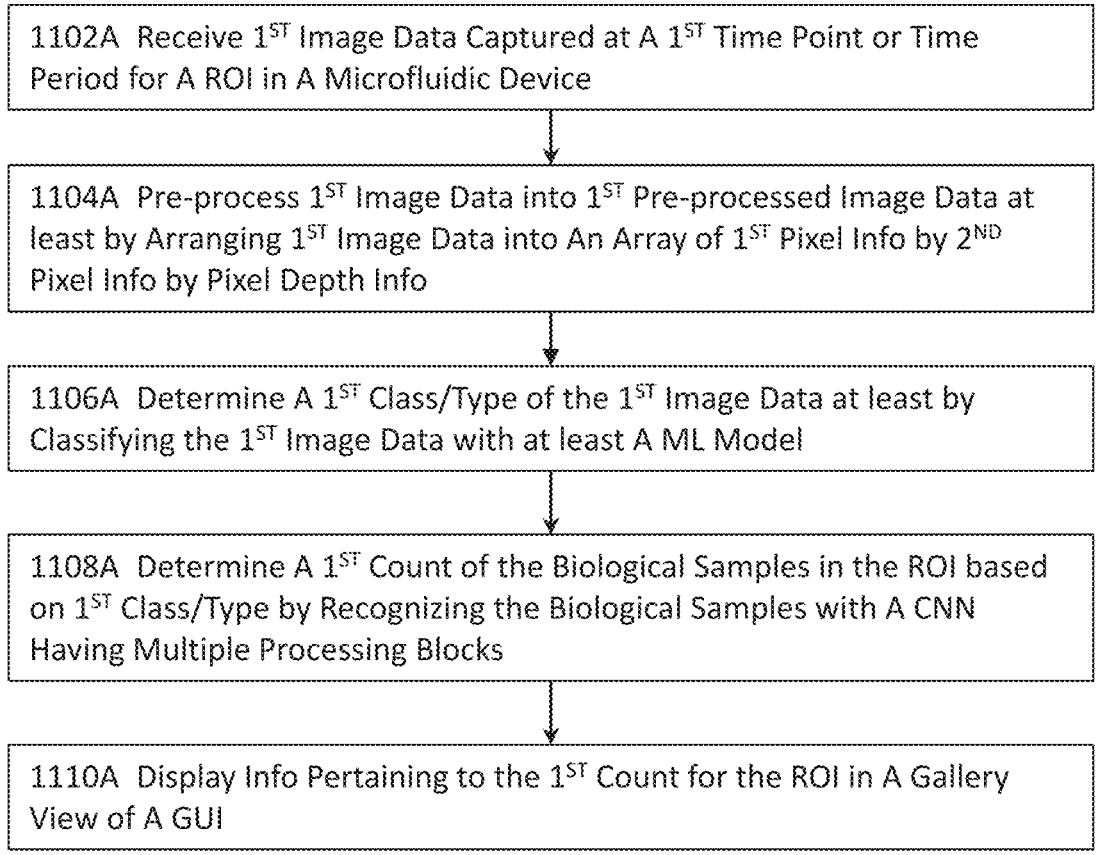
Figures 2, 11A:
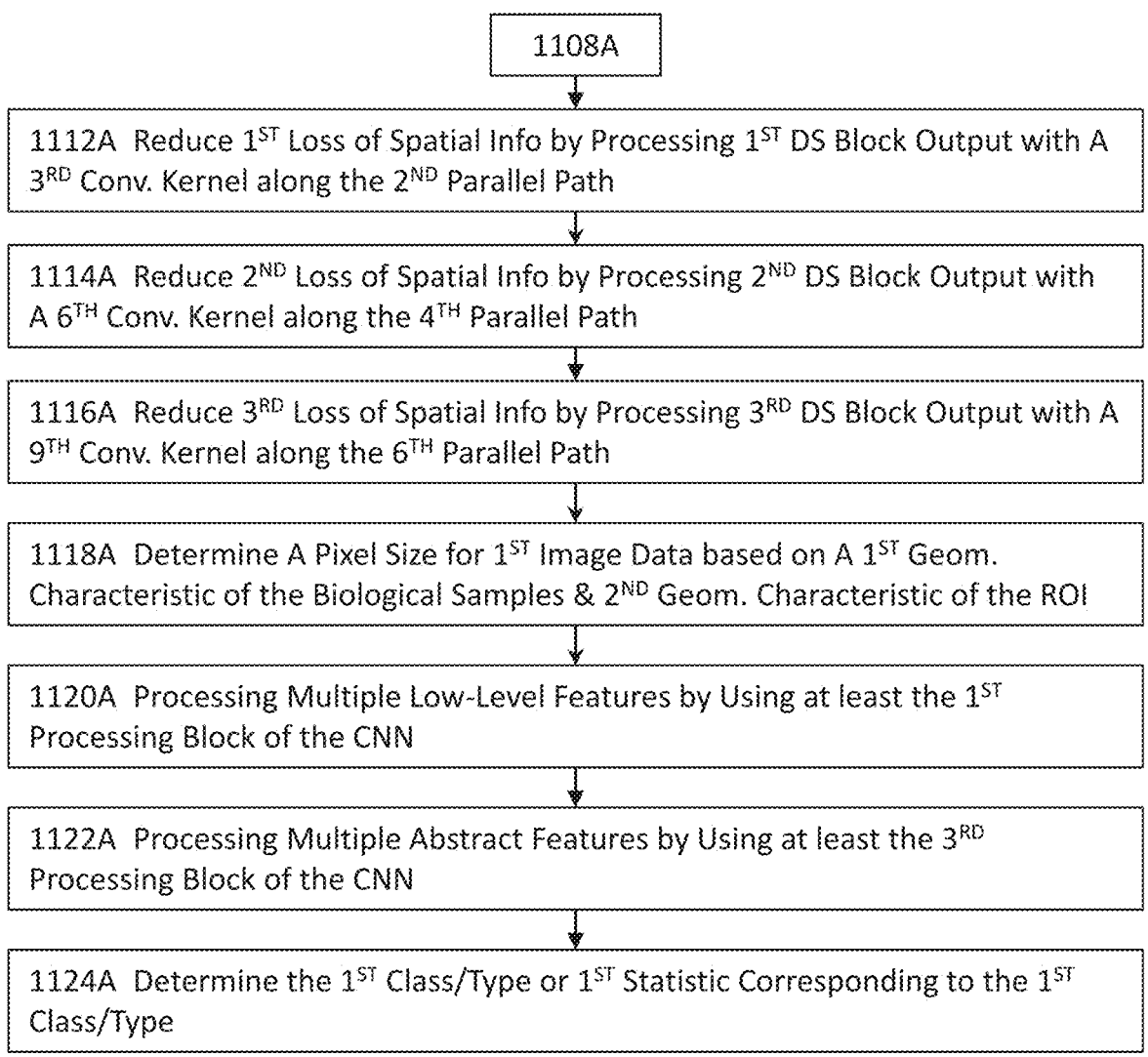

FIG. 11A-1 illustrates another high-level flow diagram of a method and/or system for analyzing biological samples using a microfluidic device having multiple chambers in one or more embodiments.

FIG. 11A-2 illustrates more details about a portion of the high-level flow diagram illustrated in FIG. 11A-1 in one or more embodiments.

Figures 1, 11B:
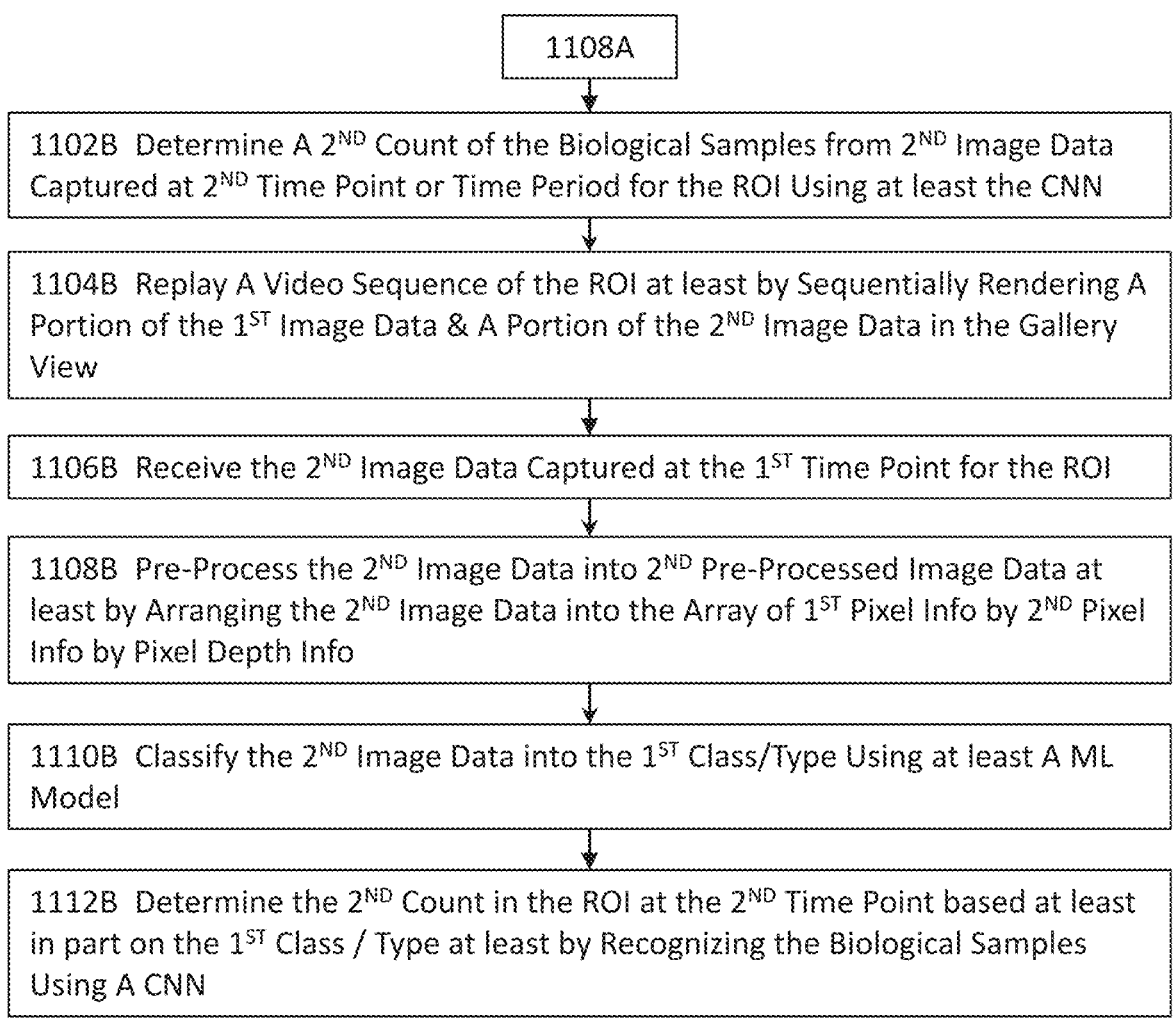
Figures 2, 11B:
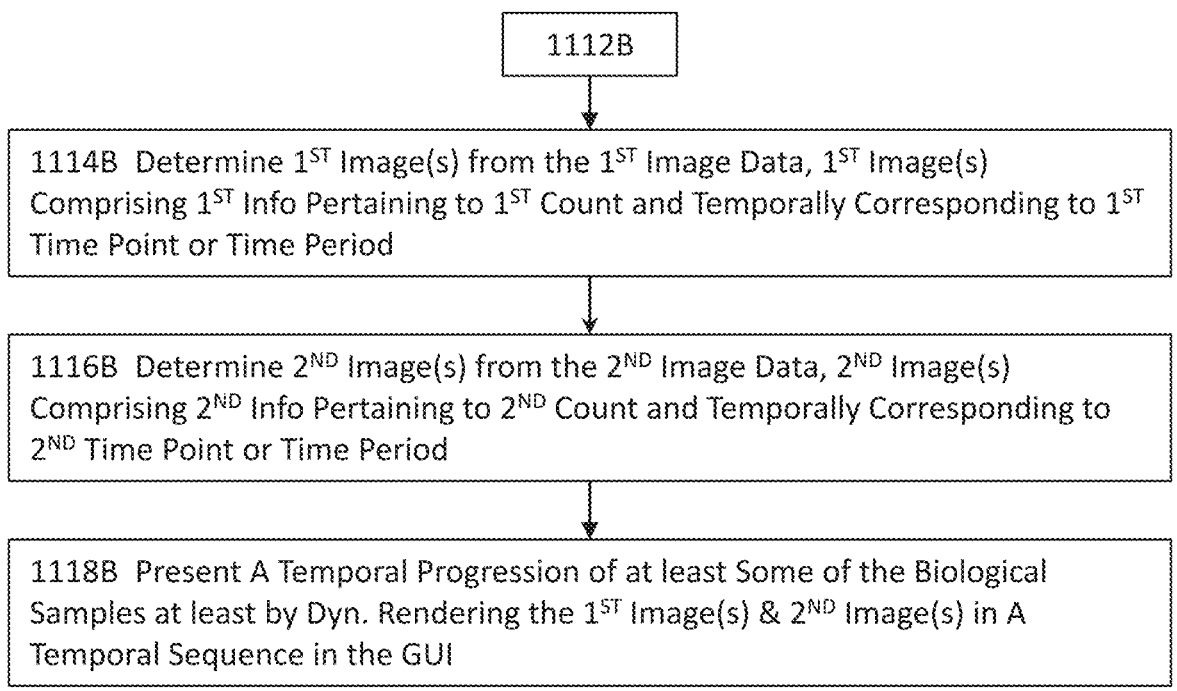

FIGS. 11B-1 and 11B-2 illustrate more details about a portion of the high-level flow diagram illustrated in FIG. 11A-1 in one or more embodiments.

FIGS. 12A-12F illustrate some example micro-object separation examples according to one or more embodiments.

Figure 13A:
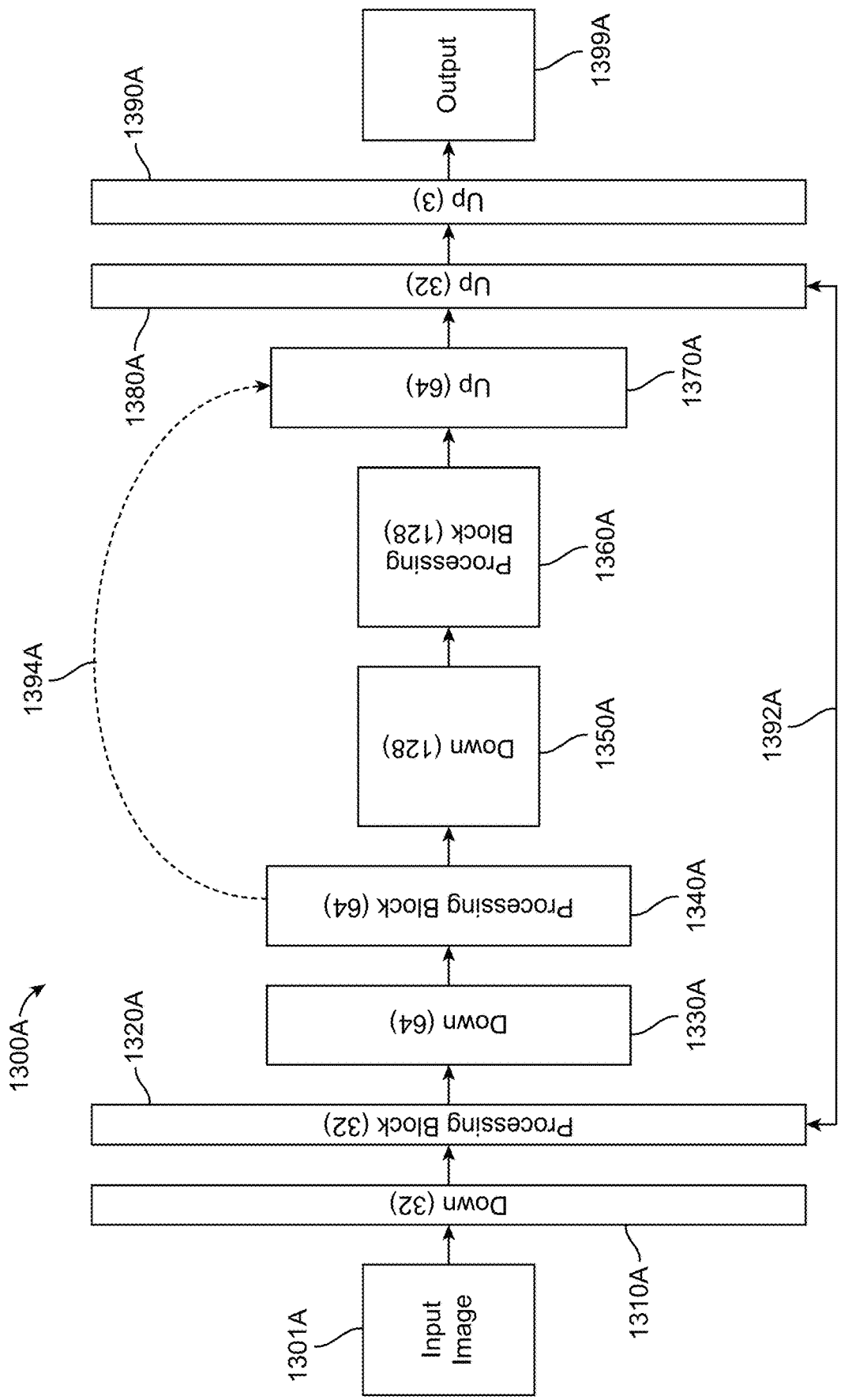

FIG. 13A illustrates a simplified schematic diagram of a convolutional neural network in accordance with one or more embodiments.

Figure 14A:
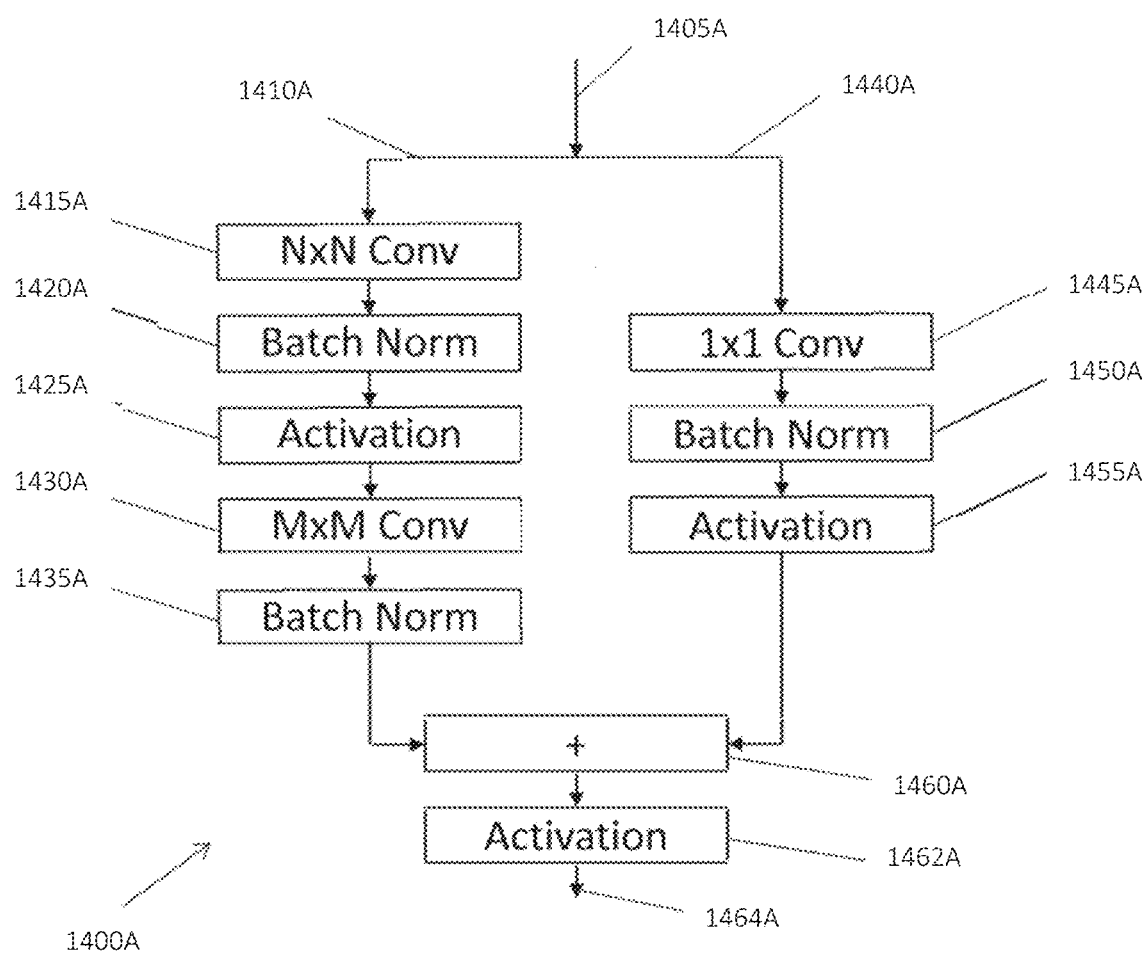
Figure 14B:
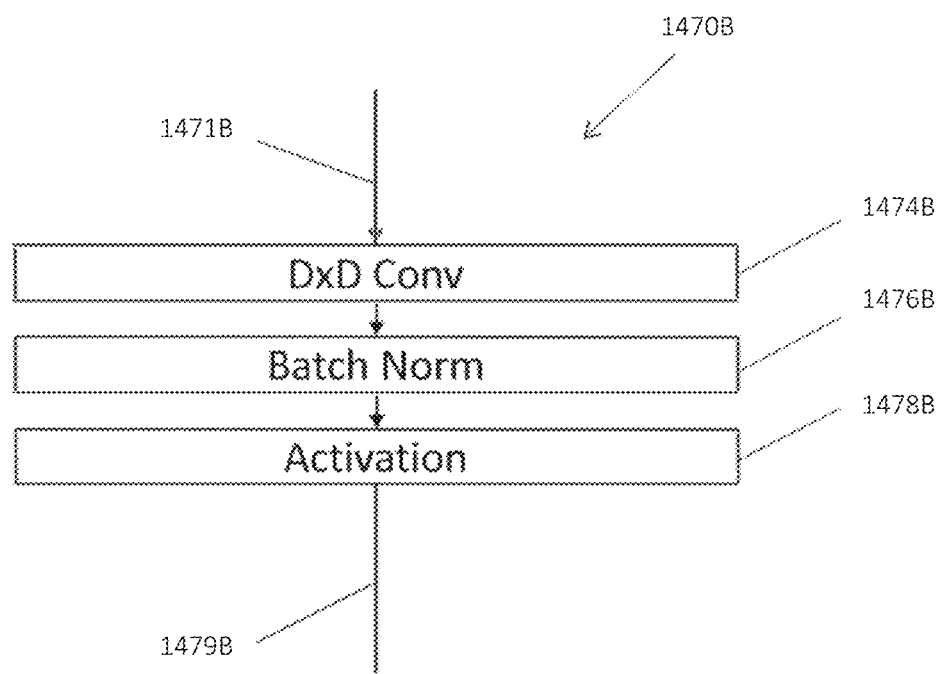
Figure 14C:
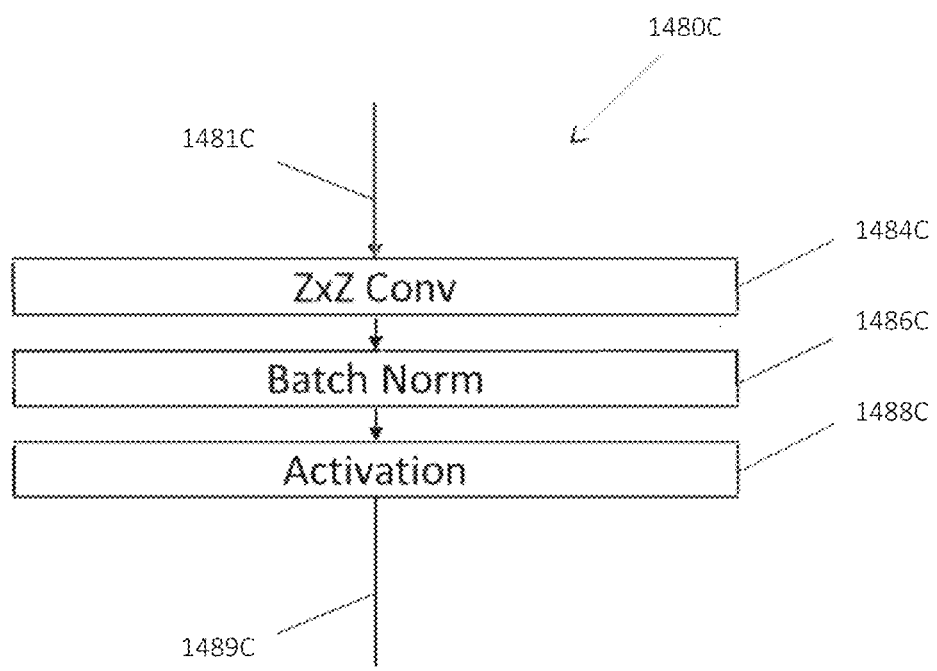

FIGS. 14A-14C illustrate schematic diagrams of a residual network, down-sampling block, and up-sampling block in accordance with one or more embodiments.

FIGS. 14D-14G illustrate more details about a convolutional neural network in one or more embodiments.

Figure 15:
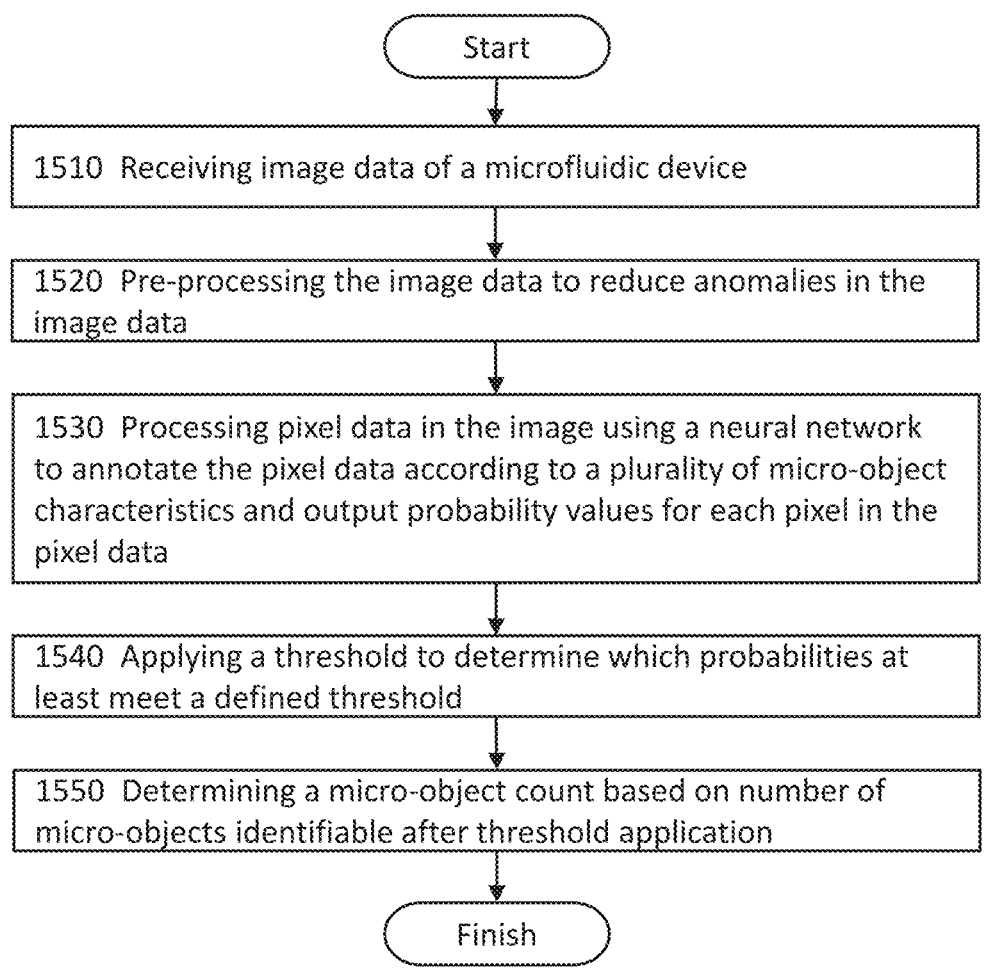

FIG. 15 illustrates a simplified example flow chart of a method for automatically detecting micro-objects in an image in accordance with one or more embodiments.

Figure 16:
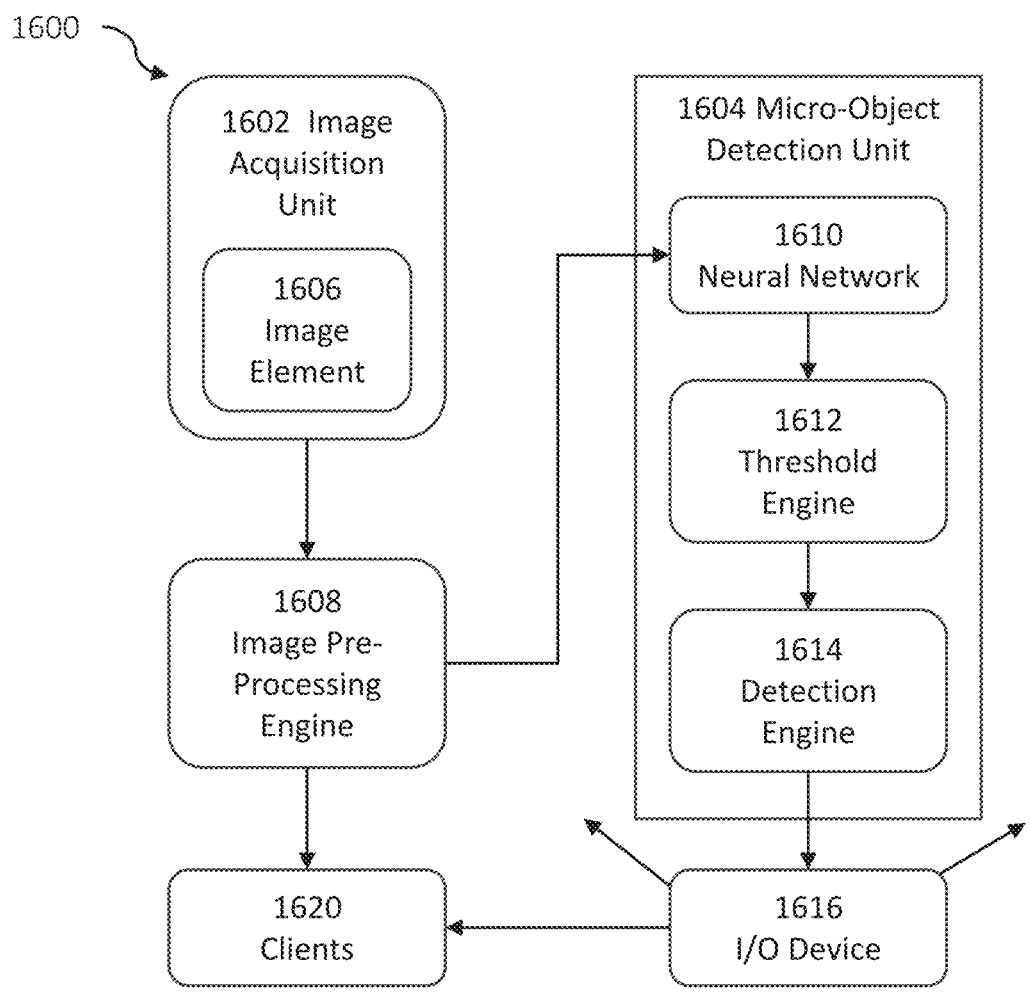

FIG. 16 illustrates a simplified example system for automatically detecting micro-objects in an image in accordance with one or more embodiments.

Figure 17:
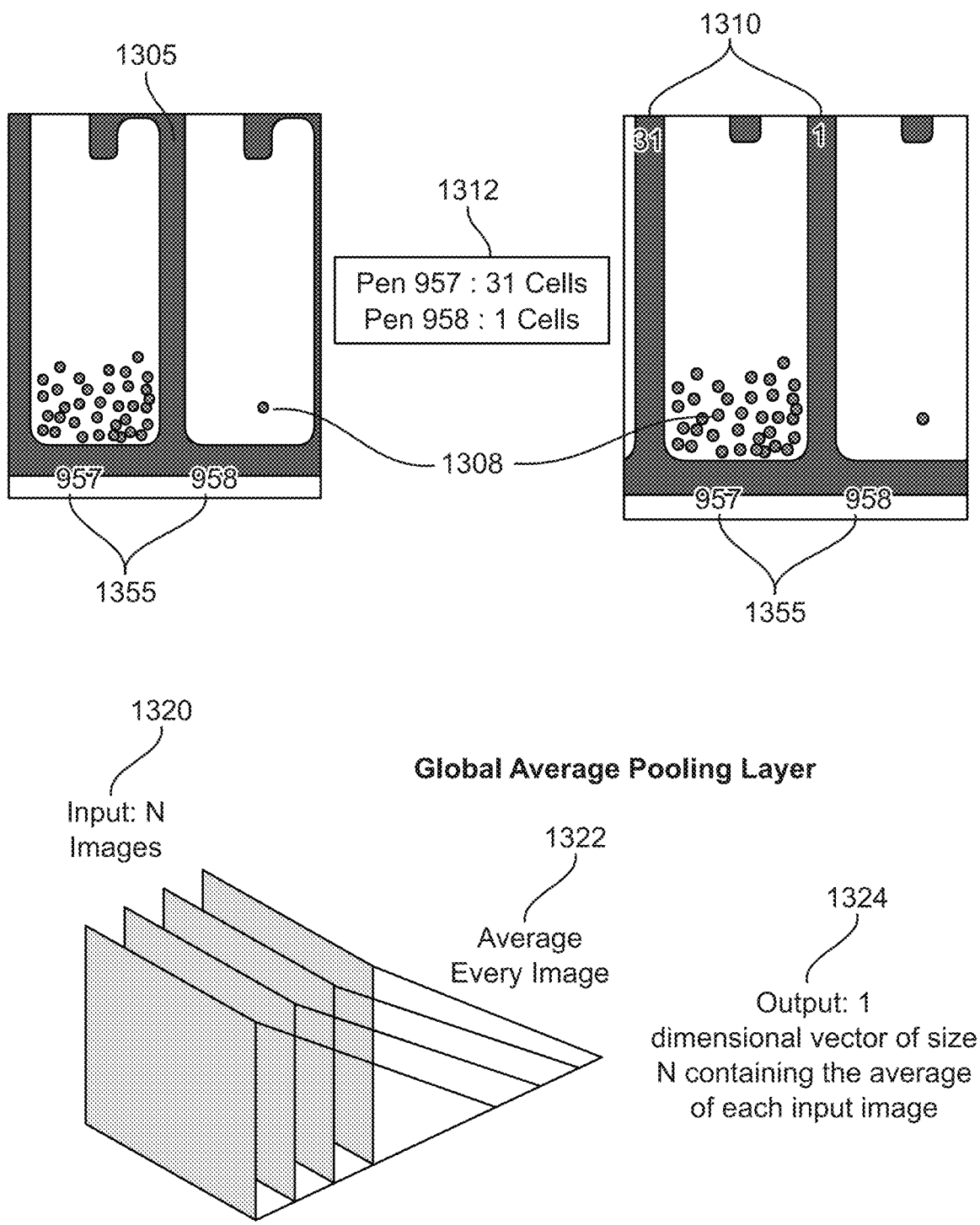

FIG. 17 illustrates example processes for performing global average pooling, and example regions of a microfluidic device for which counts may be determined by any one of the methods disclosed herein.

Figure 18:
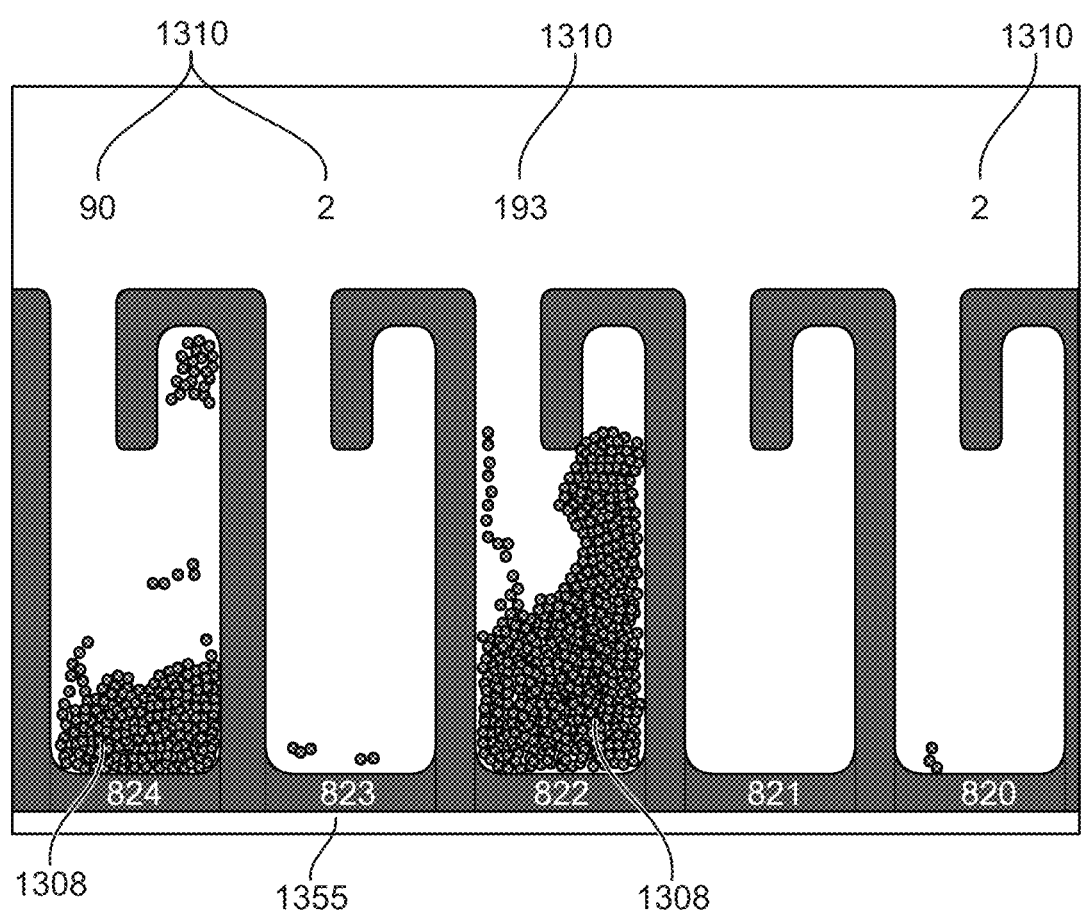

FIG. 18 illustrates some example regions of a microfluidic device for which counts may be determined by any one of the processes disclosed herein.

Figure 19:
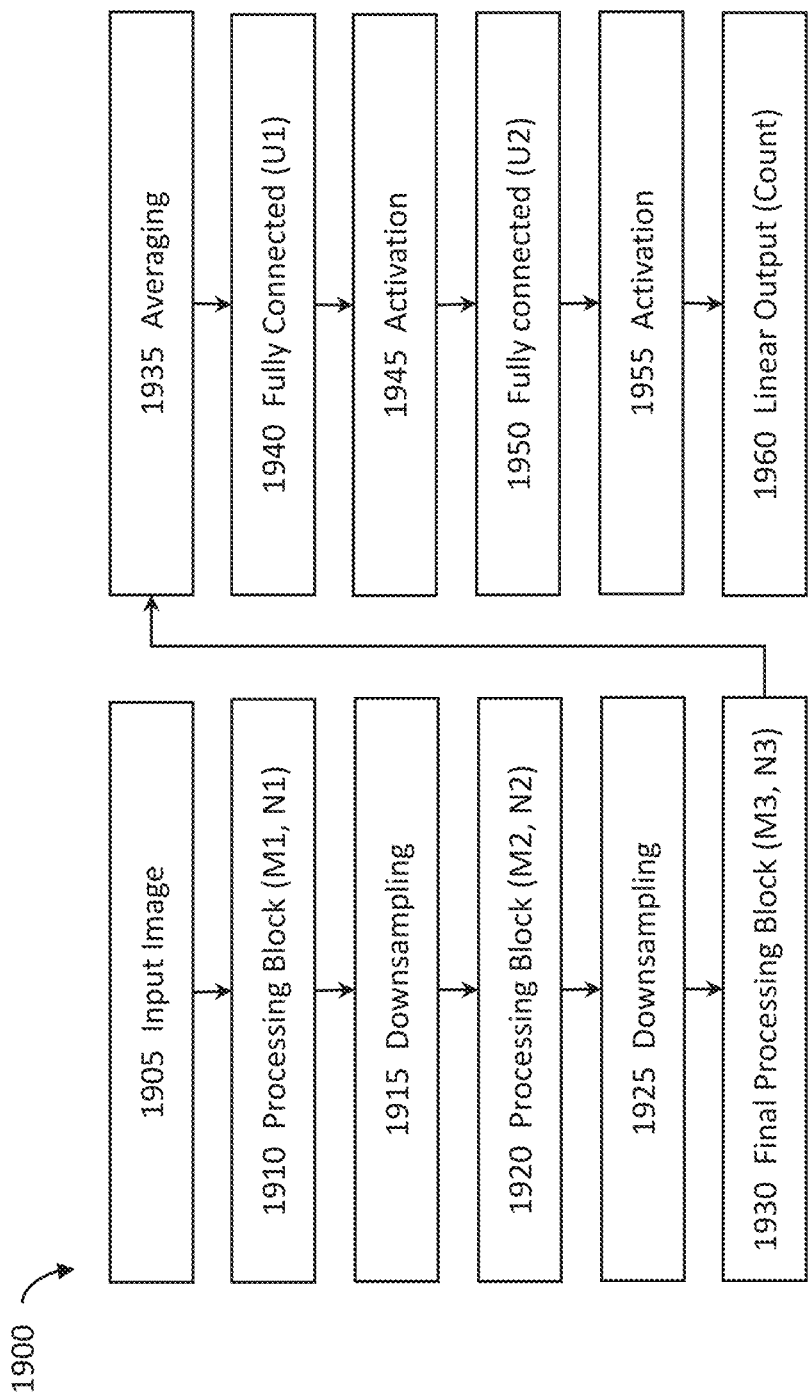

FIG. 19 illustrates a schematic diagram of a neural network in accordance with one or more embodiments.

Figure 20:
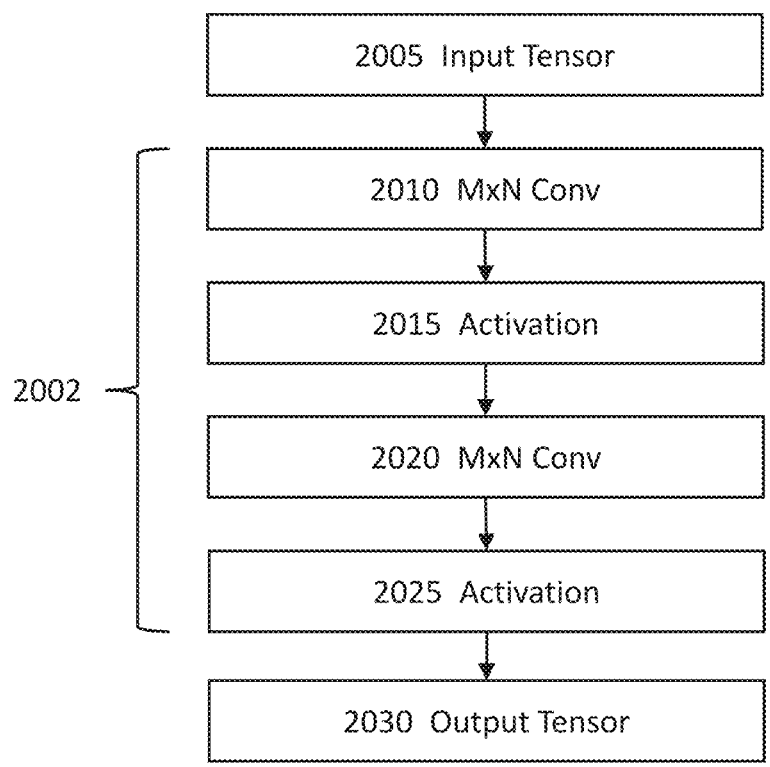

FIG. 20 illustrates a schematic diagram of a processing block in accordance with one or more embodiments.

Figure 21:
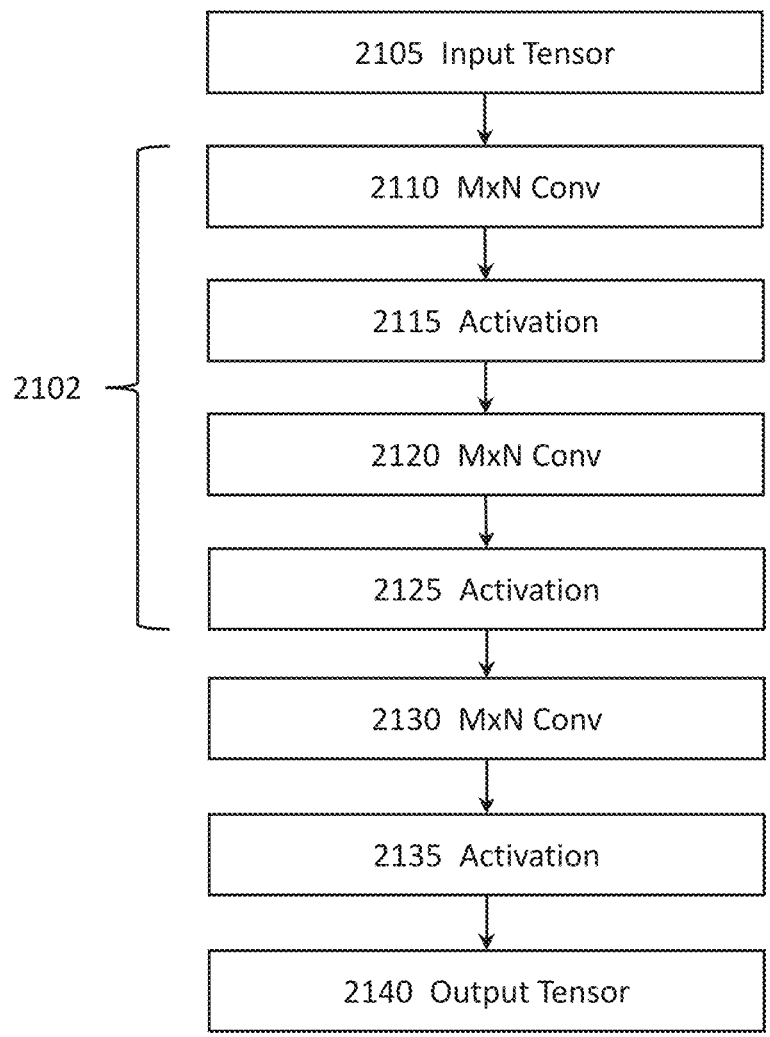

FIG. 21 illustrates a schematic diagram of a final processing block in accordance with one or more embodiments.

Figure 22A:
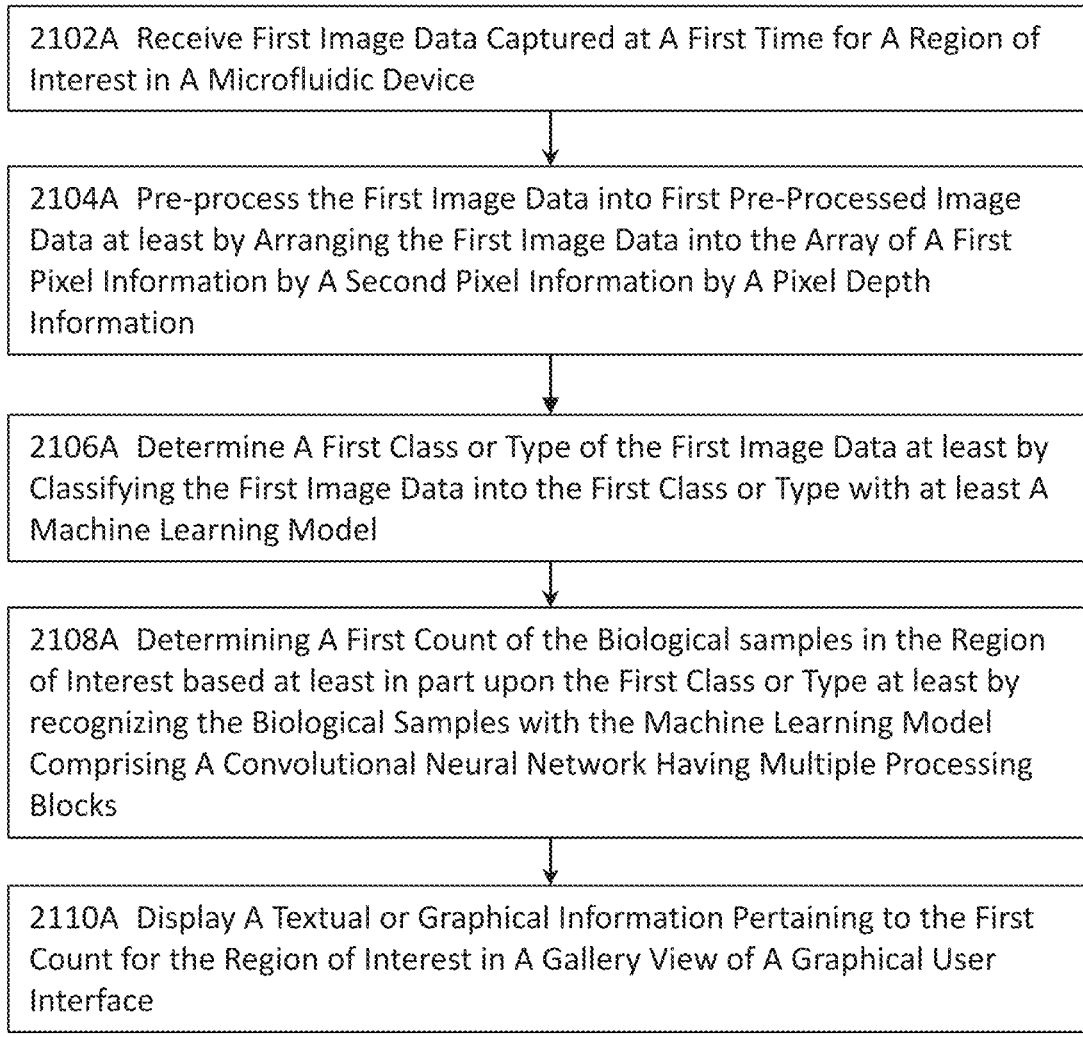
Figure 22B:
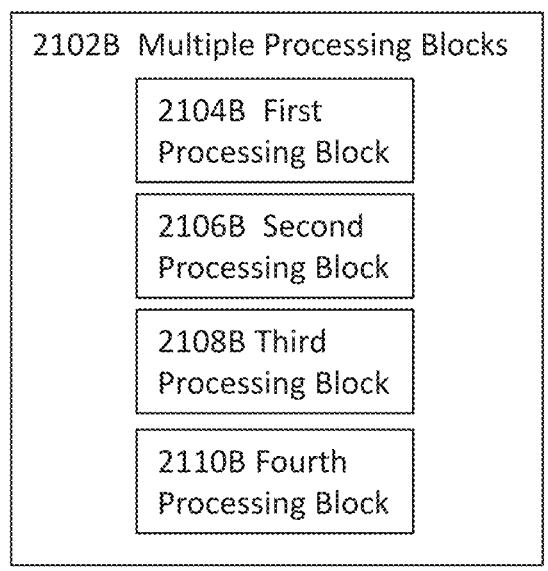

FIG. 22A illustrates a simplified high-level block diagram for a process or system for programmatically analyzing biological samples in a microfluidic device in one or more embodiments.

FIGS. 22B-22F illustrates more details about the high-level block diagram illustrated in FIG. 22A in one or more embodiments.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computer systems, server computers, and/or communications networks have not been shown or described in detail to avoid unnecessarily obscuring descriptions of the embodiments.

It shall be noted that, unless the context requires otherwise, throughout the specification and claims which follow, the word "comprise" and variations thereof, such as, "comprises" and "comprising" are to be construed in an open, inclusive sense that is as "including, but not limited to."

It shall be further noted that reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Furthermore, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Disclosed are method(s), system(s), and article(s) of manufacture for performing a process on biological samples in one or more embodiments. Some embodiments are directed at a method for performing an assay analysis or sequencing analysis for biological samples. In these embodiments, a user interface is identified and coupled to a processor of a system (e.g., an assay analyzer, a general-purpose computer, a specific-purpose computer, etc.) for processing one or more attributes of inputs captured from and/or features of a plurality of biological samples. Some embodiments are directed to a method for performing an automated count of biological samples in a region of interest in a microfluidic device having a plurality of chambers. A system for performing any of the aforementioned methods in any of the embodiments is also described herein. A non-transitory computer readable medium for storing thereupon a sequence of instructions which, when executed by a processor or a processor core, causes the processor or processor core to perform any of the aforementioned methods in any of the embodiments is also described.

These inputs include a set of images that is captured for a plurality of biological samples and is obtained at a set of time points or time periods. The plurality of biological samples includes a first biological sample and a second biological sample, and a biological sample may include a micro-object, a cell, a tissue, a protein, a gene, a virus, or an intracellular molecule such as DNA (deoxyribonucleic acid), RNA (ribonucleic acid), etc. It shall be noted that the terms "biological sample" and "micro-object" may be used interchangeably to refer to any of the aforementioned example(s) for a "biological sample", unless otherwise specifically, explicitly described to the contrary with exclusionary words such as "excluding," "not including," etc. The inputs are captured or otherwise collected for a sample that is located in a region of interest (e.g., at least a portion of a single chamber of an array of chambers, at or near an interface between a chamber and a flow channel, a chamber and a portion of a flow channel (e.g., the portion that is located immediately above and/or immediately adjacent to the chamber), etc.) in a microfluidic device, a microfluidic device, or a microfluidic apparatus, a nanofluidic device, a nanofluidic device, or a nanofluidic apparatus (collectively "microfluidic device" hereinafter). It shall be noted that the term "microfluidic device" may also be referred to as "microfluidic chip" or simply "chip", and that these terms may thus be used interchangeably in this disclosure. An output of an analysis of biological samples, as used herein, may comprise a set of images, one or more image sequences, or any data related thereto, including, for example, data derived from the set of images or the one or more image sequences.

Regions of interest in a microfluidic device may comprise a single image or image sequence taken from a discrete region of a microfluidic device. Regions of interest may be presented and displayed in an order in some embodiments or without a specific order in some other embodiments. In embodiments where the regions of interest are presented in a particular order, the order may be determined by one or more features of the region of interest, wherein the regions of interest in a set of regions of interest are sorted according to one or more characteristics or features. In some embodiments regions of interest may be stored in a region of interest list or data structure. In some of these embodiments, a region of interest list may include one or more lists that are generated from, for example, a user's review of at least a portion of the regions of interest in the list. For example, a user may use a filter builder and application module to apply one or more one- or multi-dimensional filters to identify a set of regions of interest.

As another example, a user may use, for example, a gallery view, a bioinformatics pipeline view, or one or more graphs to custom select a region of interest list comprising one or more regions of interest. The aforementioned set of regions of interest, the custom chamber list(s), etc. may also be appended to an existing region of interest list or stored in a new region of interest list. The aforementioned examples illustrate user-created region of interest lists. A region of interest list may also be automatically generated in some embodiments for the one or more regions of interest displayed or displayable in a user interface (e.g., in a gallery view). In some embodiments, a region of interest whose information is stored in a region of interest list may be derived from one or more sources such as, without limitations, one or more microfluidic devices, one or more fields of view images obtained from one or more image capturing devices or sensors, etc.

A microfluidic device (which may also be referred to as a laboratory-on-a-chip, a chip, a gene chip, a DNA chip, etc.) may include an instrument that manipulates (e.g., by using active and/or passive components and/or micro-components such as micropumps, microvalves, etc.) a very small amount of fluid (e.g., less than 1 mL, within the circuits of the microfluidic device at any given time) or fluids, reagents, soluble fluorescent reporters, etc. for exhibiting localized measurable effects in a region of interest of a microchip configured to perform one or more miniaturized processes or tests (e.g., multiplexing, automation, high-throughput screening, analysis, assays, etc.) on one or more biological samples (including an array of biological sample in excess of 100, 500, 1,000, 5,000, 7,000, 9,000, 11,000 or more biological samples). The operations performed on the microfluidic device may be configured to observe changes in one or more features/characteristics of a region of interest or regions of interest in response to control, and manipulation of the fluid or fluids, where such fluids are constrained to a small scale (e.g., sub-millimeter-scale, micro-scale, nano-scale, etc.) for the purpose of characterizing a biological sample. Manipulation of fluids may include stopping flow, starting flow, importing micro-objects, loading micro-objects into a region of the microfluidic device, isolating a micro-object, measuring changes in fluorescence in a region of the microfluidic device are around a particular target in a microfluidic device (e.g., intensity, accumulation or depletion of intensity over time, wavelength specific intensity, relative intensity at different wavelengths, etc.), measuring changes in shape or size, increase in density of micro-objects, etc.

A region of interest (ROI) includes a set of data that may be derived from a region of a microfluidic device which may be monitored over time for one or more changes (e.g., a change in fluorescence, a change in movement, a change in flow, a change indicating that a biological sample has moved into or out of a region of interest, etc.) In some embodiments, a region of interest may be target-based wherein the region of interest is identified, classified, sorted, or otherwise determined by one or more features of the region of interest. In other embodiments a region of interest may be structure-based (e.g., based on the microfluidic circuit structure). A region of interest referred to herein may be of either class (e.g., target-based or structure-based). Furthermore, the terms "region of interest," "chamber," and "pen" may be used interchangeably to refer to the aforementioned structure-based "region of interest" throughout the entire description unless otherwise specifically, explicitly described to the contrary with exclusionary words such as "excluding," "not including," etc. to limit the meaning of a pen or a chamber. It shall be noted that regions of interest may include structure-based region(s) of interest, target-based region of interest, or a combination of both structure-based and target-based region of interest.

In the former, target-based class, a region of interest may include a two-dimensional (2D) (e.g., an area in a 2D image) or a three-dimensional (3D) region that is defined based at least in part upon a target or a feature of the target. Some examples of a target may include, without limitations, a biological sample or one or more micro-objects, a feature, attribute, property, and/or characteristics thereof, a feature, attribute, property, and/or characteristic correlated with a quantifiable metric that pertains to a characteristic of a region of interest and/or is monitored or derived from analytic data collected or derived by, for example, bioinformatics pipelines, assay analyses, etc. A micro-object or a biological sample referred to in these embodiments may be determined based at least in part upon one or more criteria. For example, these one or more criteria may include any relations, constraints, requirements, limitations, etc. that are formulated based at least in part upon one or more attributes that are described with more details immediately below (e.g., the plurality of attributes selected for processing biological samples described below). Some examples of the one or more attributes may include area (e.g., number of pixels forming an area, microns (e.g., square microns or micron dimensions) of an area, background area, number of pixels of a background area, microns (e.g., square microns or micron dimensions) of a background area, centroid in microns (e.g., x-centroid, y-centroid, coordinates of a centroid, area of a centroid in square microns, etc.), centroid in pixels (e.g., x-centroid or y-centroid, coordinates of the centroid, area of centroid), circularity of a sample, diameter of a sample in microns, max brightness, median brightness, max background brightness, mean background brightness, perimeter microns of a sample, or target index (e.g., a unique identifier or label associated with a specific target), etc. Thus, a target-based region of interest may comprise a single micro-object, e.g., a cell, and include data assessed for that micro-object and is associated with the micro-object across a timeline or a selected workflow. Further, a plurality of target-based regions of interest may be defined, each comprising a single micro-object and including the data as described, where the regions of interest are distributed throughout the microfluidic device.

In the latter embodiments, a structure-based region of interest (e.g., microfluidic circuit structure-based region of interest) may include a 2D or 3D region of a microfluidic circuit or device or a portion thereof. For example, a structure-based region of interest may include, without limitation, one or more chambers, pens, isolation regions, etc. (that may also be referred to as a chamber, pen, isolation region respectively for a singular reference or multiple chambers, pens, isolation regions, etc. for plural references), a flow channel (and/or a feature thereof) in a microfluidic device, an interface between a chamber and a flow channel in a microfluidic circuit or device, a portion of a chamber, a flow channel, and/or an interface, any region in or correlated with a microfluidic circuit or device, or any combinations thereof. A chamber may be referred to as an isolation chamber because a chamber in a microfluidic device effectively, physically isolate or selectively isolate a biological sample from flow outside of the chamber and/or from one or more other biological samples outside the chamber in some embodiments.

In some embodiments, a region of interest (target-based and/or structure-based) may include any portion of or correlated with a microfluidic device and may be dynamically, automatically determined (e.g., at runtime during the generation of a gallery which is described in greater detail below) based at least in part upon, for example, a characteristic of the microfluidic device or a portion thereof. Some examples of the aforementioned characteristic may include, without limitation, a shape or a boundary of the microfluidic device or a portion thereof. In some embodiments, a region of interest may be dynamically, automatically determined based at least in part upon a workflow or a portion thereof (e.g., a step in a workflow). Pertinent data may thus be automatically generated in response to a region of interest so determined.

In an example wherein a base image captures multiple chambers of a microfluidic device, a gallery view may be generated for a region of interest at one or more timepoints of an export process from the base image. In some embodiments a base image comprising multiple regions of interest is captured by a single image capturing device (e.g., a single image sensor, a single camera, etc.) at a timepoint (while accommodating the amount of exposure time) may be cropped into individual images or image sequences for each of the multiple regions of interest in the base image and/or across base images of a microfluidic device. In further embodiments, the compiled image sequences for an array of regions of interest with each image sequence may be derived from an array of base images taken at specific time points or selected from a stack of images at specific time points. The specific time points included in the image sequences may be determined or displayed according to the time point based on the chip timeline view, where stages or operations performed on the microfluidic device are illustrated as blocks (optionally color coded) over a timeline.

For example, a region of interest for an export process may be determined to include an image of an individual chamber (or a portion thereof) at one timepoint. In response to such a determination, the system may automatically identify the chamber in the base image and crop the base image so that the individual chamber remains in the cropped image from the base image for the chamber. As another example, another region of interest may be determined to include an image of the individual chamber (or a portion thereof) plus the interface between the individual chamber and a flow channel at a subsequent timepoint. In response to such a determination, the system may automatically identify the chamber and the flow channel in the base image and crop the base image so that the individual chamber (or optionally the individual chamber with a portion of the flow channel) remains in the cropped image from the base image for the chamber. In some embodiments cropping may be performed across the base image, such that all the resulting regions of interest comprise features or characteristics that may be compared. Unless otherwise explicitly described to the contrary, the terms "chamber," "pen," and "region" may be used interchangeably throughout the entire description.

Regions of interest may be determined based on "characteristics" and "features" (e.g., a base image is split into regions of interest based on characteristics and features), where a base image is derived from images taken during a block graphically represented in the chip timeline 1304B. Additionally, "characteristics" and "features" of a "region of interest" may be used to sort the region of interest (e.g., "characteristics" or "features" may be captured in an image sequence representing the region of interest, and/or quantified for the purpose of displaying the region of interest in for example a gallery view 1804.

As another example, a third region of interest may be determined to include an image of a flow channel (optionally including the interface between the individual chamber and the flow channel) at a later timepoint. In response to such a determination, the system may automatically identify the flow channel (and optionally the interface of the flow channel with a chamber) in the base image and crop the base image so that the flow channel (and optionally the interface of the flow channel with a chamber) remains in the cropped image from the base image for the chamber. In these examples, some or all of these determinations and generations of individual images may be automatically made by the system and presented in, for example, a gallery view with the aforementioned individual images to illustrate a time-based development of the export process correlated with the biological sample(s) in the chamber.

In some embodiments, a workflow referred to herein may include a collection or series of steps and/or operations that were, are, or are to be performed on one or more biological samples in or on a microfluidic device. The performance of a workflow may include, for example but not limited to, one or more bioinformatics pipelines, one or more assays, etc. for one or more biological samples in some embodiments.

A workflow may include, for example, a series of actions or a method performed on a microfluidic device over a defined time course on said microfluidic device, optionally performed to generate an intended result and/or to filter out, assess, or monitor an ROI (region of interest) or a plurality of ROIs. For example, a workflow may have been performed on one or more biological samples in or on a microfluidic device prior to importing data correlated with the workflow is imported into a system. The system may be configured to receive the data and to employs and applies various techniques (e.g., filtering, cropping, displaying, comparing, selecting, ordering, etc.), as described herein, to characterize the data and present it to the user in a usable format, where the usable format may depend on features/characteristics of the obtained data including changes to one or more features or characteristics of images obtained from the microfluidic device (e.g., target-based or structure-based) and/or the time at which particular operations were performed on the microfluidic device (e.g., images obtained according to the chip timeline, which represents the time course of operations (e.g., changes in conditions, flow rate, import/export of micro-object, perfusion of small molecules into or out of a particular region of the microfluidic device, any operations involving the use of reagent(s) and/or non-brightfield imaging, an assay or a portion thereof, time-lapse imaging with culture, cell loading, beads loading, cells unloading, etc.)

The output of a workflow may provide the context of time and/or relevance of a temporal snapshot to the output that may be rendered and/or displayed in, for example, a chip timeline view, a gallery view, etc. described below. In some embodiments, an output and/or any other data or information derived therefrom (e.g., analytics, computational biological results, etc.) of a workflow may be stored as one or more files (e.g., a comma-separated values or csv file, a table, a database, a relational database table, or any suitable data structure, etc.) in one or more folders or directories. In some embodiments, a workflow execution unit may be separated from (e.g., in a separate assay execution system such as a cell analysis suite or CAS that controls various instruments correlated with assays, bioinformatics, etc.) one or more modules or systems described herein for performing various analytic functions. In some other embodiments, a workflow execution unit may be integrated with one or more modules or systems described herein or may even form a single system (e.g., an analyzer for both executing a workflow and performing analytics).

A workflow may be concurrently executed to generate various pieces of data while a system collects various data and performs various analytic or computational functions on the collected data in some other embodiments. That is, a system described herein may execute both a workflow collection and analysis of result data from the workflow in real-time or substantially real-time as the output data is collected. By substantially real-time, it shall be noted that a system described herein may perform an analytic function on a collected output of a workflow stage as soon as the collected output is generated and collected while the time to collect the output (e.g., capturing an image, transmitting the image data to a volatile or non-volatile storage medium for storage) an the time for performing the analytic function to generate an analytic output (e.g., invoking an analytic function, executing the analytic function, generating the analytic outputs, transmitting the analytic output for storage, and rendering the analytic output on display, etc.) may be accounted for yet neglected to satisfy the "nearly real-time" criterion due to the expedient nature of these processing tasks on a modern computing device. As used herein, a workflow stage may comprise one or more workflow tasks.

A workflow comprises workflow stage and corresponding workflow tasks, wherein each workflow task is an activity performed on a microfluidic device for the purpose of obtaining a result. A result in this context may comprise one or more of: a data set including images, analyzed quantitated features of the images, a product for example a gene product or sequence, scores/rankings or rankings of samples being analyzed in the microfluidic device, or any other output that would be reasonably expected from an assay or workflow run on a microfluidic device or obtained from the product (e.g., protein or nucleic acid sequence etc.) of a sample run on a microfluidic device. Exemplary workflow tasks may comprise any activity relevant to assaying, monitoring, perturbing, observing or otherwise interrogating a micro-object (biological or otherwise) disposed within a microfluidic device. Exemplary workflow tasks include but are not limited to: import, culture, assay, perfusion, manipulation, and export. Import may comprise flowing in a solution comprising one or more micro-objects. Culture may comprise adjusting, modulating, maintaining, or otherwise controlling or optimizing conditions of flow, temperature, light, concentration of solubilized components (e.g., oxygen, sugars, etc.) or non-solubilized components in discrete fluidic regions of the device for the purpose of expanding a population of micro-objects (e.g., cells). Assay may comprise performing an operation including but not limited to exposing (e.g., releasing, uncaging, solubilizing, perfusing in, etc.) a component (reagent, small molecule, macro-molecule, etc.) configured to elicit a measurable response from a micro-object (e.g., a micro-object). Perfusion may comprise flowing in a solution, for example via injection at the inlet or aspiration at the outlet, wherein the solution comprises a liquid for example a medium comprising one or more components (e.g., surfactants, ions, reagents, dyes, etc.). Manipulation may comprise moving, repositioning (e.g., penning or unpenning), or otherwise adjusting the spatial placement of one or more micro-objects at one or more positions within the microfluidic device. Export may comprise displacing a micro-object from inside the microfluidic device into a region of the microfluidic device and flowing a solution through the microfluidic device such that the displaced micro-object is flowed through and out of the microfluidic device.

As stated previously, image sequences may be obtained at one or more discrete or continuous time segments of the workflow associated with timestamps or with a time series that corresponds to the workflow. The image sequences may be further obtained or selected from one or more workflow tasks performed during the workflow. In embodiments disclosed herein, image sequences may be displayed in a timeline view and the inventions disclosed herein provide invokable means for selecting portions of the timeline that represent the workflow and/or workflow tasks and generating alternative views (e.g., gallery view) displaying image sequences for the corresponding selected portion of the timeline. Furthermore, the views (e.g., gallery view etc.) may be configured to further organize and display the image sequences while preserving and displaying the contextual information relevant to the workflow (e.g., the time stamp at which it was taken during the workflow and the workflow task performed at the time the selected image sequence was obtained).

As stated previously, a workflow or workflow stage may comprise a series of workflow tasks performed across a span of time. An exemplary series of workflow tasks performed on a microfluidic device comprises the following continuous or discontinuous series of tasks: {import, culture, assay, culture, assay, culture, assay, export, etc.} wherein the image sequences are taken continuously or discontinuously across the entire workflow, across one or more workflow tasks, or as a portion of one or more workflow tasks. Images in the image sequence could be obtained at a given image capture rate or at different image capture rates. Image sequences may comprise representative images (e.g., averaged, selected, or down sampled images with the subset of representative images or raw image sequences taken at discrete timepoints or at defined subsets of the workflow.

Image sequences taken at continuous or discontinuous segments across the workflow, workflow stage, and/or workflow tasks, may be presented in a timeline view. The timeline view may display the workflow (e.g., the entire workflow or any subset of the workflow, for example temporally contiguous subsets of the workflow or temporally discontinuous subsets of the workflow), with the workflow stage, and/or workflow tasks displayed, for example, as blocks, graphical representations, or graphical elements plotted across time in the timeline view. It shall be noted that the reference to the term "block" may or may not necessarily mean that a workflow is represented in a user interface as an ordered collection of solid shape such as a rectangular shape. Rather, a workflow may be represented in any suitable graphical representations. Moreover, the term "block," "graphical representation," and "graphical element" may be used interchangeably to refer to a workflow task or a workflow stage throughout this entire description. Blocks or graphical representations may correspond to respective workflow tasks and may be color coded. A graphical representation of a workflow stage may comprise one or more segments that respectively correspond to, for example, one or more workflow tasks of the workflow stage. In some embodiments where a graphical representation of a workflow stage includes multiple segments respectively representing their corresponding workflow tasks, these multiple segments may be temporally aligned or arranged with respect to each other. Moreover, each segment may correspond to its own data stored in, for example, a microfluidic device data structure or a gallery structure. In some of these embodiments, a segment may be interacted upon (e.g., by a user's zooming in to the segment and clicking on the segment), and such an interaction may trigger, for example, retrieval of the corresponding data and representation of at least a portion of the corresponding data in the user interface (e.g., in a gallery view or in a matching grid portion of a gallery view). In some embodiments where a workflow includes multiple graphical representations respectively representing their corresponding workflow stage or workflow tasks, these multiple graphical segments may be temporally aligned or arranged with respect to each other in the user interface (e.g., by positioning the multiple graphical segments along a temporal axis). Moreover, each graphical representation may correspond to its own data stored in, for example, a row or a column in a single microfluidic device data structure or a gallery structure. In some of these embodiments, a graphical representation may be interacted upon (e.g., by a user's clicking on the graphical representation), and such an interaction may trigger, for example, retrieval of the corresponding data and representation of at least a portion of the corresponding data in the user interface (e.g., in a gallery view or in a matching grid portion of a gallery view). A timeline corresponding to an analysis may include one or more blocks or graphical representations. Multiple segments in the same block may also be color coded to indicate image selections for display in other views (including but not limited to a gallery view). An image sequence collected during a workflow task may be represented in a timeline view (see, e.g., FIGS. 4B-4C, etc.), wherein a block or a graphical representation in the timeline corresponds to a workflow task (see, e.g., 404B in FIG. 4B, 408C in FIG. 4C, etc.) For example, multiple graphical representations respectively representing their corresponding workflow tasks or workflow stages in a workflow may be rendered in a user interface according to, for example, the temporal order in which the corresponding workflow tasks or workflow stages occur temporally. In some embodiments, a graphical representation may be rendered in a timeline view having a temporal axis where one end or side of the graphical representation corresponds to the beginning time point or time period when the corresponding workflow task or stage occurs, and the other end or side of the graphical representation corresponds to the end time point or time period when the corresponding workflow task or stage ended. In some embodiments, a size or dimension of a graphical representation may be rendered to be proportional to the temporal duration of the corresponding workflow task or stage.

In some embodiments, microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

In these embodiments, a plurality of characteristics may be selected for the plurality of biological samples for processing the plurality of biological samples. A first sequence of data correlated with a set of time points or time periods for the first biological sample obtained from a first region of interest (e.g., a chamber) of the microfluidic device may be populated into a data structure in an addressable space in the non-transitory computer accessible storage medium, wherein the first sequence of data corresponds to at least one or more of the plurality of characteristics.

An "characteristic" or "feature" of the plurality of characteristics may include any characteristic correlated with one or more assay analyses of biological samples, the biological samples themselves, the results of the one or more assay analyses. As used herein the term "characteristic" and "feature" may be used interchangeable. A characteristic or feature may thus be used to constrain, configure, or control a view presented in a user interface or how a view may be presented in a user interface. A characteristic or feature may also be associated with one or more functions that may be automatically invoked in response to a designation or selection of the characteristic. For example, when a user selects a cell count characteristic, a sorting function may be automatically invoked to sort various objects (e.g., interactive image objects of a plurality of chambers) in order to present the sorting result in a pertinent view. Different characteristics may be associated with the same set of one or more functions in some embodiments or different sets of one or more functions in some other embodiments.

Some examples of an characteristic of the plurality of characteristics may include, without limitation, at least one of an identifier of a chamber in the microfluidic device, a size attribute of the plurality of biological samples, a maximum brightness attribute for the plurality of biological samples, a minimum brightness attribute for the plurality of biological samples, a first pixel count attribute in a first direction for a centroid of a biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of chambers, a gate path index, an area pixel attribute, a background pixel attribute, a median brightness attribute for the plurality of biological samples, a target area pixel count attribute, a target area size attribute, a target background area size attribute, a target background pixel count attribute, a target background maximum brightness attribute, a target circularity attribute, a counting algorithm identification, an imaging cube attribute, a target diameter attribute, an export vessel identifier, an export chamber column identifier, an export chamber row identifier, an import chamber column identifier, an import chamber row identifier, an import vessel identifier, a chamber positive verification attribute, a biological sample count attribute for unpenned biological samples, or a time stamp indicating the time or time period of capture or generation of data.

A second sequence of data correlated with the set of time points or time periods for the second biological sample obtained from a second chamber of the microfluidic device may also be populated into the data structure in the addressable space in the non-transitory computer accessible storage medium, wherein the second sequence of data corresponds to at least a second portion of the plurality of characteristics.

The first and the second sequences of data may be rendered, in a first window portion of the user interface and with a graphics processing unit, in a first view, rendering the first and the second sequences of data in the first view comprising in response to a selection of a first characteristic from a first selection widget in the user interface, extracting a first characteristic value of a first characteristic from the first portion of the plurality of characteristics for the first biological sample; and extracting a second characteristic value of the first characteristic from the second portion of the plurality of characteristics for the second biological sample.

These embodiments may further render a first interactive object and a second interactive object respectively corresponding to the first and the second sequences of data into the first view, wherein the first interactive object is representative of the first characteristic value of the first biological sample and the second interactive object is representative of the second characteristic value of the second biological sample. An interactive object comprises, for example, a software object with which a user may interact via, for example, a user interface described herein. In response to a user interaction with an interactive object, the underlying system may invoke and perform one or more functions on the interactive object to modify what was presented in the user interface prior to the user interaction or generate a new or refreshed view in the user interface based on the user interaction.

In some embodiments, the data structure includes a column structure and a row structure, the column structure comprises multiple columns, the row structure comprises multiple rows, and biological sample data that is specific to an assay analysis performed on one or more biological samples in the region of interest (e.g., the single chamber) of the microfluidic device. In some of these embodiments, a column in the column structure corresponds to the biological sample data that is specific to the assay analysis performed on a chamber, and each row corresponding to the column corresponds to the biological sample data that is captured or generated for the chamber at a specific time point or for a specific time period.

In some other embodiments, a row in the row structure corresponds to the biological sample data that is specific to the assay analysis performed on a chamber, and each column corresponding to the row corresponds to the biological sample data that is captured or generated for the chamber at a specific time point or for a specific time period.

A microfluidic device comprises a device that includes one or more discrete microfluidic or nanofluidic circuits configured to hold fluid, each microfluidic or nanofluidic circuit comprises fluidically interconnected circuit elements, including but not limited to region(s), flow path(s), channel(s), chamber(s), and/or pen(s), etc. (collectively "chamber" for singular references and "chambers" for plural references) and optionally at least one port configured to allow the fluid (and, optionally, micro-objects suspended in the fluid) to flow into and/or out of the microfluidic device. In some embodiments, a microfluidic or nanofluidic circuit of a microfluidic or nanofluidic device may include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 microliters. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 microliters. The microfluidic or nanofluidic circuit may be configured to have a first end fluidically connected with a first port (e.g., an inlet) in the microfluidic device and a second end fluidically connected with a second port (e.g., an outlet) in the microfluidic device.

A "microfluidic channel" or "flow channel" as used herein refers to flow region of a microfluidic device having a length that is significantly longer than both the horizontal and vertical dimensions. For example, the flow channel may be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, glass beads, amorphous solid substrates, Luminex™ beads, or the like); magnetic beads; microrods; microwires; quantum dots, and the like; micro-objects such as cells; biological organelles; vesicles, or complexes; synthetic vesicles; liposomes (e.g., synthetic or derived from membrane preparations); lipid nano-rafts, and the like; or a combination of inanimate micro-objects and micro-objects (e.g., microbeads attached to cells, liposome-coated microbeads, liposome-coated magnetic beads, or the like). Beads may include moieties/molecules covalently or non-covalently attached, such as fluorescent labels, proteins (including receptor molecules), carbohydrates, antigens, small molecule signaling moieties, or other chemical/biological species capable of use in an assay. In some variations, beads/solid substrates including moieties/molecules may be capture beads, e.g., configured to bind molecules including small molecules, peptides, proteins or nucleic acids present in proximity either selectively or non-selectively. In one nonlimiting example, a capture bead may include a nucleic acid sequence configured to bind nucleic acids having a specific nucleic acid sequence or the nucleic acid sequence of the capture bead may be configured to bind a set of nucleic acids having related nucleic acid sequences. Either type of binding may be understood to be selective. Capture beads including moieties/molecules may bind non-selectively when binding of structurally different but physico-chemically similar molecules is performed, for example, size exclusion beads or zeolites configured to capture molecules of selected size or charge. Lipid nano-rafts have been described, for example, in Ritchie et al. (2009) "Reconstitution of Membrane Proteins in Phospholipid Bilayer Nanodiscs," Methods Enzymol., 464:211-231.

As used herein, the term "cell" may be used interchangeably with the term "biological cell" or "biological sample". Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell may be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g., about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding. As used herein, the term "expanding" when referring to cells, refers to increasing in cell number. A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like. As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion, and may encompass perfusion. For example, flow of a medium may involve movement of the fluidic medium from one point to another point due to a pressure differential between the points. Such flow may include a continuous, pulsed, periodic, random, intermittent, or reciprocating flow of the liquid, or any combination thereof. When one fluidic medium flows into another fluidic medium, turbulence and mixing of the media may result. Flowing may comprise pulling solution through and out of the microfluidic channel (e.g., aspirating) or pushing fluid into and through a microfluidic channel (e.g., perfusing).

The phrase "substantially no flow" refers to a rate of flow of a fluidic medium that, when averaged over time, is less than the rate of diffusion of components of a material (e.g., an analyte of interest) into or within the fluidic medium. The rate of diffusion of components of such a material may depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device may have different compositions (e.g., different concentrations of solutes, such as proteins, carbohydrates, ions, or other molecules) which are in flux as solutes move down their respective concentration gradients and/or fluids flow through the device.

As used herein, a "flow path" refers to one or more fluidically connected circuit elements (e.g., channel(s), region(s), chamber(s) and the like) that define, and are subject to, the trajectory of a flow of medium. A flow path is thus an example of a swept region of a microfluidic device. Other circuit elements (e.g., un-swept regions) may be fluidically connected with the circuit elements that comprise the flow path without being subject to the flow of medium in the flow path. As used herein, "isolating a micro-object" confines a micro-object to a defined area within the microfluidic device.

A microfluidic (or nanofluidic) device may comprise "swept" regions and "un-swept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region may include, for example, regions, channels, and all or parts of chambers. As used herein, an "un-swept" region is comprised of one or more fluidically interconnected circuit element of a microfluidic circuit, each of which experiences substantially no flux of fluid when fluid is flowing through the microfluidic circuit. An un-swept region may be fluidically connected to a swept region, provided the fluidic connections are structured to enable diffusion but substantially no flow of media between the swept region and the un-swept region. The microfluidic device may thus be structured to substantially isolate an un-swept region from a flow of medium in a swept region, while enabling substantially diffusive fluidic communication between the swept region and the un-swept region. For example, a flow channel of a micro-fluidic device is an example of a swept region while an isolation region (described in further detail below) of a microfluidic device is an example of an un-swept region.

As used herein, a "non-sweeping" rate of fluidic medium flow means a rate of flow sufficient to permit components of a second fluidic medium in an isolation region of the chamber to diffuse into the first fluidic medium in the flow region and/or components of the first fluidic medium to diffuse into the second fluidic medium in the isolation region; and further wherein the first medium does not substantially flow into the isolation region.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that may be expressed as numerical values, "substantially" means within ten percent. The term "ones" means more than one. As used herein, the term "plurality" may be 2, 3, 4, 5, 6, 7, 8, 9, 10, or more.

As used herein, "pen" or "penning" refers to disposing micro-objects within a chamber (e.g., a sequestration pen) within the microfluidic device in some embodiments. Forces used to pen a micro-object may be any suitable force as described herein such as dielectrophoresis (DEP), e.g., an optically actuated dielectrophoretic force (OEP); gravity; magnetic forces; locally actuated fluid flow; or tilting. In some embodiments, penning a plurality of micro-objects may reposition substantially all the micro-objects. In some other embodiments, a selected number of the plurality of micro-objects may be penned, and the remainder of the plurality may not be penned. In some embodiments, when selected micro-objects are penned, a DEP force, e.g., an optically actuated DEP force or a magnetic force may be used to reposition the selected micro-objects. In some embodiments, micro-objects may be introduced to a flow region, e.g., a microfluidic channel, of the microfluidic device and introduced into a chamber by penning.

As used herein, "unpen" or "unpenning" refers to repositioning micro-objects from within a chamber, e.g., a sequestration pen, to a new location within a flow region, e.g., a microfluidic channel, of the microfluidic device in some embodiments. Forces used to unpen a micro-object may be any suitable force as described herein such as dielectrophoresis, e.g., an optically actuated dielectrophoretic force; gravity; magnetic forces; locally actuated fluid flow; or tilting. In some embodiments, unpenning a plurality of micro-objects may reposition substantially all the micro-objects. In some other embodiments, a selected number of the plurality of micro-objects may be unpenned, and the remainder of the plurality may not be unpenned. In some embodiments, when selected micro-objects are unpenned, a DEP force, e.g., an optically actuated DEP force or a magnetic force may be used to reposition the selected micro-objects.

Some embodiments are directed at a hardware system that may be invoked to perform any of the methods, processes, or sub-processes disclosed herein. The hardware system may include at least one microprocessor or at least one processor core, which executes one or more threads of execution to perform any of the methods, processes, or sub-processes disclosed herein in some embodiments. The hardware system may further include one or more forms of non-transitory machine-readable storage media or devices to temporarily or persistently store various types of data or information. Some example modules or components of the hardware system may be found in the System Architecture Overview section below.

Some embodiments are directed at an article of manufacture that includes a non-transitory machine-accessible storage medium having stored thereupon a sequence of instructions which, when executed by at least one processor or at least one processor core, causes the at least one processor or the at least one processor core to perform any of the methods, processes, or sub-processes disclosed herein. Some example forms of the non-transitory machine-readable storage media may also be found in the System Architecture Overview section below.

According to a first aspect of the invention, a non-transitory computer-readable medium stores instructions, the instructions comprising one or more instructions that, when executed by one or more processors, cause the one or more processors to provide, for display, data derived from an assay analysis, characterized in that the data includes at least one image of at least a portion of a chamber of a lab-on-a-chip, and alphanumeric data associated with said at least one chamber, in which the display is a gallery view, a timeline view, a raw data table, or combinations thereof.

In such a non-transitory computer-readable medium, the one or more processors provide, for display, the gallery view including images of portions of the lab-on-a-chip arranged as steps of the assay. In such a non-transitory computer-readable medium, the one or more processors provide, for display, the gallery view including alphanumeric data corresponding to each image at the time the image was captured. In such a non-transitory computer-readable medium, the one or more processors provide, for display, the timeline view including image sequence markers along a timeline representing steps of the assay. In such a non-transitory computer-readable medium, the one or more processors provide, for display, the raw data view as a table.

According to another aspect of the present invention, a device comprises one or more processors to receive information that specifies a graphical scene based on data derived from an assay analysis, characterized in that the data includes at least one image of at least a portion of a chamber of a lab-on-a-chip, and alphanumeric data associated with said at least one chamber, in which the display is a gallery view, a timeline view, a raw data table, or combinations thereof.

In such a device, the information specifies, for display, the gallery view including images of portions of the lab-on-a-chip arranged as steps of the assay. In such a device, the information specifies, for display, the gallery view including alphanumeric data corresponding to each image at the time the image was captured. In such a device, the information specifies, for display, the timeline view including image sequence markers along a timeline representing steps of the assay. In such a device, the information specifies, for display, the raw data view as a table.

According to yet another aspect of the present invention, a method for displaying data derived from an assay analysis comprises providing, by a device and for display, data derived from an assay analysis, characterized in that the data includes at least one image of at least a portion of a chamber of a lab-on-a-chip, and alphanumeric data associated with said at least one chamber, and providing, by a device and for display, a gallery view, a timeline view, a raw data table, or combinations thereof.

In such a method, said providing comprises providing, for display, the gallery view including images of portions of the lab-on-a-chip arranged as steps of the assay. In such a method, said providing comprises providing, for display, the gallery view including alphanumeric data corresponding to each image at the time the image was captured. In such a method, said providing comprises providing, for display, the timeline view including image sequence markers along a timeline representing steps of the assay. In such a method, said providing comprises providing, for display, the raw data view as a table.

Still other aspects, features, and attendant advantages of the present invention will become apparent to those skilled in the art from a reading of the following detailed description of embodiments constructed in accordance therewith, taken in conjunction with the accompanying drawings.

Various embodiments will now be described in detail with reference to the drawings, which are provided as illustrative examples of the invention so as to enable those skilled in the art to practice the invention. Notably, the figures and the examples below are not meant to limit the scope of the present invention. Where certain elements of the present invention may be partially or fully implemented using known components (or methods or processes), those portions of such known components (or methods or processes) that are necessary for an understanding of the present invention will be described, and the detailed descriptions of other portions of such known components (or methods or processes) will be omitted so as not to obscure the present disclosure.

Referring to the drawing figures, like reference numerals designate identical or corresponding elements throughout the several figures.

Example embodiments may provide techniques, computer-based mediums, systems, and/or devices for displaying, in one or more of several different formats, data from an assay analyzer which is housed in a database/data space, and including filtering data based on a user's selections for the display of the filtered data.

FIG. 1 illustrates a simplified example of a block diagram of a process and/or system 150A for analyzing a biological sample or a micro-object with an enhanced user interface in one or more embodiments. Unless otherwise specifically disclaimed or described, some or all of the elements illustrated in FIG. 1 and described below apply with full and equal effects to any of the embodiments described herein, to the extent that these elements are relevant to any of the embodiments. In this simplified example, one or more analyses 104 (e.g., one or more assays analyses, one or more sequencing analyses, etc.) may be performed on a plurality of biological samples (e.g., a micro-object, a cell, a tissue, a protein, a gene, a virus, or an intracellular molecule such as DNA (deoxyribonucleic acid), RNA (ribonucleic acid), etc.) in a microfluidic apparatus with one or more corresponding workflows, pipelines, etc. 102. It shall be noted that unless otherwise specifically distinguished, the terms "biological sample," "micro-object," "cell," "tissue," "protein," "gene," "virus," and "intracellular molecule" may be used interchangeably throughout the entire disclosure. A sequencing analysis includes, for example, determining an order of a plurality of building blocks or nucleotide bases that make up a biological sample (e.g., a DNA molecule) to provide more detailed information (e.g., what genetic information is carried in a particular DNA, which stretches of DNA include genes, which stretches carry regulatory instructions, etc.) about the biological sample or one or more of the plurality of building blocks or bases therefor.

In some embodiments, an analysis of biological samples may include directing a first biological sample via a first guided path into a first structure-based or target-based region of interest in a first microfluidic device having a plurality of structure-based and/or target-based regions of interest and directing a second biological sample via a second guided path into a second structure-based or target-based region of interest in the first microfluidic device. In some of these embodiments, a single analysis apparatus may be used to performing analyses (e.g., assays, sequencing, etc.) on biological samples and computational analytics (e.g., computational biology, bioinformatics, or any other computational analyses, etc.) In some other embodiments, multiple systems may perform an analysis of biological samples. For example, a first system may perform one or more first analyses on first biological samples, a second system may perform one or more second analysis on the first or the second biological samples, one or more third systems or any of the first or the second system may perform the computational analytics. In some embodiments, the aforementioned one or more third systems may comprise, for example, a server, a laptop computer, a desktop computer, a terminal connected to a remote computer, and/or one or more virtual machines in a virtualization environment. In some embodiments, various software modules utilized herein may be located in a cloud-environment and provided as services that communicate with user or client computing nodes via one or more respective application programming interfaces (APIs) to invoke the execution of the services, to transmit input data for analyses, and/or to transmit output data from the services provisioned on the cloud environment.

In some embodiments, analysis results correlated with an analysis performed on the biological samples may be stored in an addressable space in the non-transitory computer accessible storage medium of the single analysis apparatus, wherein the result comprises one or more sequences of images of the biological substances captured during a time period. The term "analysis results" may also be referred to as "associated data" because the analysis results include various input and output data for an analysis of biological samples in a microfluidic device and are thus associated with the analysis. In some embodiments, analysis results (or associated data) may include any inputs and outputs for an analysis of biological samples in a microfluidic device. For example, associated data may include, without limitations, any inputs by user(s) for the analysis of biological samples, one or more settings and/or configurations of one or more software applications and/or one or more apparatuses utilized for the analysis, one or more parameters and one or more parameter values correlated with the biological samples, the apparatus(es), and/or the software application(s) involved in the analysis of the biological samples.

Associated data may also include intermediate and/or final output of the analysis in some embodiments. For example, associated data may include, without limitation, processed images, data from processed images, aggregated, correlated, and/or assessed data (e.g., cell count, sizes and/or shapes of cells, etc.), sequencing results, and/or metadata therefor. Associated data may include static data, dynamic data, or a combination of both static data and dynamic data. In some embodiments, dynamic data includes data that varies with time and/or data that may respond to a dynamic interaction (e.g., a user interacting with the data by manipulating a widget in a user interface, etc.) Associated data may be arranged and stored in a structured manner in a data structure such as a table, a database table, or any other suitable data structures in some embodiments. In addition or in the alternative, different portions of associated data may respectively correspond to the multiple regions of interest (e.g., structure-based and/or target-based region(s) of interest) and/or a plurality of chambers in a microfluidic device for which the associated data was acquired. For example, associated data may be stored in a structured manner in a microfluidic device data structure or a gallery structure described herein where different sub-structures (e.g., columns, rows, etc.) may respectively correspond to different regions of interest and/or different chambers in a microfluidic device.

The single analysis apparatus may then invoke various modules, functions, and/or functionalities described herein to perform the computational analytics. In some other embodiments, analyses (e.g., assays, sequencing, etc.) on biological samples and computational analytics (e.g., computational biology, bioinformatics, or any other computational analyses, etc.) may be separately performed on one or more corresponding apparatuses.

It shall be further noted that a "single analysis apparatus" comprises a system comprising a combination of hardware and software elements of one or more modules, one or more mechanisms, one or more devices, and/or one or more subsystems, etc. that is fully integrated within the system to perform one or more analyses, pre- and post-process intermediate and/or final analysis data, and present configurable analysis results in one or more user interfaces in a more efficient, effective manner to allow a user to manipulate and interact with the analysis results to gain insight into the massive intermediate and final analysis data and to facilitate the accomplishment of the objectives of these one or more analyses with various tools, modules, widgets, and functionalities described herein.

A microfluidic apparatus may include, for example, a microfluidic device, a nanofluidic device, a nanofluidic device, or a nanofluidic apparatus and is collectively reflected as a "microfluidic device" hereinafter. A microfluidic device (which may also be referred to as a laboratory-on-a-chip, a gene chip, a DNA chip, etc.) may include an instrument that manipulates (e.g., by using active and/or passive components and/or micro-components such as micropumps, microvalves, etc.) a very small amount of fluid (e.g., less than 1 mL within the circuits of the microfluidic device at any given time) or fluids, reagents, soluble fluorescent reporters, etc. for exhibiting localized measurable effects in a region of interest (e.g., a target-based ROI, or a structure-based ROI which may be at least a portion of a chamber or isolation chamber) in a microfluidic device configured to perform one or more miniaturized processes or tests (e.g., multiplexing, automation, high-throughput screening, analysis, assays, etc.) on one or more biological samples (including an array of biological sample in excess of 100, 500, 1,000, 5,000, 7,000, 9,000, 11,000 or more biological samples).

A workflow or a pipeline includes, for example, a sequence of serial and/or parallel steps, procedures, or transformations that may be performed on or for a plurality of biological samples and/or data therefor with one or more tools that are linked or chained together for qualitatively assessing or quantitatively measuring one or more characteristics (e.g., the presence, an amount, or a functional activity, etc.) of a target analyte (e.g., a biological sample, a drug, biochemical substance, etc.) A workflow or a pipeline may also include or involve one or more data manipulation operations or instructions therefor such as data retrieval/import, data filtering, cleaning-up, pruning, or normalization, etc., and/or data export in some embodiments.

One or more datasets or data structures 106 may be generated. These one or more datasets or data structures 106 may include any data that is captured during the course of or for an analysis 104 (e.g., at one or more timepoints or during one or more time periods). Some examples of such data include one or more base images 108 captured for one or more regions of interest in the microfluidic device. For example, a base image may capture an image of a plurality of chambers in the microfluidic device at a particular instant in time. Such data may further include intrinsic data 150 that pertains to a biological sample and is captured, sensed, or otherwise collected during the course of the analysis.

For example, such data may include any measurable or quantifiable characteristic of or for a biological sample such as affinity (e.g., affinity between a virus such as a Covid-19 virus and/or more antibodies), a degree of cell activation, a degree of cell secretion of a target small molecule, peptide, protein, signaling molecule, etc., a degree of response of a cell to a particular stimulus (e.g., introduction of a small molecule, etc.—such properties may be correlated with one or more target-based or structure-based properties of the region of interest including but not limited to: a size, major diameter, minor diameter, circularity, morphology, fluorescent labeling, etc. of a biological sample in some embodiments.

Such data may also include derivative or analytic data 152 derived or computed from other data correlated with a biological sample. For example, such derivative or analytic data 152 may include any computed characteristics such as any diameter(s) or geometric characteristics estimated from an image with algorithm(s), analytics, statistical measures, and/or custom created data (e.g., a computed or derived size, major diameter, minor diameter, circularity, etc., pen list(s), dataset(s), template(s), etc. custom created by applying one or more filters, clustering algorithms, ranking algorithms, etc.), or any other processed data. A computed or derived size, major diameter, minor diameter, circularity, etc. may be obtained from, for example, an image (e.g., a base image, an image of a region of interest, etc.) and may be expressed in, for example, physical dimensions such as microns or a number of unit areas of illumination (e.g., a pixel) on a display.

The intrinsic data 150 and derivative or analytic data 152 may be collectively referred to or stored as a dataset or simply data, unless otherwise specifically described. In some embodiments, the intrinsic data 150 and derivative and the analytic data 152 may respectively be stored in one or more separate data structures. In some other embodiments, at least a portion of the intrinsic data 150 and at least a portion of the derivative or analytic data 152 may be stored in a single data structure.

In some embodiments where the intrinsic data 150 and the derivative or analytic data 152 are separately stored in one or more respective data structures, the intrinsic data 150 and derivative or analytic data 152 may nevertheless be linked with each other. For example, any portion of the intrinsic data 150 and the corresponding portion of the derivative or analytic data 152 may be correlated with each other by using, for example, one or more identifiers or any other suitable links such as a microfluidic device identifier, a chamber identifier, or an aggregated identifier determined from a chamber identifier and a microfluidic device identifier, any of features, characteristics, properties, attributes, etc. correlated with a biological sample or to one or more structural features or characteristics of the microfluidic device or a portion thereof, or any other suitable links. Moreover, any of the aforementioned data structures may be indexed as described below to facilitate more efficient accesses and queries to such indexed data structure.

The data captured for the process may be stored in one or more data structures where each piece of data may be associated with a unique identifier. Due to the large number of regions of interest that may exhibit in a microfluidic device (e.g., from a single digit number of ROIs to tens of thousands of ROIs in a single microfluidic device), a unique identifier may pertain to at least one of the identification of the microfluidic device, a unique identifier for a region of interest (e.g., a specific chamber in the microfluidic device), a timestamp, a region identification, and/or any other suitable identification (e.g., barcode, etc.) that may serve to uniquely locate the base image or any region of interest captured in the base image. Data correlated with the base images may be stored in many data structures or different forms (e.g., structured data and/or non-structured data) 110 such as one or more tables, one or more databases, one or more relational database tables, or any other suitable forms or formats that correlate each piece of data captured in the dataset with a biological sample, a feature or characteristic of a biological sample, a portion of the analysis, and/or a portion of the workflow or pipeline in some embodiments. A dataset may be indexed with one or more indexing keys to facilitate efficient and expedient access, retrieval, or queries.

A dataset may be loaded into one or more modules 112 which may have read and/or write access to the dataset or a portion thereof. These one or more modules 112 may include, for example, one or more filter builder and application modules 114 that generate and apply one or more one-dimensional or multi-dimensional filters to the loaded dataset, one or more graphing modules 116 that generate or render various graphs, plots, etc. (e.g., the views 130), one or more analysis modules 118 that perform one or more analyses on or for the loaded dataset, one or more view modules 120 that generate one or more respective views (e.g., a gallery view, a chip timeline view, etc.), any other modules described herein, or any other suitable, required, or desired modules to facilitate the analysis of the plurality of biological samples. These one or more modules 112 may include, for example, a machine-learning based biological sample counting module 121 which may employ, for example, a convolutional neural network that automatically, programmatically determines the total count of biological samples in a region of interest. In some embodiments, any view (e.g., a gallery view, a chip timeline view, a bioinformatics pipeline view, a graph view, etc.) may be generated or rendered independently. In some of these embodiments, one or more views may be packaged as one or more respective objects in the context of object-oriented programming and inserted into another view.

In some embodiments, the one or more modules 112 may include one or more artificial intelligence (A.I.) modules 123 that include one or more models determined from supervised and/or unsupervised learning techniques with one or more training datasets and/or benchmark datasets. For example, a list of chambers, pens, or regions of interest may be identified by a user and incorporated into a training dataset or a benchmark dataset (e.g., as labeled training data) once the user has determined that the associated data for the list of chambers, pens, regions of interest etc. meet or exceeds one or more accuracy, performance, and/or production (e.g., tag, workflow, workflow task, biologically relevant, experimentally relevant) requirements. In addition or in the alternative, these one or more artificial intelligence modules 123 and/or the counting module 121 may perform various respective functionalities on associated data (e.g., images, or image sequences from workflow including but not limited to the portions of those images wherein the segments may include but are not limited to pens, region(s) of interest, chambers) and generate one or more metrics (e.g., a statistical measure such as a confidence level, an estimated error, etc.) which may be applied to select, sort, or otherwise identify a subset of associated data for use in compiling a training dataset or a benchmark dataset. In some instances, associated data may comprise greater than 10, 50, 100, 1000, 2000, 5000, 7000, 10000 or more individually characterized regions of interest, and the artificial intelligence module is configured to select a portion of the associated data using any of the methods disclosed herein or otherwise understood in the field for building the model. In some embodiments the one or more artificial intelligence modules 123 may identify segments of the associated data with metrics that exceed or fall below a certain threshold (e.g., a confidence level exceeding a first threshold, an estimated error below a second threshold, etc.) as a part of a training or benchmark dataset for training one or more models to improve the accuracy in their predictions of these one or more models. In further instances, a user is presented with the portion of associated data (e.g., the selected portion or an automatically generated portion) using one or more views (e.g., any one of the views disclosed herein or generated by a module disclosed herein) for presenting or otherwise visualizing the associated data such that the user may prepare a segment of the associated data or portion of the associated data based at least in part upon visual inspection, metrics or scores determined by a model, and/or applying automated steps, manual processes, or subsequent learning algorithms for the purpose of classification. Alternatively, or additionally the user may curate and prepare the segment or segments of the associated data into a benchmark dataset by combining it with other segments of associated data including but not limited to curated lists (e.g., lists compiled of pens, chambers, regions of interest etc.)

These one or more artificial intelligence modules 123 may determine or construct and/or improve one or more models with the training datasets and/or benchmark datasets by using techniques such as neural networks, convolutional neural networks, machine learning, and/or deep learning, etc. with assisted or unassisted learning.

These one or more trained or untrained models may be used to perform various predictions for new datasets. For example, these one or more models may perform functionalities such as, without limitation, image content recognition for a sequence of images correlated with an analysis, classification of associated data of an analysis, estimates of one or more characteristics of one or more biological samples or features of or regions of interest within images or images sequences obtained from an analysis of biological samples (e.g., number of pixels forming an area, microns (e.g., square microns or micron dimensions) of an area, background area, number of pixels of a background area, microns (e.g., square microns or micron dimensions) of a background area, centroid in microns (e.g., x-centroid, y-centroid, coordinates of a centroid, area of a centroid in square microns, etc.), centroid in pixels (e.g., x-centroid or y-centroid, coordinates of the centroid, area of centroid), circularity of a sample, diameter of a sample in microns, max brightness, median brightness, max background brightness, mean background brightness, target index (e.g., a unique identifier or label associated with a specific target), perimeter microns of a sample, or any combinations thereof, etc.), etc.

For example, an artificial intelligence module 123 may receive an image sequence captured for one or more regions of interest. The artificial intelligence module 123 may, for example, execute a convolutional neural network to recognize contents in the image sequence with the techniques described in, for example, FIGS. 10A-10K-2, FIGS. 11A-11-B-2, etc. Recognizing the contents of an image may be performed at multiple different resolutions for different purposes. In some embodiments, an artificial intelligence module 123 may first perform a lower-resolution content recognition on the image sequence to distinguish images showing one or more biological samples from images showing no biological images.

The artificial intelligence module 123 may classify the image sequence as two classes (e.g., a more-significant class corresponding to images showing biological sample(s) and a less-significant class showing no biological samples). For this classification of more- and less-significant classes, an artificial intelligence module 123 may employ a lower-resolution recognition process (e.g., a convolutional network having larger strides or filters such as 5×5, 7×7, 11×11, etc. filters) to conserve computational resources as the finer details in the contents of the image sequence may not be as important for this classification purpose. The artificial intelligence module 123 may further perform a higher-resolution content recognition process on the more-significant class to more precisely distinguish, for example, the boundaries of biological samples from the background so that the artificial intelligence module may more accurately capture shape of a biological sample. With the more accurately captured shape, the artificial intelligence module may estimate or compute, for example, the circularity of the biological sample and reference its knowledge base to determine whether the biological sample having the estimated circularity may be classified into a normal-sample class, an abnormal-sample class, a heathy-sample class, an unhealthy-sample class, a tumor class, etc. In these embodiments, the artificial intelligence module may thus classify a plurality of biological samples into multiple classes with computer vision and A.I. techniques described herein. It shall be noted that the counting module 121 and the one or more A.I. modules 123 may function independently of each other or in tandem with one another to facilitate the performance of their intended functionalities.

In some embodiments, a dataset may be generated concurrently with the performance of an analysis or an execution of a workflow or a pipeline. In these embodiments, various types of data (e.g., base images of one or more regions of interest, quantifiable metrics, properties, characteristics, attribute, and/or other desired or required information or data, etc.) may be acquired via one or more data acquisition tools (e.g., one or more cameras or image sensors for capturing images, one or more sensors for collecting sensory data, a computer bus or data bus for storing computational data, etc.) and store in one or more data structures.

In some embodiments, raw or processed data from the one or more data acquisition tools may be staged in an intermediate storage, and one or more data processing tools or modules may further be employed to process such data for persistent storage in one or more data structures. For example, various pieces of data from different data acquisition tools or modules may be correlated based at least in part upon, for example, an identifier of the microfluidic device, respective identifier of a plurality of chambers in the microfluidic device, and/or timestamps, etc.

The raw and/or processed data (e.g., 110, 150, and/or 152) may then be stored in one or more data structures in the forms of structured and/or non-structured data. In some embodiments, at least one of the one or more data structures may be indexed with one or more unique keys to facilitate more efficient accesses and queries to the at least one indexed data structure. For example, a chamber identifier or an aggregated identifier determined from the chamber identifier and the microfluidic device identifier, any of features, characteristics, properties, attributes, etc. correlated with a biological sample or to the structure of the microfluidic device or a portion thereof, or any other suitable keys may be used as a unique key to index the at least one data structure. For example, a data structure storing data correlated with biological samples in a plurality of chambers of a microfluidic device may be indexed by, for example, a key of total gene counts or a key of total cell counts. When a user accesses the data structure and applies a one-dimensional filter that limits the results to return chambers having no fewer than five (5) cells, the data structure may be more efficiently accessed in response to the filtering criterion to ignore any entries corresponding to chambers having fewer than a total of five cell. In this manner, any access to read from or write to an indexed data structure is more efficient.

In some other embodiments, the analysis (e.g., a biomedical, biochemical, or pharmaceutical analysis such as an assay, a sequencing, etc.) is performed ahead of time, and data correlated with the analysis is acquired during the performance of the analysis for a dataset before any additional analyses are performed on the data. That is, the analyses on biological samples are performed prior to any subsequent analyses of the data collected during the performance of the analyses. In these embodiments, the dataset may be loaded into various modules or tools described herein. Although the biomedical, biochemical, or pharmaceutical analyses of the biological samples are performed prior to additional computational analytics for the data of the biomedical, biochemical, or pharmaceutical analyses, any techniques such as arranging a vast amount of data into one or more data structures, indexing any of the one or more data structures, clustering, filtering, ranking, etc. described herein may be applied to the data of the biomedical, biochemical, or pharmaceutical analyses with full and equal effects.

One or more regions of interest 122 may be identified or determined. With these one or more regions of interest, specific data correlated with the one or more regions of interest may be extracted, derived, or otherwise automatically determined from the dataset. A region of interest 122 may be specified by a user (e.g., by clicking on a region of interest generation widget, which is not shown in FIG. 1, to select a desired or custom region as the region of interest) or automatically determined by various techniques described herein. For example, a user may specify or designate a chamber in a microfluidic device as a region of interest in some embodiments. The process or system 150A may automatically determine a region of interest based at least in part on one or more criteria. For example, the process or system 150A may consult a workflow or pipeline to identify that the analysis is concerning a cell culture and export process.

The process or system 150A may further reference the workflow or pipeline to determine that the plurality of biological samples in the microfluidic device are at the stage of cell culture for a period of time during which the process or system may determine that a region of interest includes a chamber and further automatically crop an individual image portion 126 of the chamber at one or more timepoints during the period time. During a subsequent time period, the process or system 150A may determine that an export process is to begin for another period of time. During this another period of time, the process or system 150A may automatically determine that a region of interest is a chamber plus an interface between the chamber and a neighboring flow channel in the microfluidic device. The process or system 150A may then automatically extract (e.g., by cropping) an individual image portion 126 showing the chamber and the interface from a base image including the individual image portion 126 based at least in part upon, for example, an identification of the chamber, and automatic determination of the interface portion, etc.

During another subsequent time period, the process or system 150A may determine that the export is about to end or has ended and may then automatically determine a region of interest includes a portion of the flow channel correlated with the chamber from which cells are exported. The process or system 150A may then automatically extract an individual image portion 126 showing the portion of the flow channel from the base image. With the individual ROI images 126 from a repository 124, the process or system 150A may further identify, extract, or retrieve pertinent data 128 of one or more features, attributes, characteristics, etc. correlated with a region of interest image 126 and correlate a region of interest image 126 with such pertinent data 128 with using, for example, a symbolic link, a pointer, or any other suitable link.

In some embodiments, multiple regions of interest may be determined from one or more base images 108 and the data structure(s) 110 correlated with the one or more base images to generate multiple region-of-interest (ROI) images 126 and pertinent data 128. A region of interest may be target-based or structure-based based at least in part upon, for example, one or more features that are accessed (e.g., quantitated, monitored, etc.) In some embodiments where a feature that is accessed pertains to a biological sample (e.g., a specific biological sample, a specific type of biological samples, a property/attribute/characteristic correlated with a biological sample or a portion thereof, etc.), a region of interest so determined may be termed as a target-based region of interest. On the other hand, in some embodiments where a feature that is accessed pertains to a structural characteristic (e.g., a characteristic correlated with a chamber, or any structural feature of a microfluidic device, etc.), a region of interest so determined may be termed as a structure-based region of interest. Therefore, these multiple ROI images 126 may include one or more target-based ROI images, one or more structure-based ROI images, or one or more target-based and one or more structure-based ROI images.

These region of interest images 126 and pertinent data 128 may be further provided to one or more modules in the set of modules 112 for further processing. For example, the ROI images 126 and pertinent data 128 may be provided to a filter builder and application module 114 which may apply one or more one-dimensional or multi-dimensional filters to at least a portion of the ROI images 126 and/or the pertinent data 128 to filter out data that does not satisfy the one or more filters or to maintain data that satisfies the one or more filters. As another example, the ROI images 126 and pertinent data 128 may be provided to a dimensionality reduction module (not shown) that performs, for example, a principal component analysis (PCA) on at least a portion of the ROI images 126 and/or pertinent data 128 to reduce the dimensionality of such data. As another example, the ROI images 126 and pertinent data 128 may be provided to a clustering module (not shown) to cluster, for example, the plurality of biological samples based at least in part upon one or more clustering criteria. As another example, the ROI images 126 and pertinent data 128 may be provided to a view module 120 that generates one or more views 130 such as a gallery view, a timeline view, or any other view(s) described herein to arrange the ROI images 126 and pertinent data 128 in such a way to facilitate expedient and efficient access and analyses of the data correlated with the plurality of biological samples. Similarly, the ROI images 126 and pertinent data 128 may be provided to a graphing module 116 that plots the data or a portion thereof in one or more graphs or plots.

In some embodiments, any objects described herein may be devised as an interactive object that responds to a user's interaction. Such objects may include, for example, a widget (a selection widget, an interactive widget, a sliding adjustment widget, a gallery detail widget, a processing widget, a writing widget, an identifier widget, a delete widget, an interactive folder widget, a configuration slider widget, a region of interest generation widget, a sequencing view widget, a multi-directional placement widget, etc.), an image, a module (e.g., a filter builder or filter generation module, a list generation module, etc.), a block of representations in the user interface (e.g., a block of data), an icon, a command, etc. For example, such an object may be coded with an object-oriented programming language such as Java, Python, or C++, etc. that receives a user input via a user input device, parses the user input, invokes one or more classes and/or functions coded therein or elsewhere, and generates an intermediate output (e.g., awaiting further input from a user) or a final output in response to the user input.

Figure 3B:
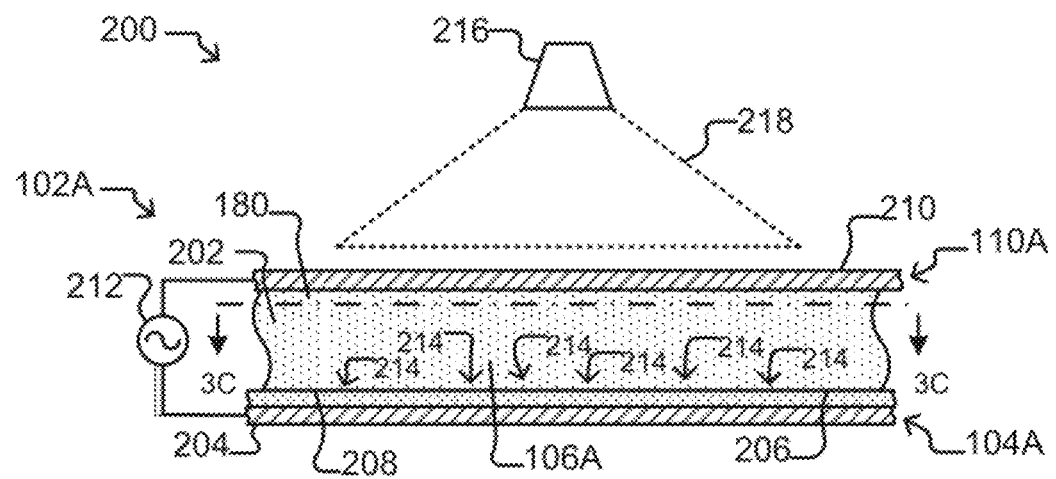
FIGS. 3A-3C illustrates example microfluidic device that may be used in one or more analyses described herein for a plurality of biological samples in one or more embodiments.
Figure 3C:
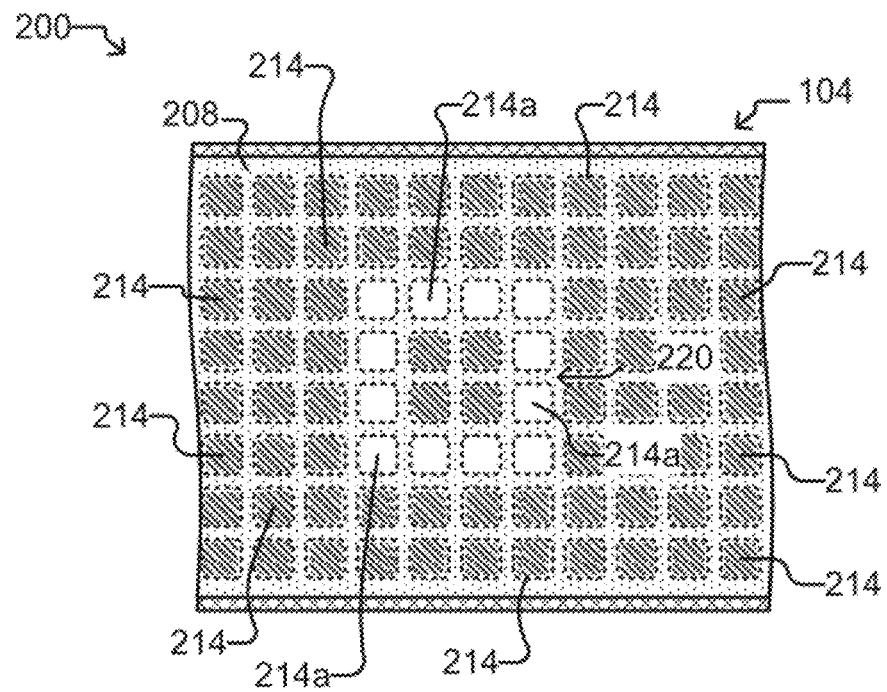
Figure 3F:
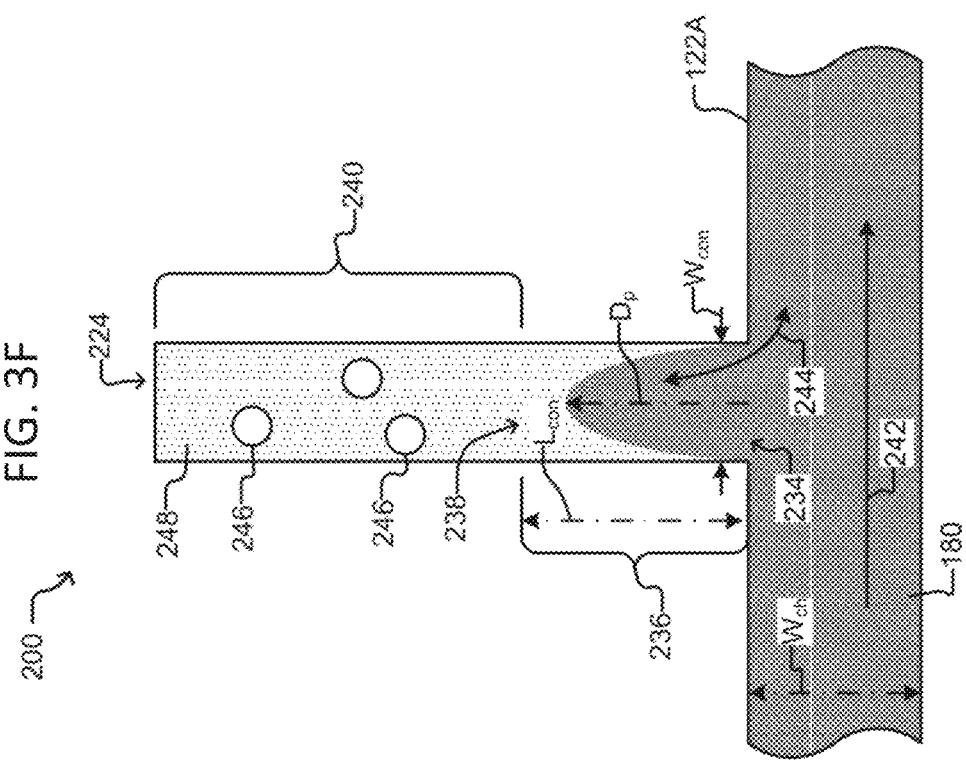
FIGS. 3D-3J illustrate example structural features of a micro-fluidic device that may be used to characterize regions of interest.
Figure 3G:
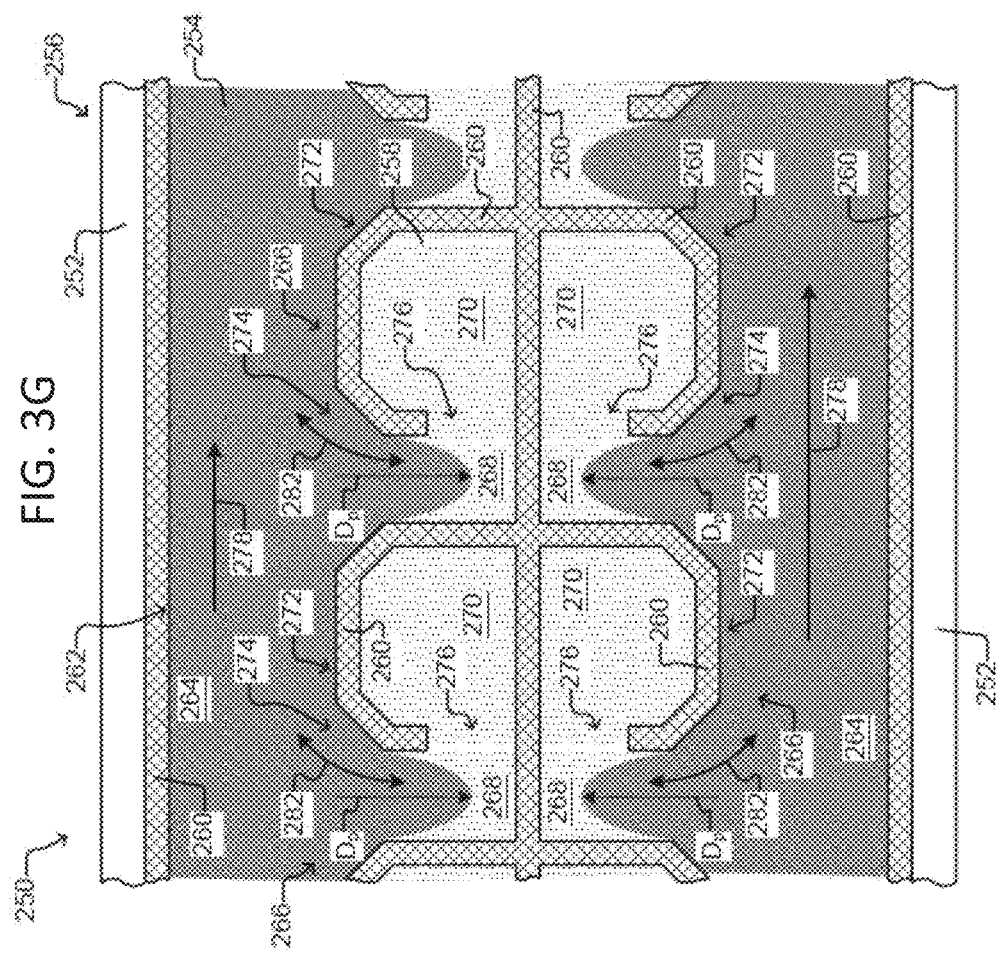
Figures 3H, 3I:
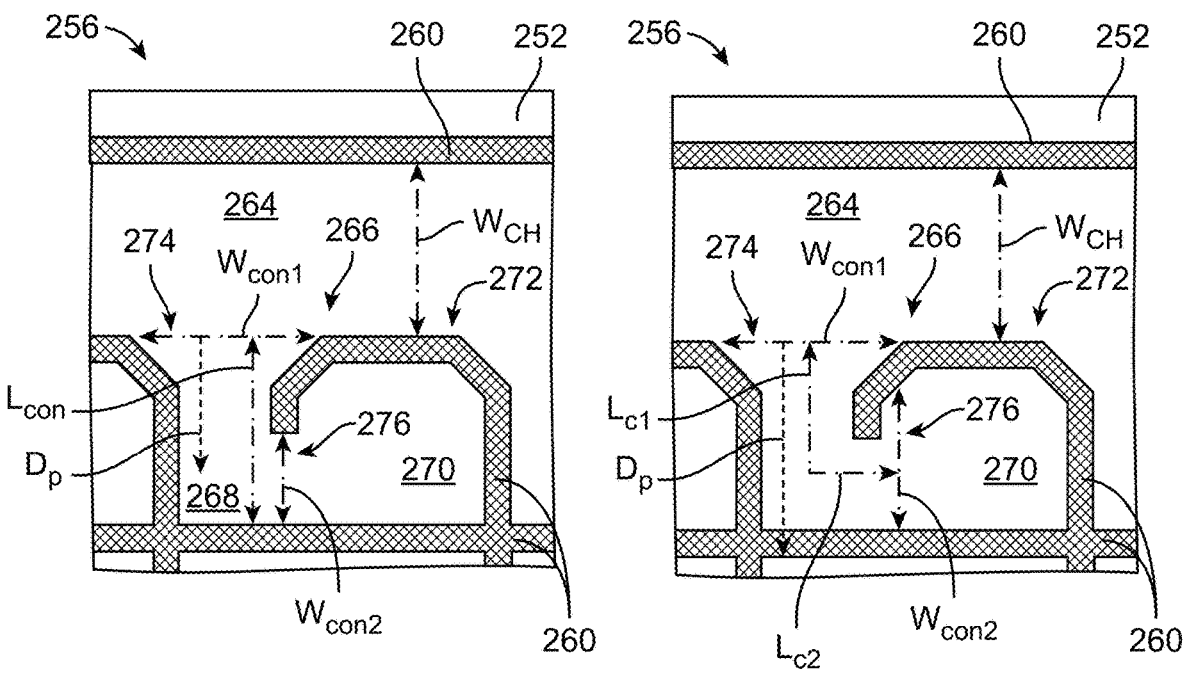
Figure 3J:
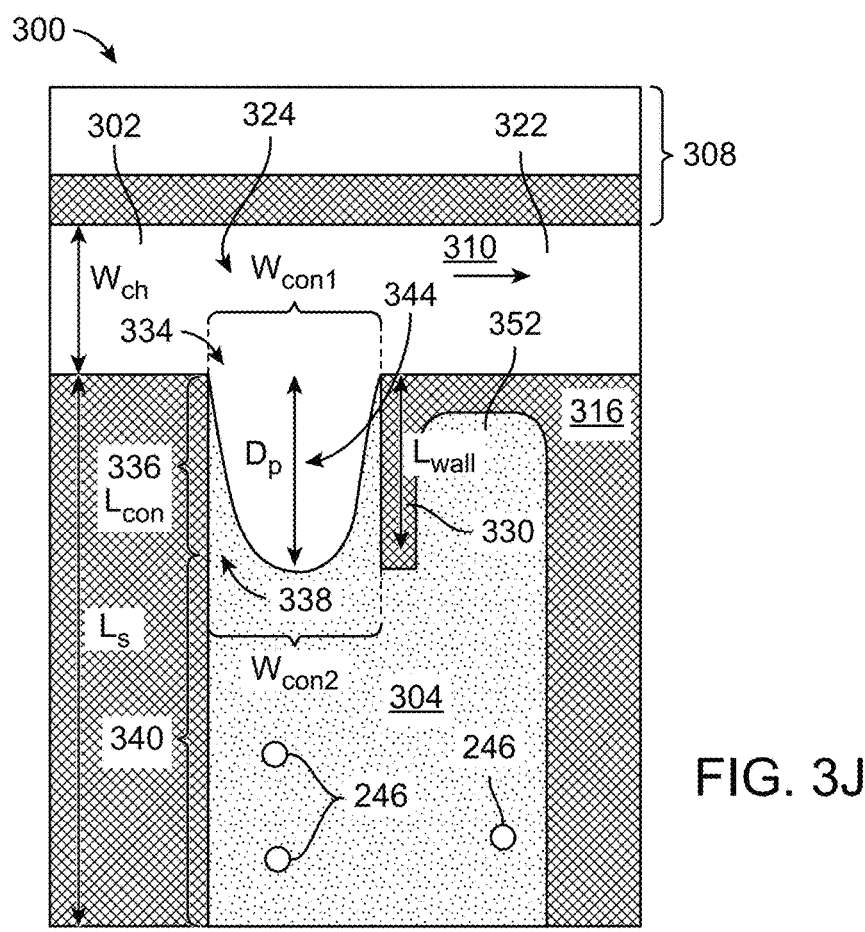
Figure 3K:
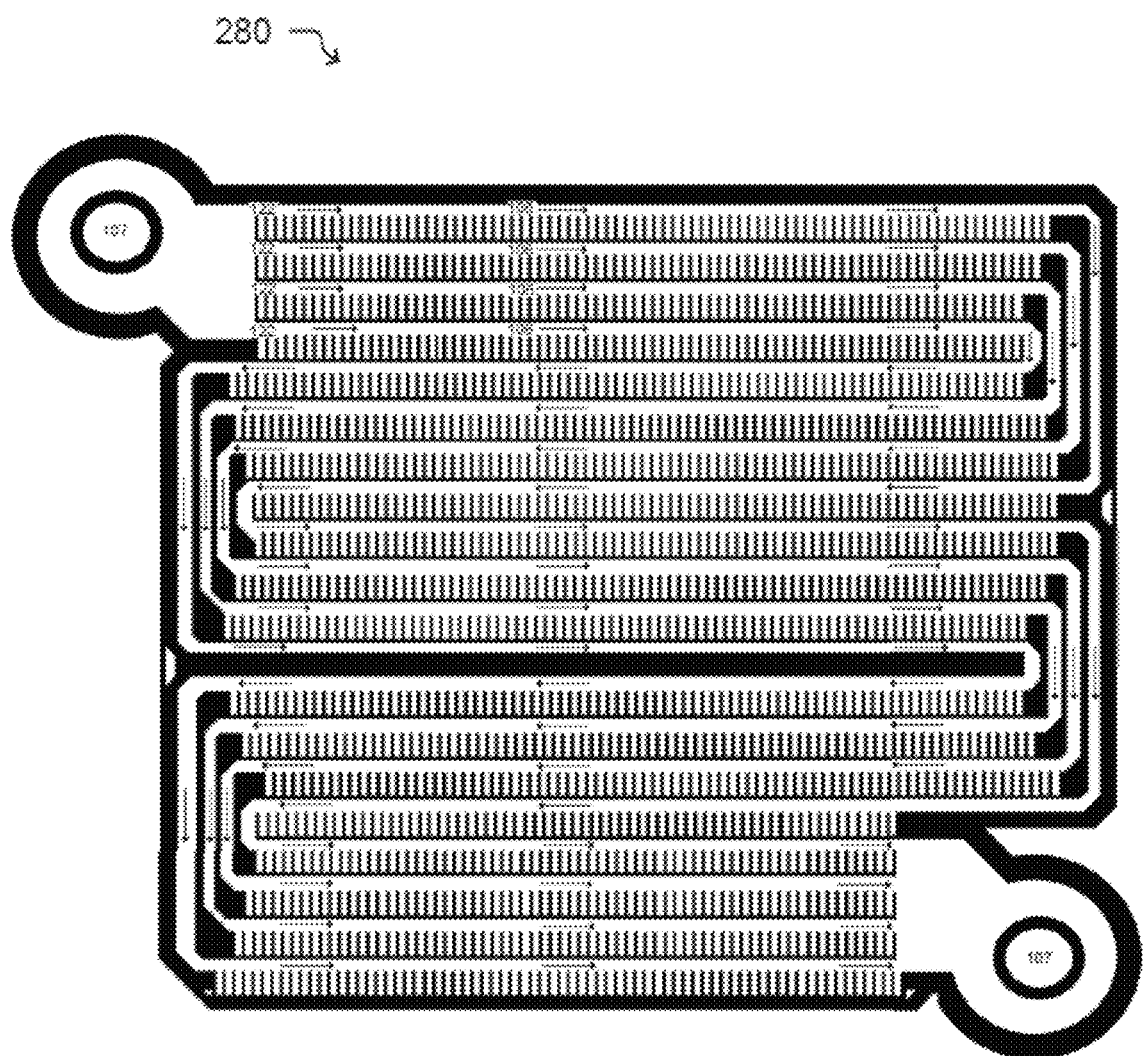
FIG. 3K illustrates a microfluidic device according to an embodiment of the disclosure.
Figure 3L:
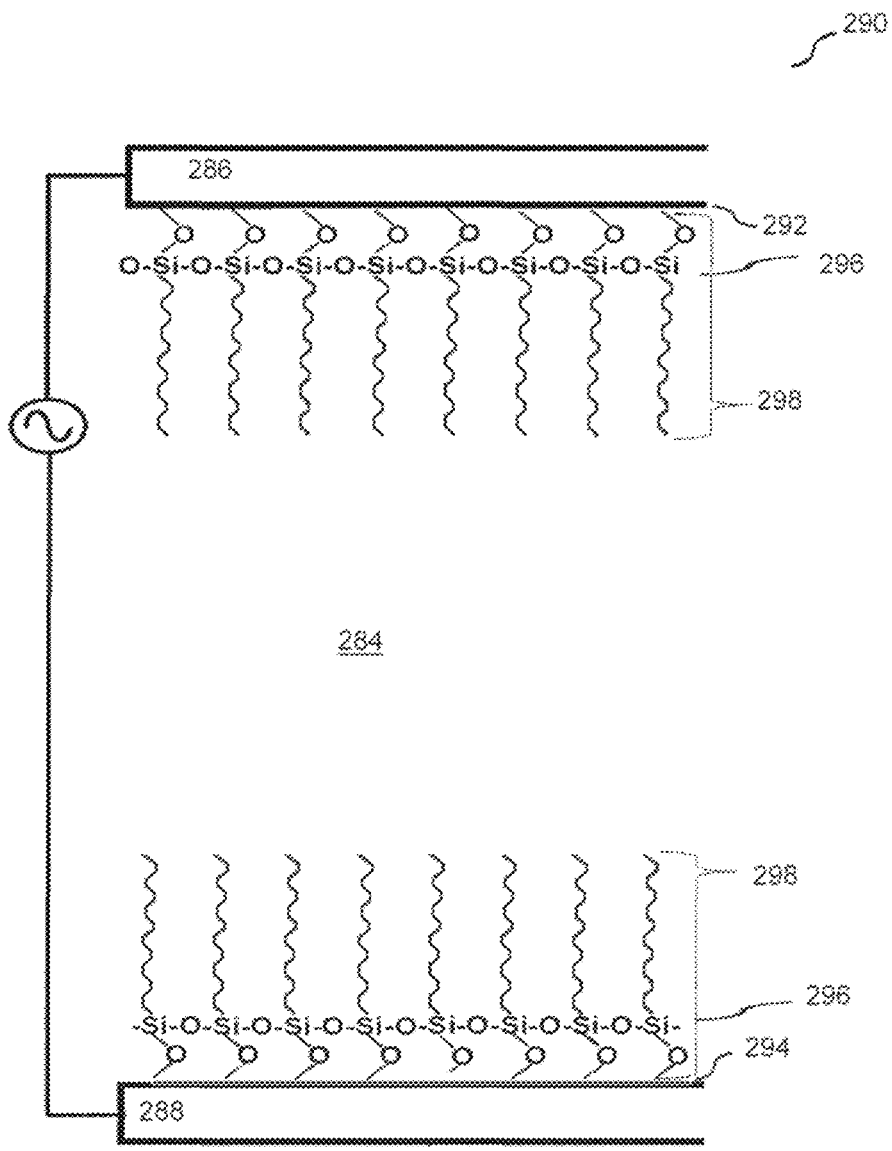
FIG. 3L illustrates a coated surface of the microfluidic device according to an embodiment of the disclosure.
Figure 3M:
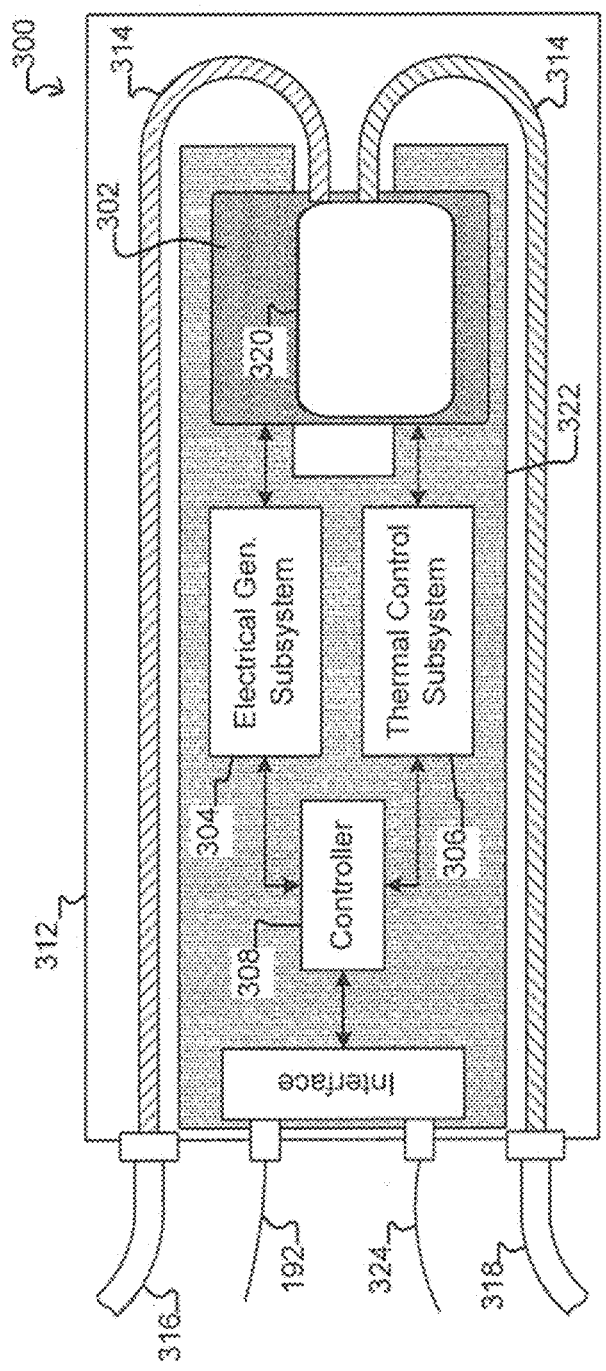
FIG. 3M illustrates a specific example of a system for use with a microfluidic device and associated control equipment according to some embodiments of the disclosure.
Figure 3N:
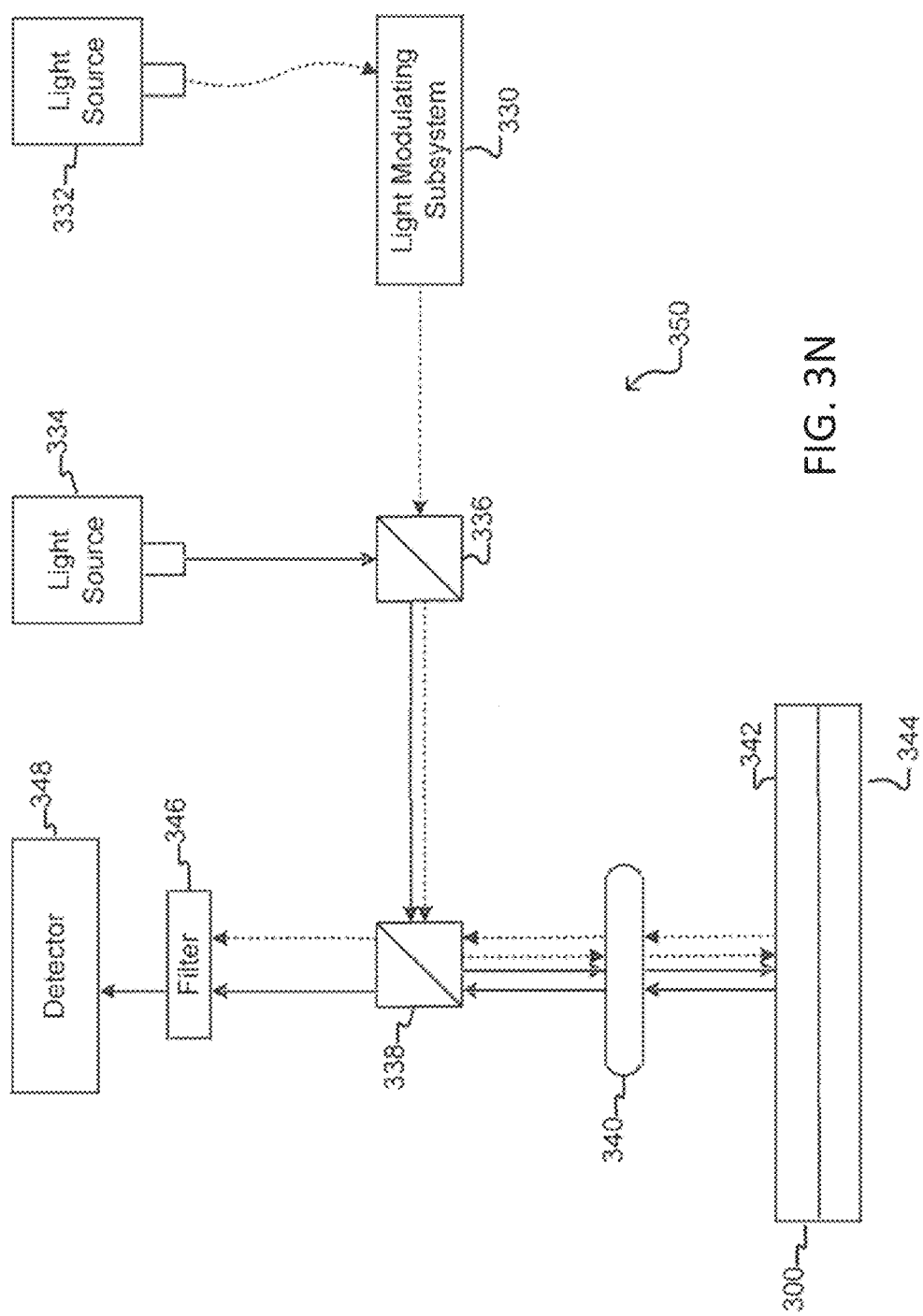
FIG. 3N illustrates an imaging device according to some embodiments of the disclosure.
Figure 3O:
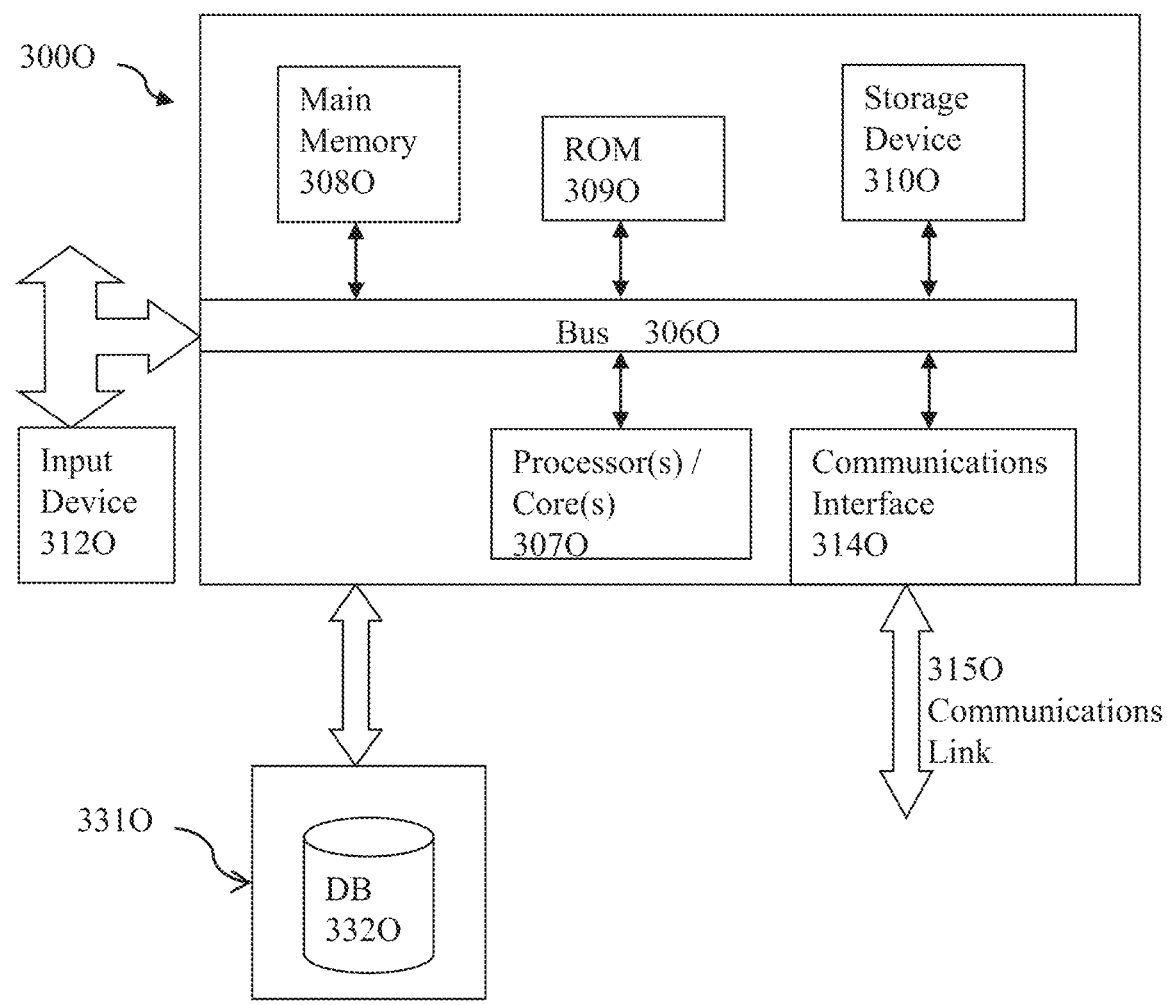
FIG. 3O illustrates a computerized system on which various processes described herein for performing an assay analysis for biological samples may be implemented in one or more embodiments.

FIG. 3O illustrates a computerized system on which various processes described herein for performing an assay analysis for biological samples may be implemented in one or more embodiments. Computer system 300O includes a bus 306O or other communication module for communicating information, which interconnects subsystems and devices, such as processor 307O, system memory 308O (e.g., RAM), static storage device 309O (e.g., ROM), disk drive 310O (e.g., magnetic or optical), communication interface 314O (e.g., modem or Ethernet card), display (e.g., CRT or LCD), input device 312O (e.g., keyboard), and cursor control (not shown).

The illustrative computing system 300O may include an Internet-based computing platform providing a shared pool of configurable computer processing resources (e.g., computer networks, servers, storage, applications, services, etc.) and data to other computers and devices in a ubiquitous, on-demand basis via the Internet in some embodiments. For example, the computing system 300O may include or may be a part of a cloud computing platform (e.g., a public cloud, a hybrid cloud, etc.) where computer system resources (e.g., storage resources, computing resource, etc.) are provided on an on-demand basis, without direct, active management by the users in some embodiments.

According to one embodiment, computer system 300O performs specific operations by one or more processor or processor cores 307O executing one or more sequences of one or more instructions included in system memory 308O. Such instructions may be read into system memory 308O from another computer readable/usable storage medium, such as static storage device 309O or disk drive 310O. In alternative embodiments, hard-wired circuitry may be used in place of or in combination with software instructions to implement the invention. Thus, embodiments of the invention are not limited to any specific combination of hardware circuitry and/or software. In one embodiment, the term "logic" shall mean any combination of software or hardware that is used to implement all or part of the invention.

Various actions or processes as described in the preceding paragraphs may be performed by using one or more processors, one or more processor cores, or combination thereof 307O, where the one or more processors, one or more processor cores, or combination thereof executes one or more threads. For example, the acts of determination, extraction, simulating, annotating, analyzing, optimizing, and/or identifying, etc. descried herein may be performed by one or more processors, one or more processor cores, or combination thereof.

The term "computer readable storage medium" or "computer usable storage medium" as used herein refers to any non-transitory medium that participates in providing instructions to processor 307O for execution. Such a medium may take many forms, including but not limited to, non-volatile media and volatile media. Non-volatile media includes, for example, optical or magnetic disks, such as disk drive 310O.

Volatile media includes dynamic memory, such as system memory 308O. Common forms of computer readable storage media includes, for example, electromechanical disk drives (such as a floppy disk, a flexible disk, or a hard disk), a flash-based, RAM-based (such as SRAM, DRAM, SDRAM, DDR, MRAM, etc.), or any other solid-state drives (SSD), magnetic tape, any other magnetic or magneto-optical medium, CD-ROM, any other optical medium, any other physical medium with patterns of holes, RAM, PROM, EPROM, FLASH-EPROM, any other memory chip or cartridge, or any other medium from which a computer may read.

In one embodiment, execution of the sequences of instructions to practice the invention is performed by a single computer system 300O. According to other embodiments of the invention, two or more computer systems 300O coupled by communication link 315O (e.g., LAN, PTSN, or wireless network) may perform the sequence of instructions required to practice the invention in coordination with one another.

Computer system 300O may transmit and receive messages, data, and instructions, including program (e.g., application code) through communication link 315O and communication interface 314O. Received program code may be executed by processor 307O as it is received, and/or stored in disk drive 310O, or other non-volatile storage for later execution. In an embodiment, the computer system 300O operates in conjunction with a data storage system 331O, e.g., a data storage system 331O that includes a database 332O that is readily accessible by the computer system 300O. The computer system 300O communicates with the data storage system 331O through a data interface (not shown). A data interface, which is coupled to the bus 306O (e.g., memory bus, system bus, data bus, etc.), transmits and receives electrical, electromagnetic or optical signals that include data streams representing various types of signal information, e.g., instructions, messages and data. In embodiments of the invention, the functions of the data interface may be performed by the communication interface 314O.

In an example system, a computing system 300O may be any computer device and/or system, such as a desktop computer, server, workstation, laptop, handheld computer, smart watch, or other form of computing or telecommunications device that is capable of communication with another device, system, or both, and that has sufficient processor power and/or memory to perform the operations described herein.

The computing system 300O may be running substantially any operating system such as a version of the Microsoft™ Windows™ operating systems, Linux operating systems (including various distros), Unix operating system, MacOS™ operating system, and the like. Implementations of computing system 300O may further operate a real-time operating system, an embedded operating system, a proprietary operating system, an open-source operating system, an operating system for mobile computing devices, and/or another type of operating system capable of running on computing system 300O and/or performing operations described herein.

Computing system 300O includes, or in general is in communication with, memory, on which a set of executable logical expressions, e.g., "software", according to at least one embodiment may be stored, processor(s) for executing software stored in the memory, and other programs for controlling system hardware.

The memory may include, among other things, a computer system memory or random-access memory (RAM), such as dynamic random-access memory (DRAM), static random-access memory (SRAM), extended data out random-access memory (EDO RAM), Magnetoresistive Random Access Memory (MRAM), and the like. A user of the system may interact with the computing system 300O through an input device, e.g., a keyboard, a pointing device, and/or a visual display device such as a computer monitor, which may include a graphical user interface (GUI). The GUI enables the user to interact with the systems described herein through the computing system 300O. The user may send an input to instruct the system using the GUI, which may in turn also display the results of the user input. The computing device 300O may also include a storage device including assay data, that is, data that has been generated from an assay, which may include both image and alphanumeric data, which will be described in greater detail below.

The computing system 300O may further include, or be in electronic communication with in general, a storage device, such as a hard-drive, compact disc-read-only memory (CD-ROM), or other computer readable medium, for storing an operating system and other related software, and for storing the display environment engine described herein. Additionally, the computing system 300O may further include one or more network interface cards, and other commonly implemented subcomponents, such as a hardware accelerator to increase a processing rate of the computing system 300O.

Figure 2A:
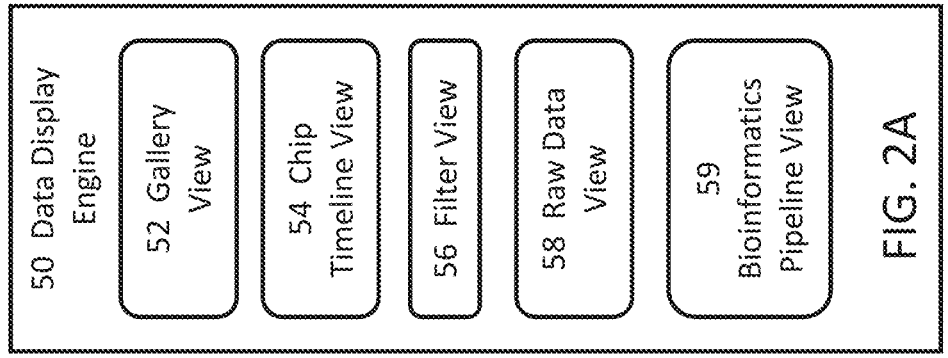
FIG. 2A illustrates an example assay data display engine in one or more embodiments.
Figure 2B:
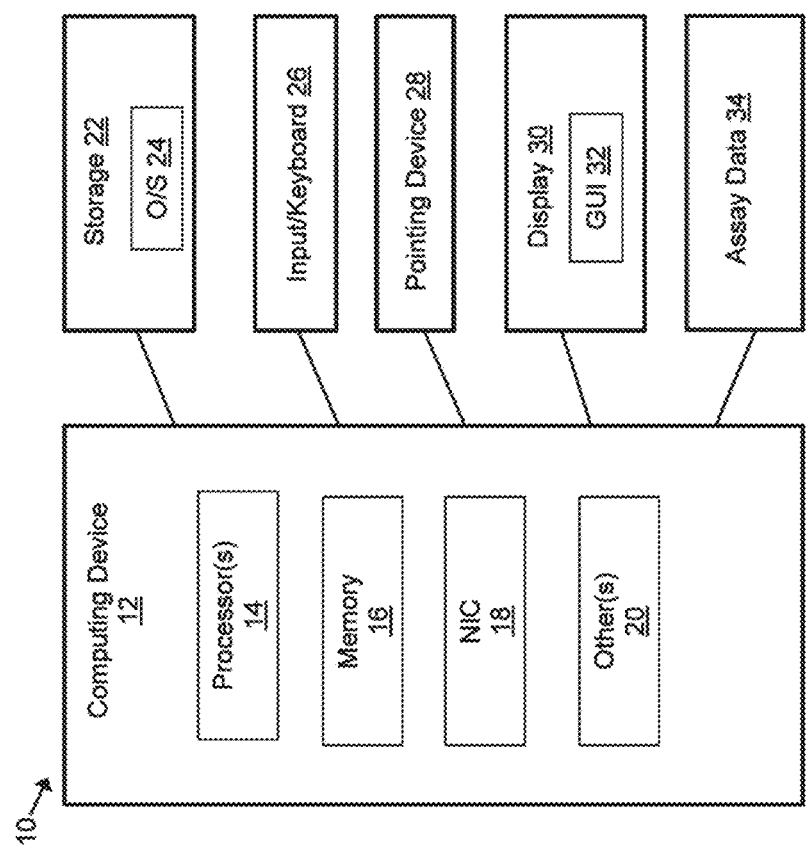
FIG. 2B illustrates an example computing node on which example computing system on which various computational tasks described herein may be implemented in one or more embodiments.

In general terms, example embodiments of a data display engine, see e.g., FIG. 2A, enables a user, e.g., a research biologist, to filter, sort, and display data from a large dataset 34, including but not limited to that described elsewhere herein. FIG. 2A illustrates an example data display engine 50 that may be part of a computing node illustrated in FIG. 2B that illustrates an example computing system 10 having a computing device 12 on which various computational tasks described herein may be implemented. The computing device 12 may include one or more processors 14, a memory 16, a network interface card 18, or other components or devices 20. The computing device executing on an operating system 24 may be operatively connected to a storage 22, an input device 26, a pointing device 28, a display 30 having a graphical user interface 32, etc. to process assay data 34. The engine 50 displays data from the assay dataset/dataspace 34 in one or more views: a gallery view 52; a chip timeline view 54; a filter view 56; a raw data view 58; and a bioinformatics pipeline view 59. One or more of these modules (e.g., 52, 54, 56, 58, and/or 59) in the data display engine 50 not only displays data or information but also perform one or more analyses either alone or in conjunction with one or more other modules (e.g., one or more modules in 112 of FIG. 1).

Referring back to FIG. 3O, a data display engine 50 may enable the user to determine the best chambers, and more specifically the best biological cells, in one or more microfluidic devices for their research, find chambers (or biological cells) that match one or more particular criteria. The data display engine 50 may display a visual history of the chambers of interest, and enable easy visualization, via a GUI, of multiple images of a single chamber over any time period of interest before, during, and after an assay is performed on micro-objects in that chamber. The data display engine 50 may enable the user to rank and/or sort chambers, and/or filter chambers, based on data associated with chambers, including data associated with micro-objects (or biological cells) included within the chambers. The data display engine 50 may enable the user to match chamber images to alphanumeric data generated during an assay analysis, and to display single chamber images from full images of the microfluidic device(s), images from multiple timepoints, and/or slices of chamber images which may optionally include area outside the chamber well, which for some assays may be important, as well as chamber data from a database, e.g., in a standardized format (e.g., CSV or "comma separated values").

FIGS. 3A-3C illustrate an example microfluidic device. Unless otherwise specifically disclaimed or described, some or all of the elements illustrated in FIGS. 3A-3C and described below apply with full and equal effects to any of the embodiments described herein, to the extent that these elements are relevant to any of the embodiments.

Each of the reference identifiers or IDs (e.g., 404D in FIG. 4D) corresponds to a microfluidic device, with the chip timeline depicting operations performed on the microfluidic device over time. Regions of interest from the microfluidic device are determined based on structural-based or target-based features of the microfluidic device, based on features that are assessed (e.g., quantitated, monitored, etc.) over the time course of the chip timeline. Images derived from the microfluidic device may be used to compile image sequences for regions of interest within the microfluidic device. Additionally, the chip timeline view is configured to represent one or more steps or operations performed on the microfluidic device over time. The microfluidic circuit 120A is illustrated as comprising a microfluidic channel 122A and chambers 124A, 126A, 128A, 130A.

In some embodiments, each chamber comprises an opening to channel 122A, but otherwise is enclosed such that the chambers may substantially isolate micro-objects inside the chamber from fluidic medium 180 and/or micro-objects in the flow path 106A of channel 122A or in other chambers. The walls of the chamber extend from the inner surface 109 of the base to the inside surface of the cover 110A to provide enclosure. The opening of the chamber to the microfluidic channel 122A is oriented at an angle to the flow 106A of fluidic medium 180 such that flow 106A is not directed into the chambers. The flow may be tangential or orthogonal to the plane of the opening of the chamber. In some instances, chambers 124A, 126A, 128A, 130A are configured to physically corral one or more micro-objects within the microfluidic circuit 120A. Chambers in accordance with the present disclosure may comprise various shapes, surfaces and features that are optimized for use with DEP (dielectrophoresis), OET (optoelectronic tweezers), OEW (optoelectric wetting), fluid flow, and/or gravitational forces, as will be discussed and shown in detail below.

The chip timeline view may record and depict operations performed on a microfluidic circuit 120A, with images taken at various timepoints or throughout the chip timeline time course. Each microfluidic circuit may comprise any number of microfluidic chambers with features or characteristics that are distinguishable in the images taken at various time points throughout the chip timeline. Although five chambers are shown in FIG. 3A, microfluidic circuit 120A may have fewer or more chambers. As shown, microfluidic chambers 124A, 126A, 128A, and 130A of microfluidic circuit 120A each comprise differing features and shapes which may provide one or more benefits useful for maintaining, isolating, assaying or culturing micro-objects, including biological cells and other micro-objects such as beads. In some embodiments, the microfluidic circuit 120A comprises a plurality of identical microfluidic chambers.

In the embodiment illustrated in FIG. 3A, the structure-based characteristic of the microfluidic device comprises a single channel 122A and flow path 106A as shown. However, other embodiments may include structure-based characteristics of multiple channels 122A, each configured to comprise a structure-based characteristic of a flow path 106A. The microfluidic circuit 120A further comprises a structure-based characteristic of an inlet valve or port 107 in fluid communication with the flow path 106A and fluidic medium 180, whereby fluidic medium 180 may access channel 122A via the inlet port 107 and may be measurable or monitorable as features or characteristics of images taken of the microfluidic device over time. In some instances, the flow path 106A comprises a single path. In some instances, the single path is arranged in, for example, a zigzag pattern whereby the flow path 106A travels across the microfluidic device 100A two or more times in alternating directions.

In some instances, microfluidic circuit 120A comprises a structure-based characteristic comprising a plurality of parallel channels 122A and flow paths 106A, wherein the fluidic medium 180 within each flow path 106A flows in the same direction. In some instances, the fluidic medium within each flow path 106A flows in at least one of a forward or reverse direction, with the direction measurable in images taken of the microfluidic device. In some instances, a plurality of chambers is configured (e.g., relative to a channel 122A) such that the chambers may be loaded with target micro-objects in parallel, with such loading measurable as features monitored over the time course of a chip timeline and in corresponding image sequences.

In some embodiments, microfluidic circuit 120A further comprises one or more micro-object traps 132A, with the micro-object traps comprising a measurable feature or characteristic of the microfluidic device. The traps 132A may be generally formed in a wall forming the boundary of a channel 122A, and may be positioned opposite an opening of one or more of the microfluidic chambers 124A, 126A, 128A, 130A. In some embodiments, the traps 132A are configured to receive or capture a single micro-object from the flow path 106A, with such operations recorded as part of an operation represented in the chip timeline and recorded in corresponding image sequences obtained for the operation performed in the chip timeline. In some embodiments, the traps 132A are configured to receive or capture a plurality of micro-objects from the flow path 106A, with such operations recorded as part of an operation represented in the chip timeline and recorded in corresponding image sequences obtained for the operation performed in the chip timeline.

In some instances, the traps 132A comprise a volume approximately equal to the volume of a single target micro-object. The traps 132A may further comprise an opening which is configured to assist the flow of targeted micro-objects into the traps 132A, with such the flow of targeted micro-objects recorded as part of an operation represented in the chip timeline and recorded in corresponding image sequences obtained for the operation performed in the chip timeline. In some instances, the traps 132A comprise an opening having a height and width that is approximately equal to the dimensions of a single target micro-object, whereby larger micro-objects are prevented from entering into the micro-object trap, with the opening operating as a structure-based feature of the micro-fluidic device and the operation of selective filtering of micro-object based on size indicated as part of an operation represented in the chip timeline and recorded in corresponding image sequences obtained for the operation performed in the chip timeline.

The traps 132A may further comprise other features configured to assist in retention of targeted micro-objects within the trap 132A. In some instances, the trap 132A is aligned with and situated on the opposite side of a channel 122A relative to the opening of a microfluidic chamber, such that upon tilting, via a tilting device 190, the microfluidic device 100 about an axis parallel to the microfluidic channel 122A, the trapped micro-object exits the trap 132A at a trajectory that causes the micro-object to fall into the opening of the chamber, with such operations represented as part of an operation represented in the chip timeline and recorded in corresponding image sequences obtained for the operation performed in the chip timeline. In some instances, the trap 132A comprises a side passage 134A that is smaller than the target micro-object in order to facilitate flow through the trap 132A and thereby increase the likelihood of capturing a micro-object in the trap 132A, with such operations represented as part of an operation represented in the chip timeline and recorded in corresponding image sequences obtained for the operation performed in the chip timeline.

In some embodiments, images taken during the chip timeline may represent or present dielectrophoretic (DEP) forces applied across the fluidic medium 180 (e.g., in the flow path and/or in the chambers) via one or more electrodes (not shown) to manipulate, transport, separate and sort micro-objects located therein, with such operations recorded as a step or series of steps in the chip timeline. For example, in some embodiments, DEP forces may be applied to one or more portions of microfluidic circuit 120A in order to transfer a single micro-object from the flow path 106A into a desired microfluidic chamber. In some embodiments, DEP forces may be used to prevent a micro-object within a chamber (e.g., chamber 124A, 126A, 128A, or 130A) from being displaced therefrom. Further, in some embodiments, DEP forces may be used to selectively remove a micro-object from a chamber that was previously collected in accordance with the embodiments of the current disclosure. In some embodiments, the DEP forces comprise optoelectronic tweezer (OET) forces.

One example of a microfluidic device 200 comprising a DEP configuration is illustrated in FIGS. 3B-3C. While for purposes of simplicity FIGS. 3B-3C show a side cross-sectional view and a top cross-sectional view, respectively, of a portion of an enclosure 102A of the microfluidic device 200 having a region/chamber 202, it should be understood that the region/chamber 202 may be part of a fluidic circuit element having a more detailed structure, such as a growth chamber, a chamber, a flow region, or a flow channel. Furthermore, the microfluidic device 200 may include other fluidic circuit elements, with such elements representing structure-based features. For example, the microfluidic device 200 may include a plurality of growth chambers or chambers and/or one or more flow regions or flow channels, such as those described herein with respect to microfluidic device 100A.

A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150A including control and monitoring equipment 152A, described above, may be used with microfluidic device 200, including one or more of the media module 160 (including media source 178), motive module 162, imaging module 164, tilting module 166, and other modules 168. Control and monitoring equipment 152A may include a master controller 154, which may further comprise a control module 156 and a digital memory 158. The monitoring equipment 152A may further include a display device 170 and an input/output device 172.

As seen in FIG. 3B, the microfluidic device 200 includes a support structure 104A having a bottom electrode 204 and an electrode activation substrate 206 overlying the bottom electrode 204, and a cover 110A having a top electrode 210, with the top electrode 210 spaced apart from the bottom electrode 204. The shapes of these electrodes may be recorded in image sequences taken of the microfluidic device and one or more characteristics of these electrodes may be utilized in determination of structure-based regions of interest. The top electrode 210 and the electrode activation substrate 206 in this example define opposing surfaces of the region/chamber 202. A medium 180 included in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 may be, for example, an alternating current (AC) power source.

In certain embodiments, the microfluidic device 200 illustrated in FIGS. 3B-3C may have an optically-actuated DEP configuration, with the optically-actuated DEP configuration producing features or characteristics represented in the chip timeline view and in images taken during the time course of the chip time line (e.g., image sequences taken of one or more regions of interest). Additionally, activation of DEP for the purpose of loading or unloading micro-objects may be represented in operations illustrated representation 1304B of operations in the chip timeline e.g., blocks in the chip timeline. Accordingly, changing patterns of light 218 from the light source 216, which may be controlled by the motive module 162, may selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.")

As illustrated in FIG. 3B, a light pattern 218 directed onto the inner surface 208 of the electrode activation substrate 206 may illuminate select DEP electrode regions 214a (shown in white) in a pattern, such as a square. Illumination may be captured in images or image sequences including base images, and image sequences or images of regions of interest. The non-illuminated DEP electrode regions 214 (cross-hatched) are hereinafter referred to as "dark" DEP electrode regions 214. The relative electrical impedance through the DEP electrode activation substrate 206 (e.g., from the bottom electrode 204 up to the inner surface 208 of the electrode activation substrate 206 which interfaces with the medium 180 in the flow path or region 106A) is greater than the relative electrical impedance through the medium 180 in the region/chamber 202 (e.g., from the inner surface 208 of the electrode activation substrate 206 to the top electrode 210 of the cover 110A) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. As such the illumination recorded in images taken of the microfluidic device provide information about electrical state of regions in the microfluidic device at a given timepoint. DEP electrodes that attract or repel micro-objects in the fluidic medium 180 may thus be selectively activated and deactivated at many different such DEP electrode regions 214 at the inner surface 208 of the region/chamber 202 by changing light patterns 218 projected from a light source 216 into the microfluidic device 200. This activation and deactivation may move micro-objects and thus may be classified as part of an operation illustrated in the chip timeline (e.g., loading or unloading of cells). Whether the DEP forces attract or repel nearby micro-objects may depend on such parameters as the frequency of the power source 212 and the dielectric properties of the medium 180 and/or micro-objects (not shown).

The square pattern 220 of illuminated DEP electrode regions 214a illustrated in FIG. 3C is an example only. Any pattern of the DEP electrode regions 214 may be illuminated (and thereby activated) by the pattern of light 218 projected into the microfluidic device 200, and the pattern of illuminated/activated DEP electrode regions 214 may be repeatedly changed by changing or moving the light pattern 218. The square pattern, or any other pattern, shape or other visually distinguishable feature or characteristic may be used to determine, identify, or establish a region of interest. Additionally, or alternatively, a shape including but not limited to those formed by an individual or combination of illuminated DEP electrode regions, may be a distinguishable feature or characteristic. The patterns of illumination used to activate DEP recording in an image or images also correspond to operations illustrated in the chip timeline (e.g., 404B in FIG. 4B), and image sequences derived for a region of interest may be presented in a gallery view under a column with a designator corresponding to a relevant block of a chip timeline.

FIGS. 3D-3J illustrate example structural features of a micro-fluidic device that may be used to characterize regions of interest. Non-limiting examples of generic chambers 224, 226, and 228 are shown within the microfluidic device 200 depicted in FIGS. 3D-3F. Each chamber 224, 226, and 228 may comprise an isolation structure 232 defining an isolation region 240 and a connection region 236 fluidically connecting the isolation region 240 to a channel 122A. The connection region 236 may comprise a proximal opening 234 to the microfluidic channel 122A and a distal opening 238 to the isolation region 240. The connection region 236 may be configured so that the maximum penetration depth of a flow of a fluidic medium (not shown) flowing from the microfluidic channel 122A into the chamber 224, 226, 228 does not extend into the isolation region 240. Thus, due to the connection region 236, a micro-object (not shown) or other material (not shown) disposed in an isolation region 240 of a chamber 224, 226, 228 may thus be isolated from, and not substantially affected by, a flow of medium 180 in the microfluidic channel 122A.

Microfluidic devices may comprise sequestration chambers and substrates (e.g., electrode activation substrates) that may comprise, for example, features useful for determining regions of interest and/or features that occur in or pertain to a region of interest that may be quantified or otherwise characterized. The sequestration chambers 224, 226, and 228 of FIGS. 3D-3F each have a single opening which opens directly to the microfluidic channel 122A. The opening of the sequestration chamber opens laterally from the microfluidic channel 122A. The electrode activation substrate 206 underlays both the microfluidic channel 122A and the chambers 224, 226, and 228. The upper surface of the electrode activation substrate 206 within the enclosure of a chamber, forming the floor of the chamber, is disposed at the same level or substantially the same level of the upper surface of the electrode activation substrate 206 within the microfluidic channel 122A (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. These features may be used to identify structure-based regions of interest. The variation of elevation in the upper surface of the substrate across both the microfluidic channel 122A (or flow region) and chambers may be less than about 3%, 2%, 1%. 0.9%, 0.8%, 0.5%, 0.3% or 0.1% of the height of the walls of the chamber or walls of the microfluidic device. Such variations of elevation may be used as indicators (features/characteristics) for determining a region of interest.

Example microfluidic devices from which images (base images, image sequences, single images, etc.) may be derived, may comprise one or more microfluidic circuits or components or regions within a microfluidic circuit. In some embodiments, structure-based regions of interest of the microfluidic circuit may comprise regions proximal to regions of flow, regions where direct flow is prevented, and/or regions separated from flow by a single opening. In further embodiments, microfluidic circuits may comprise discrete structural features including chambers (e.g., sequestration pens, pens, traps, etc.), where micro-objects may be isolation from direct flow.

In the example microfluidic device disclosed herein, the microfluidic channel 122A may be an example of a swept region, and the isolation regions 240 of the chambers 224, 226, 228 may be examples of un-swept regions. As noted, the microfluidic channel 122A and chambers 224, 226, 228 may be configured to include one or more fluidic media 180. In the example shown in FIGS. 3D-3E, the ports 222 are connected to the microfluidic channel 122A and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 includes the fluidic medium 180, the flow 242 of fluidic medium 180 in the microfluidic channel 122A may be selectively generated and stopped. For example, as shown, the ports 222 may be disposed at different locations (e.g., opposite ends) of the microfluidic channel 122A, and a flow 242 of medium may be created from one port 222 functioning as an inlet to another port 222 functioning as an outlet.

FIG. 3F illustrates a detailed view of an example of a structure-based region of interest, in this case a sequestration chamber 224 according to the present disclosure. Examples of micro-objects 246 are also shown. Structural aspects of the chamber 224 may be used to determine regions of interest in a base image derived from the microfluidic device. Regions of interest may be determined based on features recorded in any image taken of the micro-fluidic device, including target-based or structure-based features.

Regions of interest may be associated with a particular operation illustrated in a chip timeline view. Such an operation may comprise stopping, starting, increasing, or decreasing flow within the microfluidic device. In example microfluidic devices disclosed herein, a flow 242 of fluidic medium 180 in a microfluidic channel 122A past a proximal opening 234 of sequestration chamber 224 may cause a secondary flow 244 of the medium 180 into and/or out of the sequestration chamber 224. An image or images (e.g., base image or base images) may be taken of the microfluidic device and later segmented into a library of regions of interest, with the regions of interest determined based on regions where a micro-object is isolated from secondary flow. To isolate micro-objects 246 in the isolation region 240 of a chamber 224 from the secondary flow 244, the length $L_{con}$ of the connection region 236 of the chamber 224 (e.g., from the proximal opening 234 to the distal opening 238) should be greater than the penetration depth $D_p$ of the secondary flow 244 into the connection region 236. These properties provide discrete parameters and localized regions for which a region of interest may be assigned. The penetration depth $D_p$ of the secondary flow 244 depends upon the velocity of the fluidic medium 180 flowing in the microfluidic channel 122A and various parameters relating to the configuration of the microfluidic channel 122A and the proximal opening 234 of the connection region 236 to the microfluidic channel 122A. Therefore, a base image may be selected, or regions of interest within a base image may be determined based on the operations (e.g., presence/absence of flow, etc.), with the operations represented for a given microfluidic device in the chip timeline.

For a given example microfluidic device, the configurations of the microfluidic channel 122A and the opening 234 will be fixed, whereas the rate of flow 242 of fluidic medium 180 in the microfluidic channel 122A will be variable. Accordingly, for each chamber 224, a maximal velocity $V_{max}$ for the flow 242 of fluidic medium 180 in channel 122A may be identified that ensures that the penetration depth $D_p$ of the secondary flow 244 does not exceed the length $L_{con}$ of the connection region 236. As long as the rate of the flow 242 of fluidic medium 180 in the microfluidic channel 122A does not exceed the maximum velocity $V_{max}$, the resulting secondary flow 244 may be limited to the microfluidic channel 122A and the connection region 236 and kept out of the isolation region 240. The flow 242 of medium 180 in the microfluidic channel 122A will thus not draw micro-objects 246 out of the isolation region 240. Rather, micro-objects 246 located in the isolation region 240 will stay in the isolation region 240 regardless of the flow 242 of fluidic medium 180 in the microfluidic channel 122A. The effects of these flow on these micro-objects are recorded directly or indirectly in the blocks of the timeline view. Accordingly, a user may automatically or manually select images (e.g., base images, image sequences, individual images, etc.) that correspond to the properties of secondary flow or flow velocity that are relevant to the regions of interest they would like displayed or sorted in the gallery view based on features/characteristics of the region of interest under the selected conditions.

Moreover, as long as the rate of flow 242 of medium 180 in the microfluidic channel 122A does not exceed $V_{max}$, the flow 242 of fluidic medium 180 in the microfluidic channel 122A will not move miscellaneous particles (e.g., microparticles and/or nanoparticles) from the microfluidic channel 122A into the isolation region 240 of a chamber 224. Having the length $L_{con}$ of the connection region 236 be greater than the maximum penetration depth $D_p$ of the secondary flow 244 may thus prevent contamination of one chamber 224 with miscellaneous particles from the microfluidic channel 122A or another chamber (e.g., chambers 226, 228 in FIG. 3G).

Because the microfluidic channel 122A and the connection regions 236 of the chambers 224, 226, 228 may be affected by the flow 242 of medium 180 in the microfluidic channel 122A, the microfluidic channel 122A and connection regions 236 may be deemed swept (or flow) regions of the microfluidic device 230. The isolation regions 240 of the chambers 224, 226, 228, on the other hand, may be deemed un-swept (or non-flow) regions. For example, components (not shown) in a first fluidic medium 180 in the microfluidic channel 122A may mix with a second fluidic medium 248 in the isolation region 240 substantially by diffusion of components of the first medium 180 from the microfluidic channel 122A through the connection region 236 and into the second fluidic medium 248 in the isolation region 240. Similarly, components (not shown) of the second medium 248 in the isolation region 240 may mix with the first medium 180 in the microfluidic channel 122A substantially by diffusion of components of the second medium 248 from the isolation region 240 through the connection region 236 and into the first medium 180 in the microfluidic channel 122A. In some embodiments, the extent of fluidic medium exchange between the isolation region of a chamber and the flow region by diffusion is greater than about 90%, 91%, 92%, 93%, 94% 95%, 96%, 97%, 98%, or greater than about 99% of fluidic exchange. The first medium 180 may be the same medium or a different medium than the second medium 248. Moreover, the first medium 180 and the second medium 248 may start out being the same, then become different (e.g., through conditioning of the second medium 248 by one or more cells in the isolation region 240, or by changing the medium 180 flowing through the microfluidic channel 122A).

The maximum penetration depth $D_p$ of the secondary flow 244 caused by the flow 242 of fluidic medium 180 in the microfluidic channel 122A may depend on a number of parameters, as mentioned above. Examples of such parameters include: the shape of the microfluidic channel 122A (e.g., the microfluidic channel may direct medium into the connection region 236, divert medium away from the connection region 236, or direct medium in a direction substantially perpendicular to the proximal opening 234 of the connection region 236 to the microfluidic channel 122A); a width $W_{ch}$ (or cross-sectional area) of the microfluidic channel 122A at the proximal opening 234; and a width $W_{con}$ (or cross-sectional area) of the connection region 236 at the proximal opening 234; the velocity V of the flow 242 of fluidic medium 180 in the microfluidic channel 122A; the viscosity of the first medium 180 and/or the second medium 248, or the like.

In some embodiments, the dimensions of the microfluidic channel 122A and chambers 224, 226, 228 may be oriented as follows with respect to the vector of the flow 242 of fluidic medium 180 in the microfluidic channel 122A: the microfluidic channel width $W_{ch}$ (or cross-sectional area of the microfluidic channel 122A) may be substantially perpendicular to the flow 242 of medium 180; the width $W_{con}$ (or cross-sectional area) of the connection region 236 at opening 234 may be substantially parallel to the flow 242 of medium 180 in the microfluidic channel 122A; and/or the length $L_{con}$ of the connection region may be substantially perpendicular to the flow 242 of medium 180 in the microfluidic channel 122A. The foregoing are examples, and the relative position of the microfluidic channel 122A and chambers 224, 226, 228 may be in other orientations with respect to each other.

As illustrated in FIG. 3F, the width $W_{con}$ of the connection region 236 may be uniform from the proximal opening 234 to the distal opening 238. The width $W_{con}$ of the connection region 236 at the distal opening 238 may thus be any of the values identified herein for the width $W_{con}$ of the connection region 236 at the proximal opening 234. Alternatively, the width $W_{con}$ of the connection region 236 at the distal opening 238 may be larger than the width $W_{con}$ of the connection region 236 at the proximal opening 234.

As illustrated in FIG. 3F, the width of the isolation region 240 at the distal opening 238 may be substantially the same as the width $W_{con}$ of the connection region 236 at the proximal opening 234. The width of the isolation region 240 at the distal opening 238 may thus be any of the values identified herein for the width $W_{con}$ of the connection region 236 at the proximal opening 234. Alternatively, the width of the isolation region 240 at the distal opening 238 may be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g., chamfering the connection region, beveling the connection region). Further, any part or subpart of the connection region 236 may be narrowed (e.g., a portion of the connection region adjacent to the proximal opening 234).

FIGS. 3G-3I depict another example embodiment of a microfluidic device 350 including a microfluidic circuit 250 and flow channels 264, which are variations of the respective microfluidic device 100A, trap 132A, and side passage 134A of FIG. 3A. The microfluidic device 350 also has a plurality of chambers 266 that are additional variations of the above-described chambers 124A, 126A, 128A, 130A, 224, 226 or 228. In particular, it should be appreciated that the chambers 266 of device 350 shown in FIG. 3G may replace any of the above-described chambers 124A, 126A, 128A, 130A, 224, 226 or 228 in devices 100 A, 200, 230, 280, 290, 300. Likewise, the microfluidic device 350 is another variant of the microfluidic device 100A, and may also have the same or a different DEP configuration as the above-described microfluidic device 100A, 200, 230, 280, 290, 300 as well as any of the other microfluidic system components described herein.

The microfluidic device 350 of FIGS. 3G-3I comprises a support structure (not visible in FIGS. 3G-3I, but may be the same or generally similar to the support structure 104A of the microfluidic device 100A depicted in FIG. 3A), a microfluidic circuit structure (e.g., 108A in FIG. 3A, 256 in FIG. 3H, 308 in FIG. 3J, etc.) having an enclosure structural elements (e.g., 252, 262), and a cover (not visible in FIGS. 3G-3I, but may be the same or generally similar to the cover 110A of the microfluidic device 100A depicted in FIG. 3A). The microfluidic circuit structure (e.g., 108A in FIG. 3A, 256 in FIG. 3H, 308 in FIG. 3J, etc.) includes a frame 352 and microfluidic circuit material 316, which may be the same as or generally similar to the frame 114A and microfluidic circuit material of the microfluidic device 100A shown in FIG. 3A. As shown in FIG. 3G, the microfluidic circuit 250 defined by the microfluidic circuit material 316 may comprise multiple channels 264 (two are shown but there may be more) to which multiple chambers 266 are fluidically connected.

Each chamber 266 may comprise an isolation structure 272, an isolation region 270 within the isolation structure 272 having one or more walls 260, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 3E-3F, a flow 278 of a first fluidic medium 254 in a channel 264 may create secondary flows 282 of the first medium 254 from the microfluidic channel 264 into and/or out of the respective connection regions 268 of the chambers 266.

As illustrated in FIG. 3H, the connection region 268 of each chamber 266 generally includes the area extending between the proximal opening 274 to a channel 264 and the distal opening 276 to an isolation structure 272. The length $L_{con}$ of the connection region 268 may be greater than the maximum penetration depth $D_p$ of secondary flow 282, in which case the secondary flow 282 will extend into the connection region 268 without being redirected toward the isolation region 270 (as shown in FIG. 3G). Alternatively, at illustrated in FIG. 3I, the connection region 268 may have a length $L_{con}$ that is less than the maximum penetration depth $D_p$, in which case the secondary flow 282 will extend through the connection region 268 and be redirected toward the isolation region 270.

In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but may be the same or generally similar to the micro-objects 246 shown in FIG. 3F) in the isolation region 270 of a chamber 266 will not be drawn out of the isolation region 270 by a flow 278 of first medium 254 in channel 264. Nor will the flow 278 in channel 264 draw miscellaneous materials (not shown) from channel 264 into the isolation region 270 of a chamber 266.

As such, diffusion may be the mechanism by which components in a first medium 254 in the microfluidic channel 264 may move from the microfluidic channel 264 into a second medium 258 in an isolation region 270 of a chamber 266. Likewise, diffusion is the mechanism by which components in a second medium 258 in an isolation region 270 of a chamber 266 may move from the isolation region 270 to a first medium 254 in the microfluidic channel 264. The first medium 254 may be the same medium as the second medium 258, or the first medium 254 may be a different medium than the second medium 258. Alternatively, the first medium 254 and the second medium 258 may start out being the same, then become different, e.g., through conditioning of the second medium by one or more cells in the isolation region 270, or by changing the medium flowing through the microfluidic channel 264.

As illustrated in FIG. 3F, the width $W_{ch}$ of the microfluidic channels 264 (e.g., taken transverse to the direction of a fluid medium flow through the microfluidic channel indicated by arrows 278 in FIG. 3G) in the microfluidic channel 264 may be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented may be other than perpendicular and thus other than 90°. Examples of alternatively oriented angles include angles of: about 30° to about 90°, about 45° to about 90°, about 60° to about 90°, or the like.

Various dimensions and/or features of the chambers and the microfluidic channels to which the chambers open, as described herein, may be represented in a chip timeline with the features of the microfluidic device (e.g., structure-based region of interest), with the selection aimed to perform a specific operation that is measurable in images taken of the microfluidic device. Such operation include but are not limited to limiting introduction of contaminants or unwanted micro-objects into the isolation region of a chamber from the flow region/microfluidic channel; limiting the exchange of components in the fluidic medium from the channel or from the isolation region to substantially diffusive exchange; facilitating the transfer of micro-objects into and/or out of the chambers; and/or facilitating growth or expansion of any biological cells disposed within the isolation region. Microfluidic channels and chambers, for any of the embodiments described herein, may have any suitable combination of dimensions, may be selected by one of skill from the teachings of this disclosure, as follows, and these dimensions may be used for the purpose of identifying regions of interest or characterizing phenomena occurring in regions of interest. Accordingly, the structural features disclosed herein may be detected in base images represented in a chip timeline, and selected for analysis to produce image sequences for regions of interest that may be displayed in a gallery view. Quantifiable features of the regions of interest may be assessed (e.g., arranged, clustered, filtered, or otherwise manipulated) using the filter builder and application module or graph tools disclosed herein.

Microfluidic channels and chambers, for any of the embodiments described herein, may have any suitable combination of dimensions (e.g., dimensions of the chambers (e.g., 124A, 126A, 128A, 130A, 224, 226, 228, or 266), isolation region (e.g., 240 or 270), etc.). Example dimensions that may be used as features or characteristics of the microfluidic device used alone or in combination for determining a region of interest include but are not limited to: width $W_{ch}$ of the microfluidic channel (e.g., 122A), height $H_{ch}$ of the microfluidic channel, cross-sectional area of the microfluidic channel (e.g., 122A), length $L_{con}$ of the connection region (e.g., 236), width $W_{con}$ of a connection region (e.g., 236), $W_{pr}$ of a proximal opening, width $W_{pr}$ of a proximal opening of a connection region, ratio of the length $L_{con}$ of a connection region (e.g., 236) to a width $W_{con}$ of the connection region (e.g., 236), flow rate e.g., $V_{max}$, and length of a region within a microfluidic device (e.g., determined as $L_s$–$L_{con}$). Features or characteristics of the microfluidic device may be selected by one of skill from the teachings of this disclosure, as follows, and these dimensions may be used for the purpose of identifying regions of interest or characterizing phenomena occurring in regions of interest. Accordingly, the structural features disclosed herein may be detected in base images represented in a chip timeline, and selected for analysis to produce image sequences for regions of interest that may be displayed in a gallery view. Quantifiable features of the regions of interest may be assessed (e.g., arranged, clustered, filtered, or otherwise manipulated) using the filter builder and application module or graph tools disclosed herein. A list of example features and/or characteristics related to the structure of the microfluidic device are disclosed here in as various embodiments of example chambers in example microfluidic devices on which operations are performed (e.g., as recorded and illustrated in the chip timeline) and/or in images (e.g., image sequences illustrated regions of interest in gallery view, and/or as quantified representation of the regions of interest assessed using the filter builder and application module and/or graphing tools disclosed herein.

In various embodiments of chambers (e.g., 124A, 126A, 128A, 130A, 224, 226, 228, or 266), the isolation region (e.g., 240 or 270) is configured to include a plurality of micro-objects. In other embodiments, the isolation region may be configured to include one, two, three, four, five, or a similar relatively small number of micro-objects. Accordingly, the volume of an isolation region may be, for example, at least $1 \times 10^6$, $2 \times 10^6$, $4 \times 10^6$, $6 \times 10^6$ cubic microns, or more.

In various embodiments images of the microfluidic devices, features or characteristics of images taken of chambers may comprise the width $W_{ch}$ of the microfluidic channel (e.g., 122A) at a proximal opening (e.g., 234) may be about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, or 100-120 microns. In some other embodiments, the width $W_{ch}$ of the microfluidic channel (e.g., 122A) at a proximal opening (e.g., 234) may be about 200-800 microns, 200-700 microns, or 200-600 microns. The foregoing are examples only, and the width $W_{ch}$ of the microfluidic channel 122A may be any width within any of the endpoints listed above. Moreover, the $W_{ch}$ of the microfluidic channel 122A may be selected to be in any of these widths in regions of the microfluidic channel other than at a proximal opening of a chamber. In some embodiments, a chamber has a height of about 30 to about 200 microns, or about 50 to about 150 microns. In some embodiments, the chamber has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments images of the microfluidic devices, features or characteristics of images taken of chambers may comprise the height $H_{ch}$ of the microfluidic channel (e.g., 122A) at a proximal opening (e.g., 234) may be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122A) may be a height within any of the endpoints listed above. The height $H_{ch}$ of the microfluidic channel 122A may be selected to be in any of these heights in regions of the microfluidic channel other than at a proximal opening of a chamber.

In various embodiments images of the microfluidic devices, features or characteristics of images taken of chambers may comprise a cross-sectional area of the microfluidic channel (e.g., 122A) at a proximal opening (e.g., 234) may be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122A) at a proximal opening (e.g., 234) may be any area within any of the endpoints listed above.

In various embodiments images of the microfluidic devices, features or characteristics of images taken of chambers may comprise the length $L_{con}$ of the connection region (e.g., 236) may be about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) may be in any length within any of the endpoints listed above.

In various embodiments images of the microfluidic devices, features or characteristics of images taken of chambers may comprise the width $W_{con}$ of a connection region (e.g., 236) at a proximal opening (e.g., 234) may be about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, or 80-100 microns. The foregoing are examples only, and the width $W_{con}$ of a connection region (e.g., 236) at a proximal opening (e.g., 234) may be different than the foregoing examples (e.g., any value within any of the endpoints listed above).

In various embodiments images of the microfluidic devices, features or characteristics of images taken of chambers may comprise the width $W_{con}$ of a connection region (e.g., 236) at a proximal opening (e.g., 234) may be at least as large as the largest dimension of a micro-object (e.g., biological cell, which may be a B cell, a plasma cell, a hybridoma, a recombinant antibody secreting cell (ASC), such as a CHO cell or a yeast cell, or the like) that the chamber is intended for. The foregoing are examples only, and the width $W_{con}$ of a connection region (e.g., 236) at a proximal opening (e.g., 234) may be different than the foregoing examples (e.g., a width within any of the endpoints listed above).

In various embodiments images of the microfluidic devices, features or characteristics of images taken of chambers may comprise the width $W_{pr}$ of a proximal opening of a connection region, which may be at least as large as the largest dimension of a micro-object (e.g., a micro-object such as a cell) that the chamber is intended for. For example, the width $W_{pr}$ may be about 50 microns, about 60 microns, about 100 microns, about 200 microns, about 300 microns or may be about 50-300 microns, about 50-200 microns, about 50-100 microns, about 75-150 microns, about 75-100 microns, or about 200-300 microns.

In various embodiments images of the microfluidic devices, features or characteristics of images taken of chambers may comprise a ratio of the length $L_{con}$ of a connection region (e.g., 236) to a width $W_{con}$ of the connection region (e.g., 236) at the proximal opening 234, and the ratio may be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 may be different than the foregoing examples.

In various embodiments images of the microfluidic devices, features or characteristics of images taken of chambers may comprise an isolation region of a chamber, which has a length (determined as $L_s - L_{con}$) of about 40-600 microns, about 40-500 microns, about 40-400 microns, about 40-300 microns, about 40-200 microns, about 40-100 microns or about 40-80 microns. In some embodiments, an isolation region of a chamber has a length of about 30-550 microns, about 30-450 microns, about 30-350 microns, about 30-250 microns, about 30-170 microns, about 30-80 microns or about 30-70 microns. The foregoing are examples only, and a chamber may have a length $L_s$ selected to be between any of the values listed above.

In various embodiments features or characteristics of images taken of the microfluidic device may be correlated with one or more operations recorded in a chip timeline. Such operations may comprise flow rates or actions performed at specific flow rates. In such embodiments, images may be taken at time points that correspond to a max velocity of flow, $V_{max}$, which may be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, 15, 16, 17, 18, 19, or 20 microliters/sec. Additionally, or alternatively, the flow rate for a given operation illustrated in the chip timeline may be 0 microliters/sec, with no flow occurring at the timepoint in which an image (e.g., a base image) is captured.

Images of the microfluidic device may comprise one or more chambers. A base image or field of view image may comprise all or a subset of the chambers in the microfluidic device. In various embodiment, the microfluidic device has chambers configured as in any of the embodiments discussed herein where the microfluidic device has about 5 to about 10 chambers, about 10 to about 50 chambers, about 25 to about 200 chambers, about 100 to about 500 chambers, about 200 to about 1000 chambers, about 500 to about 1500 chambers, about 1000 to about 2500 chambers, about 2000 to about 5000 chambers, about 3500 to about 7000 chambers, about 5000 to about 10,000 chambers, about 7,500 to about 15,000 chambers, about 12,500 to about 20,000 chambers, about 15,000 to about 25,000 chambers, about 20,000 to about 30,000 chambers, about 25,000 to about 35,000 chambers, about 30,000 to about 40,000 chambers, about 35,000 to about 45,000 chambers, or about 40,000 to about 50,000 chambers. The chambers need not all be the same size and may include a variety of configurations (e.g., different widths, different features within the chamber).

FIG. 3J depicts another example embodiment of a microfluidic device 300 including microfluidic structure-based features of the microfluidic circuit structure 308, which include a channel 322 and chamber 324, which has features and properties like any of the chambers described herein for microfluidic devices 100A, 200, 230, 250, 280, 300 and any other microfluidic devices described herein.

The example microfluidic devices of FIG. 3J includes a microfluidic channel 322, having a width $W_{ch}$, as described herein, and including a flow 310 of first fluidic medium 302 and one or more chambers 324 (only one illustrated in FIG. 3J). These flow operations may be captured in image sequences taken during the specific steps or operations illustrated in the chip timeline. The structure-based features of the chambers 324 may also have defined features that are represented in image sequences and used to define regions of interest in a gallery view, with the gallery view corresponding to operations illustrated in the chip time line. In this example, chambers 304 each have a length $L_s$, a connection region 336, and an isolation region 340, where the isolation region 340 includes a second fluidic medium 304. The connection region 336 has a proximal opening 334, having a width $W_{con1}$, which opens to the microfluidic channel 322, and a distal opening 338, having a width $W_{con2}$, which opens to the isolation region 340. The width $W_{con1}$ may or may not be the same as $W_{con2}$, as described herein. The walls of each chamber 324 may be formed of microfluidic circuit material 316, which may further form the connection region walls 330. A connection region wall 330 may correspond to a structure that is laterally positioned with respect to the proximal opening 334 and at least partially extends into the enclosed portion of the chamber 324. In some embodiments, the length $L_{con}$ of the connection region 336 is at least partially defined by length $L_{wall}$ of the connection region wall 330. The connection region wall 330 may have a length $L_{wall}$, selected to be more than the penetration depth $D_p$ of the secondary flow 344. Thus, the secondary flow 344 may be wholly included within the connection region without extending into the isolation region 340.

The connection region wall 330 may define the structure-based feature of a hook region 352, which is a sub-region of the isolation region 340 of the chamber 324. Since the connection region wall 330 extends into the inner cavity of the chamber, the connection region wall 330 may act as a physical barrier to shield hook region 352 from secondary flow 344, with selection of the length of $L_{wall}$, contributing to the extent of the hook region. In some embodiments, the longer the length $L_{wall}$ of the connection region wall 330, the more sheltered the hook region 352. These structure-based features may be monitored in image sequences taken of the microfluidic chip, and depicted as discrete steps in the chip timeline. In chambers configured like those of FIGS. 3D-3J, the isolation region may have a shape and size of any type, and may be associated with operations in the chip timeline. Examples of operations include loading, perfusing, monitoring, and/or exporting micro-objects, and/or monitoring fluorescence. Such monitoring may be configured such that features of the image sequences correspond to biologically relevant operations including regulation of diffusion of nutrients, reagents, and/or media into the chamber to reach to a far wall of the chamber, e.g., opposite the proximal opening of the connection region to the flow region (or microfluidic channel). The size and shape of the isolation region may correspond to structure-based features of the microfluidic device with said structure-based features selected based on relevance of the biological samples to assays or assay steps that involve regulating diffusion of waste products and/or secreted products of a micro-object out from the isolation region to the flow region via the proximal opening of the connection region of the chamber.

In some other embodiments of chambers, the isolation region may have more than one opening fluidically connecting the isolation region with the flow region of the microfluidic device. However, for an isolation region having a number of n openings fluidically connecting the isolation region to the flow region (or two or more flow regions), n−1 openings may be valved. When the n−1 valved openings are closed, the isolation region has one effective opening, and exchange of materials into/out of the isolation region occurs by diffusion. Examples of microfluidic devices having pens in which micro-objects may be placed, cultured, and/or monitored have been described, for example, in U.S. Pat. No. 9,857,333 (Chapman, et al.), U.S. Pat. No. 10,010,882 (White, et al.), and U.S. Pat. No. 9,889,445 (Chapman, et al.), each of which is incorporated herein by reference in its entirety for all purposes.

FIG. 3K illustrates a microfluidic device according to an embodiment of the disclosure. More specifically, FIG. 3K illustrates a microfluidic device 280 according to one embodiment. The microfluidic device 280 illustrated in FIG. 3K includes a stylized diagram of a microfluidic device (e.g., 100 in FIG. 3A) with structure-based features that may be used to assign regions of interest for images or image sequences taken of the microfluidic device during one or more operations depicted in a chip timeline view.

In practice the microfluidic device 280 and its constituent circuit elements (e.g., channels 122A and chambers 128A in FIG. 3A) would have the dimensions discussed herein. The microfluidic circuit 120A illustrated in FIG. 3A has two ports 107, four distinct channels 122A and four distinct flow paths 106A. The microfluidic device 280 in FIG. 3K further comprises a plurality of chambers opening off of each channel (e.g., 122A in FIG. 3A). In the microfluidic device illustrated in FIG. 3K, the chambers may have a geometry similar to the pens illustrated in FIG. 3F and thus, have both connection regions and isolation regions. Accordingly, the microfluidic circuit (e.g., 120A in FIG. 3A) includes both swept regions (e.g., channels 122A and portions of the connection regions 236 in FIG. 3E within the maximum penetration depth $D_p$ of the secondary flow 244 in FIG. 3F) and non-swept regions (e.g., isolation regions 240 and portions of the connection regions 236 not within the maximum penetration depth $D_p$ of the secondary flow 244 in FIG. 3F).

FIG. 3L illustrates a coated surface of the microfluidic device according to an embodiment of the disclosure. More specifically, FIG. 3L depicts a cross-sectional view of a microfluidic device 290 having an example covalently linked coating material providing a conditioned surface. As illustrated, the coating materials 298 (shown schematically) may comprise a monolayer of densely-packed molecules covalently bound to both the inner surface 294 of a base 286, which may be a DEP substrate, and the inner surface 292 of a cover 288 of the microfluidic device 290. The coating material 298 may be disposed on substantially all inner surfaces 294, 292 proximal to, and facing inwards towards, the enclosure 284 of the microfluidic device 290, including, in some embodiments and as discussed above, the surfaces of microfluidic circuit material (e.g., 316 in FIG. 3J) used to define circuit elements and/or structures within the microfluidic device 290. In alternate embodiments, the coating material 298 may be disposed on only one or some of the inner surfaces of the microfluidic device 290.

In the embodiment shown in FIG. 3L, the coating material 298 may include a monolayer of organosiloxane molecules, each molecule covalently bonded to the inner surfaces 292, 294 of the microfluidic device 290 via a siloxy linker 296. Any of the above-discussed coating materials 298 may be used (e.g., an alkyl-terminated, a fluoroalkyl terminated moiety, a PEG-terminated moiety, a dextran terminated moiety, or a terminal moiety including positive or negative charges for the organosiloxy moieties), where the terminal moiety is disposed at its enclosure-facing terminus (i.e., the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 may include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120A, the coating material 298 may form strong hydrogen bonds with water molecules such that the resulting water of hydration acts as a layer (or "shield") that separates the micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 may form ionic bonds with the charged portions of non-covalent coating agents (e.g., proteins in solution) that are present in a medium 180 (e.g., a coating solution) in the enclosure 284.

In still other embodiments, the coating material may comprise or be chemically modified to present a hydrophilic coating agent at its enclosure-facing terminus. In some embodiments, the coating material may include an alkylene ether including polymer, such as PEG. In some embodiments, the coating material may include a polysaccharide, such as dextran. Like the charged moieties discussed above (e.g., anionic, cationic, and zwitterionic moieties), the hydrophilic coating agent may form strong hydrogen bonds with water molecules such that the resulting water of hydration acts as a layer (or "shield") that separates the micro-objects from interactions with non-biological molecules (e.g., the silicon and/or silicon oxide of the substrate). Further details of appropriate coating treatments and modifications may be found at U.S. application Ser. No. 15/135,707, filed on Apr. 22, 2016, and is incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components may provide nutrients, cell growth signaling species, pH modulation, gas exchange, temperature control, and removal of waste products from cells.

FIG. 3M illustrates a specific example of a system for use with a microfluidic device and associated control equipment according to some embodiments of the disclosure. FIG. 3N illustrates an imaging device according to some embodiments of the disclosure. More specifically, FIGS. 3M-3N show various embodiments of system which may be used to operate and observe one or more microfluidic devices according to the present disclosure. As illustrated in FIG. 3M, the system may include a structure ("nest") 300 configured to hold a microfluidic device 320, or any other microfluidic device described herein. The nest 300 may include a socket 302 capable of interfacing with the microfluidic device 320 (e.g., an optically-actuated electrokinetic device) and providing electrical connections from power source to microfluidic device 320. The nest 300 may further include an integrated electrical signal generation subsystem 304. The electrical signal generation subsystem 304 may be configured to supply a biasing voltage to socket 302 such that the biasing voltage is applied across a pair of electrodes in the microfluidic device 320 when it is being held by socket 302. Thus, the electrical signal generation subsystem 304 may be part of power source 192. The ability to apply a biasing voltage to microfluidic device 320 may or may not mean that a biasing voltage will be applied at all times when the microfluidic device 320 is held by the socket 302. Rather, in some cases, the biasing voltage may be applied intermittently, e.g., only as needed to facilitate the generation of electrokinetic forces, such as dielectrophoresis (DEP) or electro-wetting, in the microfluidic device 320.

As illustrated in FIG. 3M, the nest 300 may include a printed circuit board assembly (PCBA) 322. The electrical signal generation subsystem 304 may be mounted on and electrically integrated into the PCBA 322. The example support includes socket 302 mounted on PCBA 322, as well. In some embodiments, the electrical signal generation subsystem 304 will include a waveform generator (not shown). The electrical signal generation subsystem 304 may further include an oscilloscope (not shown) and/or a waveform amplification circuit (not shown) configured to amplify a waveform received from the waveform generator. The oscilloscope, if present, may be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement may be, for example, provided as feedback to the waveform generator, and the waveform generator may be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 3A) to perform functions and analysis. In the embodiment illustrated in FIG. 3M the controller 308 communicates with a master controller 154 through an interface 310 (e.g., a plug or connector).

In some embodiments, the nest 300 may comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit may have a +6.5V to −6.5V power supply generated by a pair of DC-DC converters mounted on the PCBA 322, resulting in a signal of up to 13 Vpp at the microfluidic device 320.

As illustrated in FIG. 3M, the support structure 300 (e.g., nest) may further include a thermal control subsystem 306. The thermal control subsystem 306 may be configured to regulate the temperature of microfluidic device 320 held by the support structure 300. For example, the thermal control subsystem 306 may include a Peltier thermoelectric device (not shown) and a cooling unit (not shown). The Peltier thermoelectric device may have a first surface configured to interface with at least one surface of the microfluidic device 320. The cooling unit may be, for example, a cooling block (not shown), such as a liquid-cooled aluminum block. A second surface of the Peltier thermoelectric device (e.g., a surface opposite the first surface) may be configured to interface with a surface of such a cooling block. The cooling block may be connected to a fluidic path 314 configured to circulate cooled fluid through the cooling block. In the embodiment illustrated in FIG. 3M, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 may be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device may be achieved, for example, by a thermoelectric power supply, such as a Pololu™ thermoelectric power supply (Pololu Robotics and Electronics Corp.). The thermal control subsystem 306 may include a feedback circuit, such as a temperature value provided by an analog circuit. Alternatively, the feedback circuit may be provided by a digital circuit.

In some embodiments, the nest 300 may include a thermal control subsystem 306 with a feedback circuit that is an analog voltage divider circuit (not shown) which includes a resistor (e.g., with resistance 1 KOhm+/−0.1%, temperature coefficient+/−0.02 ppm/CO) and a NTC thermistor (e.g., with nominal resistance 1 KOhm+/−0.01%). In some instances, the thermal control subsystem 306 measures the voltage from the feedback circuit and then uses the calculated temperature value as input to an on-board PID control loop algorithm. Output from the PID control loop algorithm may drive, for example, both a directional and a pulse-width-modulated signal pin on a Pololu™ motor drive (not shown) to actuate the thermoelectric power supply, thereby controlling the Peltier thermoelectric device.

The nest 300 may include a serial port 324 which allows the microprocessor of the controller 308 to communicate with an external master controller 154 via the interface 310 (not shown). In addition, the microprocessor of the controller 308 may communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 may communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, may be configured to plot temperature and waveform data obtained from the thermal control subsystem 306 and the electrical signal generation subsystem 304, respectively. Alternatively, or in addition, the GUI may allow for updates to the controller 308, the thermal control subsystem 306, and the electrical signal generation subsystem 304.

As discussed above, system 150A may include an imaging device 194. In some embodiments, the imaging device 194 comprises a light modulating subsystem 330 (See FIG. 3N). The light modulating subsystem 330 may include a digital mirror device (DMD) or a micro-shutter array system (MSA), either of which may be configured to receive light from a light source 332 and transmits a subset of the received light into an optical train of microscope 350. Alternatively, the light modulating subsystem 330 may include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 may be, for example, a projector. Thus, the light modulating subsystem 330 may be capable of emitting both structured and unstructured light. In certain embodiments, imaging module 164 and/or motive module 162 of system 150A may control the light modulating subsystem 330.

In certain embodiments, the imaging device 194 further comprises a microscope 350. In such embodiments, the nest 300 and light modulating subsystem 330 may be individually configured to be mounted on the microscope 350. The microscope 350 may be, for example, a standard research-grade light microscope or fluorescence microscope. Thus, the nest 300 may be configured to be mounted on the stage 344 of the microscope 350 and/or the light modulating subsystem 330 may be configured to mount on a port of microscope 350. In other embodiments, the nest 300 and the light modulating subsystem 330 described herein may be integral components of microscope 350.

In certain embodiments, the microscope 350 may further include one or more detectors 348. In some embodiments, the detector 348 is controlled by the imaging module 164. The detector 348 may include an eye piece, a charge-coupled device (CCD), a camera (e.g., a digital camera), or any combination thereof. If at least two detectors 348 are present, one detector may be, for example, a fast-frame-rate camera while the other detector may be a high sensitivity camera. Furthermore, the microscope 350 may include an optical train configured to receive reflected and/or emitted light from the microfluidic device 320 and focus at least a portion of the reflected and/or emitted light on the one or more detectors 348. The optical train of the microscope may also include different tube lenses (not shown) for the different detectors, such that the final magnification on each detector may be different.

In certain embodiments, imaging device 194 is configured to use at least two light sources. For example, a first light source 332 may be used to produce structured light (e.g., via the light modulating subsystem 330) and a second light source 334 may be used to provide unstructured light. The first light source 332 may produce structured light for optically-actuated electrokinesis and/or fluorescent excitation, and the second light source 334 may be used to provide bright field illumination. In these embodiments, the motive module 164 may be used to control the first light source 332 and the imaging module 164 may be used to control the second light source 334. The optical train of the microscope 350 may be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train may be further configured to receive unstructured light from a second light source and focus the unstructured light on at least a second region of the microfluidic device, when the device is held by the nest 300. In certain embodiments, the first and second regions of the microfluidic device may be overlapping regions. For example, the first region may be a subset of the second region. In other embodiments, the second light source 334 may additionally or alternatively include a laser, which may have any suitable wavelength of light. The representation of the optical system shown in FIG. 3N is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3N, and the laser illumination may be introduced at any suitable physical location within the optical system. The schematic locations of light source 334 and light source 332/light modulating subsystem 330 may be interchanged as well.

In FIG. 3N, the first light source 332 is shown supplying light to a light modulating subsystem 330, which provides structured light to the optical train of the microscope 350 of a system (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective lens 340 to the sample plane 342. Reflected and/or emitted light from the sample plane 342 then travels back up through the objective lens 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This may be beneficial if the first light source 332 is significantly stronger than the second light source 334. In other embodiments, the second light source 334 may emit red light, and the dichroic filter 346 may filter out visible light other than red light (e.g., visible light having a wavelength shorter than 650 nm).

Coating solutions and coating agents. Without intending to be limited by theory, maintenance of a micro-object (e.g., a biological cell) within a microfluidic device (e.g., a DEP-configured and/or EW-configured microfluidic device) may be facilitated (i.e., the micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and micro-object(s) maintained therein. In some embodiments, one or more of the inner surfaces of the microfluidic device (e.g., the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of micro-object(s), or may be introduced concurrently with the micro-object(s). In some embodiments, the micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the micro-object(s) into the microfluidic device.

In some embodiments, at least one surface of the microfluidic device includes a coating material that provides a layer of organic and/or hydrophilic molecules suitable for maintenance and/or expansion of micro-object(s) (e.g., provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating agent/Solution. Any convenient coating agent/coating solution may be used, including but not limited to: serum or serum factors, bovine serum albumin (BSA), polymers, detergents, enzymes, and any combination thereof.

Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether including polymers may be suitable for use in the microfluidic devices described herein. One non-limiting example class of alkylene ether including polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer may have a hydrophilic-lipophilic balance (HLB) greater than about 10 (e.g., 12-18). Specific Pluronic® polymers useful for yielding a coated surface include Pluronic® L44, L64, P85, and F127 (including F127NF). Another class of alkylene ether including polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer including carboxylic acid moieties. The carboxylic acid subunit may be an alkyl, alkenyl or aromatic moiety including subunit. One non-limiting example is polylactic acid (PLA). In other embodiments, the coating material may include a polymer including phosphate moieties, either at a terminus of the polymer backbone or pendant from the backbone of the polymer. In yet other embodiments, the coating material may include a polymer including sulfonic acid moieties. The sulfonic acid subunit may be an alkyl, alkenyl or aromatic moiety including subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer including saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer including nucleotide moieties, i.e., a nucleic acid, which may have ribonucleotide moieties or deoxyribonucleotide moieties, providing a polyelectrolyte surface. The nucleic acid may include only natural nucleotide moieties or may include unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer including amino acid moieties. The polymer including amino acid moieties may include a natural amino acid including polymer or an unnatural amino acid including polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum may be from any convenient source, including but not limited to fetal calf serum, sheep serum, goat serum, horse serum, and the like.

In some embodiments, BSA in a coating solution is present in a concentration from about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a concentration of about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, may include, but is not limited to, a collagen, an elastin, an RGD-including peptide (e.g., a fibronectin), or a laminin. In yet other embodiments, growth factors, cytokines, hormones or other cell signaling species may be provided within the coating material of the microfluidic device.

In some embodiments, the coating material may include a polymer including more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of micro-object(s).

In some embodiments, the covalently linked moiety configured to provide a layer of organic and/or hydrophilic molecules suitable for maintenance/expansion of micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups including an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group may be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether including polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Example reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino including moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms may help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties. Aside from the composition of the conditioned surface, other factors such as physical thickness of the hydrophobic material may impact DEP force. Various factors may alter the physical thickness of the conditioned surface, such as the manner in which the conditioned surface is formed on the substrate (e.g., vapor deposition, liquid phase deposition, spin coating, flooding, and electrostatic coating). In some embodiments, the conditioned surface has a thickness of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a surface prepared by spin coating, for example, which may typically have a thickness of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which may lead to breakdown of the coating material. Defects in the coating material may increase charge trapping and lead to further breakdown of the coating material. Similarly, different coating materials have different dielectric strengths (i.e., the minimum applied electric field that results in dielectric breakdown), which may impact charge trapping. In certain embodiments, the coating material may have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that includes fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-part conditioned surface. The covalently linked coating material may be formed by reaction of a molecule which already includes the moiety configured to provide a layer of organic and/or hydrophilic molecules suitable for maintenance/expansion of micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of micro-object(s) to a surface modifying ligand that itself has been covalently linked to the surface.

Methods of preparing a covalently linked coating material. In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

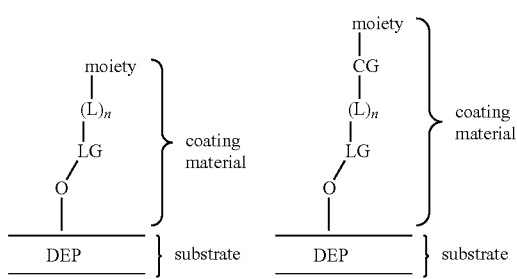

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of micro-object(s) in the microfluidic device may be any of the moieties described herein. The linking group LG may be directly or indirectly connected to the moiety configured to provide a layer of organic and/or hydrophilic molecules suitable for maintenance/expansion of micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and/or phosphorus atoms, subject to chemical bonding limitations as is known in the art. It may be interrupted with any combination of one or more moieties, which may be chosen from ether, amino, carbonyl, amido, and/or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process may be optionally improved, for example, by pre-cleaning the cover 110A, the microfluidic circuit material 116A, and/or the substrate (e.g., the inner surface 208 of the electrode activation substrate 206 of a DEP-configured substrate, or a dielectric layer of the support structure 104A of an EW-configured substrate), by exposure to a solvent bath, sonication or a combination thereof. Alternatively, or in addition, such pre-cleaning may include treating the cover 110A, the microfluidic circuit material 116A, and/or the substrate in an oxygen plasma cleaner, which may remove various impurities, while at the same time introducing an oxidized surface (e.g., oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102A defining a microfluidic circuit 120A. Without intending to be limited by theory, depositing such a coating material on a fully-assembled microfluidic circuit 120A may be beneficial in preventing delamination caused by a weakened bond between the microfluidic circuit material 116A and the electrode activation substrate 206 dielectric layer and/or the cover 110A. In embodiments where a two-step process is employed the surface modifying ligand may be introduced via vapor deposition as described above, with subsequent introduction of the moiety configured provide a layer of organic and/or hydrophilic molecules suitable for maintenance/expansion of micro-object(s). The subsequent reaction may be performed by exposing the surface modified microfluidic device to a suitable coupling reagent in solution.

Figure 4A:
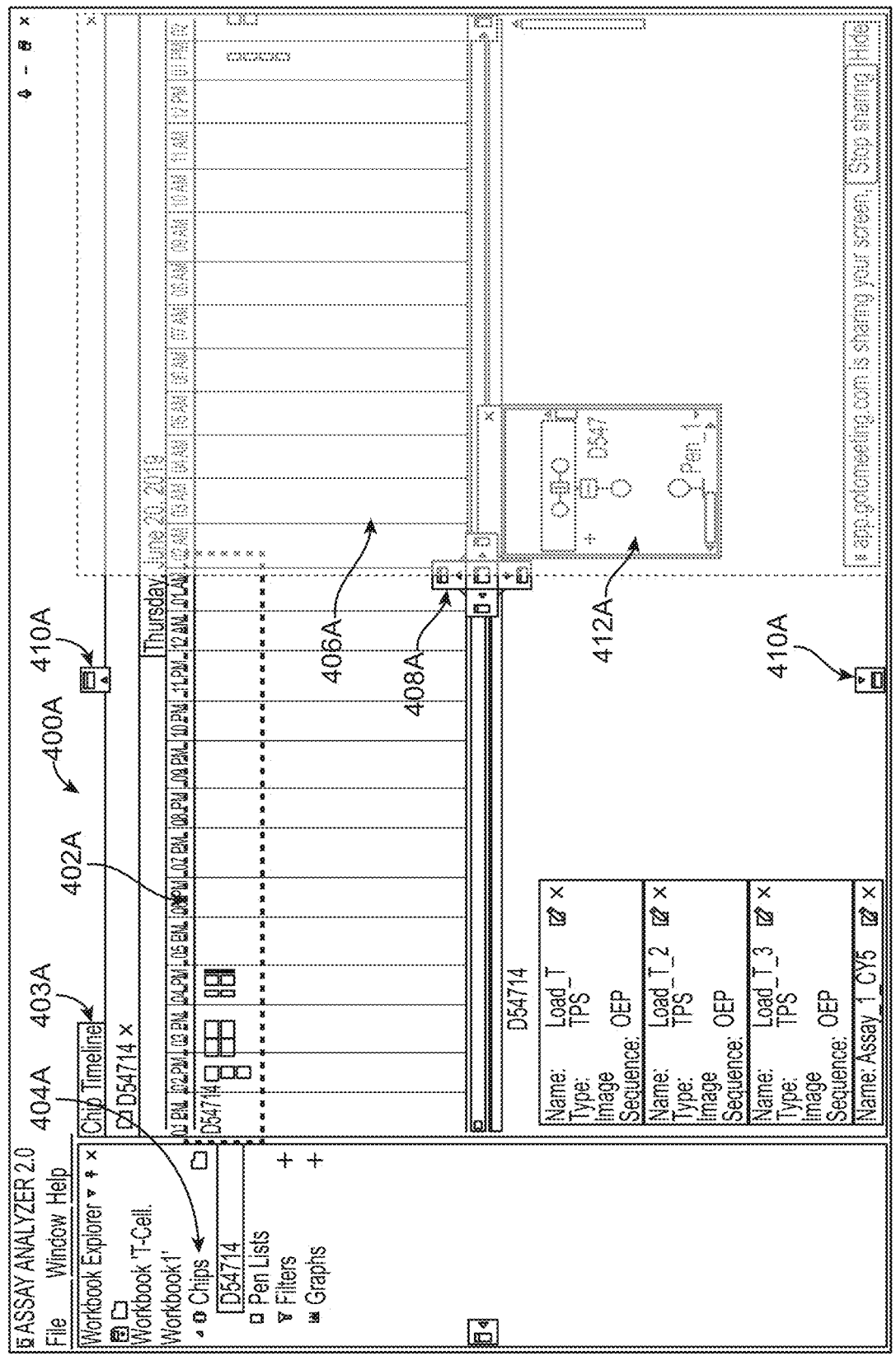
FIG. 4A illustrates a portion of an example simplified user interface showing a part of a chip timeline view in one or more embodiments.

FIG. 4A illustrates a portion of an example simplified user interface showing a part of a chip timeline view in one or more embodiments. In this example, the chip timeline view 400A includes data representation or a matching grid portion 402A that is temporally arranged for one or more microfluidic devices 404A, each having a respective plurality of chambers, which may be selected from a menu in the left column. The one or more microfluidic devices 404A may be implemented as an interactive progress widget which, when interacted upon, causes a processor at least to populate the matching grid portion with at least a portion of the first sequence of data or at least a portion of the analysis result. A chip timeline view includes information that provides, for example, the context for one or more workflows. For example, a chip timeline view may provide temporal information of one or more operations that are executed or performed on a microfluidic device. As described herein, a workflow may comprise a set of operations performed on a microfluidic device and/or one or more biological samples therein or thereon. A chip timeline view may be generated via, for example, a timeline view activation interactive widget (e.g., a menu command, a command in a context menu, an on-screen widget, or a tab identifier (403A) for a chip timeline view, or any other suitable widget(s), etc.

Some examples of operations may include, without limitations, loading micro-objects, selection of particular micro-objects based on one or more features/characteristics, perfusing one or more reagents into the microfluidic device, iterative processes of perfusing reagents and/or selection of micro-objects based on one or more features/characteristics, and exporting micro-objects from the microfluidic device. In some embodiments, the set of operations or a portion thereof may be pre-determined and coded. In some other embodiments, the set of operations or at least a portion thereof may be detected, observed, recorded, or otherwise represented in one or more regions of interest. A chip timeline may be associated with at least a portion of the operations in the set of operations, and these at least a portion of the operations in the set may be temporally aligned in a chip timeline view to indicate, for example, an absolute temporal relationship (e.g., exact timepoint(s) or time period(s)) or a relative temporal relationship among these at least a portion of the operations in the set.

Operations that may be presented in a chip timeline view may comprise any operation that captures an image or a sequence of multiple images. Some exemplary operations in the set of operations may include, without limitation, loading or exporting of micro-objects, which may include capture beads, wherein the capture beads may be used to detect biological products secreted by biological cells or may be used to capture biological cell products including but not limited to nucleic acids or proteins for identification, e.g., by sequencing, mass spectrometry or any other method of identification; loading or exporting of biological samples; loading or exporting of memory B cells; loading or exporting of plasma B cells (B lymphocyte); loading or exporting plant, bacterial, fungal, other non-mammalian cells, or viral particles and the like; an import or export operation, including introduction of reagents, nutrients, assay components and the like; measurement(s) of optical density; a small volume import or export operation; an optimized penning or unpenning analysis where penning or unpenning may involve moving a micro-object from a flow region of the microfluidic device to an isolated region of the microfluidic device and/or the reverse thereof, and further where penning or unpenning may optionally involve dielectrophoresis (DEP); culturing biological cells of any kind; monitoring a chamber (e.g., a pen) of the microfluidic device; monitoring a pen target number, where the target number may include a desired or selected number of cells within a chamber (e.g., a pen); unpenning micro-objects from regions of interest comprising multiple micro-objects or biological samples; imaging and counting the number of micro-objects or biological samples; multi-spectral time-lapsed imaging; TPS (target pen selection) imaging (e.g., where TPS comprises one or more of identifying, selecting, and/or moving micro-objects to or from a chamber/pen); TPS imaging subsequent to adjustments to microfluidic chip conditions (e.g., temperature, medium, etc.) for the purposes of monitoring the culturing of a biological sample; capturing assay (e.g., monitoring kinetics or thermodynamic properties of visualizable molecules for example fluorescent or fluorescently labeled molecules, where kinetic or thermodynamic properties including but are not limited to diffusion rates and binding kinetics); capturing assay with or without template(s) (e.g., where templates comprise established criterion for assigning one or more regions of interest, generating a score, or performing one or more other characterizations of the biological samples); a capturing assay with unload list generation (e.g., where unload list comprises a list of regions of interest comprising one or more biological sequences that meet one or more pre-set criterion, wherein the criterion is established from one or more characteristics associated with an image sequence or data sequence derived from a region of interest); diffusion assays, including non-limiting examples such as DiGr (Spotlight Diffusion Gradient or "digger") assay (e.g., wherein diffusion of a fluorescent molecule is monitored in a region of interest), DiGr spotlight assay (e.g., wherein a fluorescent molecule including but not limited to accumulation of fluorescence resulting from a fluorescent molecule is monitored in a region of interest), DiGr spotlight reference images (e.g., images taken prior to the start of a DiGr assay and/or images taken prior to the start of a DiGr assay compared with images taken at a later time); detection of a detectable signal from a micro-object, which may be a bead, e.g., a capture bead or which may be a cell; detection of a detectable signal from a soluble reporter molecule: secreted biological product complex; detection of a detectable signal from a region of interest surrounding a micro-object; unloading, e.g., unpenning, of CLD (cell line development), e.g., unloading a micro-object or biological sample from a chamber such as a pen; unloading of OptoSeq B-cell receptor (BCR) (e.g., unloading a micro-object including but not limited to a bead comprising one or more DNA or RNA sequences); unloading of cell (e.g., a B cell, eukaryotic cell, prokaryotic cell, yeast cell, mammalian cell, t-cell, or any other type of biological cell); or unloading a micro-object or other object disposed within a region of interest; or any other operations that capture an image or images.

The multi-directional placement widget 408A shown in FIG. 4A may be activated via an on-screen widget 410A and may include five actuatable switches (e.g., up, down, right, left, and center) although it shall be noted that other combinations or arrangement of the same or different number of actuatable switches are also contemplated. A user may actuate one or more of these actuatable switches to control placement of a software object (e.g., a view window) in the user interface. For example, a user may click on "up" and "center" actuatable switches to indicate to the system that the user intends to place the separate object near the top central part on the display. After receiving the user's actuations of these one or more actuatable switches, the system automatically scans the real estate on display to determine which portion(s) of the real estate is not occupied by semantic information or other objects and automatically determines one or more candidate placement positions and/or sizes in response to the user's request.

In some embodiments, a user interface may provide multiple tabs where each tab may be configured by an administrator or a user to display one or more views and their associated data or information. In the example illustrated in FIG. 4A, the current view tab showing a chip timeline view 400A in the current, active tab. In addition, a user may actuate the center actuatable switch of the multi-directional placement widget 408A (e.g., the center square providing a separate function different from the functions respectively provided by the other four squares in the multi-directional placement widget 408A). In response to the user's actuation of the center actuatable switch of the multi-directional placement widget 408A, the system automatically determines a candidate space 406A that may be claimed by the object for insertion 412A which, in this example, is represented as a miniaturized view of a gallery view or a portion thereof. It shall be noted that a candidate space (e.g., 406A) denotes the space that may be claimed by an object for insertion although the object for insertion may or may not necessarily occupy the entire candidate space.

Figure 4B:
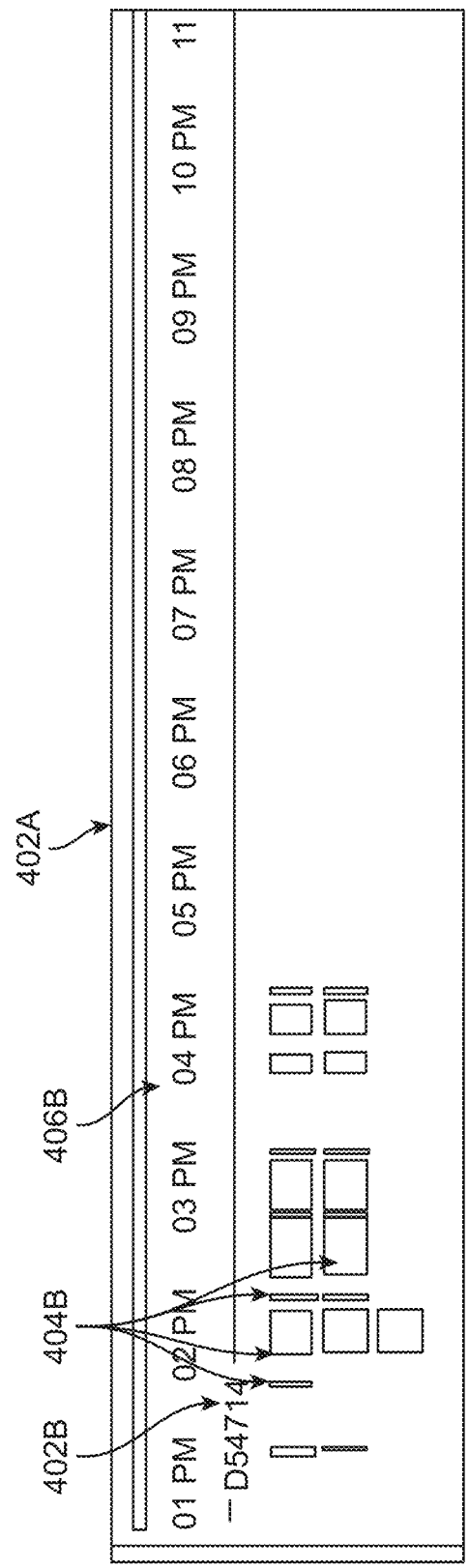
FIG. 4B illustrates a zoom-in view of the data region 402A in FIG. 13A in some embodiments.
Figure 4C:
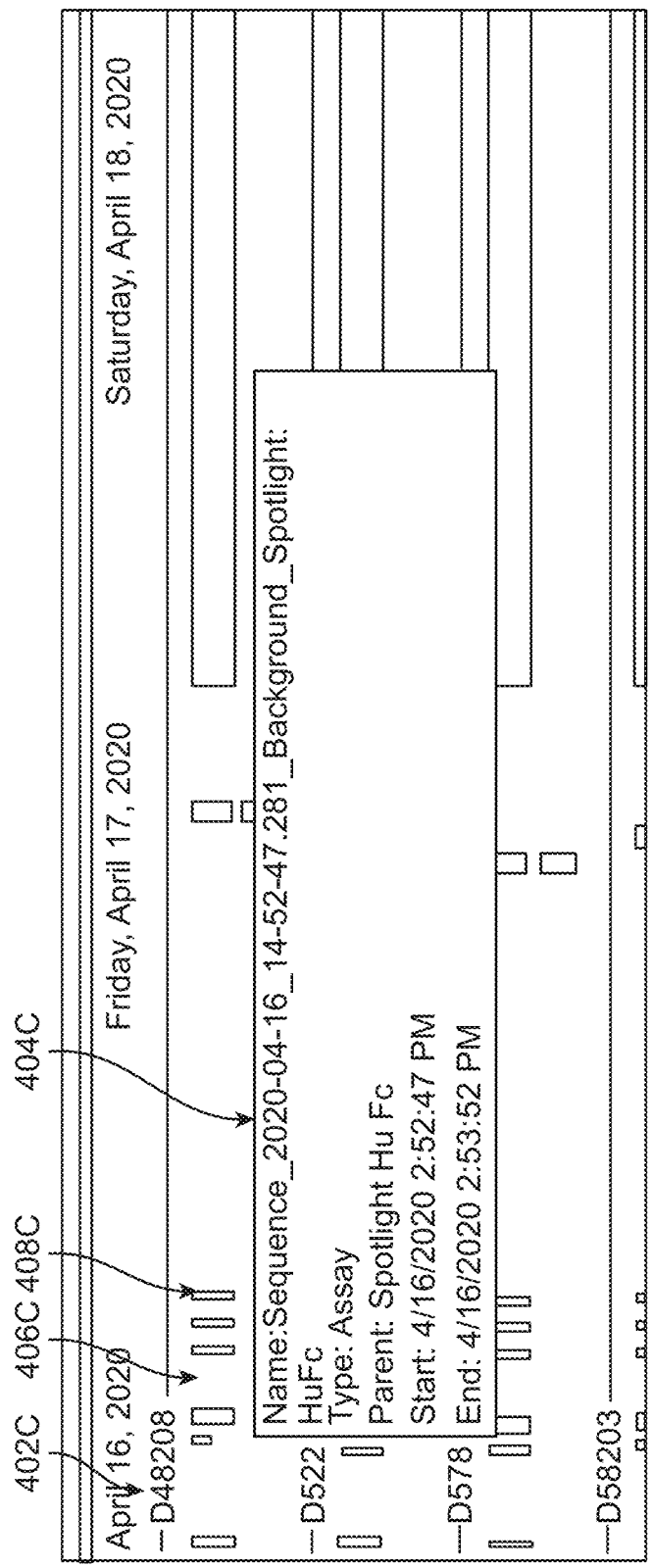
FIG. 4C illustrates more details about a chip timeline view in one or more embodiments.

FIG. 4B illustrates a zoom-in view of the data region 402A in FIG. 4A in some embodiments. FIG. 4C illustrates more details about a chip timeline view in one or more embodiments. More specifically, FIG. 4B illustrates a zoom-in view of the data region 402A in FIG. 4A where a chip timeline view may include a chip timeline for each of one or more microfluidic devices (e.g., a microfluidic device associated with a microfluidic device identifier 402B). In the example illustrated in FIG. 4B, the chip timeline view may include one or more representations or blocks (404B) each of which respectively indicate a corresponding operation in a workflow as well as the corresponding timepoint(s) and/or time period(s), such as time period 406B. In some embodiments, the one or more representations may be color coded to indicate respective, different image sequence types (e.g., TPS (target pen selection), culture and load, assay, selected/mapped, etc.) corresponding to the at least a portion of operations of the set of operations.

Each of these one or more graphic representations may thus graphically indicate a corresponding operation that is done at the timepoint(s) or during the time period (406B). It shall be noted that the temporal label illustrated in FIG. 4B is "hour" although other temporal units (e.g., "day," "minute," etc.) may be used. In some embodiments, the temporal labeling may be altered by, for example, a menu item or command, a user interface action (e.g., by scrolling a wheel on a pointing device), etc. FIG. 4C illustrates more details about a chip timeline view in one or more embodiments. More specifically, FIG. 4C illustrates an example where a graphic representation (e.g., 404B in FIG. 4B) may be interactive. In this example, a graphic representation 402C may be interacted upon to bring up additional information associated with the graphic representation 402C.

For example, a user may hover the cursor of a pointing device over the graphic representation 402C (or click on the graphic representation 402C or other suitable types of user interface actions), and the system automatically shows a pop-up window including additional information or details 404C correlated with the graphic representation 402C. In the example illustrated in FIG. 4C, the additional information or details 404C comprise the name of the image sequence, the type of the workflow (assay), the exact starting timepoint and the exact ending timepoint of an operation corresponding to the graphic representation 402C. It shall be noted that the additional information or details 404C may also comprise static and/or interactive information or details may also be presented in addition to or in the alternative of the information or details illustrated in FIG. 4C.

FIG. 4C further illustrates a summary 406C of the chip timeline that corresponds to the one or more graphic representations plotted with respect to a temporal dimension ("date" in this example). The summary 406C represents a miniaturized or compressed view of the entire chip timeline and includes one or more miniaturized graphic representation 408C. A miniaturized graphic representation, when actuated (e.g., being clicked on), causes a corresponding graphic representation (e.g., 404B in FIG. 4B) to be highlighted or otherwise emphasized in some embodiments. In some embodiments, an activation or actuation (e.g., by clicking on or by hovering a cursor of a pointing device over) of a graphic representation (e.g., 404B in FIG. 4B) also causes a corresponding miniaturized graphic representation 408C to be emphasized graphically, textually, or both.

Figure 4D:
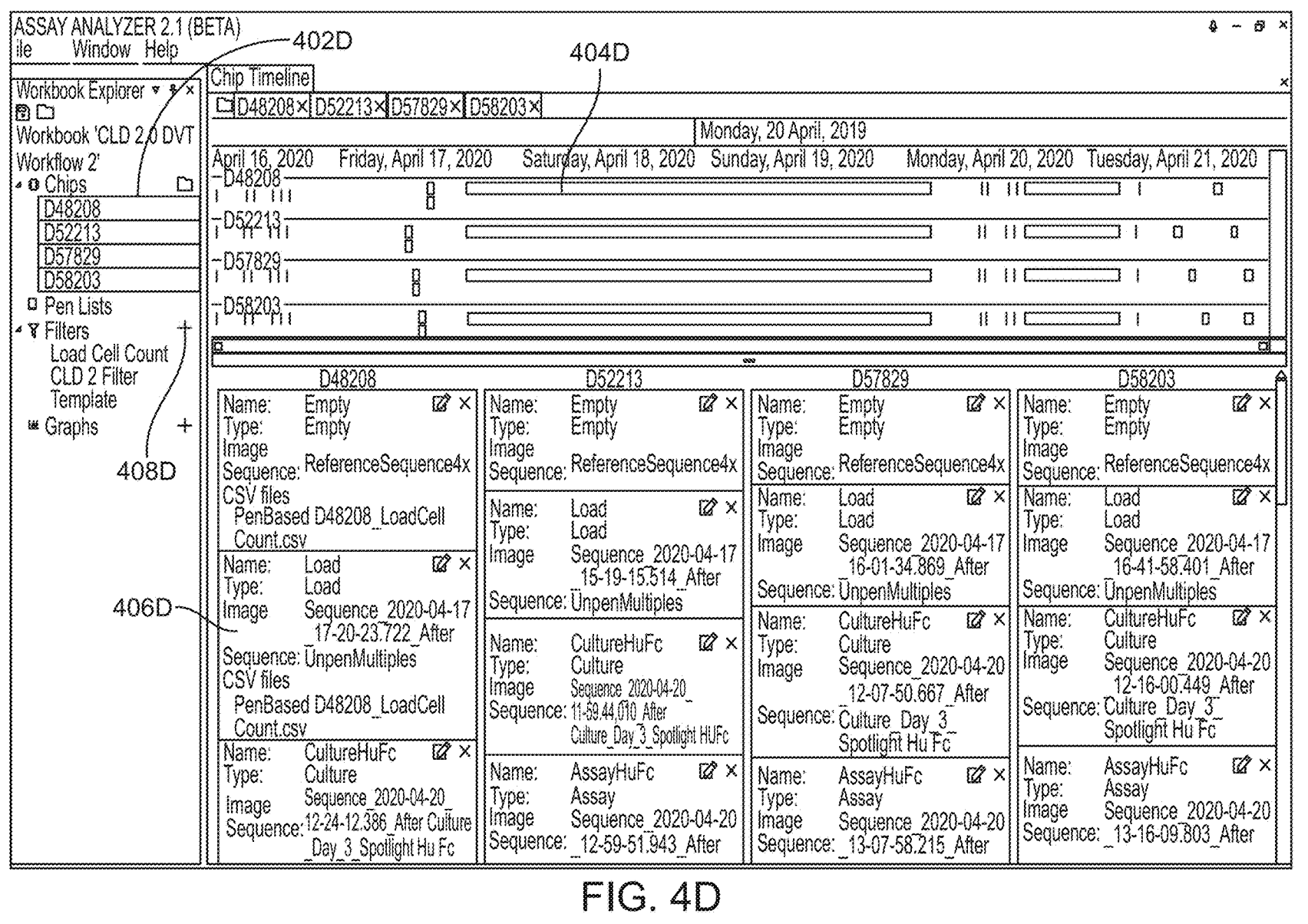

FIG. 4D illustrates another example of a chip timeline view in one or more embodiments. More specifically, FIG. 4D illustrates another example of a chip timeline view in one or more embodiments where the chip timeline view includes four microfluidic device operations 404D, with the horizontal bar or graphical representation (which may be represented in a color such as red), indicating that imaging is being performed with images taken at discrete time points over the time course illustrated in the chip timeline for each of the respective four microfluidic devices 402D identified in the user interface. In this example, each of the four microfluidic devices 402D has an operation 404D that is conducted for the same length of time, e.g., length of the horizontal bar or graphical representation. The operations 404D may be the same operation, e.g., culturing for each of the four microfluidic devices, or in some other embodiments, the operations may be different operations 404D, each performed for the same period of time (e.g., begin and end on the same dates) although different operations may include the same or different workflow tasks and/or workflow stages that may occur (e.g., being and/or end) at exactly the same time point(s) or at different time points due to, for example, different control variables for the different operations. The microfluidic devices identified in this example have microfluidic device identifiers (ID's), unique identifiers associated with the specific microfluidic device (e.g., D48208, D52213, D57829, D58203). These microfluidic device IDs allow the presently disclosed system to correlate the microfluidic device with the timeline and with regions of interest that may be extracted from one or more base images taken at the different time points in the chip timeline. The base images may be segmented (e.g., based on target-based or structure-based features) to generate individual images or image sequences for each region of interest on a microfluidic device, or across multiple microfluidic devices (e.g., across the four microfluidic devices as shown). The images may be quantified or otherwise characterized and displayed in a gallery view, in graphs or plots, the images may be filtered and sorted then displayed, etc.

This example of FIG. 4D further illustrates additional information or details 406D for each of the graphic representations in the chip timeline view. As described above, a graphic representation in the chip timeline view may correspond to an operation performed on a microfluidic device or a portion thereof. The graphic representation of the microfluidic device view may correspond to one or more microfluidic devices, where each block depicted in the chip timeline view corresponds to measurable changes occurring within the microfluidic device (e.g., at region of interest or to features of a region of interest). The changes to the graphic representation may be important to the user and otherwise difficult to identify from an array of hundreds or thousands of biological samples disposed across a microfluidic device where the sample is within or near a region of interest or regions of interest, with image sequences taken from chip timelines exceeding an hour (e.g., hours, days, weeks, etc.). In some embodiments, each graphic representation may correspond to a corresponding block of additional information or details 406D. Such a block of additional information or details 406D may be expandable (and collapsible) to reveal (or hide) additional information or details about the corresponding graphic representation. The example illustrated in FIG. 4D further shows a filter selector switch 408D which, when interacted upon by a user action (e.g., by clicking on the filter selector switch widget in the user interface, etc.), invokes one or more actions to determine one or more filters of one or more filter types. A filter selector switch may further correspond to an attribute selector switch which, when interacted upon, triggers a presentation of one or more filter types and one or more corresponding lists of one or more filter attributes for each filter type. An example of the presentation (e.g., 602I) is illustrated in FIG. 6I described below.

Regions of interest may be determined based on "characteristics" and "features" (e.g., a base image is split into regions of interest based on characteristics and features), where a base image is derived from images taken during a block graphically represented in the chip timeline 404B. Additionally, "characteristics" and "features" of a "region of interest" may be used to sort the region of interest (e.g., "characteristics" or "features" may be captured in an image sequence representing the region of interest, and/or quantified for the purpose of displaying the region of interest in for example a gallery view (e.g., 504E in FIG. 5E).

Figure 4E:
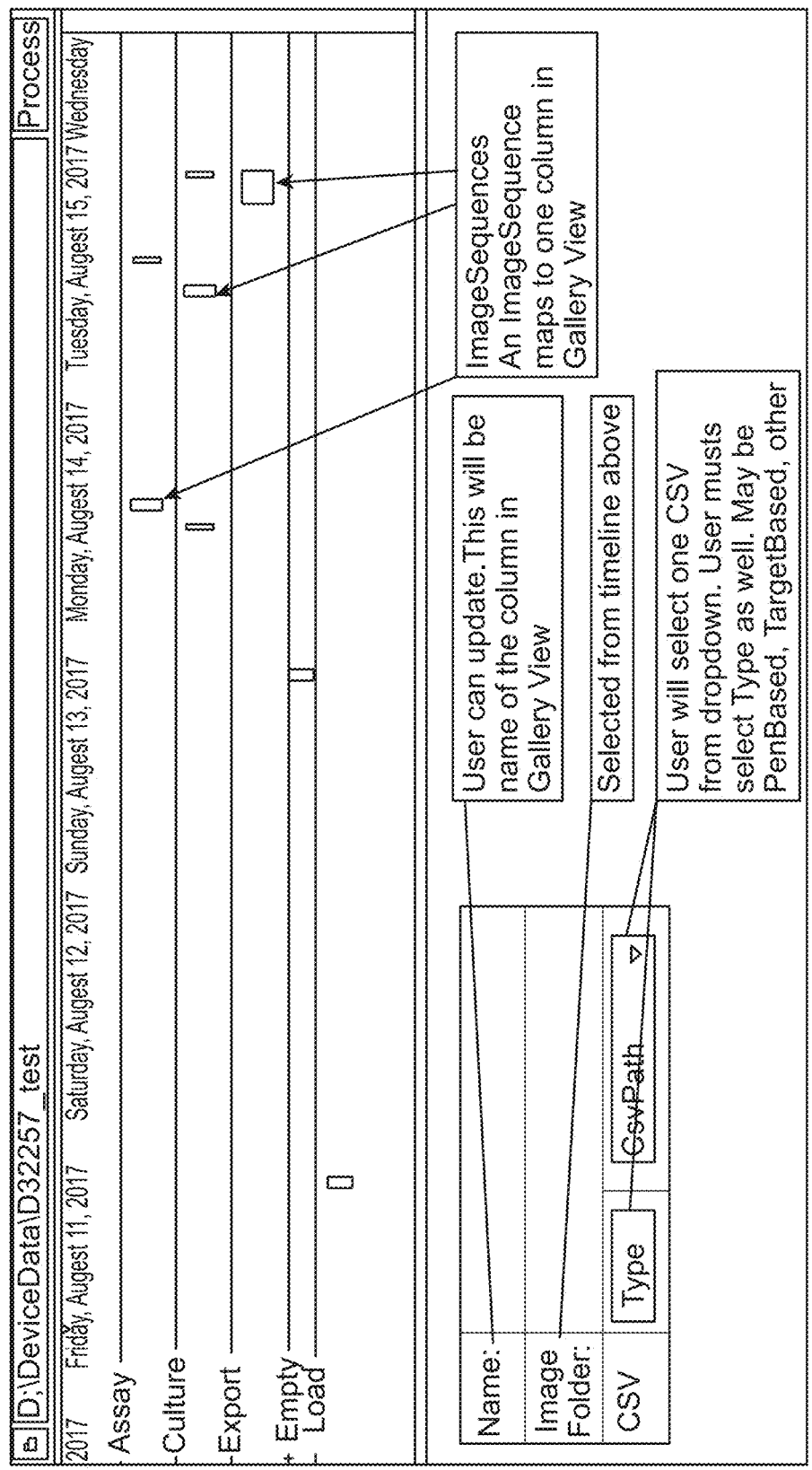
FIG. 4E illustrates an example of a chip timeline view in one or more embodiments.

FIG. 4E illustrates an example of a chip timeline view in one or more embodiments. More specifically, FIG. 4E illustrates that an engine (e.g., a data display engine 50 in FIG. 2A) may display filtered data from the dataset. For example, a data display engine 50 may also display filtered data from a dataset in, for example, a chip timeline view, an example of which is shown in, for example, FIG. 4E. Among other things, a chip timeline view may allow a user to see, via the GUI, a history of image-sequences on or from one or more microfluidic devices. A user may select an image-sequence, the associated data in CSV files, and generate a file in which to store that selection.

Moreover, the engine 50 may operate on a history file to generate a microfluidic device model, and the chip timeline view may be used to create the history file; however, if a history file already exists, a user may update it using the chip timeline view. Recalling that images are captured of the microfluidic device(s), are associated together in image sequence(s), and stored in a dataset. The image sequences are digitally analyzed using known image processing, and data is generated from that analysis. The image analysis may occur when an image is captured, or much later, e.g., at a time of the user's choosing. A user may also elect to have the analysis performed multiple times on the same image sequence. Therefore, to create a microfluidic device model, an image sequence must be matched to the correct data. In this manner, the timeline view may be used to create a mapping of the image sequences and data (408E), the output is the history file, the history file is used to generate the microfluidic device model, and the microfluidic device model is then used by the filter builder and application module, gallery view, and raw data view.

The engine 50 may display a chip timeline view which may include the timeline of one or more microfluidic devices, optionally up to a maximum number (e.g., 4, 6, 8, 10, 12, 14, 16, or the like) of microfluidic devices. Each timeline may show when each image sequence was captured, and optionally may show when analysis was performed. Given all the image sequences for a microfluidic device, the engine 50 allows the user to match an image sequence with a CSV file that includes data for that image sequence. The engine 50 also may allow a user to change other characteristics of the image sequence, e.g., its name.

By way of a non-limiting example, and with reference to FIG. 4E, a user may load one microfluidic device in timeline view, and wants to create a new history file for that microfluidic device's data; the history file may or may not exist at that time. The top half of a pane in timeline view, generated and displayed by the engine 50, may show the timeline for the microfluidic device, based on the image sequence types, and initially the bottom half of the timeline pane may be empty. When the user selects an image sequence in the timeline, in the example of FIG. 4E displayed as small vertical lines or blocks, it will be populated in the bottom matching grid, which is then displayed by the engine 50. In the matching grid, the user may change the "Name" (402E), for example, and the user selects the type and path of data (406E), e.g., a CSV file for that image sequence from a dropdown list of all available data files present in the dataset or a selected subset of the dataset, such as a particular folder (404E), which may include all CSV files being present in the same folder as the image sequence file. The engine 50 may optionally not permit the user to continue if they have not selected at least one data CSV file for all selected image sequences. The engine 50 may permit the user to select as many image sequences from the timeline view as desired. The engine 50 may then display a button or the like, clicking on which generates a history file or a history data structure, or updates a previously created history file or history data structure, and optionally may display another button or the like, clicking on which generates a microfluidic device model.

Figure 5A:
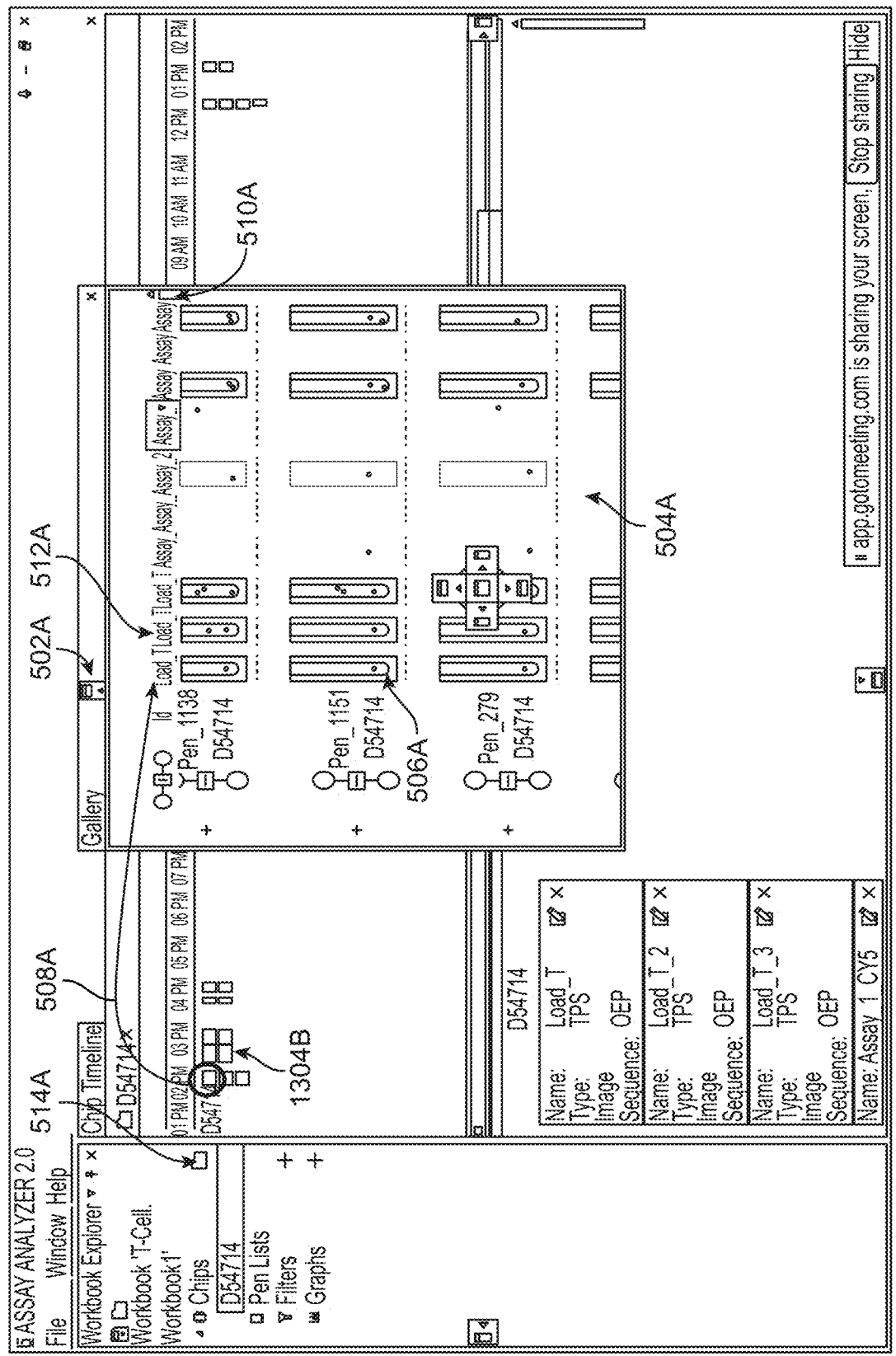
FIG. 5A illustrates another example of actuating a placement widget to insert another object into the chip timeline view in some embodiments.
Figure 5B:
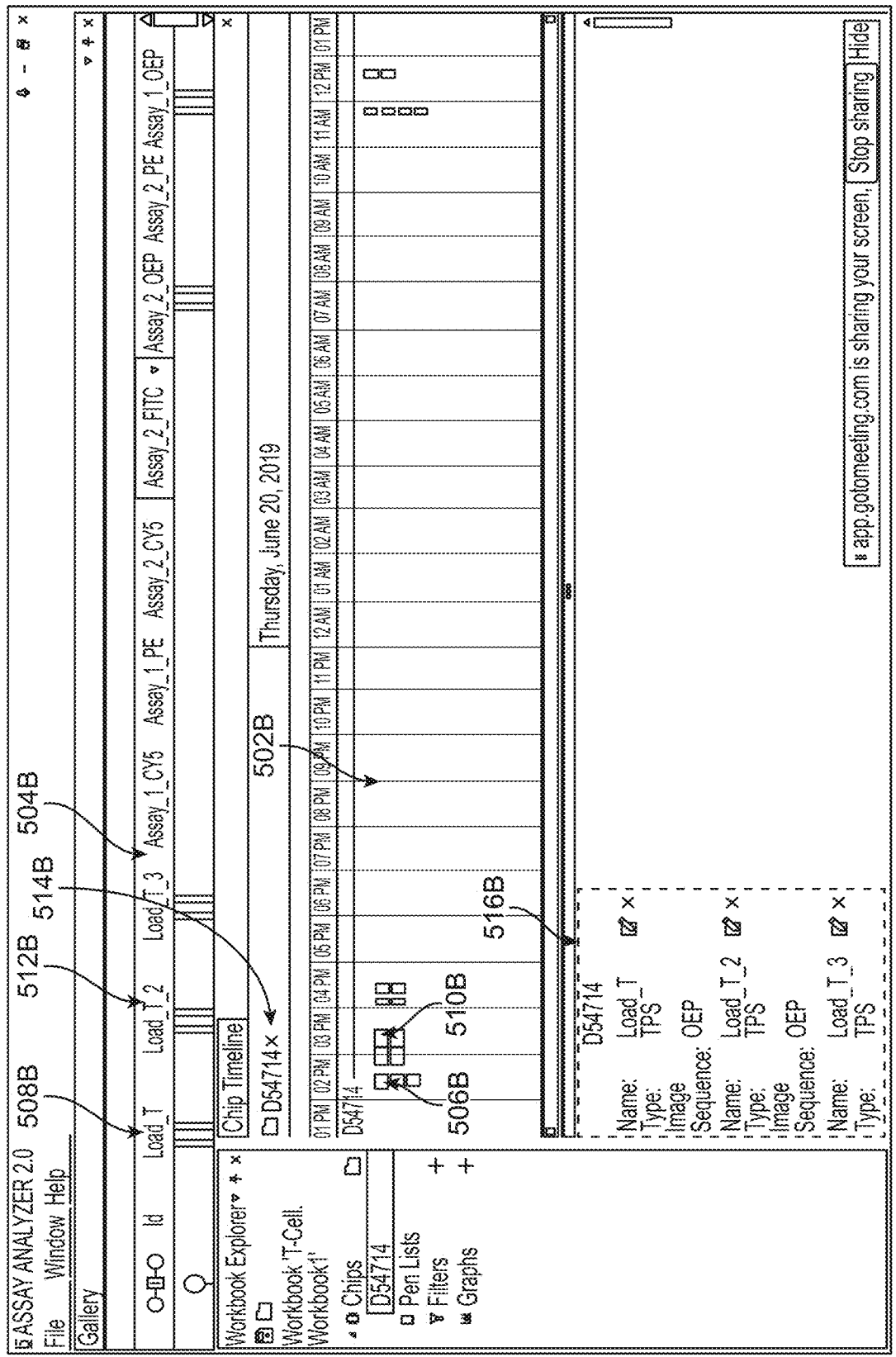
FIG. 5B illustrates the chip timeline window with the inserted gallery view 1604 at the top of the original chip timeline view in some embodiments.
Figure 5C:
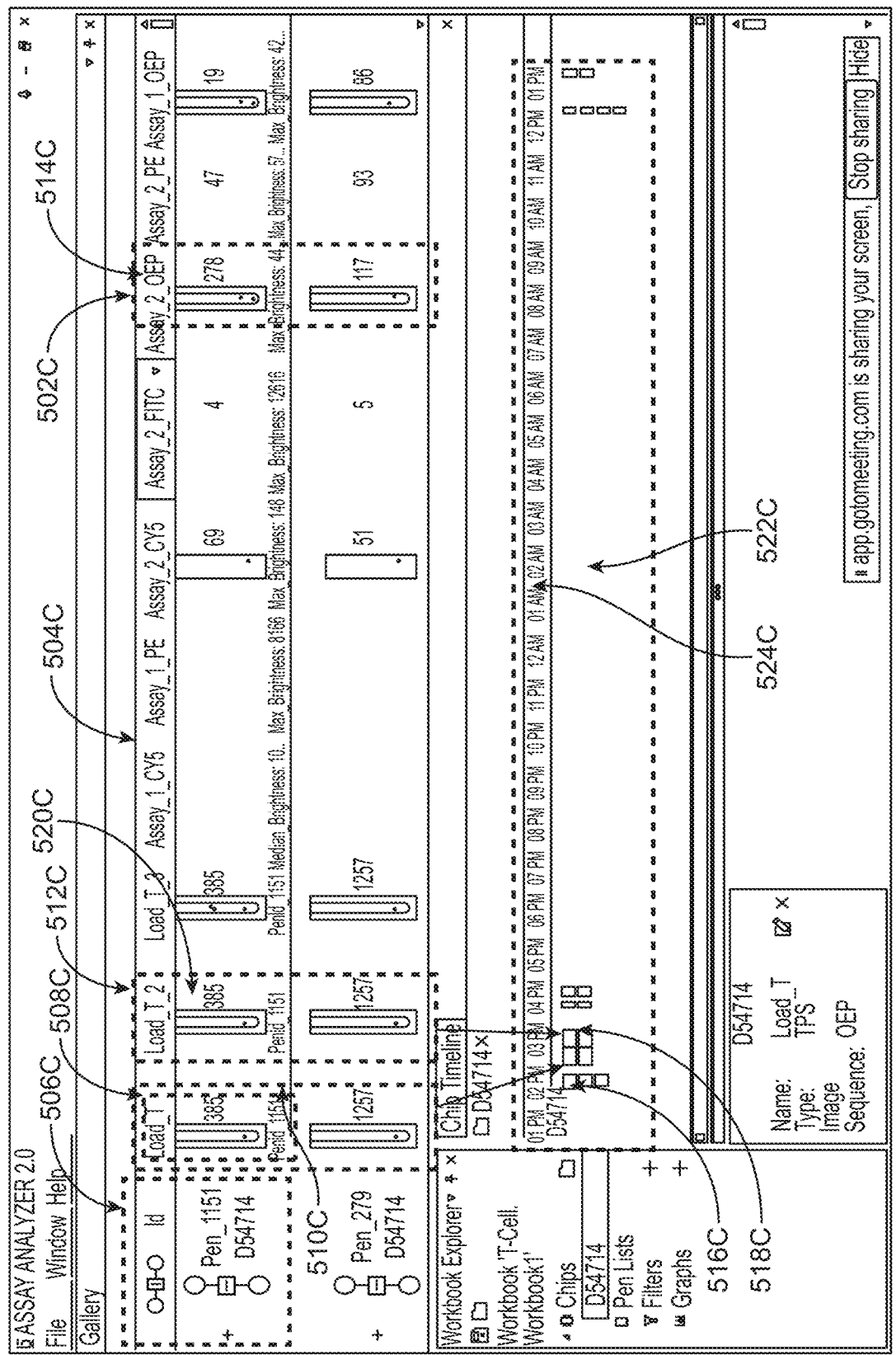
FIG. 5C illustrates the chip timeline window with the inserted gallery view at the top of the original chip timeline view after adjusting the height for the inserted object.
Figure 5D:
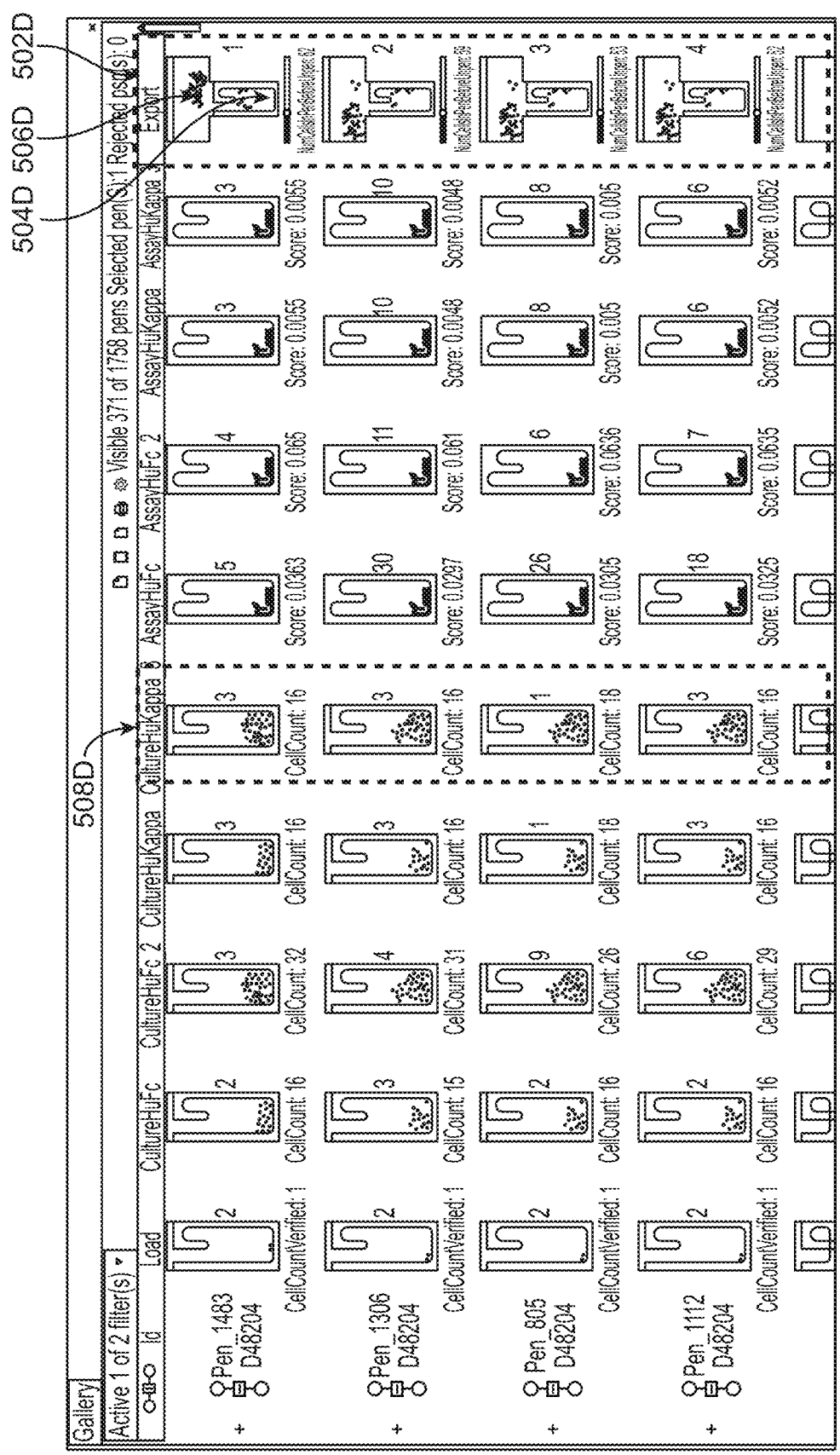
FIG. 5D illustrates another example of a gallery view object that may be displayed in a user interface or a portion thereof in one or more embodiments.
Figure 5E:
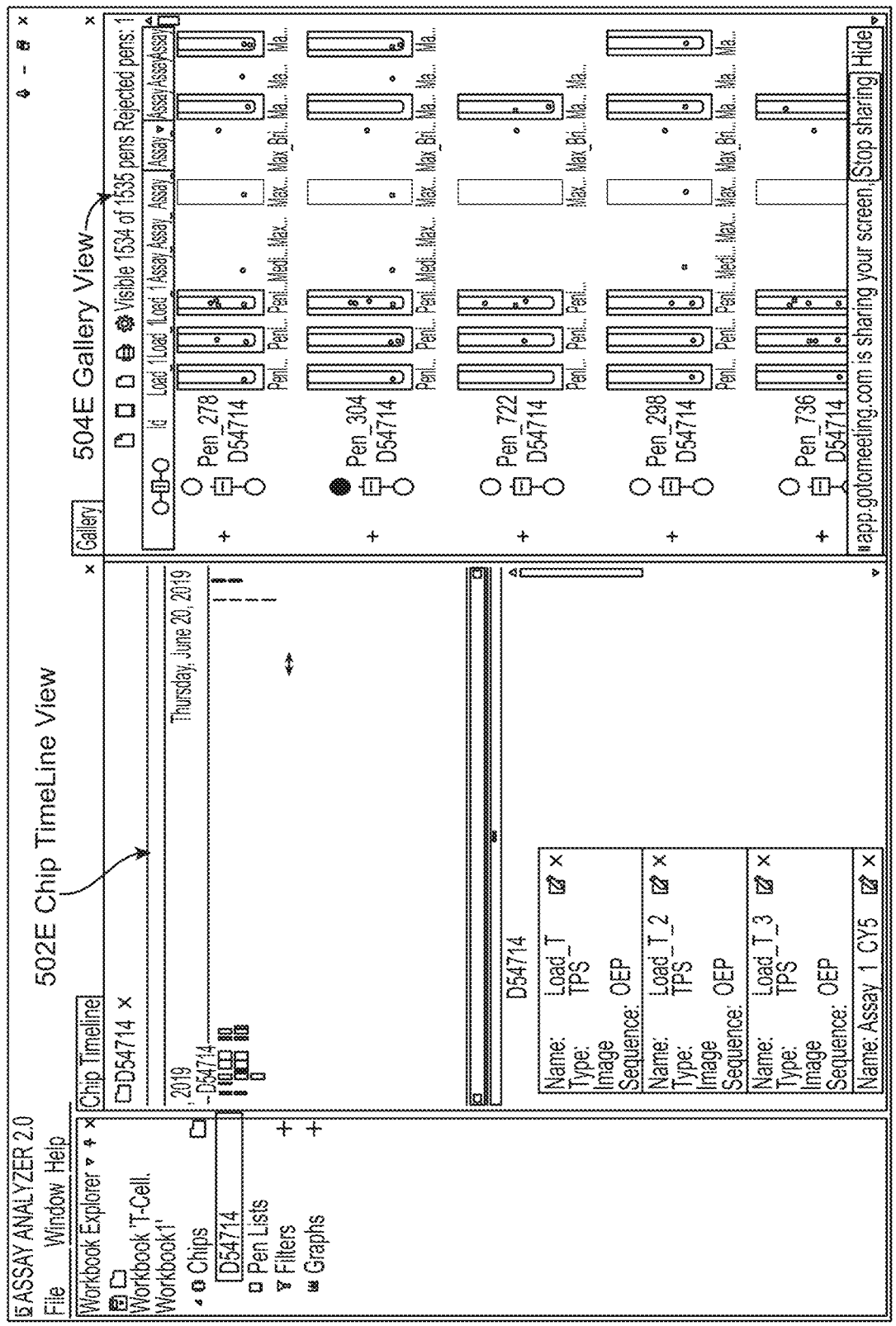
FIG. 5E illustrates an example of adding a gallery view to right of the original chip timeline window or view in FIG. 4A in some embodiments.
Figure 5F:
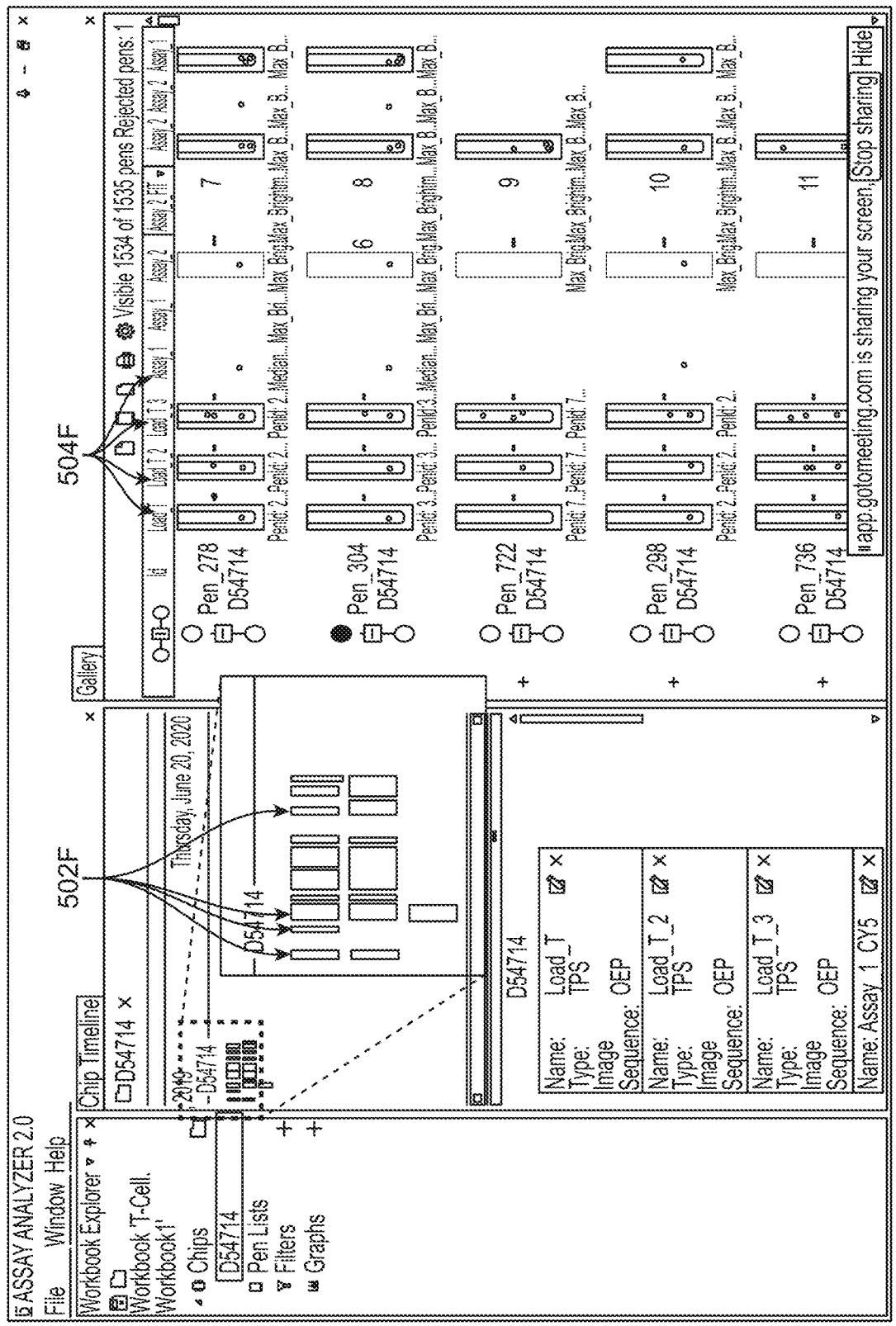
FIG. 5F illustrates the chip timeline window with the inserted gallery view to the right of the original chip timeline view after adjusting the height for the inserted gallery view.
Figure 5G:
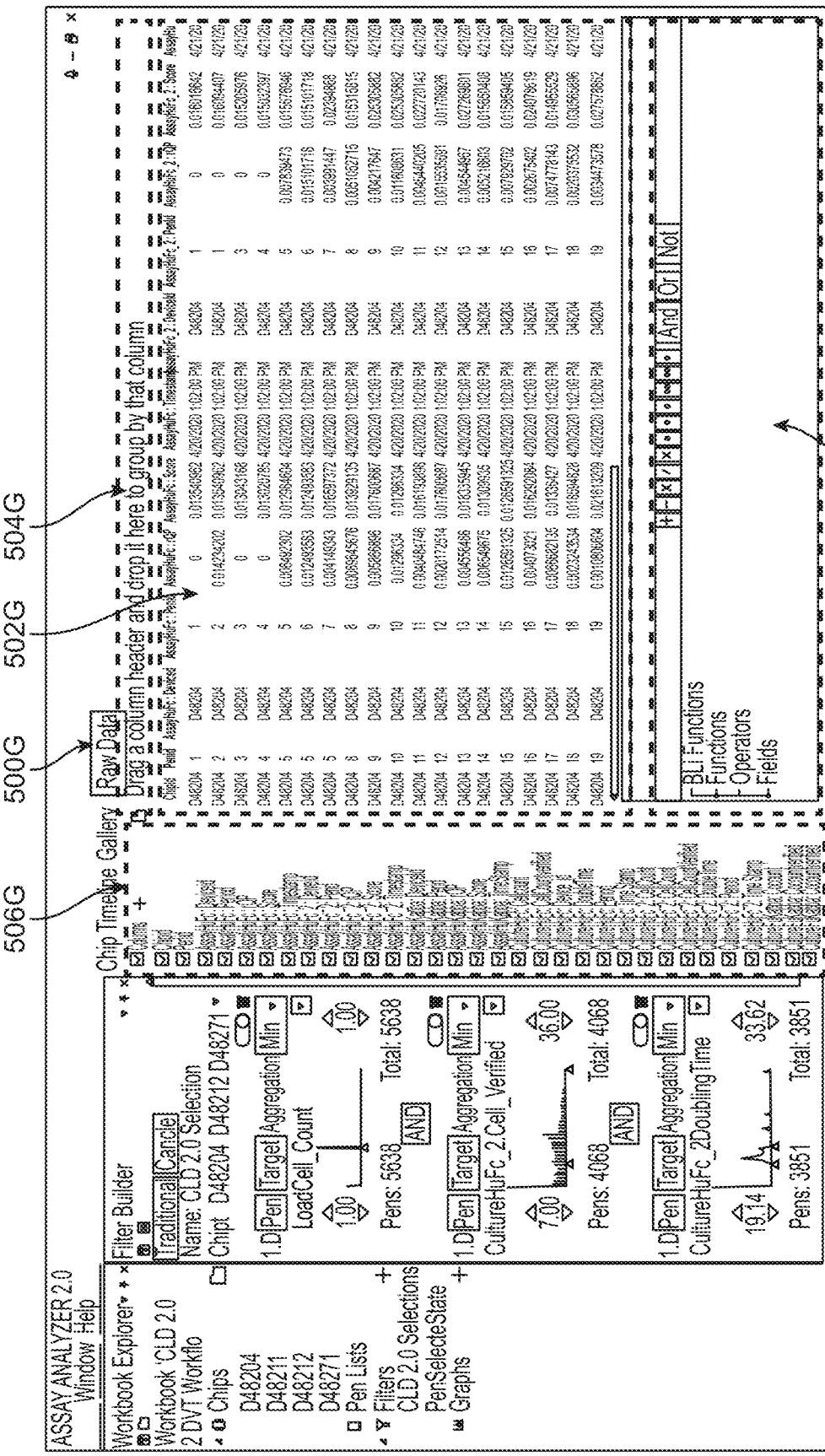
FIG. 5G illustrates an example display of an example data structure that stores raw data for a chip timeline view in one or more embodiments.
Figure 5I:
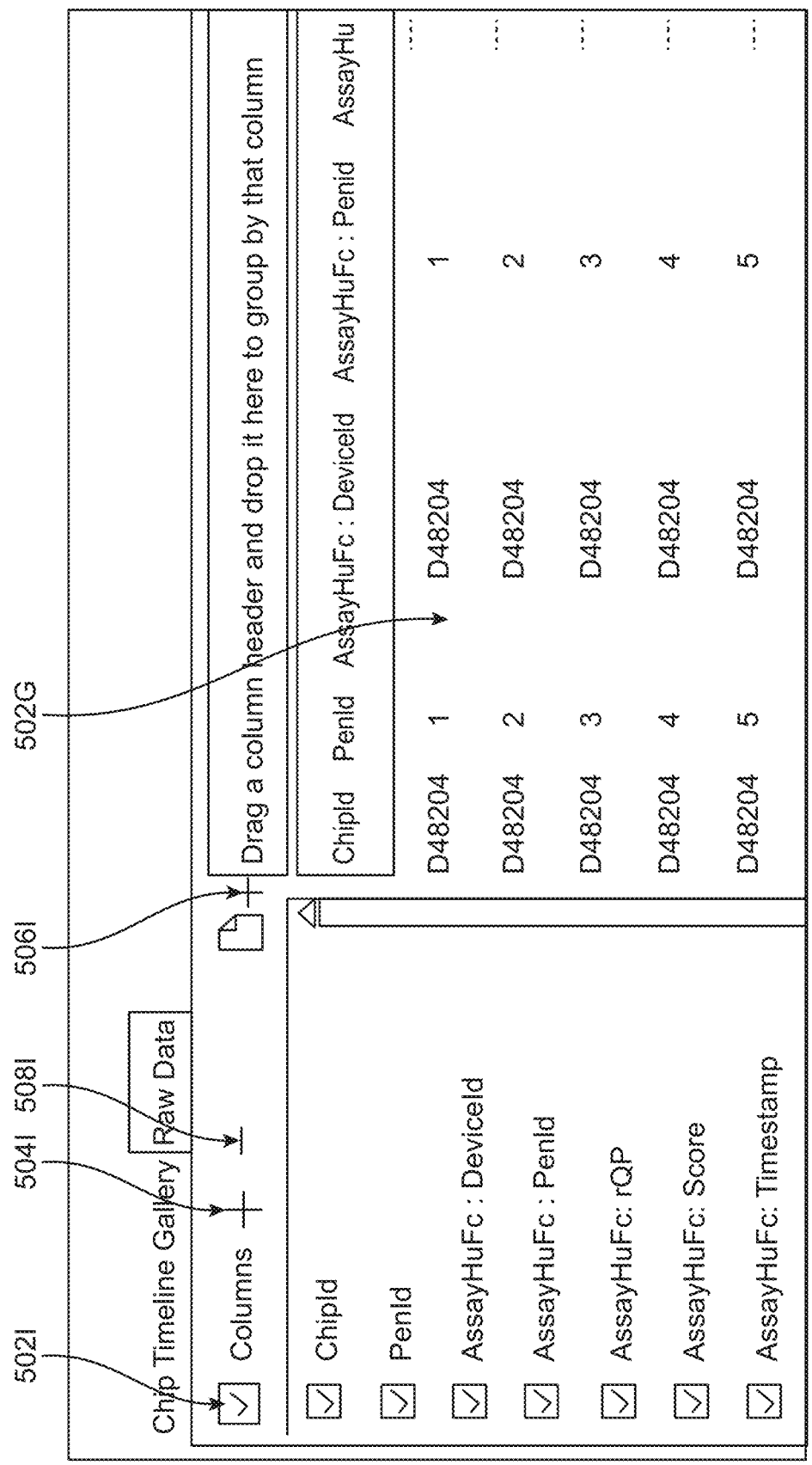
FIG. 5I illustrates more details about a portion of the example display of the example data structure illustrated in FIG. 5G in one or more embodiments.

Another example view that the engine 50 may display is a raw data view, an example of which is shown in FIG. 5I. An example raw data view may be a 2-D (two-dimensional) grid or array with the alphanumeric data of each chamber presented in columns, without corresponding image data; a raw data view may be presented of the entire dataset, or of a subset of that data after filtering as dictated by the user in a filter builder and application module as described elsewhere herein. A raw data view may be more like a traditional spreadsheet view of data, and may include: fields for the user to input formulae to group, sort, filter and select chambers; and/or create new characteristics for chambers; and/or change/update specific values of the data; and/or select/reject large sets of chambers with a single action; or use the data subset the user creates using this view to instruct the engine 50 to generate a gallery view of the results.

Each of the views displayed by the engine 50 described herein may be integrated into a single engine 50, or they may each be a stand-alone engine/application, module, script, plug-in, or program that responds to calls from the user via the GUI (graphical user interface).

While the invention has been described in detail with reference to example embodiments thereof, it will be apparent to one skilled in the art that various changes may be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

FIG. 5A illustrates another example of actuating a placement widget to insert another object into the chip timeline view in some embodiments. More specifically, FIG. 5A illustrates another example of actuating another placement widget 502A to insert another object 504A into the chip timeline view. Once actuated, this placement widget 502A automatically scans the upper portion of the chip timeline window or the display area to determine how to insert the object 504A into the current view or window. In this example, the separate object 504A may comprise a gallery view showing a plurality of chambers having corresponding biological samples therein. By default, the placement widget may automatically determine a top portion of the current window or view for insertion of a new object. The placement widget may be configured or customized to automatically determine another portion (e.g., right, left, bottom, etc.) of the current window or view for insertion of a new object. In this case the object for insertion 504A is the gallery view. The gallery view displays an array of regions of interest 506A with the regions of interest corresponding to the chip timeline. In some embodiments, the user interface may include a processing widget 514A which, when invoked, may generate or identify a data structure (e.g., a data structure storing analysis data for biological samples in a microfluidic device) based at least in part upon an identification of the data structure, one or more other instructions, one or more calls (e.g., an inter-process call or IPC), or any other data (e.g., a pen list, etc.) from another module or interface.

For example, the first graphic representation 508A in the chip timeline corresponds to the first column 512A in the gallery view to be placed. It shall be noted that although the placement of the gallery view is not yet finalized in FIG. 5A, the miniaturized gallery view (e.g., a snapshot of the corresponding gallery view or the object for insertion 504A) may dynamically reflect the correspondence between the timeline (e.g., the specific designator 508A of a plurality of designators 510A that correspond to respective blocks of the chip timeline) and the corresponding portion of the gallery view (e.g., 512A). In some embodiments, the images for regions of interest (e.g., 506A) illustrated in the gallery view are clipped from a base image captured for a microfluidic device or a portion thereof during the chip timeline. The designations above the columns in the gallery view correspond to the blocks of the chip timeline. A user may customize these dependent on the workflow being performed or other needs or interests of the user.

A region of interest may be target-based or structure-based as described herein with reference to, for example, FIG. 1. Based at least in part upon whether a region of interest is structure-based or target-based, data correlated with one or more corresponding attributes, characteristics, or properties, etc. related to the region of interest may be identified and correlated with the region of interest. For example, one or more attributes, characteristics, or properties, etc. correlated with a biological sample may be identified and correlated with a target-based region of interest. Similarly, one or more attributes, characteristics, or properties, etc. correlated with a structure of a microfluidic device or a portion thereof may be identified and correlated with a structure-based region of interest. Moreover, a gallery view may include or illustrate data correlated with only target-based regions of interest, only structure-based regions of interest, or both target-based and structure-based regions of interest. Multiple regions of interest in a gallery view may be further processed or manipulated (e.g., filtered, clustered, ranked, analyzed, etc.) based at least in part upon one or more of the aforementioned attributes, characteristics, or properties, etc. correlated with these multiple regions of interest by using various functionalities, processes, and/or techniques described herein.

In some embodiments, a gallery view may be compiled based at least in part upon one or more characteristics correlated with a region of interest. A characteristic may be accessed over an image sequence for the region of interest in some embodiments. In some of these embodiments, a characteristic corresponding to a region of interest may be associated with one or more timepoints of a workflow. In some embodiments, a characteristic correlated with a region of interest may be accessed based at least in part upon one or more structural features of a microfluidic device and/or one or more features of a target (e.g., a biological sample, a characteristic thereof, etc.) that is disposed in or on the microfluidic device.

Some examples of characteristics with a target may include, without limitations, a size attribute of a plurality of biological samples in the microfluidic device or a region of interest, a maximum brightness attribute for the plurality of biological samples, a minimum brightness attribute for the plurality of biological samples, a first pixel count attribute in a first direction for a centroid of a biological sample, a second pixel count attribute in a second direction for the centroid of the biological sample, a size attribute for the centroid of the biological sample, a biological sample count attribute, a verified biological sample count attribute, a biological sample type attribute, or any other suitable, required, or desired attributes, or any combinations thereof. The brightness attribute, as described above may be determined by brightfield (e.g., visible wavelengths), fluorescent, infrared, ultraviolet, or luminescent illumination detection.

Some examples of characteristics associated with a structure-based feature or characteristic (e.g., a chamber or portion thereof, a flow channel, a portion of the microfluidic circuit that is located immediately above and/or immediately adjacent to the chamber for example between a chamber and a flow channel such as a connection region of a sequestration pen as described herein, etc.) may include, without limitations, one or more of a total count of biological samples, a score correlated with the structure feature or characteristic, one or more filter attributes, one or more characteristics correlated with at least one aspect of an analysis (e.g., an assay, a sequencing, etc.) and/or the result thereof, a time lapse index characteristic, a device identifier for the microfluidic device, a score characteristic of the plurality of chambers, a gate path index, an area pixel characteristic, a background pixel characteristic, or a median brightness characteristic for the plurality of biological samples, or any other suitable, required, or desired characteristics, or any combinations thereof.

Structural features of a microfluidic device may be responsible for functional effects detectable at the region of interest and captured in the image sequences of a region of interest. Structural features may comprise features associated with chambers (e.g., pens) disposed on the microfluidic device. Chambers, like other circuit elements of the microfluidic device, may comprise structural characteristics that restrict flow or isolate one or more biological samples (e.g., isolate the one or more biological samples from direct flow) such that images taken of a region of interest comprising the biological sample express features that are measurable, dynamic, and/or result in changes that are detectable in images or image sequences representing the one or more regions of interest. Measurable features may be correlated with a biologically relevant property and may be associated with a score or other quantifiable metric.

Two aspects may be of importance for assessing or analyzing a biological sample disposed within the microfluidic device—specifically the region of the microfluidic device (e.g., structure-based region of interests) and the phenomena that a particular object (e.g., biological sample, micro-object, etc.) is exposed to within the microfluidic device (e.g., a target-based region of interests). In the above microfluidic device and in other such microfluidic devices with target-based and structure-based regions of interest, a user is interested in understanding the phenomena occurring at the region of interest (e.g., where a biological sample for example a single biological sample is disposed, or in a region proximal to where a biological sample is disposed), therefore associating base images with a particular operation is critical to determining the base images that are relevant to the regions of interest that a user is most interested in. In some cases, the filter selection tool or graphing tool (e.g., a filter builder and application module) may be used in accordance with the chip timeline to generate a gallery view of the regions of interest that are most relevant to the user's interest or needs. Without this tool, performing this type of assessment for hundreds, thousands, or even tens of thousands of biological samples across one or more fields of view, and/or one or more microfluidic devices, etc. may be prohibitive without tools equipped to perform such an operation and to provide and display the automatically assessed results for interpretation by the user.

Example microfluidic devices from which images (base images, image sequences, single images, etc.) may be derived, may comprise one or more microfluidic circuits or components or regions within a microfluidic circuit. In some embodiments, structure-based regions of interest of the microfluidic circuit may comprise regions proximal to regions of flow, regions where direct flow is impaired, and/or regions separated from flow by a single opening. In further embodiments, microfluidic circuits may comprise discrete structural features including chambers (e.g., sequestration pens, pens, traps, etc.), where micro-objects may be isolation from direct flow.

FIG. 5A further illustrates the insertion of a separate object 504A (e.g., a gallery view object) into the chip timeline view (E.G., 400A in FIG. 4A) after a user initiates the addition of an object (e.g., 504A) by using an view activation interactive widget (not shown) represented as a menu command or a clickable icon in the user interface, invokes a placement widget (e.g., 502A), and confirms the placement position of the separate object by using, for example, one or more user interface commands (e.g., dropping the inserted object 504A at a specific location in the user interface or selecting a position by manipulating a multi-directional placement widget, etc.) The size of the separated object on display may be adjusted either before or after the separate object is placed on display. The system may optionally adjust the position, aspect ratio, and/or size of another object on display to accommodate the inserted separate object.

FIG. 5B illustrates the chip timeline window with the inserted gallery view 504B at the top of the original chip timeline view in some embodiments. More specifically, FIG. 5B illustrates the chip timeline window with the inserted gallery view 504B having a gallery structure at the top of the original chip timeline view 502B. In some embodiments, the size, aspect ratio, and/or position of this inserted object may be adjusted before or after the insertion of this object. Moreover, a first graphical representation 506B indicating an occurrence of an activity in the chip timeline 502B corresponds to a first subset of a gallery view (e.g., a first column 508B in the gallery view 504B); and a second graphical representation 510B indicating an occurrence of another activity in the chip timeline 502B corresponds to a second subset of a gallery view (e.g., a second column 512B in the gallery view 504B).

A gallery structure includes a structured arrangement of static and/or dynamic information or data such as textual, graphical, and/or image analysis results, input data, information correlated with the biological samples in an analysis, metadata, etc. A gallery structure may be arranged in many different ways, and FIG. 5B merely illustrates one specific arrangement. Moreover, a gallery structure may be structured based on one or more characteristics such as one or more identifiers (e.g., device identifier of a microfluidic device, chamber identifiers), one or more characteristics correlated with the analysis (e.g., fluorescent labeling molecules such as FITC or fluorescein isothiocyanate, Cy3 dye, Cy5 dye, Phosphatidylethanolamine or PE, etc.), one or more properties of the analysis and/or the biological samples, one or more quantifiable metrics correlated with the analysis and/or to the biological samples, time labels, and/or identifiers of workflow items in a workflow, etc.

A gallery structure may be indexed with a unique key (e.g., a unique identifier from the aforementioned identifiers) or a combination of keys (e.g., a combination of multiple identifiers from the aforementioned identifiers) each of which uniquely identifies a specific gallery substructure (e.g., a column or a row) in the gallery structure. For example, a gallery structure may include one or more columns or rows of one or more keys that may be used in indexing the gallery structure. Each gallery substructure comprises one or more gallery fields, and each gallery field may store an object that comprises, for example, various data or information described herein. As another example, a gallery structure may be indexed with a first key column storing respective unique chamber identifiers for a plurality of chambers in a microfluidic device. As another example, a gallery structure may be indexed with a first key column storing respective unique chamber identifiers for a plurality of chambers in a microfluidic device and a second key column storing a device identifier of the microfluidic device. Yet as another example, a gallery structure may be indexed with a first key column storing a combination of respective unique chamber identifiers for a plurality of chambers and the microfluidic device identifier of the microfluidic device. It shall be noted that although what a gallery view having a gallery structure in FIG. 5B appears to be a two-dimensional table structure having each column corresponding to a specific identifier for a plurality of chambers at multiple time points, a gallery structure is not limited only to a two-dimensional data structure (e.g., database table(s)) and may have more than two dimensions in some embodiments. On a two-dimensional display device such as a computer monitor, only two-dimensional representations may be displayed. Therefore, the techniques described herein retrieve pertinent data from a gallery structure for proper display on such two-dimensional display devices.

Moreover, the gallery structure illustrated in FIG. 5B includes multiple columns each of which corresponds to a specific identifier. Each column has one or more rows that respectively represent data that was computed, gathered, generated, and/or captured for one or more corresponding chambers at the same time point or temporal period of a plurality of time points or temporal periods. Different columns correspond to different attributes, characteristics, properties, etc. correlated with the analysis (or analyses) of interest and/or the biological samples therefor. Because the gallery structure may be structured or even indexed (e.g., indexed based on one or more keys).

With this correspondence between a chip timeline view and a gallery view, the actuation or activation of one corresponding item (e.g., the first subset 508B) may be configured to automatically trigger the actuation or activation of the other corresponding item (e.g., the corresponding first graphical representation 506B) so that one or both of these two entities on display may be emphasized (e.g., graphically emphasized). It shall be noted that the correspondence between a chip timeline view and a gallery view may be optional. In some embodiments, such correspondence may be configurable in one or more user interface views described herein.

FIG. 5B further illustrates a delete widget (514B) which, when invoked in the user interface, causes at least the processor to remove the microfluidic device and data correlated with the microfluidic device from the second view. FIG. 5B further illustrates a representation (516B) of a chip folder structure that comprises a plurality of chip fields for the microfluidic device having the array of chambers. Chip data of a microfluidic device may be populated into a first chip field in the chip folder structure. The first chip field in the chip folder structure may be rendered as the representation (516B) in a user interface by for example, clicking on an interactive folder widget (not shown) which, when interacted upon, invokes one or more candidate actions that are correlated to a view in the user interface and may be performed on a folder (e.g., a folder that stores data correlated with data of biological samples in a microfluidic device).

FIG. 5C illustrates the chip timeline window with the inserted gallery view at the top of the original chip timeline view after adjusting the height for the inserted object. More specifically, FIG. 5C illustrates the chip timeline window with the inserted gallery view (or any other inserted object) 504 at the top of the original chip timeline view after adjusting the height for the inserted object. As described herein, the inserted gallery view 504 may include the corresponding images of a plurality of regions of interest that may be only target-based, only structure-based, or both target-based and structure-based. The image of each region of interest corresponds to pertinent data such as one or more attributes, characteristics, or properties, etc., that are determined based at least in part upon the type (e.g., target-based or structure-based) of the region of interest.

Moreover, FIG. 5C further illustrates an example structure of a gallery view. It shall be noted that although FIG. 5C illustrates a chip timeline window with an inserted gallery view object, the example structure of the gallery view illustrated in FIG. 5C may also apply to other any gallery views in one or more other views in some embodiments. In these embodiments, a gallery view 504C may include a plurality of gallery sub-structures such as the columns 502C, 510C, and 512C. It shall be noted that although the gallery substructures are arranged in respective columns, a gallery substructure may also be arranged in a row or in any other manner in some other embodiments.

A gallery sub-structure (e.g., 510C) may include one or more gallery fields 508C. That is, in some embodiments where only one row is displayed in a user interface (e.g., in a timeline view), a gallery sub-structure includes only one gallery field. In some other embodiments where multiple rows are displayed, a gallery sub-structure includes multiple gallery fields. A gallery sub-structure may be configured to include a sufficient number of gallery fields that accommodate at least the total number of target-based and/or structure-based regions of interest in a microfluidic device in some embodiments so that the corresponding data (e.g., an image or image sequence of a region of interest) of each region of interest may be displayed in the respective gallery field. Regardless of whether a sub-structure is arranged in a column, a row, or any other form, the sub-structure may also be interchangeably referenced as a linear structure of data in some embodiments where the sub-structure is arranged in a linear manner. Other arrangements of data different from a linear arrangement such as a circular arrangement, a portion of a circular arrangement, or any other suitable arrangement in a user interface may also be implemented in some other embodiments.

In some embodiments, a gallery field in a gallery sub-structure corresponds to an image of a target-based or structure-based region of interest. As described herein, this image may be displayed as a static image or as an dynamic interactive object with which a user may interact by, for example, clicking on and/or right clicking on the image object or clicking on one or more widgets, icons, menu items, etc. in the user interface, In addition or in the alternative, the size, shape, and/or content of an image for a region of interest may be dynamically determined from, for example, a base image based at least in part upon, for example, an analysis type, a specific workflow stage or workflow task at which the base image is captured, the type of the region of interest (e.g., target-based or structure-based), or any other suitable, desired, and/or required attributes, characteristics, properties, or metrics.

A gallery sub-structure may also correspond to an identifier or an attribute correlated with a region of interest 514C which may further correspond to a target-based or a structure-based attribute, characteristic, property, or quantifiable metric, etc., which in this case is identified as "Assay_2_OEP" indicating a point in the assay performed on the biological micro-objects within pen 1151. In some embodiments, an identifier or an attribute 514C may correspond to a specific target-based attribute, characteristic, property, or quantifiable metric (e.g., Fluorescein isothiocyanate or FITC, a major diameter, a minor diameter, centroid, circularity, affinity to, for example, antibodies, etc.) correlated with the biological samples analyzed with a plurality of chambers of a microfluidic device. As another example, a particular structure-based attribute, characteristic, property, or metric correlated with any aspect of a microfluidic device or a portion thereof may include a region of interest, any geometric, physical, or other characteristics of a microfluidic device or a portion thereof, etc. That is, various embodiments described herein include regions of interest that may include only one or more target-based regions of interest, only one or more structure-based regions of interest, or both at least one target-based region of interest and at least one structure-based region of interest. Various embodiments may also include one or more attributes, characteristics, properties, or metrics that may further include only one or more target-based attributes, characteristics, properties, or metrics correlated with a biological sample, only one or more structure-based attributes, characteristics, properties, or metrics correlated with a microfluidic device or a portion thereof, or at least one target-based attribute, characteristic, property, or metric and at least one structure-based attribute, characteristic, property, or metric.

In some embodiments, a gallery sub-structure may thus be sorted, ranked, ordered, filtered, clustered, or otherwise processed with respect to its identifier. In some embodiments where a plurality of regions of interest rendered in a gallery sub-structure are ranked, sorted, or ordered with respect to the identifier of gallery sub-structure, the respective orders or ranks (520C) for the corresponding regions of interest may be displayed in relation to the corresponding regions of interest. In this example illustrated in FIG. 5C, the respective orders or ranks of a plurality of regions of interest are displayed in the respective vicinity of the plurality of regions of interest. In some embodiments as illustrated in FIG. 5C, a multi-state selector 506C may be rendered for a row where a column corresponds to a plurality of rows. A multi-state selector 506C allows a user to select a state for a specific row to which the multi-state selector corresponds. For example, a user may select a state among "selected," "deselected," "undecided," or any other suitable state(s), etc. The identifier or attribute 514C may be created as a widget such as an identifier widget which, when receiving an identifier change input from the user interface, triggers an instruction that changes a first identifier of the first sequence of data.

FIG. 5C further demonstrates an example of the respective correspondence between a plurality of gallery sub-structures and a plurality of graphic representations in a chip timeline view (522C) having an interactive, matching grid portion (524C) indicating temporal relationships of a plurality of workflow tasks and/or workflow stages in an analysis of biological samples in a plurality of chambers in a microfluidic device. For example, a first gallery sub-structure 510C corresponds to a first graphic representation 516C in a chip timeline view; and a second gallery sub-structure 512C corresponds to a second graphic representation 518C in a chip timeline view. It shall be noted that the correspondence between a gallery view and a chip timeline view may be optional. Moreover, the correspondence therebetween may be established or enabled at least by correlating or linking various pieces of data pertaining to the analysis of biological samples in a plurality of regions of interest of a microfluidic device with each other. Such a correlation or linking is described with reference to, for example, FIG. 1 above.

Moreover, FIG. 5C illustrates adjusting the size and/or aspect ratio of one or more objects on display. Compared with FIG. 5B, FIG. 5C illustrates the on-screen display after the height of the object (504B in FIG. 5B and 504C in FIG. 5C) has been increased. The tool automatically adjusts the size and/or aspect ratio of other objects on display to become the resized and/or repositioned chip timeline view (e.g., 502B in FIG. 5B and 522C in FIG. 5C) in order to accommodate the adjusted object.

In some embodiments, the current view tab showing a chip timeline view 522C in the current, active tab may be configured to accommodate one or more addition objects (e.g., a gallery view object, a graph view object, etc.) A user may actuate the center actuatable switch of the multi-directional placement widget (e.g., a multi-directional placement widget 408A in FIG. 4A). In response to the user's actuation of the center actuatable switch of the multi-directional placement widget, the system automatically determines a candidate space that may be claimed by the object for insertion (e.g., 504B) which, in this example, is represented as a miniaturized view of a gallery view or a portion thereof. It shall be noted that a candidate space (e.g., 406A in FIG. 4A) denotes the space that may be claimed by an object for insertion although the object for insertion may or may not necessarily occupy the entire candidate space.

FIG. 5D illustrates another example of a gallery view object that may be displayed in a user interface or a portion thereof in one or more embodiments. More specifically, FIG. 5D illustrates the example of dynamically generating one or more sequences of images for corresponding regions of interest based at least in part upon, for example, a workflow or pipeline, a workflow or pipeline stage, etc. In this example illustrated in FIG. 5D, a first sequence of images 502D may be generated for, for example, an export process (for exporting cells cultured in chambers of a microfluidic device) where a region of interest may include not only a chamber or a portion thereof 504D but also at least a portion of a neighboring flow channel 506D.

The system may parse the workflow or one or more workflow stages or workflow tasks and automatically determine that for an export process, a region of interest includes the aforementioned chamber or chamber portion as well as a portion of the flow channel and thus crop or extract one or more base images to create the first sequence of images 502D as shown in FIG. 5D. In addition, the system may determine that for another workflow, workflow stage, or workflow tasks during which biological samples are cultured, a region of interest for this workflow, workflow stage, or workflow tasks may need to include only a chamber and optionally an interface between the chamber and a neighboring flow channel portion. The system may then crop or extract one or more base images to create the second sequence of images 508D as shown in FIG. 5D.

FIG. 5E illustrates an example of adding a gallery view 1804 to right of the original chip timeline window or view in FIG. 4A in some embodiments. More specifically, FIG. 5E illustrates an example of adding a gallery view 504E to right of the original chip timeline window or view in FIG. 4A. This placement of the gallery view object 504E may be accomplished by using, for example, the aforementioned multi-directional placement widget or the placement widget described above with reference to FIG. 5A. The original chip timeline view or window in FIG. 4A is automatically resized as 502E to accommodate the inserted object 504E.

FIG. 5F illustrates the chip timeline window with the inserted gallery view to the right of the original chip timeline view after adjusting the height for the inserted gallery view. More specifically, FIG. 5F illustrates the chip timeline window (502E in FIG. 5E) with the inserted gallery view (504E in FIG. 5E) to the right of the original chip timeline view after adjusting the height for the inserted gallery view. A chip timeline view in, for example, FIGS. 5E-5G, provides complementary content to other views including, for example, a gallery view (e.g., 504E in FIG. 5E), in that a chip timeline view includes important information that is temporally aligned with the progression of an analysis (e.g., one or more operations) performed on biological samples. For example, the chip timeline view may represent the multiple states in an analysis as corresponding graphical representations 502F. In this example illustrated in FIG. 5F, a color-coded rectangle is used to represent a corresponding stage in the analysis. Moreover, the span or width of the color-coded rectangle also visually indicates the time span of the corresponding stage in the analysis. Different colors of color-coded rectangles represent different stages (e.g., load, culture, export, etc.) In addition, a graphical representation 502F may correspond to a specific column 504F in the corresponding gallery view.

In some embodiments, a timeline as presented in a chip timeline view is thus associated with any of the data correlated with the analysis during which the data is collected (e.g., from a chamber in a microfluidic device) or generated (e.g., by a computational biology module or any computational modules). Various types of data may be collected or generated for an analysis. For example, a base image of a plurality of target-based and/or structure-based regions of interest may be captured. Such base images, although not displayed in a chip timeline view, are also associated with a chip timeline view to enable a user to manipulate a chip timeline view with all the functionalities, tools, widgets, etc. described herein. For example, any of the attributes, characteristics, properties, etc. correlated with a structure-based or a target-based region of interest will be available to a user so that the user may invoke, for example, a filter builder and application module even from within a chip timeline view to build and apply one or more one- or multi-dimensional filters to a result dataset.

In addition or in the alternative, the size and/or shape of a chip timeline view, a gallery view, or any other views or inserted objects may be adjustable, and the underlying system may invoke, for example, a rendering engine to re-render the content within an adjusted view in some embodiments. For example, the width (and/or height) of the chip timeline view or portion in FIG. 5F or that of the gallery view may be adjusted by, for example, dragging a boundary of the portion or view or specifying an exact size (e.g., in pixels, in inches, etc.) to a desired position or value to alter the size and/or shape of the view or portion.

In some of these embodiments where a user interface accommodates multiple views, and the size and/or shape of one of these multiple views is adjusted, the system may automatically adjust the contents of at least one remaining window in response to the adjustment of size or shape of the view. For example, a user may adjust the size and/or shape of the chip timeline window (e.g., the portion showing 502F) to a new size and/or shape. In response to this new size and/or shape, the system may modify the contents in the gallery view (e.g., the portion showing 504F in FIG. 5F). Such a modification to the gallery view may include, for example, scaling the size and/or shape of the gallery view, adding one or more additional columns and/or one or more additional rows to the existing columns, removing one or more additional columns and/or one or more additional rows to the existing columns, etc. in response to the new size and/or shape of the chip timeline view to the left of the gallery view. Similar adjustments to another view or portion of a view may also be performed to another view or a portion thereof other than the chip timeline view example described above. For example, the portion of the display area in the user interface for the microfluidic device builder module may also be adjusted, and the system may automatically or based on user configurations or confirmations adjust the remaining portion(s) of the user interface in response to the adjustment to the portion of the display area.

FIG. 5G illustrates an example display of an example data structure that stores raw data for a chip timeline view in one or more embodiments. More specifically, FIG. 5G illustrates an example data structure that stores raw data for a chip timeline view in one or more embodiments. More specifically, FIG. 5G illustrates a raw data view for a chip timeline that may be selected by a user for display in a chip timeline view. For example, a user may choose to view the raw data associated with a chip timeline by clicking on an interactive element 500G in the user interface. In response to the invocation of the interactive element 500G, the system may read all or a portion of one or more data structures that store therein the raw data correlated with the chip timeline for display in a raw data display region 502G.

In some of these embodiments, the one or more data structure may include multiple column sub-structures as described herein, and the respective information (e.g., column header or identifier) corresponding to these multiple columns may also be optionally displayed in the user interface (e.g., in a column display region 506G). The respective information corresponding to these multiple columns may be displayed as static, non-interactive information in some embodiments or as dynamic, interactive information in some other embodiments to enable users to interact with each respective piece of information. For example, a user may click on a respective piece of information in the column display region 506G, the system may automatically scroll to or display the data of the corresponding column in the raw data display region 502G.

The raw data display region 502G may display data or information such as, without limitation, the identifier of a microfluidic device, the respective identifiers for corresponding data in the microfluidic device, the respective identifiers or description of one or more assays to which the data pertains, one or more attributes and/or characteristics (.g., a rate of product production, e.g., QP, of for example antibodies, a score related to a biological property such as, but not limited to cell surface markers, etc.), timestamps, or any other suitable, desired, or required data or information. The raw data display region 502G may be configurable by users by, for example, using the grouping widget 504G described herein.

In addition or in the alternative, a user may further configure which column or columns for raw data display. For example, a user may select one or more columns in the column display region 506G so that the data respectively corresponding to the one or more selected columns is displayed in the raw data display region. As another example, a user may deselect one or more columns in the column display region 506G so that the data respectively corresponding to the one or more deselected columns will be suppressed, hidden, or otherwise not displayed in the raw data display region. The column display region 506G may be configurable by a user to add, remove, enable, and/or disable one or more columns into the column display region 506G. For example, a user may add, remove, enable (e.g., activate), and/or disable (e.g., deactivate) a device identifier column for an assay, a score column for an assay, a chamber identifier column for an assay, an rQP column for an assay, a cell count column for an assay, a verified cell count column for an assay, a timestamp column for an assay, one or more respective columns for one or more corresponding assays, or any other suitable or desired columns, etc.

The example chip timeline view may further optionally include a function display area 508G showing a list of functions, operators, etc. that has been or may be applied to any of the data or column sub-structures described herein. The function display area 508G may also be configurable by a user to display desired data or information therein. For example, a user may add, in addition to function(s) and/or operator(s), one or more fields, parameters, characteristics, input variables, output variables, etc. into the function display area 508G. A chip timeline view may also optionally include a grouping widget 504G for a user to quickly group various pieces of data by using the grouping widget 504G. For example, a user may drag a column header from 502G or 506G and drop the column header to the grouping widget 504G that automatically triggers a grouping action on some or all of the raw data (e.g., only the raw data on display or all of the raw data correlated with the timeline of a microfluidic device) based on that column header. As described above, a column header may be coded as an interactive object to correspond to a target-based or structure-based attribute, characteristic, property, or metric. Therefore, dropping a column header of a column may effectively instruct the system to sort some or all of the raw data according to the corresponding target-based or structure-based attribute, characteristic, property, or metric.

FIG. 5H illustrates more details about a portion of the example display of the example data structure illustrated in FIG. 5G in one or more embodiments. More specifically, FIG. 5H illustrates more details about the raw data display region 502G in FIG. 5G. In some embodiments, the raw data display region 502G may include one or more of a microfluidic device identifier 502H, a chamber identifier 504H, a first assay device identifier 506H, a first assay chamber identifier 508H, a first assay rQP (dr, dq, dp molecules) 510H, a first assay score 512H, a first assay time stamp 514H, a second assay device identifier 516H, a second assay chamber identifier 518H, a second assay rQP (dr, dq, dp molecules) 520H, a second assay score 522H, and/or a second assay time stamp 524H, etc.

FIG. 5I illustrates more details about a portion of the example display of the example data structure illustrated in FIG. 5G in one or more embodiments. More specifically, FIG. 5I illustrates more details about the raw data display region 502G. In this example illustrated in FIG. 5I, the raw data display region 502G may include a column enable/disable on-screen widget 502I which toggles the display or suppression of display of all columns. The raw data display region 502G may also presents a configurable list of columns for displaying in the raw data display region 502G. The configurable list of columns may be configured in one or more different ways. For example, a new column may be added with the add-new-column widget 504I.

An existing column may be removed from the configurable list with a remove-column widget 508I. A column in the configurable list may be individually enabled (e.g., displayed in the raw data display region 502G) or disabled (e.g., not displayed in the raw data display region 502G) by, for example, checking the check box or other on-screen widget(s), menu command(s), contextual command(s) (e.g., commands invoked by right-clicking on a column or its identifier), etc. The columns displayed in the raw data display region 502G may also be grouped in a variety of different manners. For example, a user may drag a column identifier into the filed 506I to arrange, sort, or organize the data displayed in the raw data display region 502G by that column identifier. Such sorting, arrangement, or organization may also be achieved by other suitable commands (e.g., a contextual command invoked by a right-click of pointing device cursor in the raw data display region 502G, a menu command, etc.)

Figure 5J:
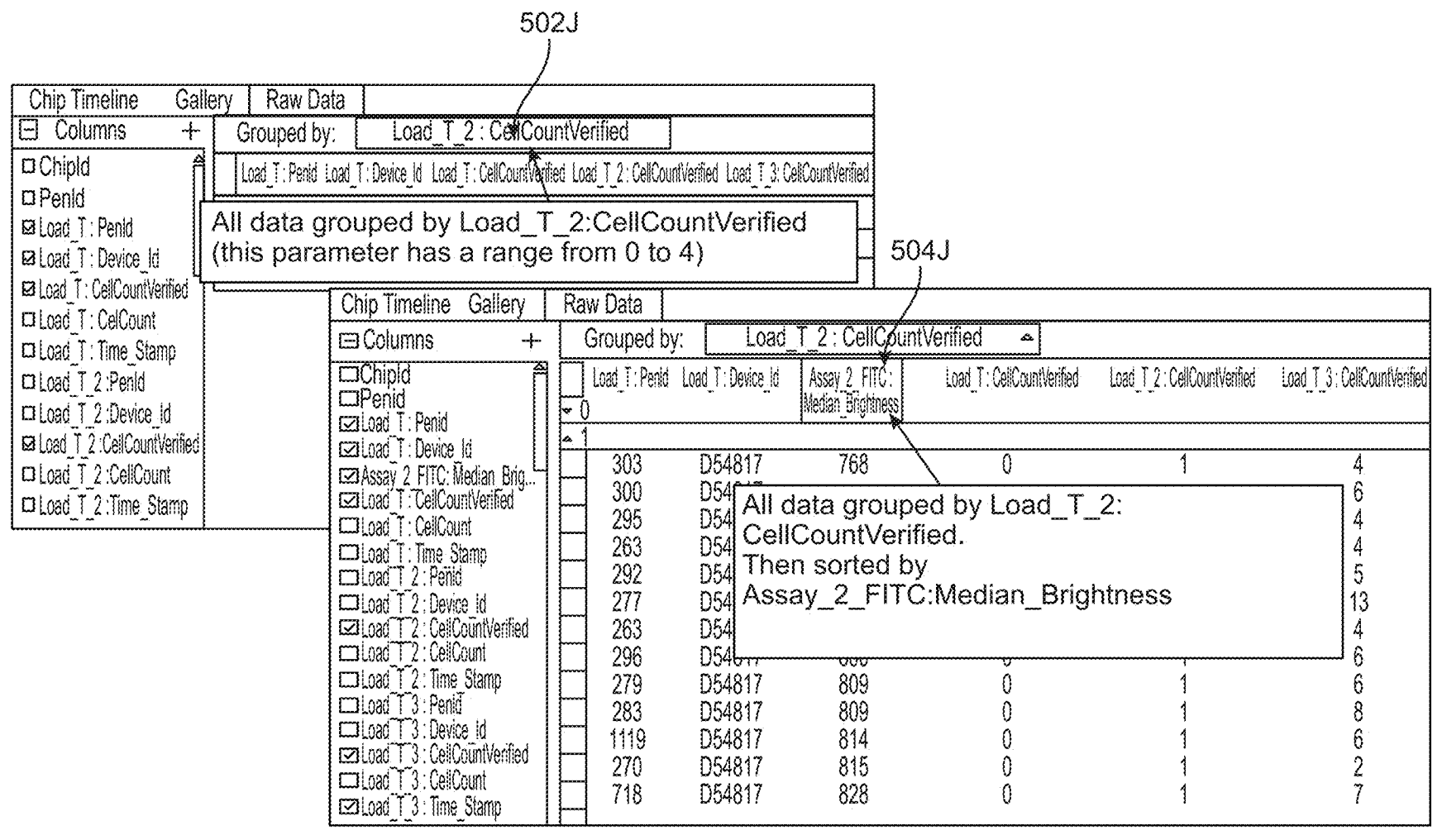

FIG. 5J illustrates an example grouping of an example data structure that stores raw data in one or more embodiments. As illustrated in the example in FIG. 5J, data may be grouped by one or more characteristics (e.g., dragging a column identifier into the field 506I in FIG. 5I). In these embodiments, grouping 502J may be done for all data (either enabled or disabled in the raw data display region 502G), all enabled data in the raw data display region 502G, or a smaller subset of all data. FIG. 5J further illustrates a set of compounded, nested, or hierarchically-arranged actions (e.g., 504J) that may be performed on the data displayed in the raw data display region (e.g., 502G). For example, a user may select multiple characteristics by clicking on multiple characteristics (e.g., characteristics in field 506I of FIG. 5I) so that the data displayed may be first grouped by the first selected characteristic, then sorted by the second selected characteristic, etc.

Figure 5K:
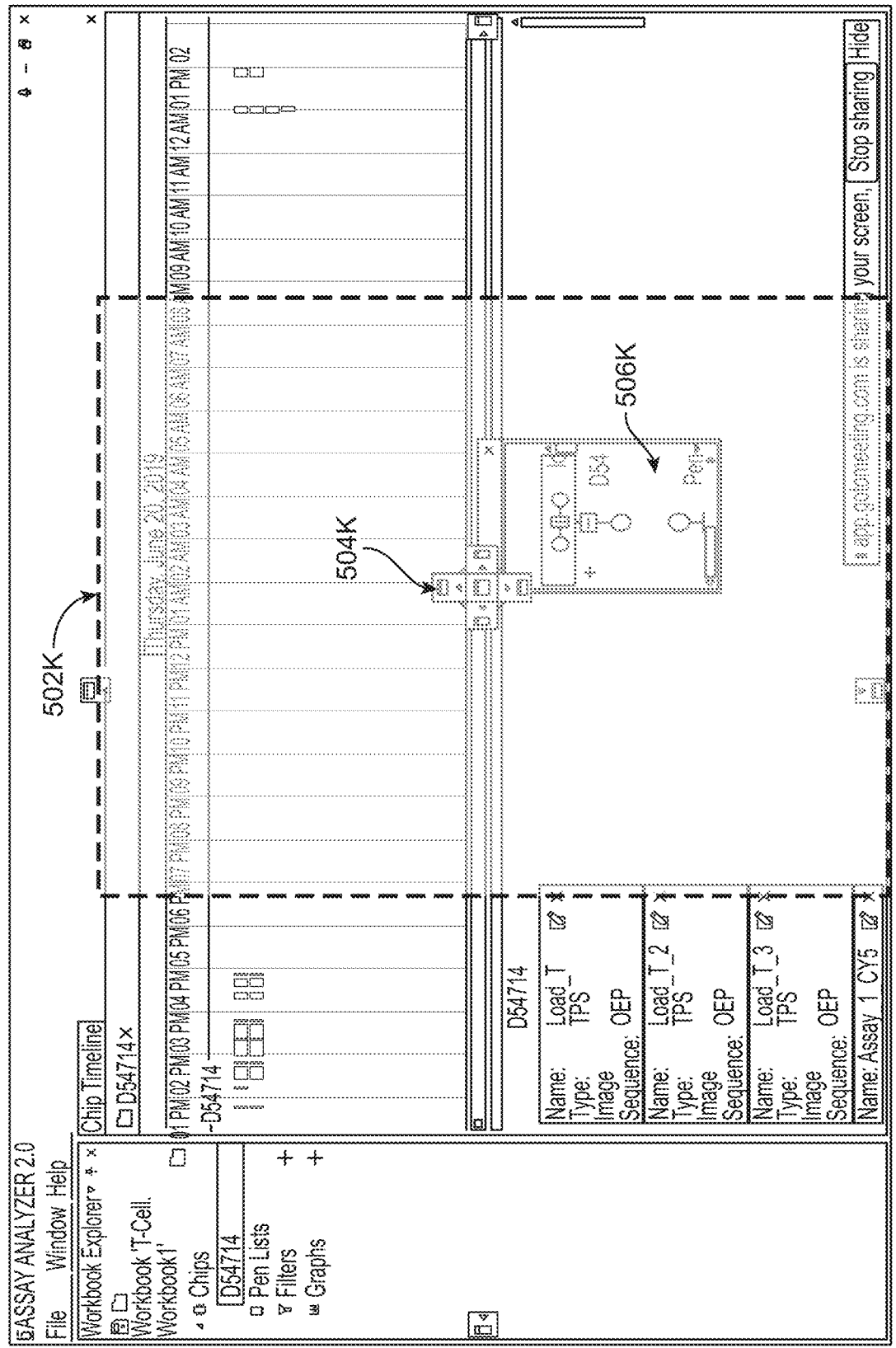
FIG. 5K illustrates another example of inserting an object into the chip timeline view or window by using the multi-directional placement widget in one or more embodiments.

FIG. 5K illustrates another example of inserting an object into the chip timeline view or window by using the multi-directional placement widget in one or more embodiments. More specifically, FIG. 5K illustrates another example of inserting an object 506K into the chip timeline view or window (e.g., FIG. 4A) by using the multi-directional placement widget 504K. In this example, the user selects the center actuatable switch in the multi-directional placement widget 504K. In response to the user's actuation of the center actuatable switch in the multi-directional placement widget 504K, the system automatically determines a candidate space to accommodate the object 506K and may optionally show a translucent ghosting bounding box 502K within which the object 506K may be placed.

Figure 6A:
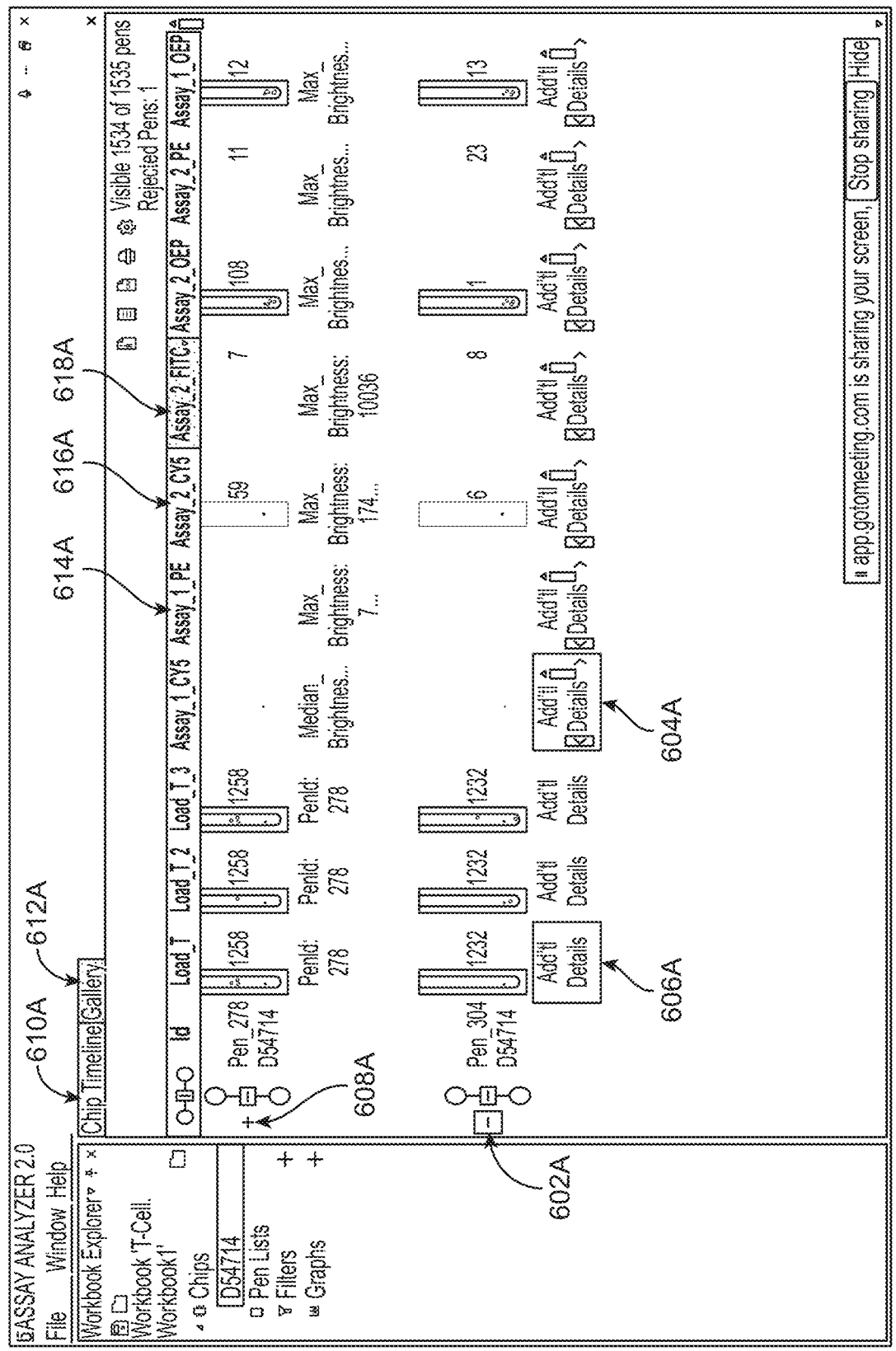
FIG. 6A illustrates an example of actuating an expansion widget to display additional contents associated with each chamber in the form of an object in one or more embodiments.

FIG. 6A illustrates an example of actuating an expansion widget to display additional contents associated with each chamber in the form of an object in one or more embodiments. FIG. 6A illustrates an example of actuating or expanding an expansion/collapsing widget 602A to display additional contents (e.g., 604A, 606A, etc.) associated with each chamber in the form of an object. The expansion/collapsing widget 602A automatically changes its graphical representation based on user's manipulations. For example, the expansion/collapsing widget 602A may illustrate an expansion representation (e.g., a plus sign such as 608A) for an expandable feature and a collapsing representation (e.g., a minus sign such as 602A) when a feature may only be collapsed. The system automatically determines the size and position of a sub-window or sub-area to display the additional content of a chamber without any obstruction or with reduced obstruction to other contents on the display. In some embodiments where the additional content cannot be fully accommodated or displayed in the determined sub-window or sub-area (e.g., 604A), the system may further render one or more sliders in one or more respective dimensions (e.g., up-and-down as well as left-and-right) for the user to scroll through the contents.

FIG. 6A further illustrates an expansion/collapsing widget or a gallery detail widget 608A which, when actuated, may change its appearance and may cause addition information or contents to be displayed. An expansion widget may be expanded when needed or collapsed when not needed in some embodiments to avoid cluttering the user interface with additional information, functionality, etc. The example user interface illustrated in FIG. 6A shows these expansion widgets in a collapsed state.

Moreover, the user interface in FIG. 6A includes a gallery view or a portion thereof. The various types of data populated into a gallery view include, for example, individual images of corresponding regions of interest that may be derived or extracted from one or more base images. These corresponding regions of interest may be determined by a user or automatically by the system based at least in part upon, for example, the corresponding chip timeline and/or the workflow or the pipeline. These regions of interest may be purely target-based, purely structure-based, or both target-based and structure-based. Depending on whether a region of interest is target-based or structure-based, one or more attributes, characteristics, properties, and/or quantifiable metrics, etc. may also be captured and associated with the other data (e.g., base image(s), individual image of a region of interest, etc.) and may be used to manipulate (e.g., filter, rank, cluster, etc.) data that is associated with each other.

In some embodiments, these individual images of corresponding regions may be arranged in a gallery view according to the chip timeline that tracks the flow of the underlying analysis of the biological samples in a microfluidic device. For example, a gallery view may present specific stages of an analysis in respective columns where each column corresponds to a specific stage, and these specific columns in the gallery view also correspond to the information presented chip timeline (e.g., the graphic, color-coded representations 502F in FIG. 5F). In some embodiments where a column in a gallery view presents data for multiple regions of interest according to one of the aforementioned one or more attributes, characteristics, properties, or quantifiable metrics, the system may further determine the correspondence between this column and the stage that is more or most pertinent to the attribute, characteristic, property, or quantifiable metric in the chip timeline. In this manner, various different views described herein may efficiently leverage or employ any of the functionalities described herein so that a user may easily switch among different views to perform any of the desired or required functionalities to facilitate the derivation computational analytics and/or the analysis of the data correlated with the analysis of biological samples.

FIG. 6A illustrates the example where it is confirmed (e.g., by the user or by the system) that the object for insertion is to occupy the entire candidate space, the system may determine that some semantic or meaningful contents on display may be obstructed by the insertion of the object. In response, the system may add a new tab 612A to accommodate the object for insertion while the original chip timeline view remains in the original tab (e.g., the current, active tab). In this example, the object for insertion includes a gallery view object. FIG. 6A further illustrates that a user interface may include multiple tabs such as a chip timeline view 610A and a gallery view that is added to the user interface. In some embodiments, any other views may be added to the user interface that currently displays a specific view. For example, a user interface displaying a gallery view may also be augmented by adding a chip timeline view.

Moreover, FIG. 6A further illustrates some examples of interactive widgets (e.g., 614A, 616A, and 618A). An interactive widget, when interacted upon, triggers a performance of one or more functions. In the example illustrated in FIG. 6A, the interactive widget 618A for the corresponding gallery sub-structure (e.g., column in the example) may trigger the performance of one or more functions that may be associated with or custom defined for the interactive widget. For example, when a user selects target-based or structure-based attribute, characteristic, property, or metric for rendering in a gallery view, the system may use the description of or notation associated with the target-based or structure-based attribute, characteristic, property, or metric as the heading or title for the gallery sub-structure.

This heading or title block may be generated as a parameterized block of code awaiting the description or notation as an input to be displayed as the heading or title therefor. In addition, one or more functions correlated with the selected target-based or structure-based attribute, characteristic, property, or metric may be associated with the heading or title block so that when the heading or title block is interacted upon (e.g., being clicked on), the one or more function may be executed or be presented to the user for selection for execution. In addition or in the alternative, the heading or title block (e.g., 612A) may also be configured to serve as an identifier widget or to have the functionality of an identifier built into the aforementioned parameterized block of conde. An identifier widget, when invoked, changes an identifier. For example, a user may invoke the identifier widget functionality to change the identifier for the heading or title block.

Figure 6B:
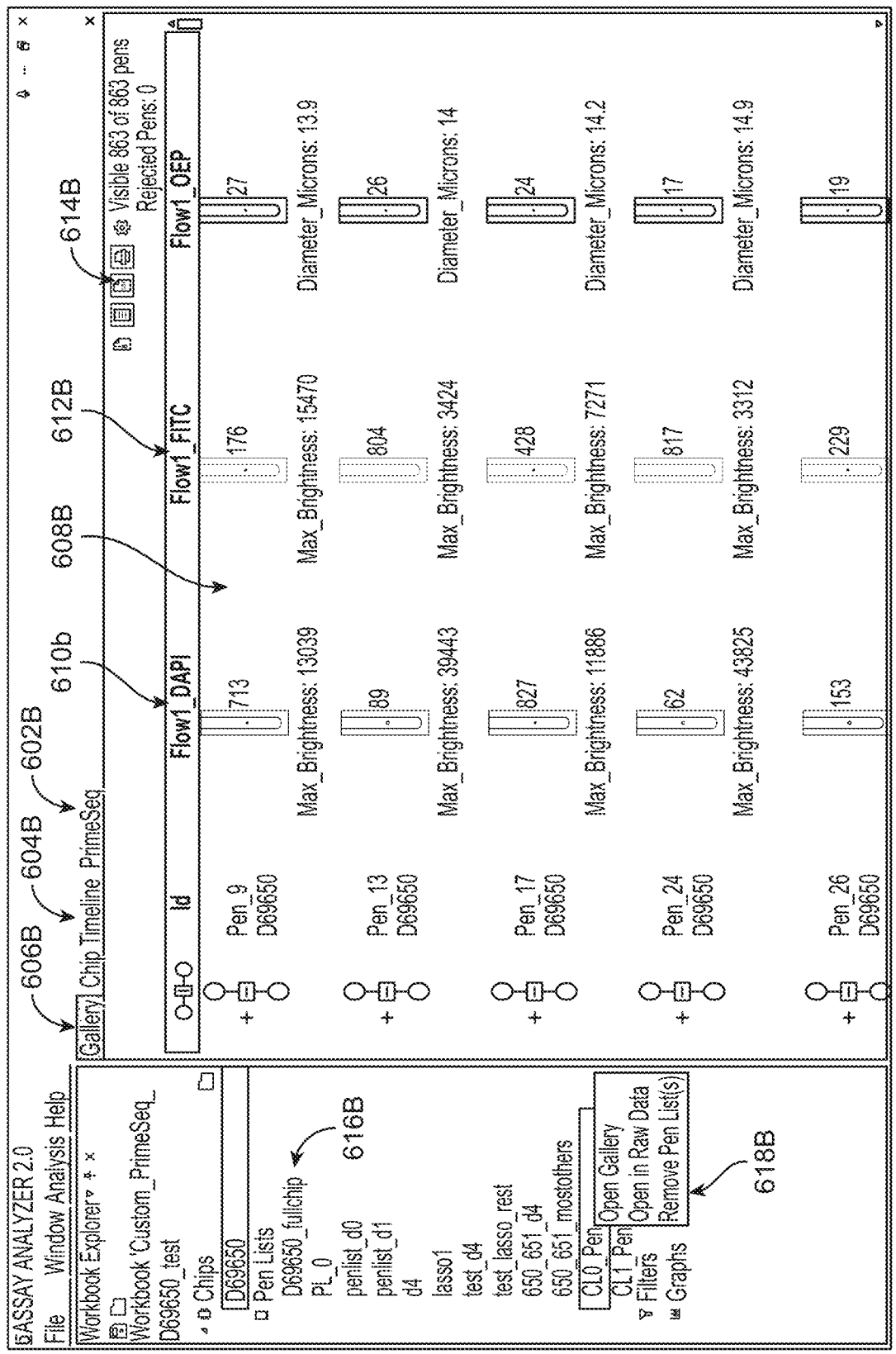
FIG. 6B illustrates an example of the integration of a bioinformatics pipeline user interface and one or more other user interfaces or views described herein in some embodiments.

FIG. 6B illustrates an example of the integration of a bioinformatics pipeline user interface and one or more other user interfaces or views described herein in some embodiments. FIG. 6B illustrates an example of the integration of a bioinformatics pipeline user interface (e.g., 702A in FIG. 7A described below) and one or more other user interfaces or views described herein in some embodiments. More specifically, FIG. 6B illustrates the integration of a bioinformatics pipeline user interface 602B, a gallery view or user interface 606B, and a chip timeline view 604B or user interface, etc. Each of these views or user interfaces may be presented in its respective tab. In addition, one view (or user interface) may be added as an object into another view or user interface as described above with reference to, for example, FIG. 5A. In some embodiments, a gallery view or user interface 606B may be devised for, for example, an assay analyzer that performs one or more assays to determine, for example, the presence of a substance (e.g., the aforementioned biological samples), the amount of that substance, or biological or pharmacological potency of a drug, etc.

A bioinformatics pipeline user interface (602B) may be separately devised for a sequencer that employs bioinformatics or computational biology to determine, for example, the sequence, domain, and/or structure of a biological sample. With the vast amount of sequencing data generated by a sequencer, conventional tools could merely present the vast amount of data to the user without any useful tools or functionality. As a result, a user must rely on his or her close observation and attention to details to hopefully cipher through a vast amount of data to identify useful information.

Various techniques described herein apply with full and equal effects to assay analyses and bioinformatics pipelines analyses by providing various functionalities for a user to quickly identify and determine pertinent information or data of interest and even provide the functionalities for the user to visually validate the results. For example, with the integrated bioinformatics pipeline user interface and a gallery view, a user may employ all or nearly all of the functionalities described therefor in manipulating, analyzing, and/or further processing both assay analysis data and bioinformatics pipeline data. Moreover, the gallery view 608B includes multiple flows. For example, the gallery view 606B includes a fluorescence DAPI (4', 6-diamidino-2-phenylindole) flow 610B that uses a blue-fluorescent DNA stain that exhibits about 20-fold enhancement of fluorescence upon binding to AT regions of dsDNA, a FITC (fluorescein isothiocyanate) flow 612B, and one or more other flows 614B (e.g., TRITC or tetramethylrhodamine isothiocyanate, OEP or opto-electro positioning, etc.) Moreover, the gallery view 608B showing these multiple flows (610B, 612B, 614B, etc.) may be generated from a single timeline or a single block of a timeline of one or more microfluidic devices.

For example, as illustrated in FIG. 6B, a user may load a bioinformatics pipeline dataset, select a subset of bioinformatics pipeline data and store the subset as a chamber list (e.g., by selecting a chamber list of interest 616A via the sub-menu item or widget) by using the functionalities described above for gallery views. The underlying system may then automatically identify and link pertinent data (e.g., a sequence of images of a chamber captured at a sequence of timepoints) by using, for example, the identifier of a microfluidic device in which the chamber is located and/or the identifier of the chamber to link the bioinformatics pipeline data and the pertinent data.

In this manner, the gallery view provides visual representations of the chamber at each of the sequence of timepoints so that a user may visually identify and even visually validate the results by, for example, visually observing the sequence of images of the chamber. Moreover, a user may also employ the filter configuration and definition functionalities and apply one or more one-dimensional or multi-dimensional filters to both assay analysis data and bioinformatics pipeline data.

FIG. 6B further illustrates an expandable and collapsible chamber list menu (616B) that provides a list of existing chamber lists each of which, when activated (e.g., by clicking or right-clicking), provides a context menu (618B) for a user to determine which further action is to be performed for a selected chamber list. Some example actions may include open the selected chamber list in a gallery view, open the raw data of the selected chamber list, and/or delete the selected chamber list, or any other suitable, desired, or required actions correlated with manipulation of and/or operations on a chamber list, etc.

Figure 6C:
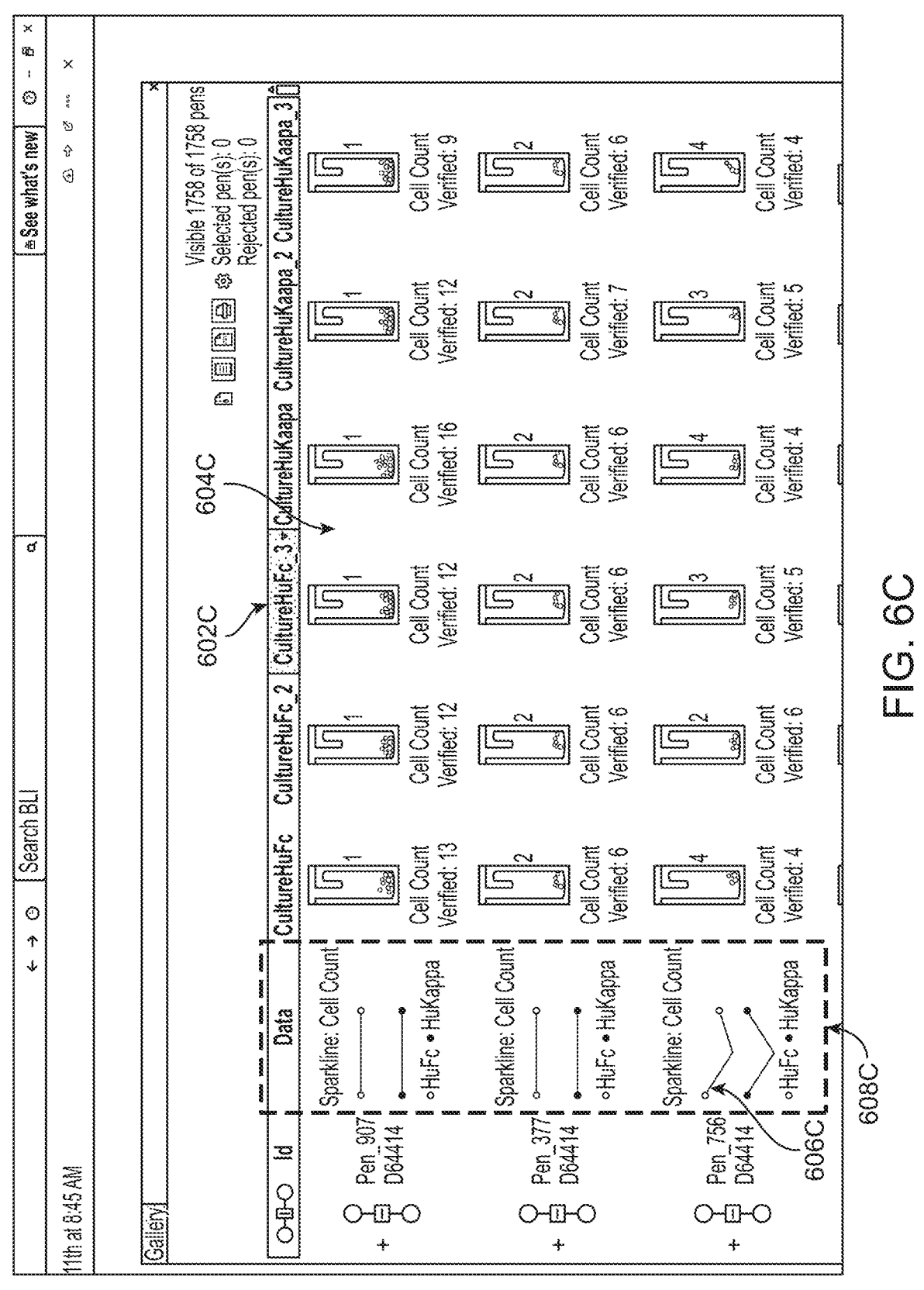

FIG. 6C illustrates more details of the gallery view illustrated for a loaded bioinformatics pipeline dataset in some embodiments. FIG. 6C illustrates more details of the gallery view illustrated in FIG. 6B for a loaded bioinformatics pipeline dataset in some embodiments. In these embodiments, in addition to one or more previously described features and functionalities of a gallery view, FIG. 6C further illustrates the arrangement of images captured for a chamber at a sequence of timepoints (with three chambers arranged in three rows in FIG. 6C). Each chamber may be associated with a sparkline 606C in the Data area 608C that provides a quick representation of numerical or statistical information (e.g., cell count in FIG. 6C). A sparkline 606C illustrated in FIG. 6C has a form of a graph without axes although a sparkline may also be represented with one or more axes in some other embodiments. Moreover, a chamber may be associated with more than one sparkline in some embodiments. It shall be noted that although a sparkline in FIG. 6C appears to be built upon three data points, a sparkline may be constructed with any number of data points over time.

FIG. 6C further illustrates an example of dynamically replaying a sequence of images captured for a chamber at a plurality of timepoints in some embodiments. The user interface (e.g., a gallery view as illustrated in FIG. 6C) may include a widget 602C which, when activated (e.g., via clicking), causes the sequence of images captured for the chamber of interest. For example, a user may click on a replay widget implemented as a part of the column menu 602C. Upon receiving the click on the replay widget, the underlying system may replay the sequence of images for the particular chamber at the portion 604C of the user interface allocated for displaying the image of the chamber. For instance, the replay of the sequence of images may illustrate the expansion of a clonal population of biological micro-objects within a chamber over time, progression of a biological micro-object labelling experiment, progress of lysis of biological micro-objects over time, capture of a biological product to a capture bead over time, diffusion of a soluble reporter molecule: biological product complex over time, and the like.

Figure 6D:
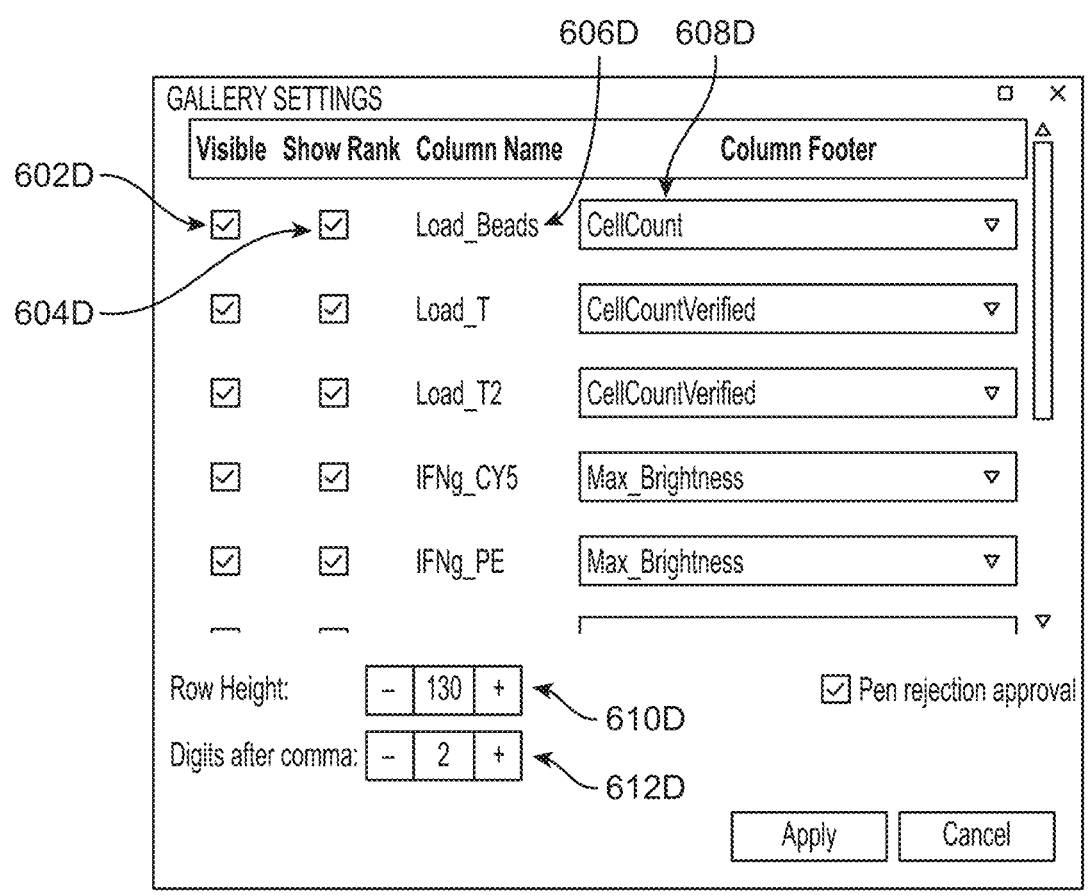
FIG. 6D illustrates an example pop-up window over an example gallery view for configuring the settings for the example gallery view in one or more embodiments.

FIG. 6D illustrates an example pop-up window over an example gallery view for configuring the settings for the example gallery view in one or more embodiments. More specifically, FIG. 6D shows an example of the gallery view, as generated by the engine (e.g., data display engine 50), after a user has selected a settings button or the like in the GUI, which may include a pop-up window or pane of one or more settings that the engine may then use to generate the gallery view of the filtered data. While not limited to these particular parameters, settings may include, for each step of the assay (represented by "column name"), whether or not that column is visible, if the column's rank is visible, and the text to be displayed at the footer of each image (here, called a "column footer"). Furthermore, the engine 50 may present settings such as row height, digits after a comma, and the like, as well as permitting the user to require chamber rejection approval; the engine 50 may present options to apply these settings to the gallery view, or cancel the changes to the gallery view.

In the example illustrated in FIG. 6D, a user may configure various aspects, attributes, characteristics, etc. of a gallery view. In some embodiments, a user may configure such various aspects, attributes, characteristics, etc. for each column (e.g., the columns corresponding to 610B, 612B, etc. in FIG. 6B). For example, a user may configure whether a column (e.g., a column corresponding to analysis data such as images, analysis results, and/or other relevant data correlated with a chamber in a microfluidic device at a plurality of time points) is visible or invisible in a gallery view by respectively checking the visibility widget 602D. A user may also turn or off the ranking of respective columns by checking the ranking widget 604D.

A user may configure or revise the default column identifier 606D by, for example, issuing a command (e.g., through a menu, a context menu, click, double-click, etc.) on the respective column identifier 606D. A user may also configure the column footer 608D, which corresponds to a plurality of selectable characteristics (e.g., total cell count for a chamber, verified total cell count for a chamber, maximum brightness, minimum brightness, etc.) concerning the display of the corresponding column in a gallery view by selecting a desired characteristic from a pull-down menu. In addition or in the alternative, a user may configure the size of a column (e.g., height and/or width of a column) in a gallery view through the column size adjustment widget 610D. In some embodiments, a user may configure the displayed precision of the number(s) for a column (e.g., the number of decimal places) in a gallery view through the precision adjustment widget 612D.

Figure 6E:
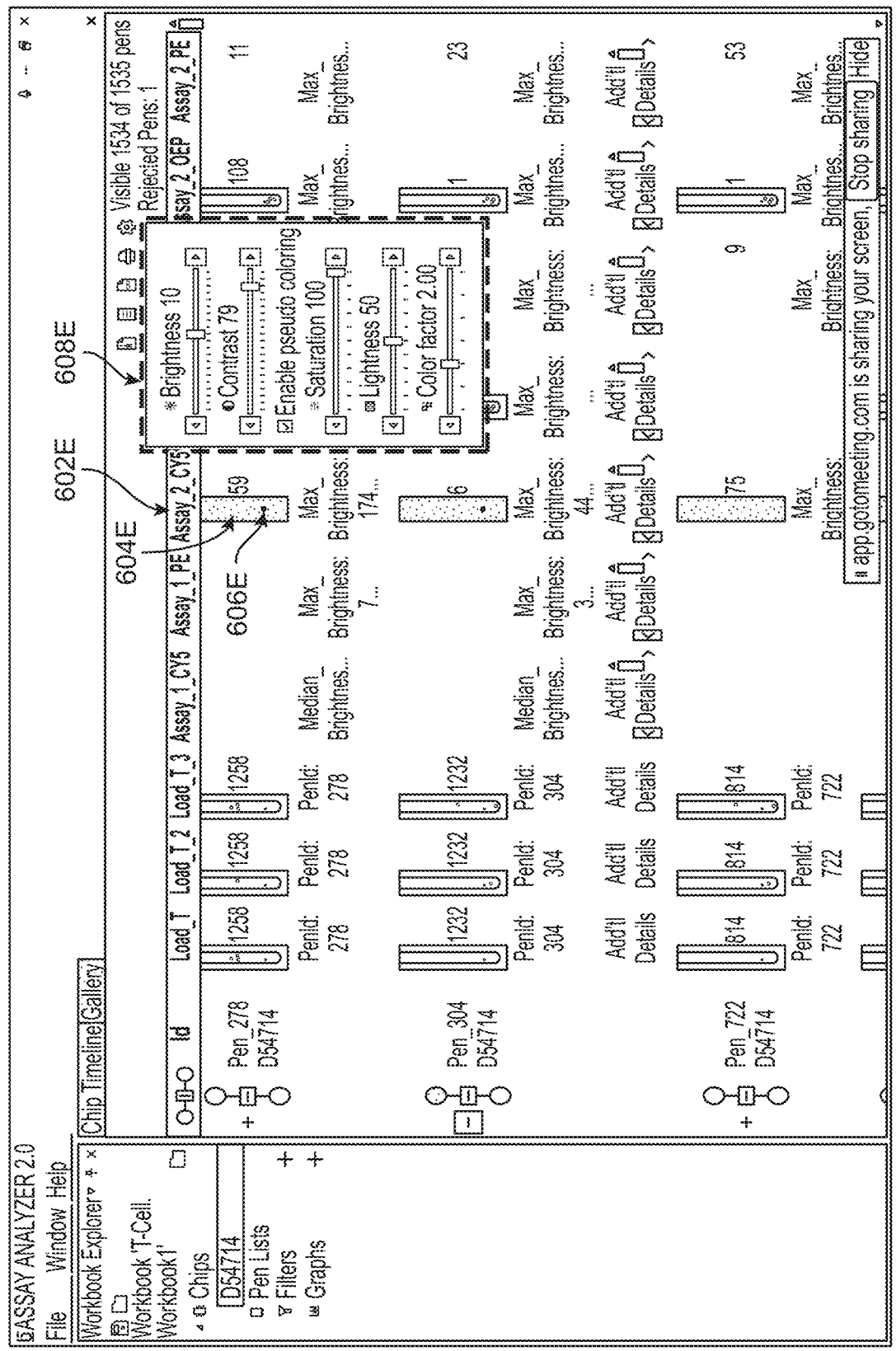
FIG. 6E illustrates an example result of pseudo coloring in an example gallery view in some embodiments.

FIG. 6E illustrates an example result of pseudo coloring in an example gallery view in some embodiments. More specifically, FIG. 6E illustrates an example result of enabling pseudo coloring of a column of chambers (e.g., by selecting the Assay_2_CV5 column title 602E) that colors the background 604E of these chambers in green with a fluorescent-labeled cell 606E having a determined size that approximates the size of the fluorescent-labeled cell 606E. Pseudo coloring may be utilized to recover an image of a chamber that was captured with certain characteristics (e.g., insufficient contrast, low brightness, etc.) that prohibit or reduce proper visibility of the image on a display device.

FIG. 6E further illustrates an example of a configuration widget 608E that provides a user with the ability to adjust various characteristics or other aspects of a specific view or the entire user interface. Some examples of characteristics that may be configured through the configuration widget 608E include, without limitations, brightness, contrast, pseudo-coloring enablement or disablement, saturation, gamma, lightness, color factor, or any other suitable, desirable, or required characteristics.

Figure 6F:
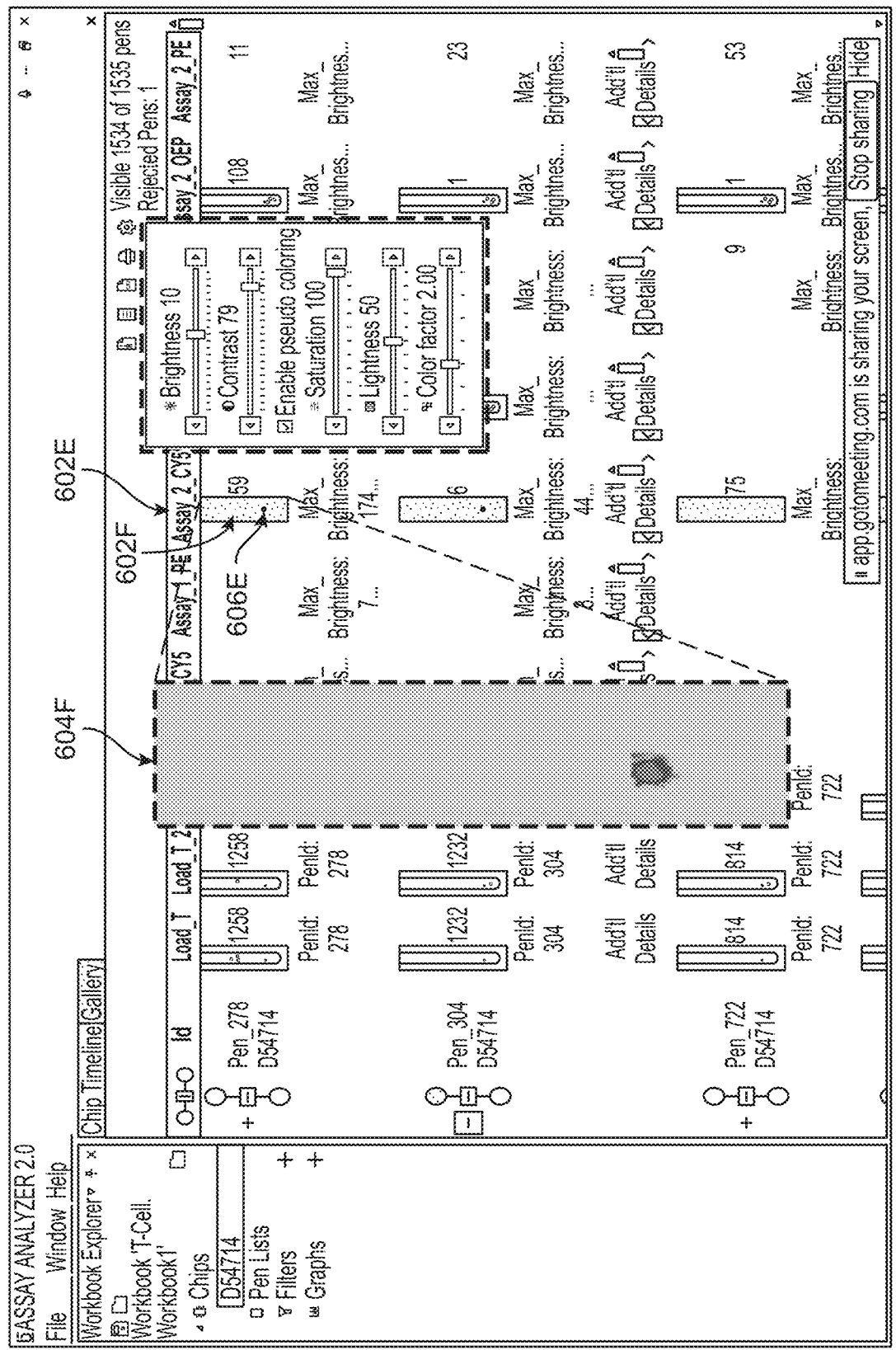
FIG. 6F illustrates an example result of altering the color factor of a column of chambers in an example gallery view and a zoom-in feature of one or more individual chambers in some embodiments.

FIG. 6F illustrates an example result of altering the color factor of a column of chambers in an example gallery view and a zoom-in feature of one or more individual chambers in some embodiments. More specifically, FIG. 6F illustrates an example result of altering the color factor of a column of chambers (e.g., by selecting the Assay_2_CV5 column title 602E in FIG. 6E) that colors the background 602F of these chambers in blue with a fluorescent-labeled cell 606E (in FIG. 6E) having a determined size that approximates the size of the fluorescent-labeled cell 606E in FIG. 6E. FIG. 6F further illustrates that a user may select a chamber 602E to zoom in to the cell 606E in FIG. 6E. A zoomed-in image (e.g., an enlarged image 604F) of the fluorescent-labeled cell 606E is generated with a size that is determined to approximate or to scale the actual size of the cell in the corresponding chamber to provide better visibility, especially for fine feature(s) in the image.

Figure 6G:
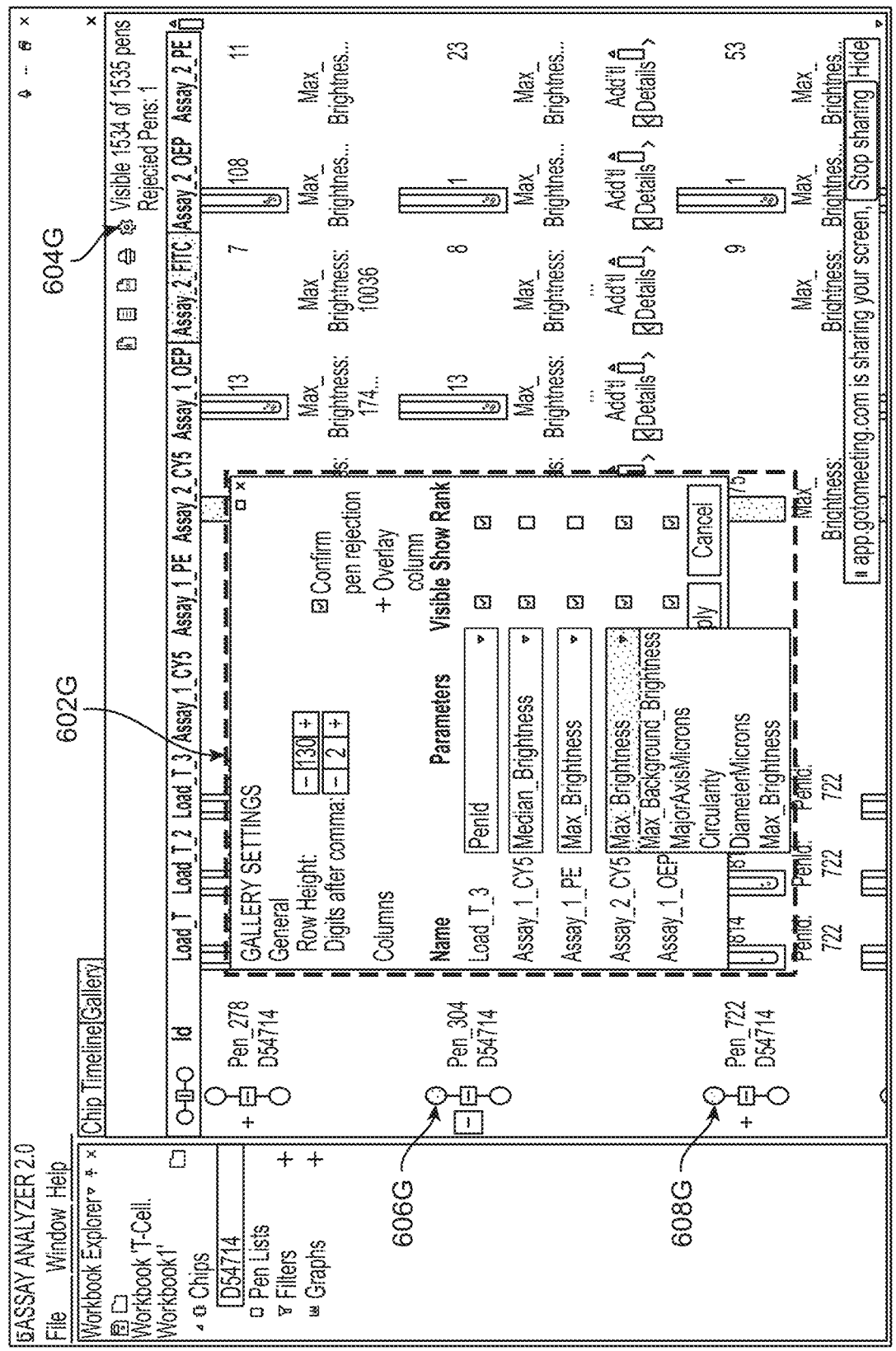
FIG. 6G illustrates another example of a configuration widget for configuring a view in some embodiments.

FIG. 6G illustrates another example of a configuration widget for configuring a view in some embodiments. More specifically, FIG. 6G illustrates another example of a configuration widget for configuring a view (e.g., a gallery view, a chip timeline view, etc.) In this example, the configuration widget 602G lists the columns in the view according to their respective titles (e.g., assay types as the titles) and provide a drop-down menu for a user to choose from to control the view. For example, a user may click on the drop-down menu for a column (e.g., Assay_2_CY5 in this example) to change characteristics of an assay including, without limitations, the height of the column, the number of digits after comma (e.g., 1, 2, 3, . . . ), the respective identifiers of chambers, the maximum brightness, the maximum background brightness, the major axis size (e.g., in microns), the minor axis size, circularity, the diameter size, chamber identifier, and/or medium brightness, etc.

The configuration window may include one or more fields each of which corresponds to a drop-down or pop-up window for configuring a corresponding column in, for example, a gallery view. Each field may be further configured to be, for example, visible or invisible, whether ranks are to be displayed, etc. The user may further configure whether each of the selected characteristic is visible or not, whether the ranking of a chamber (compared to the other chambers in a microfluidic device) in the column is to be displayed, or any other information the user may desire to see or hide. For example, a user may click on the configuration widget 604G in a gallery view to configure or adjust configurations, settings, attributes, and/or characteristics, etc. In some embodiments, this configuration menu 602G may also provide the capability to adjust the height of a row on display and/or the number of digits after comma.

For example, a user may configure the size of a column (e.g., height and/or width of a column) in a gallery view through the column size adjustment widget (e.g., 610D in FIG. 6D). In some embodiments, a user may configure the displayed precision of the number(s) for a column (e.g., the number of decimal places) in a gallery view through the precision adjustment widget (e.g., 612D in FIG. 6D). A user may determine whether one or more columns are visible or invisible by checking the visibility icon (e.g., 602D in FIG. 6D). A user may also turn or of off the ranking of respective columns by checking the ranking widget (e.g., 604D in FIG. 6D). A user may also configure the column footer 608D, which corresponds to a plurality of selectable characteristics (e.g., total cell count for a chamber, verified total cell count for a chamber, maximum brightness, minimum brightness, etc.) concerning the display of the corresponding column in a gallery view by selecting a desired characteristic from a pull-down menu.

Figure 6H:
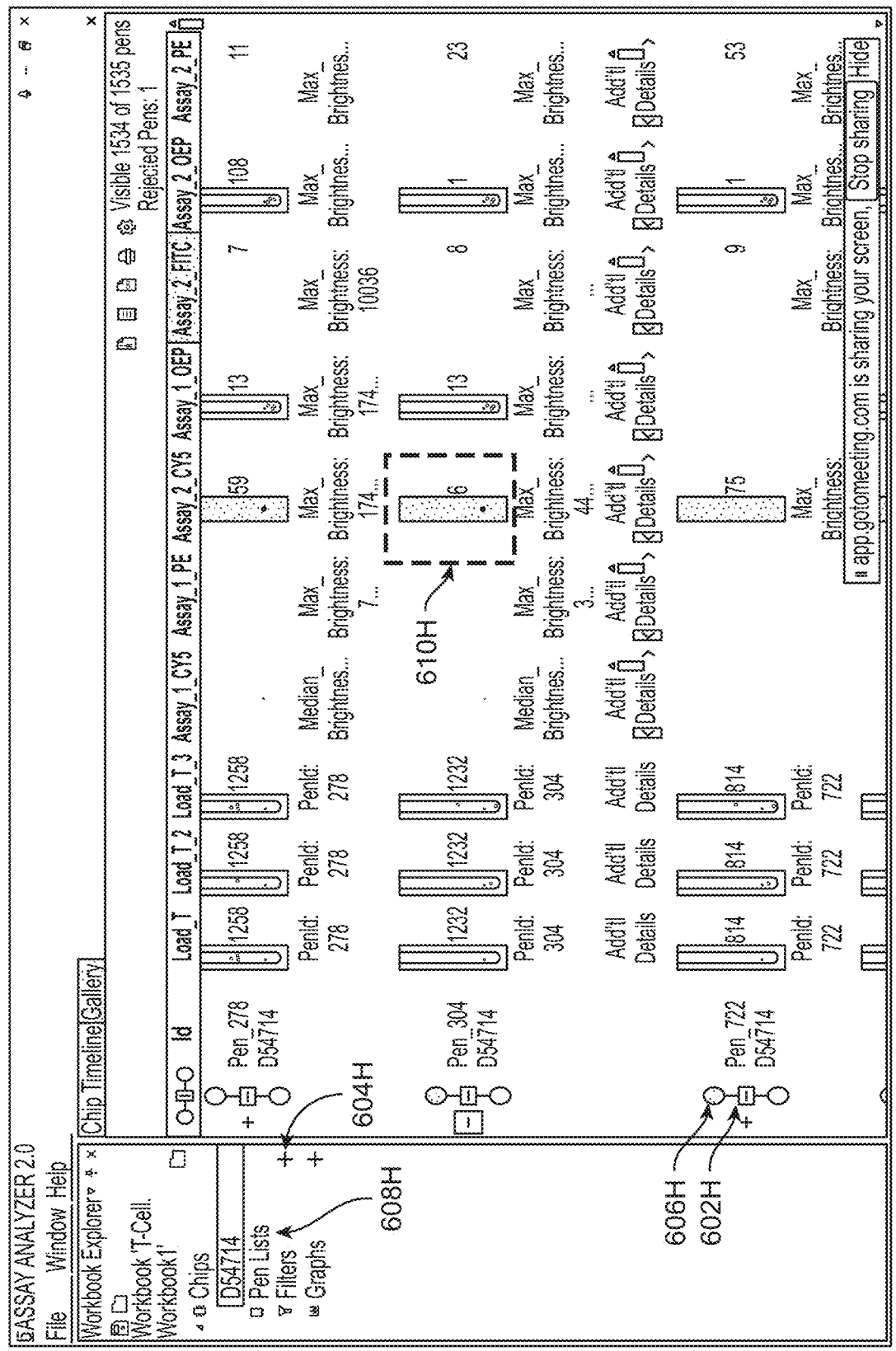
FIG. 6H illustrates an example where a user changed the status of the chamber in FIG. 6G from a "selected" status to an "undecided" status in some embodiments.
Figure 6I:
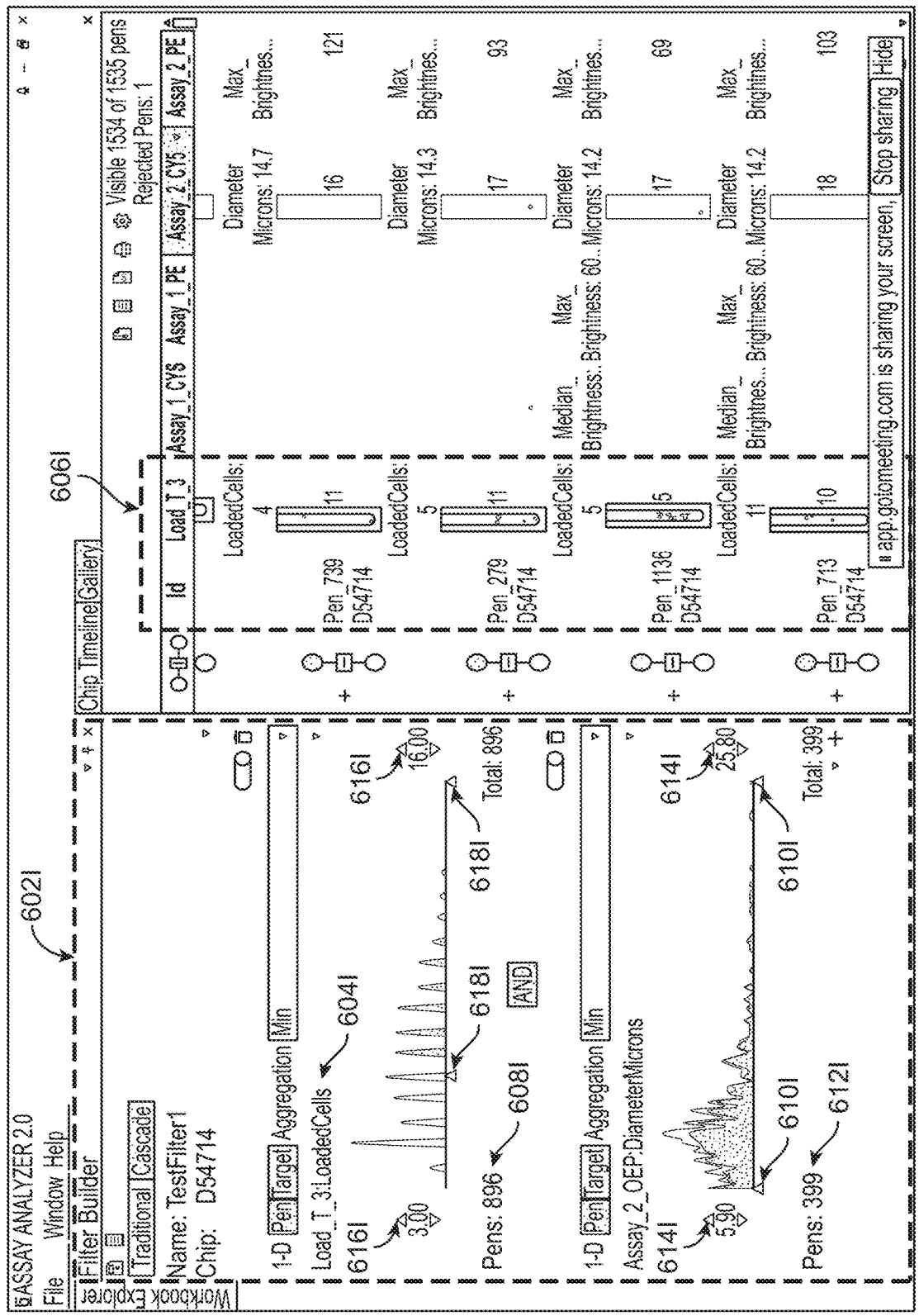
FIG. 6I illustrates an example of a filter builder and application module for adding one or more filters of one or more filter types in some embodiments.

FIG. 6H illustrates an example where a user changed the status of the chamber in FIG. 6G from a "selected" status to an "undecided" status in some embodiments. FIG. 6H illustrates an example where a user changed the status of the chamber in FIG. 6G from "selected" (e.g., with the upper bubble filled in the multi-state selector as shown by 606G or 608G in FIG. 6G) to undecided (e.g., with a minus sign icon "−" in the multi-state selector and no bubble filled in 602H). FIG. 6H further illustrates a filter selector switch 604H which, when invoked, is used to determine one or more filter types and/or one or more attribute selectors as illustrated in FIG. 6I described below.

FIG. 6H further illustrates the refreshed display of a gallery view object after adjusting one or more characteristics described above with reference to FIG. 6G. FIG. 6H further illustrates a multi-state switch or multi-state selector 606H for a user to select a chamber, to reject a chamber, or to label a chamber as "undecided" (e.g., undecided as to whether to select or reject the chamber). In this example illustrated in FIG. 6H, the chamber enclosed in 610H is currently showing as "selected" as graphically emphasized in the user interface. It shall be noted that although FIG. 6H only shows one chamber as selected, more than one chamber may be selected in some embodiments, and the techniques described herein may automatically, programmatically arrange the user interface to accommodate the additional operations (e.g., zoomed-in views) associated with the multiple selected chambers. FIG. 6H also illustrates a list generation switch 608H which, when actuated, invokes instructions for the generation of a list (e.g., a "pen list" or "chamber list") that includes one or more regions of interest. For example, a user may apply one or more filters to filter a plurality of regions of interest in a microfluidic device down to a filtered list of regions of interest and clicks on the list generation switch 608H to create a pen list that includes the filtered list of regions of interest satisfying the one or more filters. The analysis data and/or the computational analytic data correlated with this filtered list of regions may be used to generate a gallery view while leveraging some or all of the functionalities therefor.

FIG. 6I illustrates an example of a filter builder and application module for adding one or more filters of one or more filter types in some embodiments. More specifically, FIG. 6I illustrates an example of a filter builder and application module 602I for adding one or more filters of one or more filter types (e.g., one-dimensional filter controlling one characteristic, two-dimensional filter controlling two characteristics, etc.) A characteristic or a filter attribute (e.g., 604I) described herein may be interactive in some embodiments. A characteristic or a filter attribute may include or pertain to a target-based or a structure-based characteristic, attribute, property, or a quantifiable metric. Some examples of a target-based characteristic, attribute, property, or a quantifiable metric may include, without limitation, a characteristic of or correlated with a biological sample such as a size, circularity, affinity, major and/or minor diameter, fluorescent intensity, or count, etc. that may be actually measured or derived or computed for the biological sample Examples of structure-based characteristic, attribute, property, or a quantifiable metric may include, without limitation, any information correlated with an aspect or any chamber, or any portion of a microfluidic device. A filter attribute may be selected from a list of filter attributes and may correspond to one or more gallery sub-structures (e.g., one or more columns in a gallery view) in some embodiments.

The filter builder and application module 602I allows a user to custom build and apply one or more filters to a view by selecting one or more characteristics and further by changing or defining a value or a range of values for a characteristic so that the filter, when applied to a view, identifies one or more objects that satisfy the value or the range of value which may be called a filtering criterion (or criteria). Various modules described herein (e.g., a filter builder and application module) are configured or devised to filter, sort, and/or rank, etc. multiple regions of interest and may function in tandem with or in conjunction with one or more graphic processing and/or rendering modules to display the results of such filtering, sorting, and/or ranking, etc.

Moreover, a filter builder and application module or filter generation module 602I may include one or more filtering criterion configurators or one or more configuration slider widgets 610I or 618I (which may also be referred to as a sliding adjustment widget) that allow a user to determine one or more required or desired filtering criteria. In the example illustrated in FIG. 6I, a filtering criterion configurator includes a set of filter configurators (e.g., one or more sliders 610I or 618I and/or a set of one or more corresponding adjustment widgets 614I) that allows a user to adjust or define a filtering criterion. It shall be noted that other types of filtering criterion configurators may also be used and are thus contemplated. For example, another filtering criterion configurator may allow a user to specify a dynamic constraint such as a value or a range of values by typing in such a value or range of values. As another example, a filter criterion may allow a user to select any chambers having a minimum of three samples and a maximum of 16 samples by manipulating the sliders 610I or 618I and/or the corresponding adjustment widget 614I or 616I. As another example, a filter criterion may allow a user to select any chambers having a minimum diameter of 5.90 microns and a maximum diameter of 25.80 microns by manipulating the sliders (610I or 618I) and/or the corresponding adjustment widgets (614I or 616I). Once a filter is applied, a region of interest that satisfies the one or more filtering criteria (and hence rendered in the user interface) may be termed a filtered region of interest in some embodiments.

In some embodiments, the filter builder and application module 602I automatically determines the number of samples after the application of a filter. For example, in response to the adjustment of the set of one or more sliders (610I or 618I) and/or the set of one or more corresponding adjustment widgets (614I or 616I), a filter builder and application module 602I automatically determines that 896 samples (608I) satisfy the first filter, and 399 samples (612I) of these 896 samples further satisfy the second filter after the adjustment of the second set of one or more sliders (610I or 618I) and/or the second set of respective adjustment widgets (614I or 616I) for the second filter criterion/criteria.

Moreover, with the adjustment of the filtering criterion or criteria, the gallery view (e.g., the gallery view including 606I) on the right-hand portion of FIG. 6I is automatically updated to reflect the application of a filter. It shall be noted that a filter criterion may be target-based or structure-based. Moreover, a filter builder and application module 602I allows a user to build and apply more than multiple one- or multi-dimensional filters. In some embodiments where multiple filters are applied, these multiple filters may include one or more target-based filters, one or more structure-based filters, or both one or more target-based filters and one or more structure-based filters. In some embodiments where a multi-dimensional filter is applied, the multi-dimensional filter may include a first-dimensional target-based filter and a second-dimensional structure-based filter.

Figure 7A:
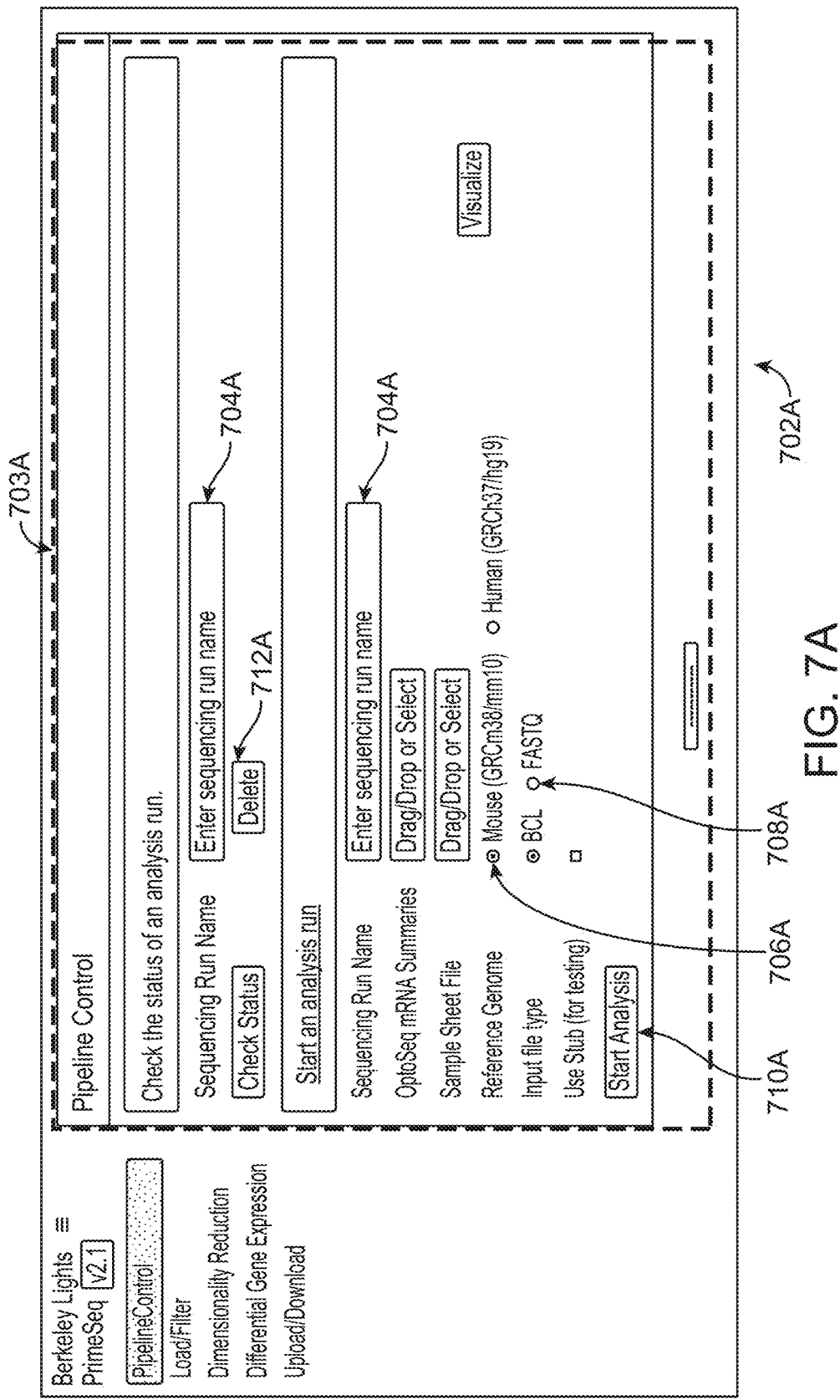
FIG. 7A illustrates an example bioinformatics pipeline user interface for a bioinformatics pipeline engine in one or more embodiments.

FIG. 7A illustrates an example bioinformatics pipeline user interface for a data control view 703A (e.g., a bioinformatics pipeline engine, an assay analysis control, etc.) in one or more embodiments. More specifically, FIG. 7A illustrates an example portion (e.g., data control view 703A) of a bioinformatics pipeline user interface for configuring or setting up a bioinformatics pipeline engine or a display engine (e.g., the display engine 50 in FIG. 2A) in one or more embodiments. In this example, a bioinformatics pipeline user interface 702A may receive a name of a sequencing run (704A) and the reference genome (706A) such as mouse (GRCm38/mm10) genome, a human genome (GRCh37/hg19), etc. A user may start an analysis run (e.g., by clicking on Start Analysis 710A). The bioinformatics pipeline user interface 702A may further allow the user to specify the input file type or format (708A) such as a binary base call (BCL) file type or format, a FASTQ file type or format, etc. in some embodiments.

In some other embodiments, the built-in intelligence of the input module that automatically determines the input file type of an input file. A BCL or binary base call file includes raw data generated by a genomics sequencing tool (e.g., an Illumina sequencer). A FASTQ file is a text-based sequencing data file format that stores, for example, raw sequence data, quality scores, and/or other pertinent data and may be used as an input for a bioinformatics analysis. In addition, FIG. 7A further illustrates the provisioning of a delete widget 712A which, when invoked, triggers deletion of certain designated data. In this example illustrated in FIG. 7A, the delete widget 712A, when invoked, causes the execution of instructions (e.g., by a processor in connection with a data bus) to delete a designated sequencing run. A delete widget may also be implemented in any other user interfaces or portions thereof to effectuate deletion of designated data.

Any of the reference numerals 704A, 706A, 708A, 710A, and/or 712A may be implemented as an interactive data control widget which, when interacted upon by a user input, invokes one or more respective candidate actions as described herein.

A bioinformatics user interface may provide alternative or additional functionalities that will be described below. The bioinformatics pipeline user interface is integrated seamlessly with one or more other modules, engines, and user interfaces described above. For example, the bioinformatics pipeline user interface may be integrated with one or more other views described above (e.g., gallery view, chip timeline view, etc.) so that a user may utilize these various other views as well as the functionalities provided by the underlying engines and modules described above with reference to FIGS. 4A-4E, 5A-5K, and 6A-6I. Some examples for integrating the bioinformatics user interface, the underlying bioinformatics pipeline engine, etc. are illustrated in FIGS. 7A-7O.

Moreover, sequencing analyses whose results are presented in, for example, FIGS. 7A-7O, the sequencing may be performed on a separate sequencing module that is seamlessly integrated with all the other views described herein in some embodiments. More specifically, various types of data populated into a view illustrated in FIG. 7C or 7J may include, for example, the representations of genes in corresponding regions of interest. These corresponding regions of interest may be determined by a user or automatically by the system based at least in part upon, for example, the corresponding chip timeline and/or the workflow or the bioinformatics pipeline. These regions of interest may be purely target-based, purely structure-based, or both target-based and structure-based. Depending on whether a region of interest is target-based or structure-based, one or more attributes, characteristics, properties, and/or quantifiable metrics, etc. may also be captured and associated with the other data and may be used to manipulate (e.g., filter, rank, cluster, generate custom chamber list(s), etc.) data that is associated with each other.

Figure 7B:
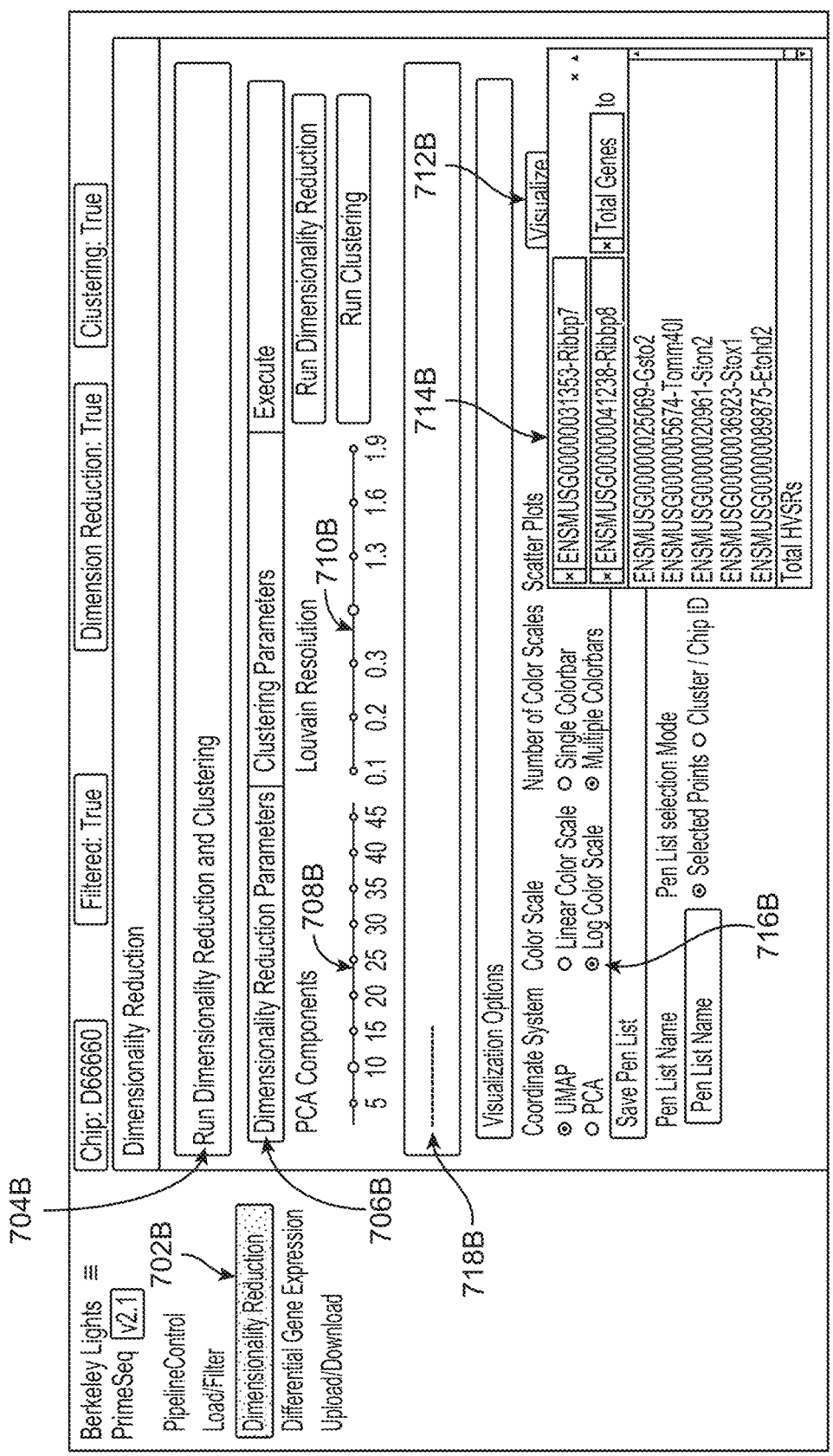
FIG. 7B illustrates an example where a user is provided with the capability to configure one or more dimensionality reduction parameters for dimensionality reduction of a bioinformatics pipeline dataset as well as some additional features of the example bioinformatics pipeline user interface in one or more embodiments.
Figure 7C:
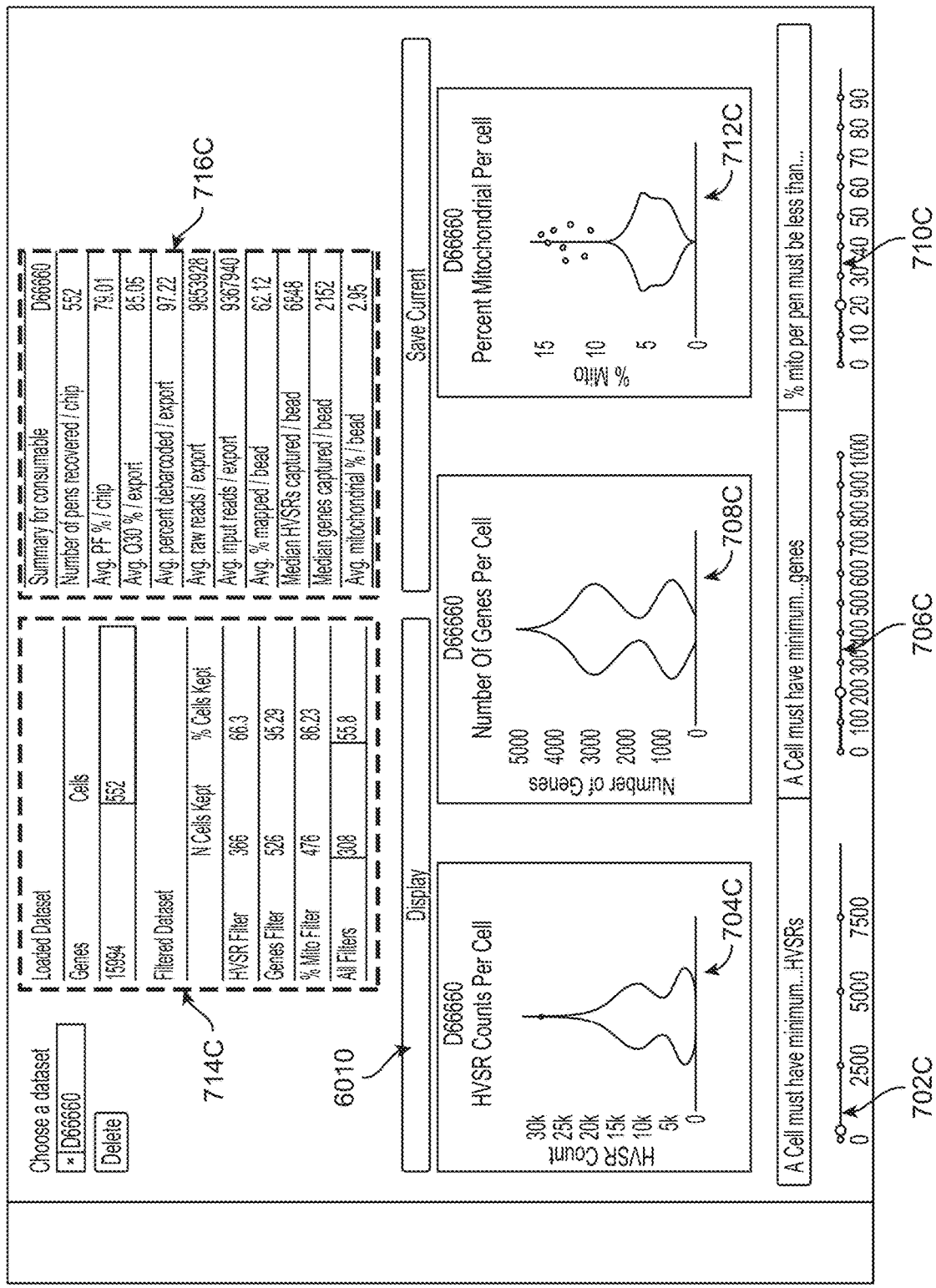
FIG. 7C illustrates an example representation of a bioinformatics pipeline dataset in one or more embodiments.
Figure 7E:
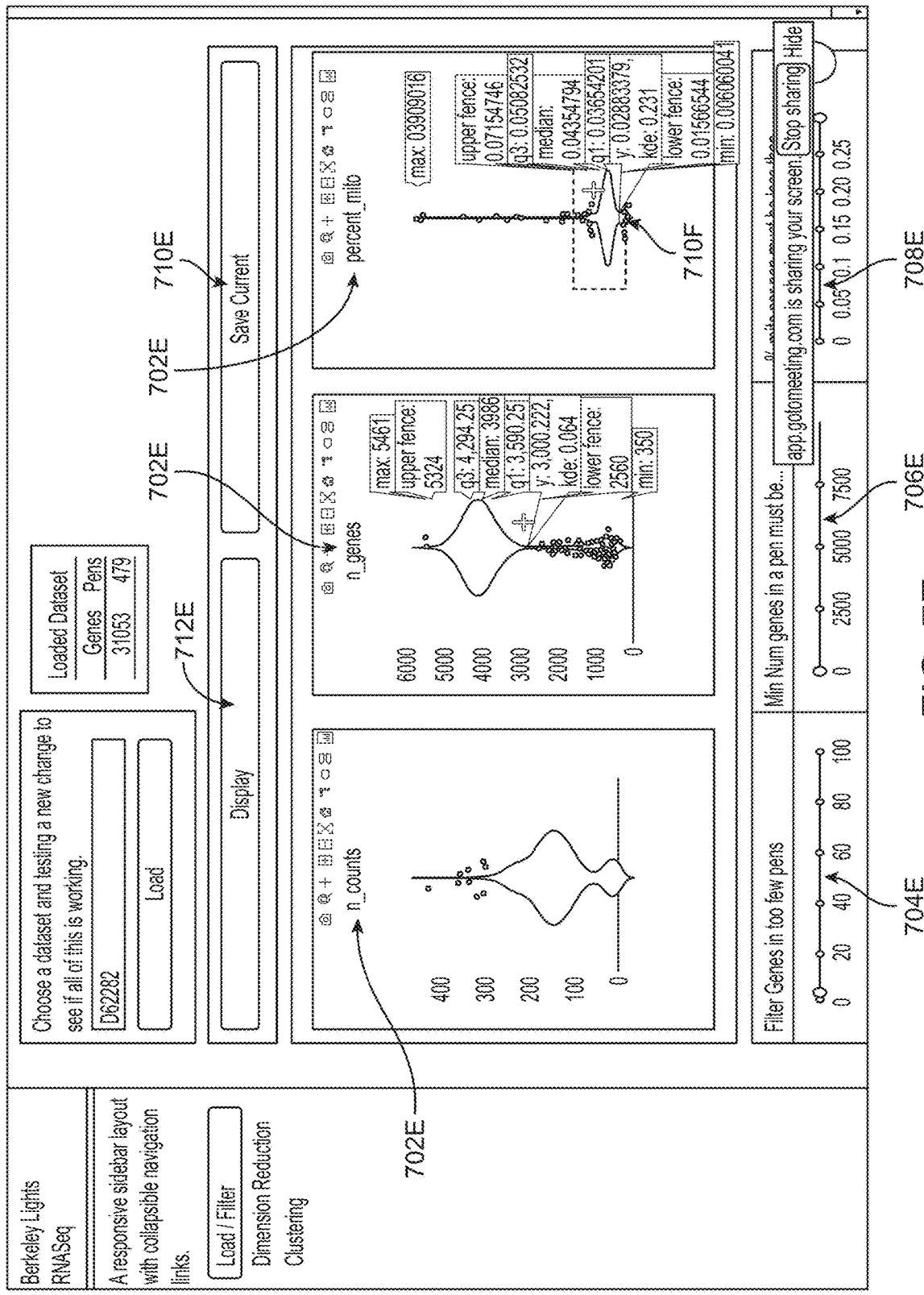
FIG. 7E illustrates some example dynamic aspects of an example user interface described herein in one or more embodiments.
Figure 7F:
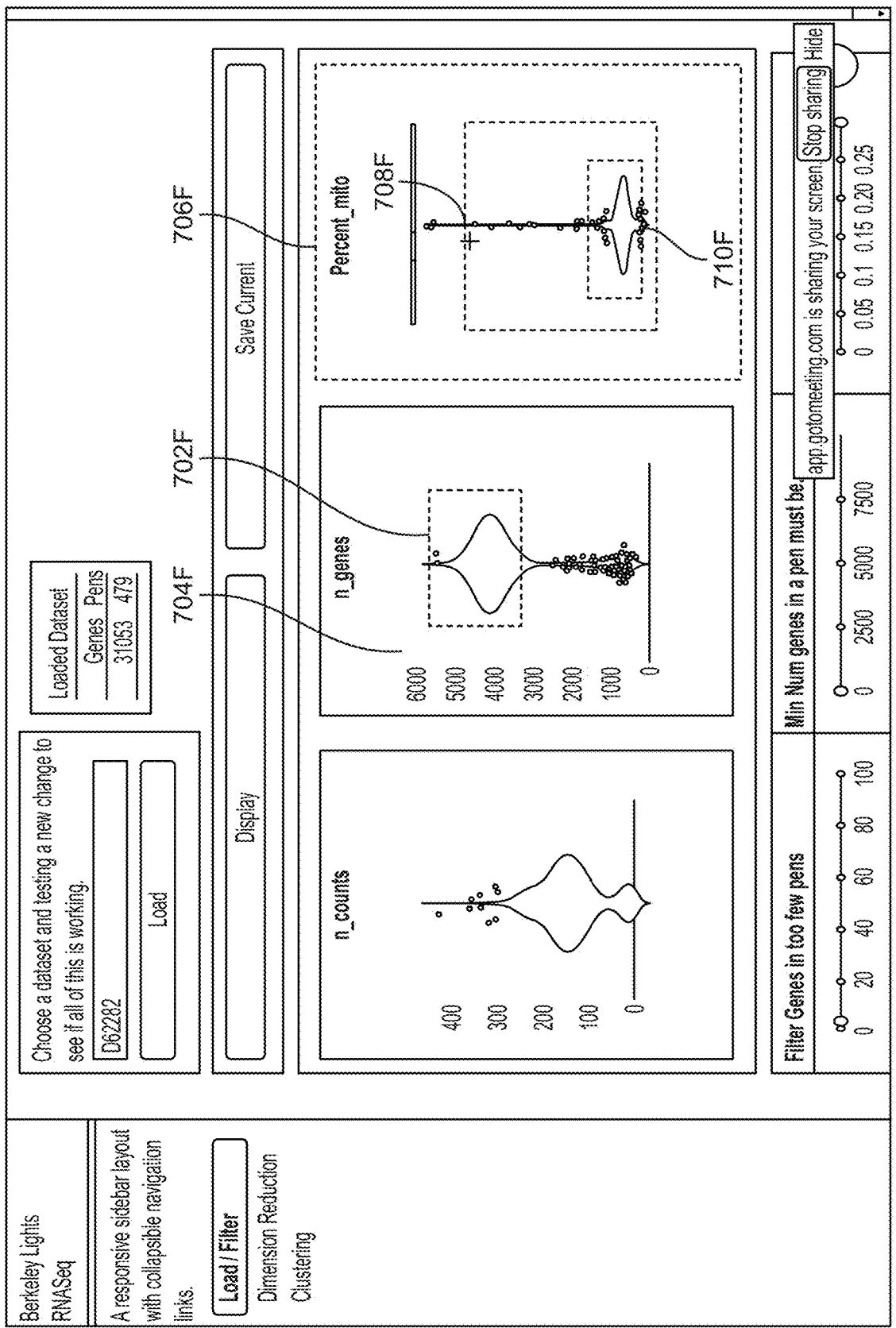
FIG. 7F illustrates an example of another selection tool for selecting a portion of the bioinformatics pipeline dataset in one or more embodiments.
Figure 7G:
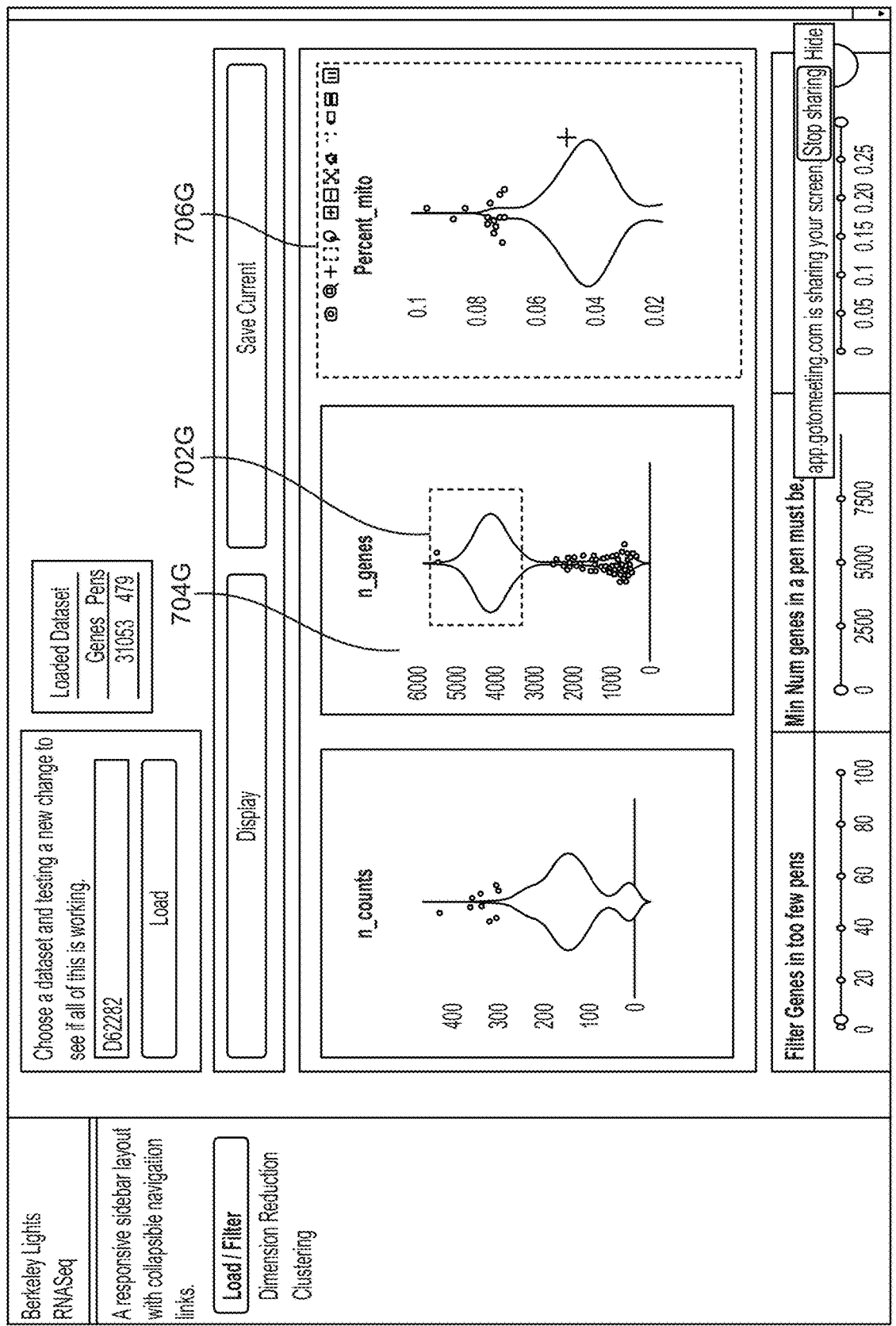
FIG. 7G illustrates an example result of selection in FIG. 7F in an example user interface described herein in one or more embodiments.
Figure 7H:
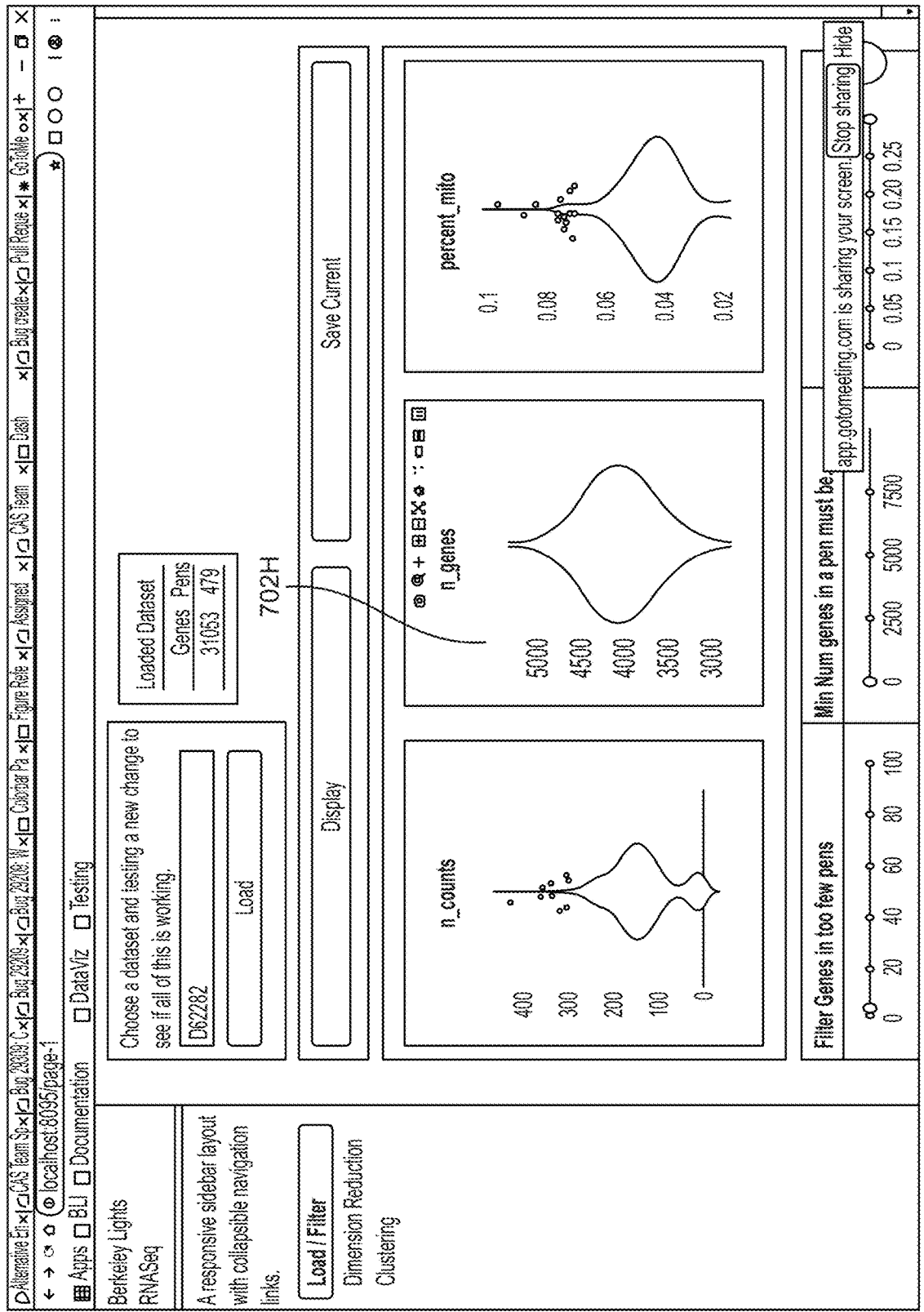
FIG. 7H illustrates the result of selection from FIG. 7G in an example user interface described herein in one or more embodiments.
Figure 7I:
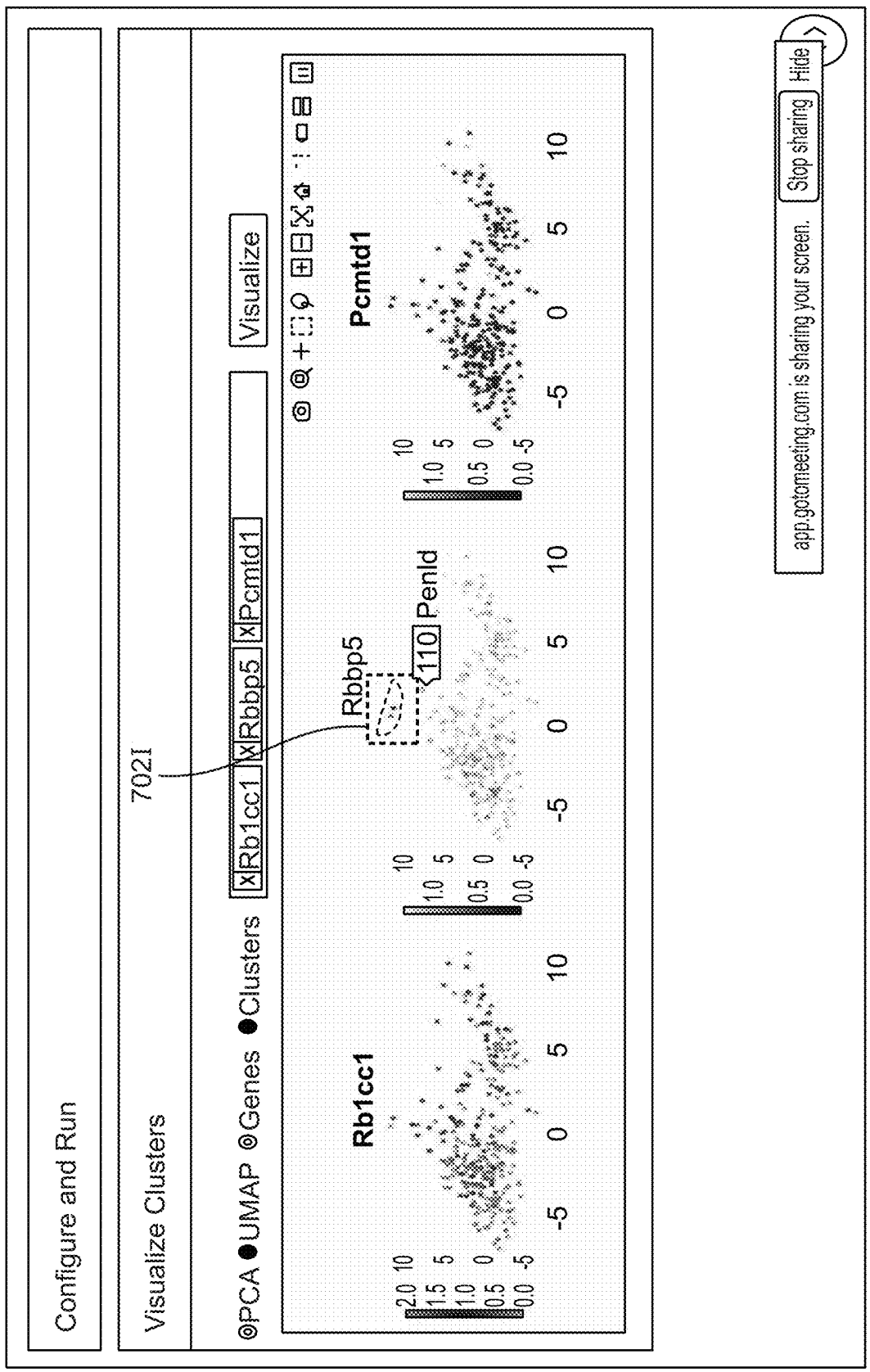
FIG. 7I illustrates the result of selection from FIG. 7G in an example user interface described herein in one or more embodiments.

Moreover, the graphs illustrated in, for example, FIG. 7C or 7I may also be correlated with any other views (e.g., a gallery view, a chip timeline view, etc.) For example, a gallery view may present specific stages of an analysis in respective columns where each column corresponds to a specific stage, and these specific columns in the gallery view also correspond to the information presented chip timeline (e.g., the graphic, color-coded representations 502F in FIG. 5F). In some embodiments where a column in a gallery view presents data for multiple regions of interest according to one of the aforementioned one or more attributes, characteristics, properties, or quantifiable metrics, the system may further determine the correspondence between this column and the stage that is more or most pertinent to the attribute, characteristic, property, or quantifiable metric in the chip timeline. In this manner, a graph illustrated in FIGS. 7A to 7O for sequencing may also be correlated with various different views described herein to efficiently leverage or employ any of the functionalities described herein so that a user may easily switch among different views to perform any of the desired or required functionalities to facilitate the derivation computational analytics and/or the analysis of the data correlated with the analysis of biological samples.

FIG. 7B illustrates an example where a user is provided with the capability to configure one or more dimensionality reduction parameters for dimensionality reduction of a bioinformatics pipeline dataset as well as some additional features of the example bioinformatics pipeline user interface in one or more embodiments. More specifically, FIG. 7B illustrated additional features of the example bioinformatics pipeline user interface illustrated in FIG. 7A in one or more embodiments. More specifically, FIG. 7B illustrates the user interface for dimensionality reduction and/or clustering (e.g., clustering of biological samples). As it may be seen from FIG. 7B, the dimensionality reduction functionalities are integrated into the interface for loading a dataset in these embodiments. The size of a typical full dataset obtained from the biological samples in or on a microfluidic device is usually large which substantially slows down computation. Therefore, applying one or more filters in the interface for loading a dataset to narrow down the scope of further processing before saving any information, proceeding to dimensionality reduction, or performing clustering may further conserve compute resources.

As illustrated in FIG. 7D described below, the bioinformatics pipeline dataset is a large data structure comprising 15994 genes and 552 cells. This data structure may comprise a tabular structure where each gene is stored in a respective column, and each cell is stored in a respective row. The dimensionality reduction and/or clustering functionality may be invoked by, for example, clicking on "Dimensionality Reduction" 702B in the bioinformatics pipeline user interface although other ways of invoking the dimensional reduction functionality (e.g., by selecting from a menu, clicking on an icon, etc.) are also contemplated. The example bioinformatics pipeline user interface further provides a user to invoke the configuration and/or execution of dimensionality reduction and/or clustering (704B) as well as to view the dimensionality reduction and/or clustering results (718B).

For example, a user may click on "dimensionality reduction and clustering" 704B in the bioinformatics pipeline user interface. In response, the bioinformatics pipeline user interface automatically expands and shows one or more menu items for configuring and/or executing dimensionality reduction as well as configuring and/or executing clustering. In this example illustrated in FIG. 7B, the user is provided with the capability to configure one or more dimensionality reduction parameters 706B for dimensionality reduction of a bioinformatics pipeline dataset in one or more embodiments. These one or more clustering parameters 706B may include, for example, the number of PCA (principal component analysis) components (708B) to reduce to, or any other suitable parameter(s) for dimensionality reduction. For example, some embodiments may first perform a PCA (Principal Component Analysis) to produce a smaller number of dimensions and then perform UMAP (Uniform Manifold Approximation and Projection) with the smaller number of dimensions. Moreover, the user is provided with the ability to configure one or more clustering parameters 716B. These one or more clustering parameters 716B may include, for example, a resolution parameter 710B (e.g., Louvain parameter) used for a clustering algorithm (e.g., Louvain clustering algorithm), or any other suitable parameter(s) for clustering. In some embodiments, these one or more clustering parameters include a Louvain resolution parameter which further includes, for example but not limited to, the number of clusters where a larger value leads to more clusters.

FIG. 7B illustrates an example of configuring the visualization options of the aforementioned clustering result in one or more embodiments. More specifically, a user may click on "Visualize Clusters" 718B. In response, the bioinformatics pipeline user interface automatically expands and shows one or more menu items for configuring one or more visualization characteristics of the clustering analysis of the biological samples. In this example, a user may be provided with the options to select the coordinate system (e.g., UMAP or Uniform Manifold Approximation and Projection, PCA or Principal Component Analysis, etc.), the color scale (e.g., linear scale, logarithmic scale, etc.), the number of color scales (e.g., single color bar, multiple color bars, etc.), and/or any other visualization attributes or characteristics.

A user may further configure (e.g., specify or select from a pull-down menu) one or more types of plots each of which characterizes a specific characteristic or statistical measure correlated with a loaded dataset with the provisioning 714B in the bioinformatics pipeline user interface. The drop-down list for 714B includes all genes available after filter, if previously applied. In some embodiments where clustering has been performed, the drop-down list for 714B may further include options correlated with clustering. For example, a user may select one or more of the total HVSRs (highly variable signal regions), the total genes per cell, by clusters, etc. to configure visualization of the clustering (which may be subject to dimensionality reduction if the user opts for and configures dimensionality reduction). With the visualization configuration done, a user may generate a graphical representation by, for example, clicking on "Visualize" (e.g., a "sequencing view widget") 712B in the bioinformatics pipeline user interface.

FIG. 7C illustrates an example representation of a bioinformatics pipeline dataset in one or more embodiments. More specifically, FIG. 7C illustrates an example representation of the bioinformatics pipeline dataset described above with reference to FIG. 7M in one or more embodiments. It shall be noted that although three specific types of plots are illustrated in FIG. 7C, some embodiments may also provide one or more other types or numbers of graphical representations for a bioinformatics pipeline dataset as a part of a bioinformatics pipeline user interface (e.g., 702A in FIG. 7A). This example illustrated in FIG. 7C presents a first plot for the HVSR (highly variable signal region) counts per cell 704C with a filtering slider 702C that constrains the first plot by the minimum HVSR. For example, a user may desire to view the results of cells that have a minimum or a maximum HVSR by adjusting the slider 702C. FIG. 7C further includes a second plot for the total number of genes per cell 708C with a filtering slider that constrains the second plot by the minimum or maximum total number of genes per cell. For example, a user may desire to view the results that have a minimum or a maximum number of genes per cell by adjusting the slider 706C.

FIG. 7C further includes a third plot for the percentages of mitochondrial per cell 712C with a filtering slider 710C that constrains the third plot by the minimum or maximum percentage of mitochondrial genes per cell. For example, a user may desire to view the results that have a minimum or a maximum percentage of mitochondrial genes per cell by adjusting the slider 710C. It shall be noted that although FIG. 7C illustrates the provisioning of sliders, other ways of constraining or limiting the dataset to be graphically represented (e.g., in 704C, 708C, and/or 712C) may be used in place of or in addition to these illustrated sliders. For example, the example bioinformatics pipeline user interface may provide a field for a user to enter an exact value or an expression (e.g., a logical expression) to filter or constrain the dataset for graphical representation.

For example, a user may use the filtering slider 702C to filter out any cells that fail to satisfy a minimum number (e.g., 1000) of HVSRs as controlled by the user. The graph 704C is updated automatically in response to the manipulation of the filtering slider 702C. As another example, a user may use the filtering slider 706C to filter out any cells that fail to satisfy a minimum number (e.g., 200) of genes as controlled by the user. The graph 708C is updated automatically in response to the manipulation of the filtering slider 706C. As another example, a user may use the filtering slider 710C to filter out any cells that fail to satisfy a maximum percentage (e.g., 15%) of mitochondrial genes as controlled by the user. The graph 712C is updated automatically in response to the manipulation of the filtering slider 710C.

FIG. 7D illustrates more details about an example bioinformatics pipeline user interface illustrated in FIGS. 7A-7C in one or more embodiments. More specifically, as illustrated in FIG. 7D, in response to the user's adjustment of one or more sliders, the system automatically updates the summary 714C and 716C to reflect the effect of adjusting these one or more sliders. For example, the bioinformatics pipeline user interface shows that the loaded dataset corresponds to 15994 genes and 552 cells. The bioinformatics pipeline user interface further shows the respective number of cells retained and the respective percentage of cells retained for each of the sliders as well as the total number of cells retained and the total percentage of cells retained with the combination of all of the filters that are placed in effect.

For example, FIG. 7D illustrates that the number of micro-objects retained after the application of the HVSR filter is 366; the number of micro-objects retained after the application of the genes filter is 526; the number of micro-objects retained after the application of the % mitochondrial filter is 476; and the total number of micro-objects retained after the application of all filters is 308. In some embodiments, the bioinformatics pipeline user interface may further show the respective percentages of the micro-objects retained for the application of each filter and the application of all filters.

The bioinformatics pipeline user interface may further display addition information in the summary 716C. In some embodiments, the additional information may include at least one of, the number of chambers recovered per microfluidic device (e.g., 552 in FIG. 7D), the average PF percentage per microfluidic device (e.g., 79.01% in FIG. 7D), the average Q30 percentage per export (e.g., 85.05% in FIG. 7D), the average percent of the de-barcoded per export (e.g., 97.22% in FIG. 7D), the average raw reads per export (e.g., 9,853,928 in FIG. 7D), the average input reads per export (e.g., 9,367,940 in FIG. 7D), the average percentage mapped per bead (e.g., 62.12% in FIG. 7D), the median HVSRs captured per bead (e.g., 6,848 in FIG. 7D), the median genes captured per bead (e.g., 2,152 in FIG. 7D), the average mitochondrial percentage per bead (e.g., 2.95% in FIG. 7D), and/or any other desired or relevant information or data.

FIG. 7E illustrates some example dynamic aspects of an example user interface described herein in one or more embodiments. More specifically, FIG. 7E illustrates an example of a dynamic aspect of the user interface illustrated in FIG. 7E. More specifically, when a user moves a pointing device cursor near a designated area (e.g., near the top, the bottom, etc.) of a view, a context menu may pop up in the view to provide the user with option(s) or command(s) to, for example, further configure the view or analyze the bioinformatics pipeline dataset. In some embodiment, the context menu may also appear on display by other user interactions (e.g., by right click with a pointing device in the view). In addition, a bioinformatics pipeline dataset that comprises nucleotide sequence data such as gene sequence data, DNA sequence data, RNA sequence data, and/or viral sequence data, etc. to which various techniques and functionalities described herein apply.

FIG. 7E illustrates a bioinformatics view that may be displayed in the user interface and may leverage the other modules, widgets, and functionalities described herein to view and analyze bioinformatics pipeline dataset that comprises nucleotide sequence data such as gene sequence data, DNA sequence data, RNA sequence data, and/or viral sequence data, etc. The example dataset illustrated in FIG. 7E includes around 500 chambers with over 31,000 genes that span across a data structure of about 30,000 columns with about 1,000 rows. The three subtitles 702E (e.g., "n_counts," "n_genes," and "percent mito" representing their corresponding characteristics in FIG. 7E) refer to the names of genes in the respective scatter plots. These labels, when interacted upon, sorts or ranks the corresponding chambers or regions of interest in a descending or ascending order in some embodiments. In some embodiments, one of such plots or graphs may be generated with a color scheme or range that corresponds to a range of values for an attribute, characteristic, property, or metric of a plurality of biological samples and may be referred as a heat map.

FIG. 7E further illustrates an example of a user interface for loading the bioinformatics pipeline dataset in some embodiments. More specifically, a bioinformatics pipeline dataset that comprises nucleotide sequence data such as gene sequence data, DNA sequence data, RNA sequence data, and/or viral sequence data, etc. to which various techniques and functionalities described herein apply.

FIG. 7E also illustrates the on-screen display of the distribution of the bioinformatics pipeline dataset. Each of the views may be static or dynamic in relation to user interactions. Again, the example data on which the view illustrated in FIG. 7E is generated may include a bioinformatics pipeline dataset that comprises nucleotide sequence data such as gene sequence data, DNA sequence data, RNA sequence data, and/or viral sequence data, etc. to which various techniques and functionalities described herein apply. Moreover, FIG. 7E illustrates the provisioning of filtering controls (704E, 706E, and 708E). For example, a first filtering control 704E provides a user with the capability of filtering biological samples (e.g., genes in this FIG. 7E) based at least in part a number of regions of interest (e.g., chambers) that exhibit a specific type of genes.

For example, genes that are detected in fewer than (or equal to) a threshold number of regions of interest (e.g., 20 or twenty ROIs) will be filtered out by adjusting the filtering control 704E. A second filtering control 706E provides a user with the capability of filtering biological samples based at least in part upon a minimum number of genes in a region of interest. For example, filtering control 706E may filter out regions of interest that fail to satisfy a minimum number of, for example, 200 genes as controlled by the filtering control 706E. A third filtering control 708E provides a user with the capability of filtering biological samples based at least in part upon a maximum percentage of mitochondrial genes in a region of interest. For example, filtering control 708E may filter out regions of interest that fail to satisfy a maximum percentage of, for example, 15% of mitochondrial genes as controlled by the filtering control 708E.

FIG. 7E further illustrates an example implementation of a writing widget 710E which, when invoked, triggers the storage of data or information (e.g., processed data) into a volatile or non-volatile storage medium. For example, a user may click on the writing widget 710E to trigger the storage of any of the data (e.g., the applied filter(s) and filtering criterion (or filtering criteria), the filtered results or a portion thereof, the plots, or any desired, required data, etc.) correlated with the display in FIG. 7E into a volatile or non-volatile storage medium. The writing widget 701E may further optionally present one or more options for saving data to the user so that the user may choose what is to be saved. In some embodiments, a delete widget (not shown) may be rendered in any of the user interfaces or a portion thereof to provide users with the functionality to delete data. A sequencing view widget 712E may be used to generate a sequencing view in the user interface.

FIG. 7E illustrates another example of a dynamic aspect of the user interface. More specifically, when a user moves a pointing device cursor near the distributed data in a view, the data (e.g., the maximum value, the upper fence, the median, the lower fence, the minimum value, etc.) associated with the nearest point to the cursor may be displayed in the view. When the user moves the cursor away, the data will be automatically suppressed or hidden. In some embodiments, FIG. 7E illustrates another example of a dynamic aspect of the user interface. More specifically, when a user moves a pointing device cursor near the distributed data in a view, the data (e.g., the maximum value, the upper fence, the median, the lower fence, the minimum value, etc.) associated with the nearest point to the cursor may be displayed in the view. When the user moves the cursor away, the data will be automatically suppressed or hidden.

FIG. 7F illustrates an example of another selection tool for selecting a portion of the bioinformatics pipeline dataset in one or more embodiments. More specifically, FIG. 7F illustrates an example of another selection tool for selecting a portion of the bioinformatics pipeline dataset. For example, a user may draw a polygonal shape (e.g., 708F or 710F) in a view 706F to select interested data. As described above, the example data on which the view illustrated in FIG. 7F is generated may include a bioinformatics pipeline dataset that comprises nucleotide sequence data such as gene sequence data, DNA sequence data, RNA sequence data, and/or viral sequence data, etc. to which various techniques and functionalities such as the selection tool apply.

FIG. 7F further illustrates another example of a dynamic aspect of the user interface. More specifically, when a user moves a pointing device cursor near the distributed data in a view, the data (e.g., the maximum value, the upper fence, the median, the lower fence, the minimum value, etc.) associated with the nearest point to the cursor may be displayed in the view. When the user moves the cursor away, the data will be automatically suppressed or hidden.

FIG. 7F also illustrates an example of another selection tool for selecting a portion of the bioinformatics pipeline dataset. For example, a user may draw a polygonal shape 710F in a view to select interested data. As described above, the example data on which the view illustrated in FIG. 7F is generated may include a bioinformatics pipeline dataset that comprises nucleotide sequence data such as gene sequence data, DNA sequence data, RNA sequence data, and/or viral sequence data, etc. to which various techniques and functionalities such as the selection tool apply.

FIG. 7F further illustrates an example of another selection tool for selecting a portion of the bioinformatics pipeline dataset. For example, a user may draw a polygonal shape 702F in a view 704F to select interested data which, in this example illustrated in FIG. 7F, includes nucleotide sequence data such as gene sequence data, DNA sequence data, RNA sequence data, and/or viral sequence data, etc. to which various techniques and functionalities such as the selection tool apply.

FIG. 7G illustrates an example result of selection in FIG. 7F in an example user interface described herein in one or more embodiments. More specifically, FIG. 7G illustrates the result of selection from FIG. 7F. The view 706G is a result of selection according to the selection shape 708F in FIG. 7F from the original view 706F in FIG. 7F. As described above, the example data on which the view illustrated in FIG. 7F is generated may include a bioinformatics pipeline dataset that comprises nucleotide sequence data such as gene sequence data, DNA sequence data, RNA sequence data, and/or viral sequence data, etc. to which various techniques and functionalities described herein apply.

FIG. 7G further illustrates an example of another selection tool for selecting a portion of the bioinformatics pipeline dataset. For example, a user may draw a polygonal shape 702G in a view 704G to select interested data which, in this example illustrated in FIG. 7G, includes nucleotide sequence data such as gene sequence data, DNA sequence data, RNA sequence data, and/or viral sequence data, etc. to which various techniques and functionalities such as the selection tool apply.

FIG. 7H illustrates the result of selection from FIG. 7G in an example user interface described herein in one or more embodiments. More specifically, FIG. 7H illustrates the result of selection from FIG. 7G. The view 702H is a result of selection according to the selection shape 702G from the original view 704G in FIG. 7G. As described immediately above, the view illustrated in FIG. 7H is generated with various techniques described herein and leverages various functionalities described here based on a bioinformatics pipeline dataset that may comprise nucleotide sequence data such as gene sequence data, DNA sequence data, RNA sequence data, and/or viral sequence data, etc. to which various techniques and functionalities such as the selection tool apply.

FIG. 7I illustrates an example bioinformatics pipeline user interface described herein in one or more embodiments. More specifically, FIG. 7I illustrates an example of selecting samples from one or more scatter plots (e.g., the scatter plots having the respective identifiers or labels of "Rb1cc1," "Rbbp5," and "Pcmtd1" corresponding to their respective characteristics in FIG. 7I) of a bioinformatics pipeline dataset. In this example, the user interface may provide a user with the capability to draw, for example, one or more polygonal shapes, lassos, or other appropriate shapes 702I to enclose samples of interest. In some embodiments, the user interface may also provide a user with the capability of selecting individual samples by, for example, clicking on or in the vicinity of a sample. Once the samples or points of interests are selected, the system may transmit the data associated with these selected samples or points to one or more other views so that a user may invoke various functions and capabilities provided in these one or more other views.

Moreover, FIG. 7I illustrates an example user interface for configuring the presentation and analysis of bioinformatics pipeline dataset. For example, a user may configure the minimum mean value or range, the maximum mean value or range, the mid-dispersion, etc. A user may also select or specify a solver for analyzing the dataset, the convergence criterion, etc. for the analysis. The interface may also allow the user to invoke PCA (principal component analysis), UMAP (uniform manifold approximation and projection), or any other analyses from within the interface.

FIG. 7I further illustrates some example scatter plots of the dataset. In some embodiments, a view may be configured with various display attributes, coloring schemes (e.g., maximum and minimum colors for a heat map) so that the samples or points (each one representing, e.g., one biological sample in a chamber) in the scatter plots may be visually distinguished. The interface also allows a user to select points from any of the scatter plots and sends the selected points to, for example, a gallery view for further analyses, viewing, etc. as described above. Further, results from one assay, e.g., staining for a cell surface marker may be linked with the results from another assay, e.g., a gene expression plot for the same samples, and obtain more highly discriminating heat maps. In one example, phenotypic data 702P, staining intensity in CY5 for CD3 cell surface markers for peripheral blood mononuclear (PBMC) cells is shown in FIG. 7P, overlaid on the overall gene expression clusters for this sample, where the staining phenotypically identifies the sample as T cells. This data may be further interrogated by examining the gene expression results from these cells for specific genetic markers as shown in FIG. 7Q. Panel 702Q shows CD3D gene expression; Panel 704Q shows CD8A gene expression; Panel 706Q shows CD4 gene expression, and Panel 708Q shows CD8B gene expression. Examining the distribution of these specific gene expression markers allows for identification of particular sub-types of T cell. Thus, different assay results performed at different time points along a chip timeline may be linked together in some embodiments.

Figure 7J:
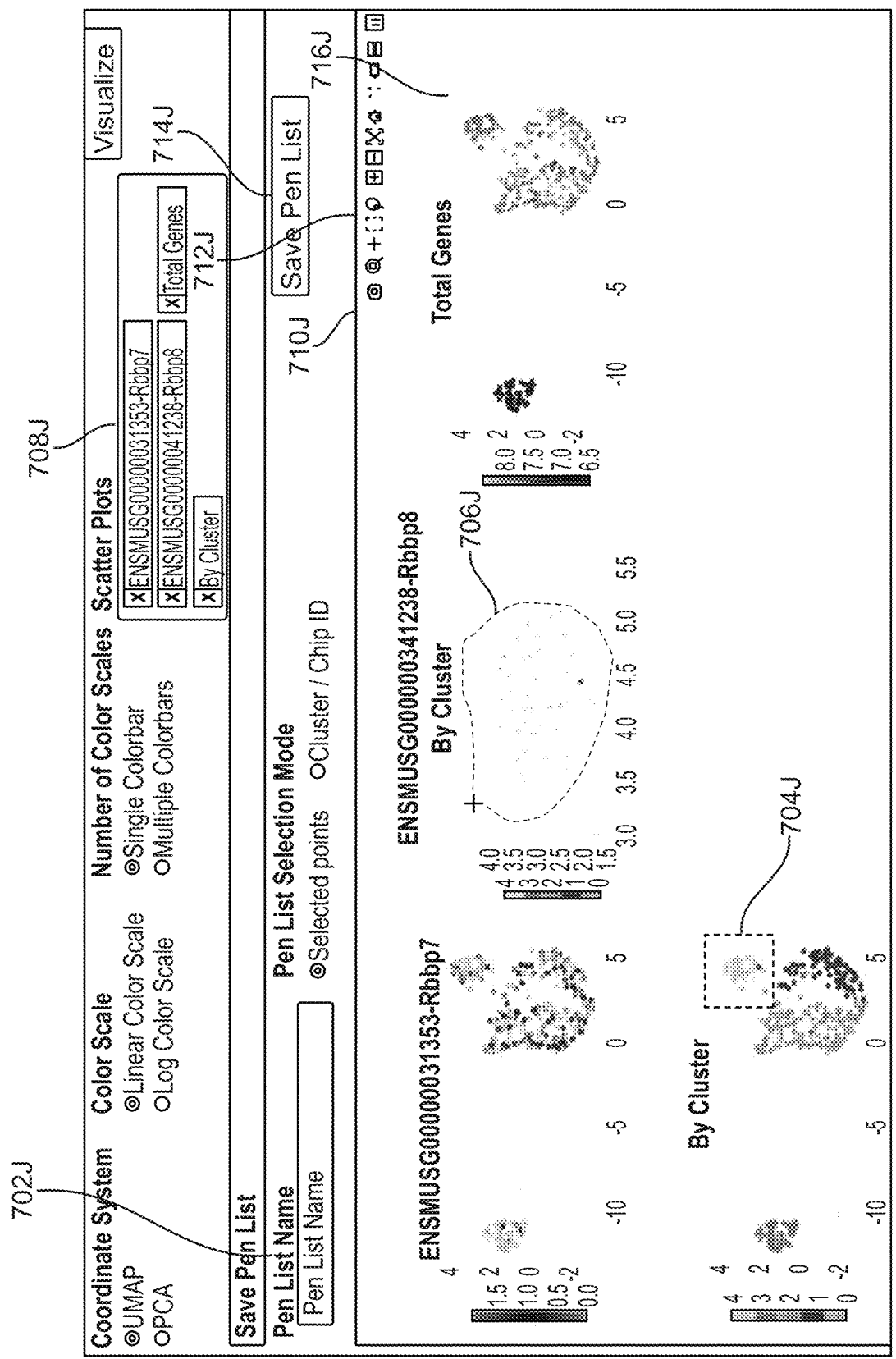
FIG. 7J illustrates some example scatter plots of clustering results of biological samples in a loaded bioinformatics pipeline dataset, an interactive plot or graphical representation, as well as an example where a user configures an interactive plot presented in a user interface in one or more embodiments.

FIG. 7J illustrates some example scatter plots of clustering results of biological samples in a loaded bioinformatics pipeline dataset, an interactive plot or graphical representation, as well as an example where a user configures an interactive plot presented in a user interface in one or more embodiments. More specifically, FIG. 7J illustrates some example scatter plots of clustering results of the biological samples in a loaded bioinformatics pipeline dataset in one or more embodiments after the user, for example, has configured and executed the clustering module and the visualization module to view the results.

The plots presented in the bioinformatics pipeline user interface may be generated based at least in part on how a user configures the scatter plots (e.g., 714B in FIG. 7B). In some embodiments where PCA or UMAP have been performed during dimensionality reduction, a plot may be generated using at least the PCA or UMAP data. In the examples illustrated in FIGS. 7A-7B, the user identifies four scatter plots each corresponding to a characteristic or statistical measure for the biological samples in the bioinformatics pipeline dataset. In response to the user's selection, the underlying system generates four scatter plots that respectively correspond to the four selected characteristic(s) and/or statistical measure(s). A user may also configure the number of colors or color schemes for the plotting engine to generate a plot. Each dot in the scatter plot represents a region of interest (e.g., a chamber), and the color of the dot may depend on, for example, the title. For example, if the title is one of gene id, cluster, or phenotypic information, the color represents the expression of that gene in that region of interest, the cluster the region of interest belongs to, or the value of the phenotypic measure for that region of interest, respectively.

Each of the plots or graphical representations illustrated in FIG. 7J may be a static plot in some embodiments or an interactive plot in some other embodiments. FIG. 7J illustrates an example of an interactive plot or graphical representation 716J in one or more embodiments. The bioinformatics pipeline user interface may automatically reveal one or more icons, menu items, widgets, etc. providing respective widget menu having a plurality of widgets (710J) when an interactive plot or graphical representation (e.g., 716J) is interacted upon (e.g., by moving a pointing device cursor over the interactive plot 716J, by clicking on the interactive plot 716J, etc.) For example, a user may invoke a curvilinear or rectilinear selection widget 712J from the respective widget menu 710J. Any suitable functionalities, commands, widgets, or menu items correlated with displaying the interactive plot (e.g., changing coloring scheme, contrast, color, etc., zoom-in, zoom-out, etc.) or correlated with data points in the interactive plot (e.g., one or more selection tools for the data represented in the interactive plot, etc.) may be provided in the aforementioned icons, menu items, widgets, etc.

A user may further configure (e.g., specify or select from a pull-down menu) one or more types of plots each of which characterizes a specific characteristic or statistical measure correlated with a loaded dataset with the provisioned plot or graph configuration interface 708J in the bioinformatics pipeline user interface. The plot or graph configuration interface may include a drop-down list which may further include, for example, one or more genes or biological micro-objects available for selection. In some embodiments where clustering has been performed, the drop-down list for the plot or graph configuration interface 708J may further include options, configurations settings, or parameter value(s), etc. correlated with clustering. For example, FIG. 7J illustrates an example where a user configures an interactive plot presented in a user interface to further zoom into some of the data points in the interactive plot in some embodiments. In this example, the user may define a zoom-in window 704J with the aforementioned one or more icons, menu items, widgets, etc. (710J) to draw a custom window that encloses some data points of interest. In response, the underlying system may display the data points of interest enclosed by the zoom-in window 704J as shown in FIG. 7J. FIG. 7J further illustrates the provisioning of a selection tool 706J for a user to select one or more data points of interest from an interactive plot in one or more embodiments. In this example illustrated in FIG. 7J, a lasso selection tool is provided for a user to select one or more data points of interest.

The bioinformatics pipeline user interface may be seamlessly integrated with one or more other user interface components described herein in some embodiments although each of the user interface components including the bioinformatics pipeline user interface may be a stand-along software construct in some other embodiments. FIG. 7J illustrates an example of seamlessly interfacing a bioinformatics pipeline user interface with one or more other user interface components described herein in one or more embodiments. As described above with reference to, for example, FIG. 7K described below, a user may select one or more chambers or biological samples via the tools provided by various techniques described herein. Once these one or more chambers or biological samples are selected, a user may create a custom chamber list or chamber list (e.g., by clicking on "Save Pen List" 714J) with an identifier 702J and store the pen list or chamber list for subsequent references.

Figure 7K:
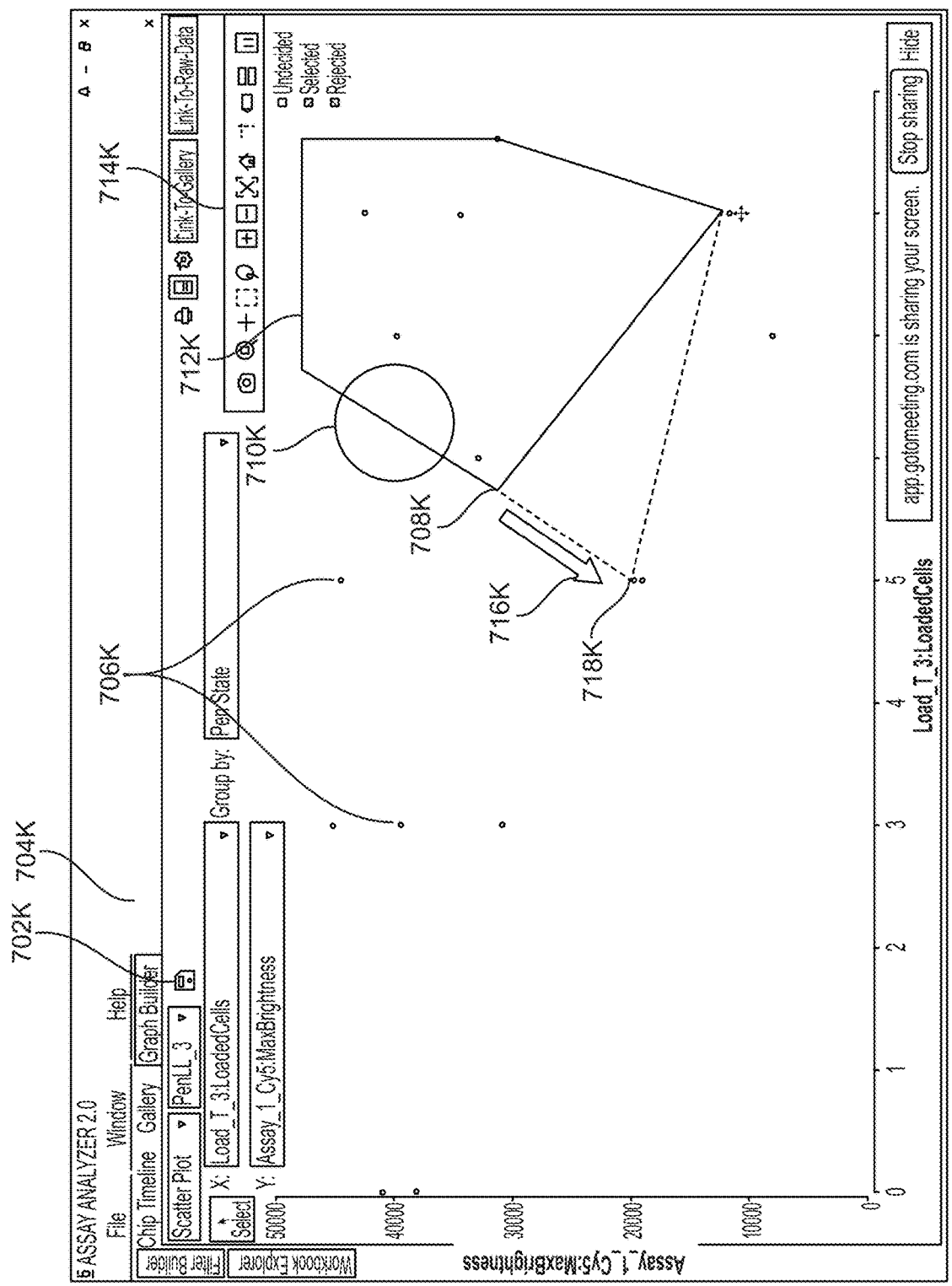
FIG. 7K illustrates a built-in selection widget that may be incorporated with any graphs or views, if applicable, for a user to select objects in some embodiments.

FIG. 7K illustrates a built-in selection widget that may be incorporated with any graphs or views, if applicable, for a user to select objects in some embodiments. More specifically, FIG. 7K illustrates an example of a graph building module 704K that allows a user to, for example, define what is to be used for the axes (e.g., X-axis for loaded cells, Y-axis for a specific assay or characteristic such as maximum brightness, etc.) The graph building module 704K may also permit the user to group the displayed items by one or more grouping criteria (e.g., by the state of chambers, etc.) FIG. 7K further illustrates an example of a sequencing result so that each dot (data notes or data points) 706K on display represents, for example, a gene in a structure-based region of interest (e.g., a chamber in a microfluidic device). These dots 706K may be obtained by, for example, lysing the biological samples in chambers of a microfluidic device so that DNA or RNA is attracted to beads (e.g., magnetic beads) and by exporting the beads for clustering. FIG. 7K further illustrates an example implementation of a writing widget 702K which, when invoked, triggers the storage of data or information (e.g., processed data) into a volatile or non-volatile storage medium.

For graphs of a sequencing analysis presented in, for example, FIGS. 7A-7O, the sequencing may be performed on a separate sequencing module that is seamlessly integrated with all the other views described herein in some embodiments. More specifically, various types of data populated into a view illustrated in FIG. 7K may include, for example, the representations of genes in corresponding regions of interest. These corresponding regions of interest may be determined by a user or automatically by the system based at least in part upon, for example, the corresponding chip timeline and/or the workflow or the bioinformatics pipeline. These regions of interest may be purely target-based, purely structure-based, or both target-based and structure-based. Depending on whether a region of interest is target-based or structure-based, one or more attributes, characteristics, properties, and/or quantifiable metrics, etc. may also be captured and associated with the other data and may be used to manipulate (e.g., filter, rank, cluster, generate custom chamber list(s), etc.) data that is associated with each other.

Moreover, the graph illustrated in FIG. 7K also be correlated with any other views (e.g., a gallery view, a chip timeline view, etc.) For example, a gallery view may present specific stages of an analysis in respective columns where each column corresponds to a specific stage, and these specific columns in the gallery view also correspond to the information presented chip timeline (e.g., the graphic, color-coded representations 502F in FIG. 5F). In some embodiments where a column in a gallery view presents data for multiple regions of interest according to one of the aforementioned one or more attributes, characteristics, properties, or quantifiable metrics, the system may further determine the correspondence between this column and the stage that is more or most pertinent to the attribute, characteristic, property, or quantifiable metric in the chip timeline. In this manner, a graph illustrated in FIG. 7K for sequencing may also be correlated with various different views described herein to efficiently leverage or employ any of the functionalities described herein so that a user may easily switch among different views to perform any of the desired or required functionalities to facilitate the derivation computational analytics and/or the analysis of the data correlated with the analysis of biological samples.

FIG. 7K also illustrates a result of altering the polygonal shape 712K by dragging the vertex 708K of the shape 712K along the direction 716K in FIG. 7K to the new position 718K in order to alter the original polygonal shape 712K into the new polygonal shape. In some embodiments, FIG. 7K illustrates another example of the selection widget that allows the user to alter an existing selecting shape 712K. For example, if a user wishes to add a vertex or node to the bottom edge of the existing shape, the user may click on the bottom edge to activate the bottom edge and may use, for example, a context menu (not shown) to add a node. The selection widget may, in response to the user's invocation of the instruction to add a node or vertex, show a region 710K within which the node or vertex may be added. In some embodiments, the selection widget may add the node or vertex approximately to the location where the user clicks on the bottom edge.

In addition or in the alternative, the user interface may also provide many other adjustable settings for a user to customize a scatter plot such as FIG. 7K. For example, the user interface may allow the user to specify the shape of the scatter plot (e.g., circle, ellipse, etc.), whether the shape of scatter plot is filled or unfilled, the height and/or width of the scatter plot (which will be identical if circle is selected), the stroke, the thickness of the stroke, the palette, the color of selection, etc. and may provide a live preview when a user changes any of the settings. The user interface may also allow a user to select which tooltip(s) is (are) to be displayed, minimum color for a heatmap, maximum color for a heatmap, etc.

FIG. 7K further illustrates an example of using a built-in selection widget that may be incorporated with any graphs or views, if applicable, for a user to select objects (e.g., regions of interest, samples of interest, etc.) in some embodiments. A user may invoke the built-in selection widget to select objects by, for example, drawing a shape 712K (e.g., a polygonal shape, a lasso, a circle, etc.) to enclose the objects that the user wishes to select. The selection widget may also allow the user to change the shape 712K after the shape is drawn. For example, a user may drag a vertex 708K of a polygonal shape to alter the shape. A user may also add one or more vertices to an existing shape to alter the shape for selection. One or more selection widgets (e.g., a rectilinear selection widget used to define a rectilinear area including the objects of interest for selection, a curvilinear selection widget used to define a rectilinear area including the objects of interest for selection, etc.) may be implemented in a widget bar 714K or in a pop-up menu (e.g., a menu that appears when a view with one or more cursor associated commands such as a right click in a view), built-in menu, or a context menu (e.g., a pop-up menu that appears when a view that may be subject to selection is activated), etc.

In addition or in the alternative, data associated with selected samples or points from a view or window in a bioinformatics pipeline interface to another view or window (e.g., a gallery view described above) in some embodiments. For example, the data associated with the samples or points of interest selected in, for example, the bioinformatics pipeline user interface (e.g., selection via the polygonal selection shape 712K) may be transmitted to a gallery view described above and rendered in the gallery view for a user to invoke various functions provided by the gallery view described above.

Various example embodiments of the disclosure are described herein. Reference is made to these examples in a non-limiting sense. Examples are provided to illustrate more broadly applicable aspects of the invention. Various changes may be made to various embodiments described herein and equivalents may be substituted without departing from the true spirit and scope of the invention. In addition, many modifications may be made to adapt a particular situation, material, composition of matter, process, process act(s) or step(s) to the objective(s), spirit or scope of the present disclosure. Further, as will be appreciated by those with skill in the art that each of the individual variations described and illustrated herein has discrete components and features which may be readily separated from or combined with the features of any of the other several embodiments without departing from the scope or spirit of the present disclosures. All such modifications are intended to be within the scope of claims associated with this disclosure.

Figure 7L:
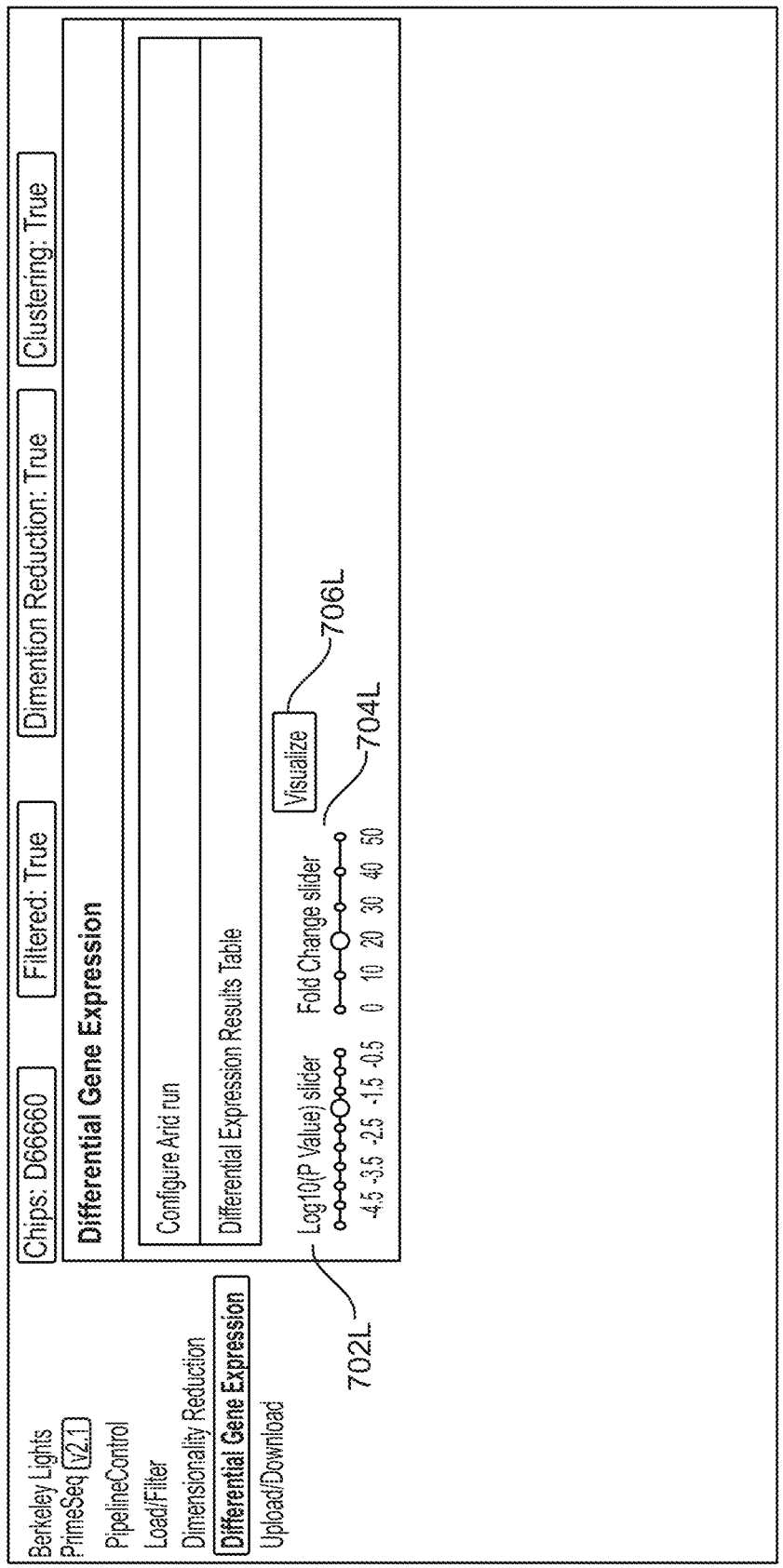
FIG. 7L illustrates another example of configuring differential gene expression in some embodiments.

FIG. 7L illustrates another example of configuring gene expression or differential gene expression in some embodiments. More specifically, FIG. 7L further illustrates another example of configuring differential gene expression in some embodiments. For example, a user may adjust a $log_b$ slider widget 702L and/or the fold change slider widget 704L to their respective desired values and click on "Visualize" widget 706L to present the differential gene expression results that are further illustrated in FIG. 7O described below. It shall be noted that various techniques described herein apply not only to analysis of gene expression data but also from other experiments and/or analyses such as RNA-seq (Ribonucleic acid-sequencing), DNA-seq (Ribonucleic acid-sequencing), genome sequencing, or any other analyses and/or experiments that reveal the presence and quantity of biological samples. It shall be also noted that the base of the logarithm may comprise a value of 2, 10, the Euler's number e (~2.71828), etc.

Figure 7M:
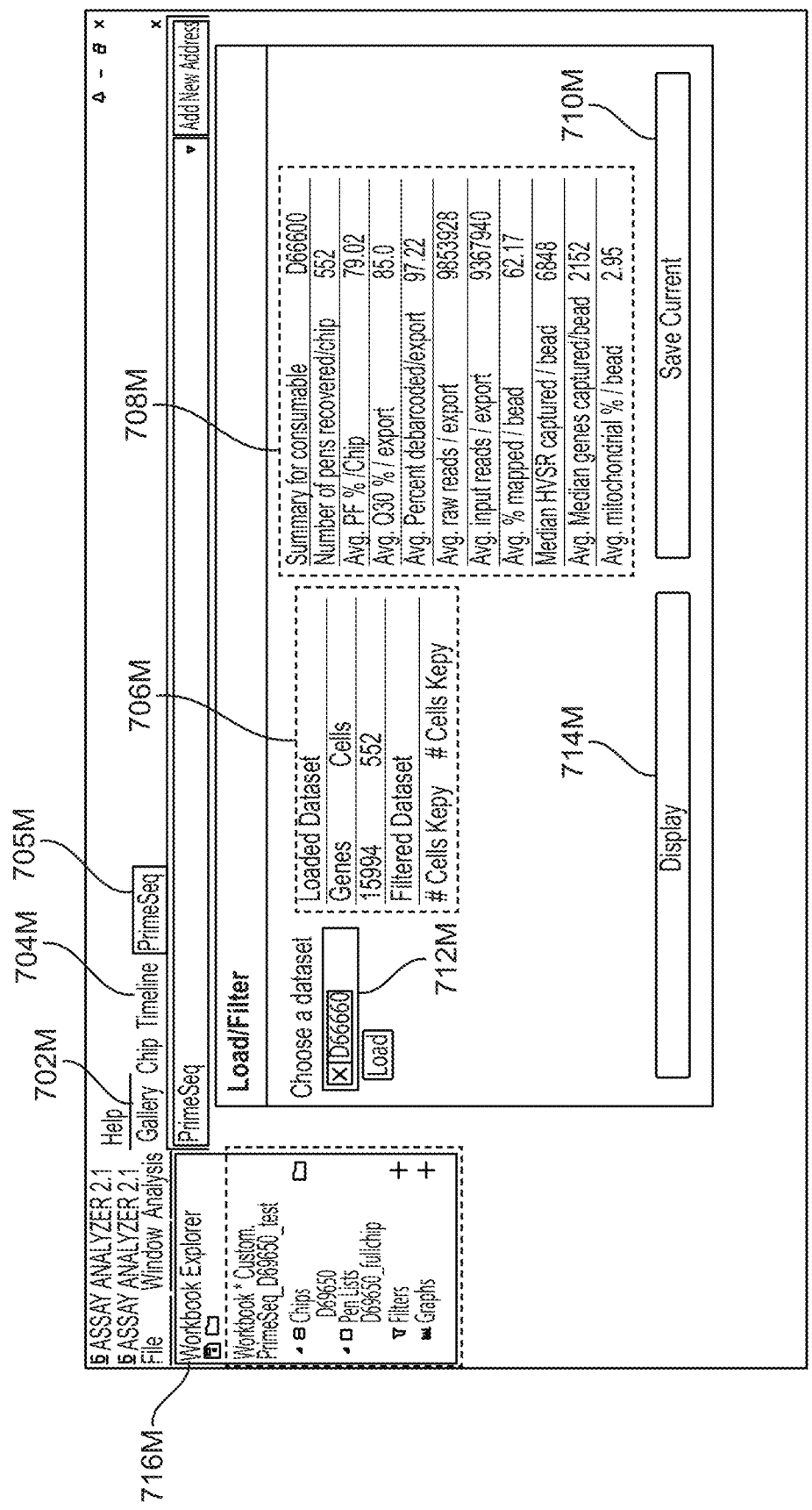
FIG. 7M illustrates additional features of the example bioinformatics pipeline user interface in one or more embodiments.

FIG. 7M illustrates additional features of the example bioinformatics pipeline user interface in one or more embodiments. More specifically, FIG. 7M illustrates additional features of the example bioinformatics pipeline user interface illustrated in FIG. 7A in one or more embodiments. More specifically, a user may load a dataset of a previously executed bioinformatics pipeline (or workflow) via the example bioinformatics user interface by, for example, selecting or entering the identifier of the dataset or any identifier correlated with a previously executed bioinformatics pipeline at the field 712M that may present a list of previously executed bioinformatics pipelines or may allow a user to enter an identifier correlated with a previously executed bioinformatics pipeline. Once a dataset of a previously executed bioinformatics pipeline is loaded, the system may present a summary of one or more characteristics of the dataset, the biological samples for which the dataset is generated, the analysis performed, and/or statistic measure(s), etc. Moreover, FIG. 7M further illustrates an example sequencing view widget 714M which, when invoked, triggers execution of instructions to render a sequencing view.

For example, the example bioinformatics pipeline user interface may provide a first summary 706M including, for example but not limited to, total number of genes in the analysis, the total number cells for the analysis, etc. In some embodiments where one or more filters are applied to the dataset, the first summary 706M may also include the number of cells filtered out and/or the number of cells kept after the application of the one or more filters. The example bioinformatics pipeline user interface may also provide a second summary 708M including, for example but not limited to, the total number of chambers recovered for the microfluidic device in the analysis, one or more statistical measures. For example, these one or more statistical measures may include average percentage of exported cells, one or more statistical measures for HVSR (highly variable signal region), one or more statistical measures for genes captures, one or more statistical measures for mitochondrion or mitochondria, and/or any other characteristics, measures, attributes, etc. The second summary 708M may represent a snapshot of bioinformatics data that include, for example, the total number of chambers recovered in a microfluidic device, average percentage of exported cells, median HVSRs captured, median genes captured, and/or average mitochondrial percentage, etc.

FIG. 7M further illustrates the system's summary response after a user adjusted the sliders (e.g., 704E, 706E, 708E in FIG. 7E). As illustrated in FIG. 7M, in response to the user's adjustment of one or more sliders, the system may automatically update the summary (706M and/or 708M) to reflect the effect of adjusting these one or more sliders. For example, the bioinformatics pipeline user interface shows that the loaded dataset corresponds to 15994 genes and 552 cells as shown in the first summary 706M. The bioinformatics pipeline user interface further shows the respective number of cells retained and the respective percentage of cells retained for each of the sliders as well as the total number of cells retained and the total percentage of cells retained with the combination of all of the filters that are placed in effect.

FIG. 7M also illustrates an example bioinformatics pipeline user interface for loading a bioinformatics pipeline dataset in one or more embodiments. For example, a user may click on a field 712M to select a bioinformatics pipeline dataset from a pulldown list or may enter the identifier (e.g., name) or the first one or more characters of the identifier of a desired bioinformatics pipeline dataset to load the bioinformatics pipeline dataset. A bioinformatics pipeline user interface in FIG. 7M may be integrated with one or more other user interfaces or portions thereof.

For example, the bioinformatics pipeline user interface illustrated in FIG. 7M may be constructed as a software construct that appears to be a tab (e.g., 705M having a label of "PrimeSeq") of an integrated user interface that may further include one or more other user interfaces or views such as a chip timeline user interface or view, a gallery user interface or view, or any other user interface or views described herein, etc. so that each of these user interfaces or views may leverage the functionalities of another user interview or view. In some embodiments, the user interface may include one or more tabs in addition to the tab 705M for the bioinformatics pipeline view. For example, the user interface may include a gallery view tab 702M, a chip time view tab 704M, etc.

In addition, FIG. 7M illustrates more details about the bioinformatics pipeline user interface for loading a bioinformatics pipeline dataset in one or more embodiments. More specifically, FIG. 7M illustrates that once a dataset is loaded into the system, the bioinformatics pipeline user interface may provide a summary of the loaded bioinformatics pipeline dataset in 706M and/or 708M. The summary may include information such as the total number of genes, the total number of cells, and/or any other information correlated with the microfluidic device, a specific chamber, or a biological sample, etc. in some embodiments. The summary (706M and/or 708M) may further incudes filtering results when a user defines or configures one or more filters and applies the one or more filters to the bioinformatics pipeline dataset either before or after the entire dataset is loaded into the system for further processing (e.g., rendering, analyses, etc.) The bioinformatics pipeline user interface may further present additional details 708M (e.g., one or more characteristics of a microfluidic device having multiple chambers, a chamber, and/or a biological sample, one or more statistical measures correlated with a microfluidic device having multiple chambers and/or multiple biological samples, etc.)

The bioinformatics pipeline user interface further provides the options for a user to display the loaded bioinformatics pipeline dataset (714M), to load or define one or more filters to constrain or limit the data to be displayed and/or processed via the filter submenu (716M), and/or to save a custom template for the loaded dataset (710M). For example, a user may define one or more one- or multi-dimensional filters for a specific bioinformatics pipeline dataset via the filter submenu 716M. A one-dimensional filter includes a filter that applies a single rule or filtering criterion to data. A multi-dimensional filter includes a filter that applies a nested or hierarchically-arranged set of multiple filters or filtering criteria successively. For example, a two-dimensional filter may apply a first rule or filtering criterion to certain data to reduce the data to first filtered data and then apply a second rule or filtering criterion to the first filtered data to generate second filtered data.

Figure 7N:
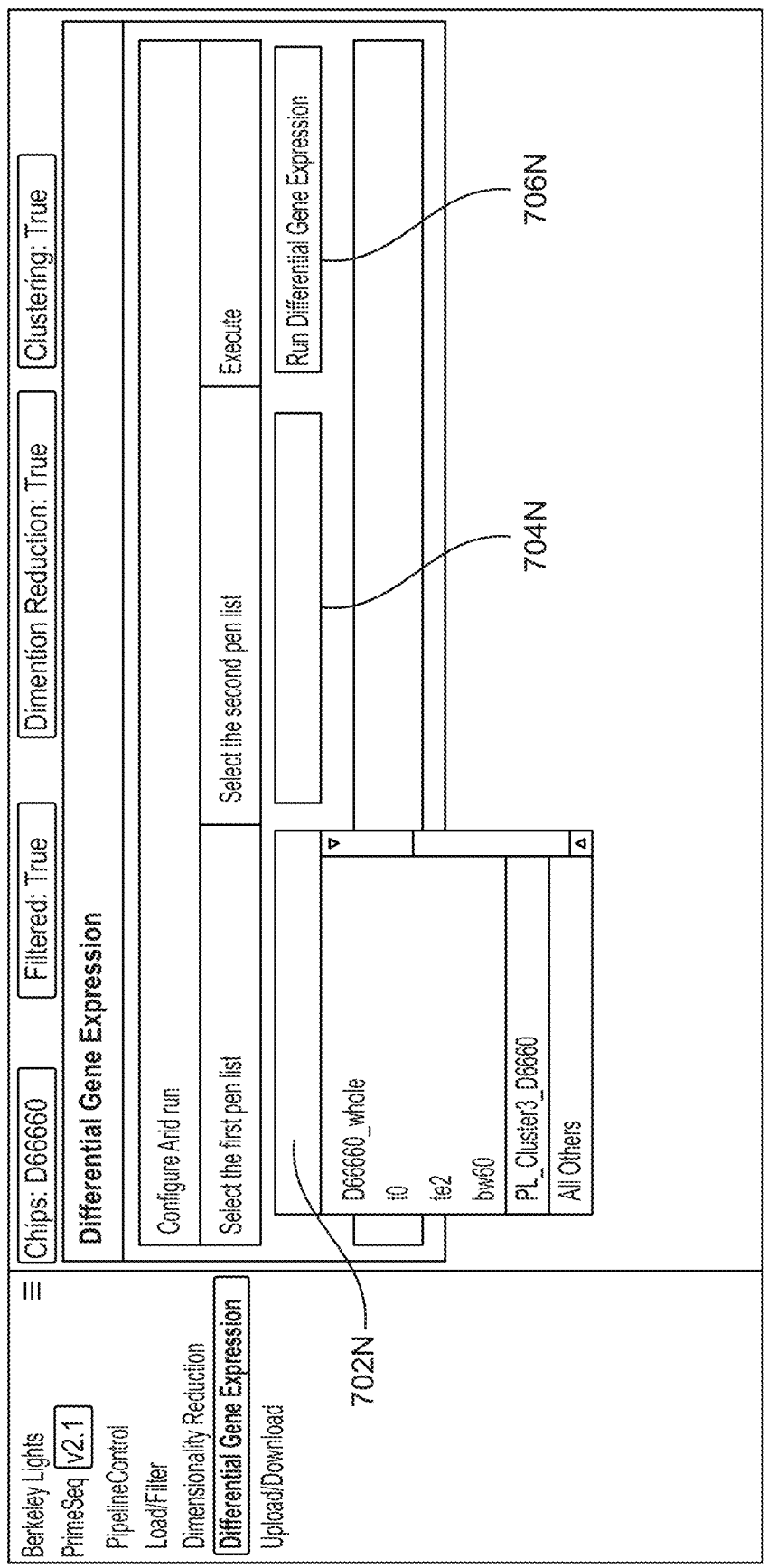
FIG. 7N illustrates an example of an additional functionality for differential gene expression of a bioinformatics pipeline user interface in one or more embodiments.
Figure 70:
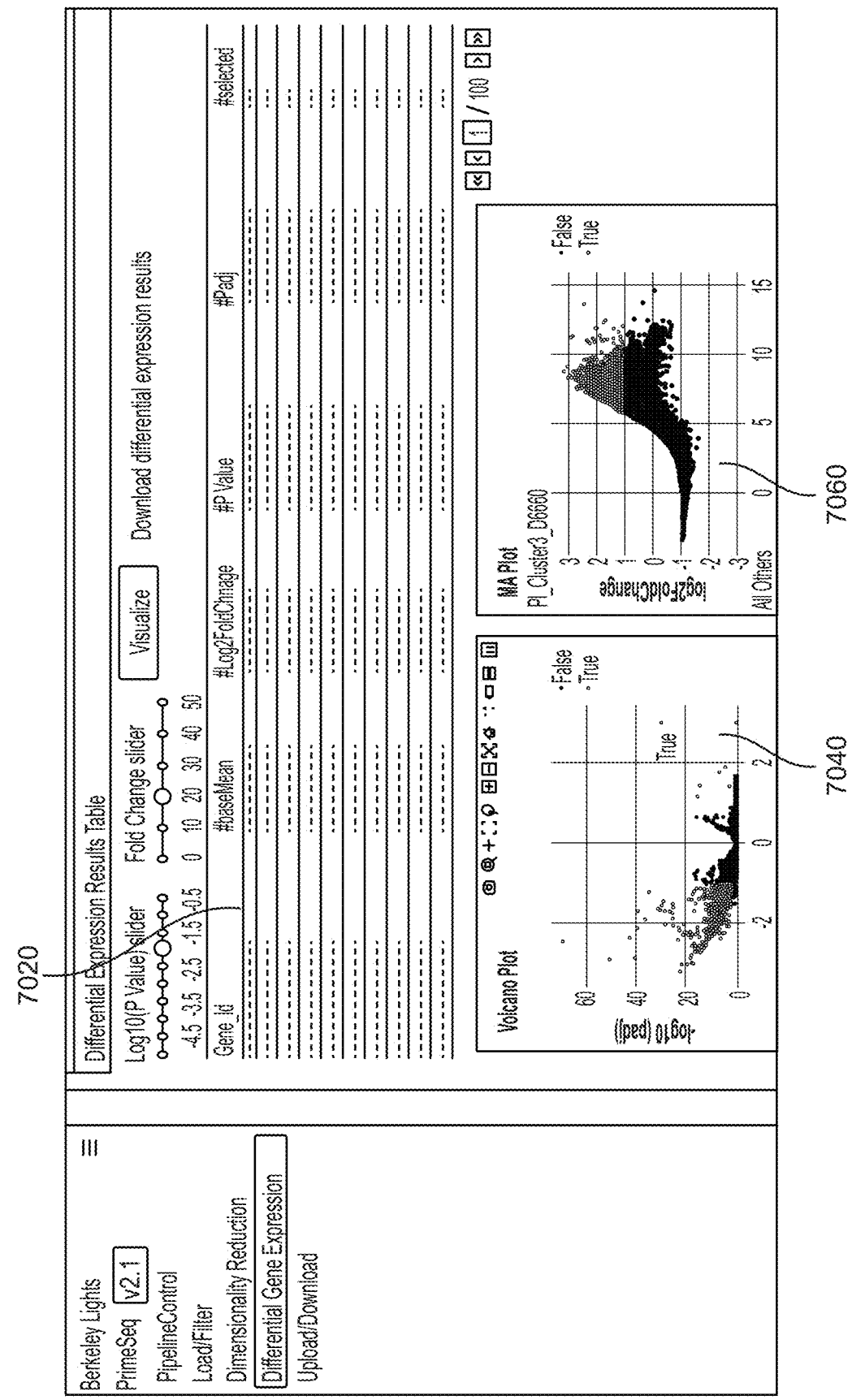
Figure 7P:
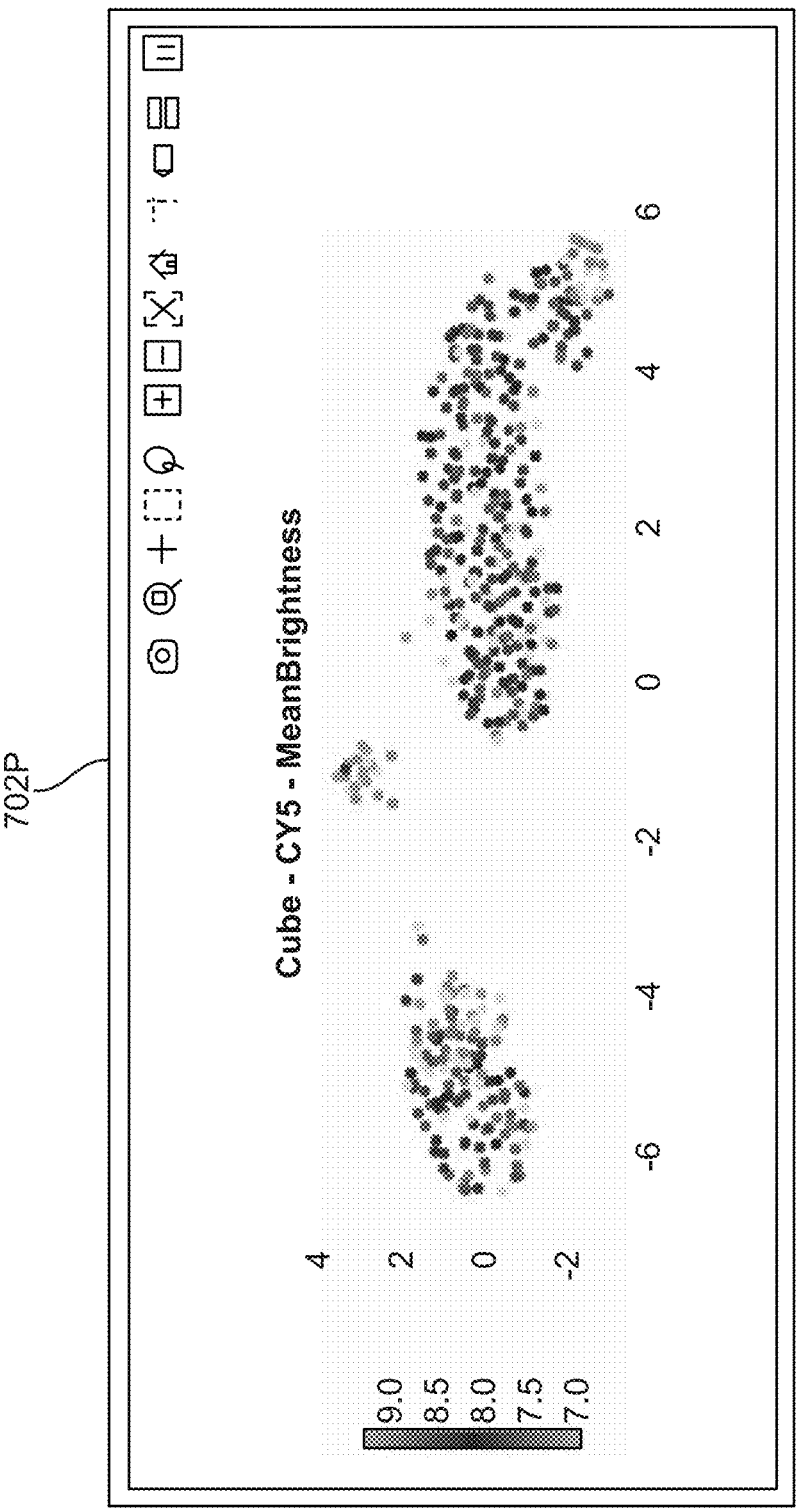
FIG. 7P illustrates some example phenotypic data results.
Figure 7Q:
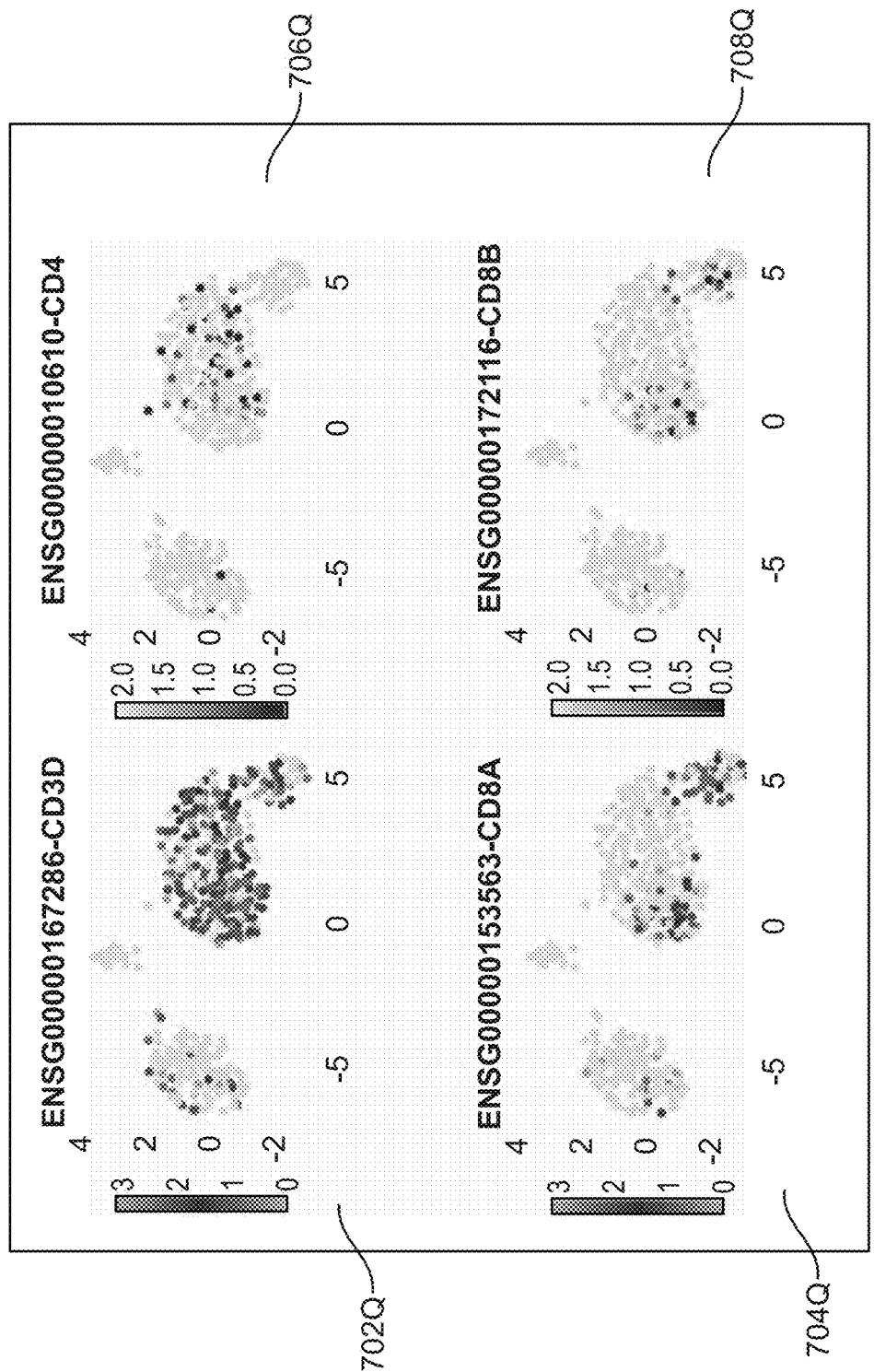
FIG. 7Q illustrates an example differential gene expression results linked with the phenotypic data results of FIG. 7P.

FIG. 7N illustrates an example of an additional functionality for differential gene expression of a bioinformatics pipeline user interface in one or more embodiments. In this example, a user may select or identify a chamber list (e.g., select from a pull-down list having one or more chamber lists or specify the identifier or a portion of the identifier of a chamber list) as the first gene expression 702N.

The user may further select or identify another chamber list or a group of chamber lists (e.g., "all other chamber lists" but the selected chamber list) as the second gene expression 704N and initiate the differential gene expression by, for example, clicking on the "Run Differential Gene Expression" 706N. In some embodiments, multiple sets of regions of interest may be identified (e.g., imported from another view such as a gallery view) or created for a differential gene expression analysis. In some other embodiments, only one set of regions of interest is needed for a differential gene expression analysis. For example, a user may identify or create a chamber list for the first gene expression 702N and choose "all others" as the second gene expression 8304 for a differential gene expression analysis.

FIG. 7O illustrates an example differential gene expression results from FIG. 7N in some embodiments. More particularly, the example results illustrated in FIG. 7O include various suitable, desired, or required differential analysis results 702O, a volcano plot 704O, and a MA (Bland-Altman) plot 706O that graphically presents the differences between measurements taken in two samples (e.g., the two selected chamber lists described above with reference to FIG. 7N), by transforming the data onto M (log ratio) and A (mean average) scales and further by plotting these values. A volcano plot 704O graphically represents the relationship between the p-values of a statistical test and the magnitude of the difference in expression values of the samples in the groups.

FIG. 8A illustrates an example image captured for a plurality of chambers in a microfluidic device in some embodiments. In this example, an image capturing device (e.g., a camera) having a field of view captures a single image 802A for a plurality of chambers at a timepoint. Although FIG. 8A illustrates the example of capturing multiple chambers in a single image, an individual single image may be captured for a single chamber, rather than a plurality of chambers, at one or more timepoints in some other embodiments. In some embodiments, a microfluidic device and each of the multiple chambers in the microfluidic device may be respectively barcoded with, for example, a respective unique identifier.

An image captured for a plurality of chambers may be not only timestamped but also associated with the corresponding microfluidic device identifier and/or the chamber identifiers for the plurality of chambers in the image. When an individual image 804A of a chamber is requested (e.g., to be presented in a gallery view), the image illustrated in FIG. 8A may be sliced, cropped, and/or processed on the fly while referencing the respective identifier of the chamber. This individual image of the chamber may then be presented in a user interface (e.g., a gallery view) based at least in part upon the respective identifier of the chamber.

The slicing or cropping of an individual image from an image illustrated in FIG. 8A may be performed based at least in part on one or more requirements. An example of such one or more requirements may include a type of analysis, whether the flow channel (the area 808A above the chamber or pen 806A) is to be included in the individual image, or any other suitable, desired, and/or required requirements, etc. For example, the flow channel area 808A may be included in the dynamic, on-the-fly slicing of the individual image 804A for exporting biological samples. The example individual image 804A illustrated in FIG. 8A shows that there are no biological samples in the channel area 808A at the timepoint at which the image is captured.

As described above, an analyzer performing various analytic, rendering, and displaying functions described herein may be a separate, independent system from a system for executing one or more workflows for one or more biological samples with one or more microfluidic devices in some embodiments or may be an integrated with the system for executing one or more workflows in some other embodiments. In both cases, a full or partial image of a microfluidic device (or even multiple microfluidic devices) may be captured. In some embodiments, an image (full or partial) such as a base image may be captured based at least in part upon a field of view (FOV) or the field of view plus a margin of an image capturing device (e.g., an imaging sensor, a camera, etc.)

In some embodiments where an image in a sequence of images is captured for more than one region of interest (e.g., individual chamber images, individual target images, or any combinations thereof, etc.), one or more individual images of an individual region of interest (e.g., an individual image of an individual target or an individual chamber) may be derived from the image. For example, an individual target image or an individual chamber image may be extracted from the image of multiple regions of interest.

A process for deriving an individual image of an individual region of interest may include, for example, identifying one or more features correlated with an individual region of interest and cropping the image into the individual image of an individual region of interest based at least in part upon the one or more features. For example, one or more features such as a feature correlated with a target for the individual region of interest may be identified for a target-based region of interest, and the image comprising information of multiple regions of interest may be cropped based at least in part upon the one or more identified feature. As another example, one or more features such as a feature correlated with a structure for the individual region of interest may be identified for a structure-based region of interest, and the image comprising information of multiple regions of interest may be cropped based at least in part upon the identified feature into the individual image for the structure-based region of interest.

An image may be stored in various formats such as one or more raw formats, one or more raster graphics formats (e.g., TIFF or Tagged Image File Format, a bilevel format, a grayscale format, a palette-color format, an RGB (red-green-blue) or full-color format, etc.), one or more lossless formats, one or more lossy formats, etc. In some embodiments where one image captures only a smaller portion of a microfluidic device, the image may comprise image data for one or more regions of interest.

An image captured may be associated with one or more identifiers that may be used to correlate the image with other data. For example, an image may be associated with a timecode or a timestamp indicating the time point at which the image is captured, a chamber identifier indicating a chamber for which the image is captured in a microfluidic device, a microfluidic device identifier of the microfluidic device for which the image is captured, and/or a flow channel identifier of the microfluidic device for which the image is captured, or any combinations thereof. In some embodiments, information correlated with any aspects of the image (e.g., information correlated with the image capture process) may also be stored (e.g., in an XML file) and associated with the image captured. An image and even the aforementioned identifier(s) and/or information correlated with any aspects of the image may be collectively referred as an image sequence or a sequence of images that may be correlated with each other as well as other data and the time point(s) at which the image(s) is (are) captured. In a context of an execution of a workflow, one or more image sequences or sequences of images of the same type or of two or more different types may be generated.

In some embodiments, images in a sequence of images may be captured by one or more image capturing devices or sensors over multiple timepoints or one or more time periods to produce a time-lapsed image sequence. A sequence of images may include one or more brightfield images, fluorescent images, or any other required or desired image, or any combinations thereof. In some embodiments where an image sequence comprises images captured from one or more filter cubes (e.g., Fluorescein Isothiocyanate (FITC), Texas Red or TxRed, synthetic dyes (cyanines), etc.), a resulting image sequence may be referred to as a multi-spectral image sequence.

In some embodiments, a workflow may correspond to one or more templates for computational biology or analytic purposes. A template may include a set of instructions which, when executed by a microprocessor or a processor core, causes the microprocessor or processor core to map a sequence of images to other data by using, for example, regular expressions (REGEX) so that the sequence of images is correlated to such other data (e.g., a quantifiable metric, a target, a chamber, a microfluidic device, a biological chamber, or a characteristic, attribute, property, or metric of a biological chamber, or any combinations thereof) to, for example, reduce or even minimize the amount of tasks related to correlating image sequence(s) with other data.

A regular expression includes a group of characters or symbols that may be used to define a specific pattern in data (e.g., textual data) and may be used to define a mapping between a sequence of images and a workflow output (e.g., a CSV file, a table, a database, or any other suitable data structures). A regular expression may be constructed by using, for example, meta characters in some embodiments. Meta characters may or may not stand for themselves but may be interpreted in some special way in some embodiments. For example, some meta characters may have a special meaning and may be expressed, for example, inside square brackets.

Some examples of meta characters include, but not limited to, "." That matches any single character except a line break; "[ ]" indicating a character class that matches any character included between the square brackets; "[^]" indicating a negated character class that matches any character that is not included between the square brackets; "*" that matches zero (0) or more repetitions of the preceding symbol; "+" that matches one or more repetitions of the preceding symbol; "?" that renders the preceding symbol optional; "(xyz)" indicating a character group that matches the characters "xyz" in that exact order; "|" indicating alternation that matches either the characters before or the characters after the symbol "|"; "\" that escapes the next character to match reserved characters such as "[", "]", "(", ")", etc.; "^" that matches the beginning of an input; and/or "$" that matches the end of an input in some embodiments.

Some examples of templates include, without limitations, one or more cell line discovery templates for discovery of cell lines, a T-cells template for importing and/or exporting data or information correlated with T cell (which may also be called T lymphocyte) type of leukocyte (white blood cell) that is an essential part of an immune system, a B-cells template (which may be used for importing and/or exporting lymphocytes—B cells that determine the specificity of immune response to antigens in a body), an AbD (antibody discovery) template for importing and/or exporting information or data correlated with antibody discovery, a multiplex cytokine assay template. Templates may be added, edited (e.g., modified to accommodate an updated workflow, etc.), copied (e.g., an existing template may be copied to provide a starting point for a, for example, different workflow), removed, imported (e.g., shared among users from different systems or versions), and/or exported in some embodiments.

One or more workbooks may be created for the biological sample(s) in or on a microfluidic device in some embodiments. A workbook may include information about any attributes, characteristics, properties, and/or metrics of the microfluidic device or a portion thereof in these embodiments. In some of these embodiments, a workbook may include one or more filters that are to be or that have been applied to one or more regions of interest (e.g., a plotted or displayed region of interest). In addition or in the alternative, a workbook may include one or more layout views and/or any existing or new characteristic (e.g., a characteristic created during a session or a characteristic that is specific to a particular workflow or a portion thereof).

A workbook may facilitate efficient import of information or data (e.g., textual data, image data, etc.) as well as rendering or display various other data. For example, a chip timeline view may be generated based at least in part on a workflow executed for one or more biological samples in or on a microfluidic device. The workflow may also be configured or correspond to, at least in part, a chip timeline view.

Figure 8B:
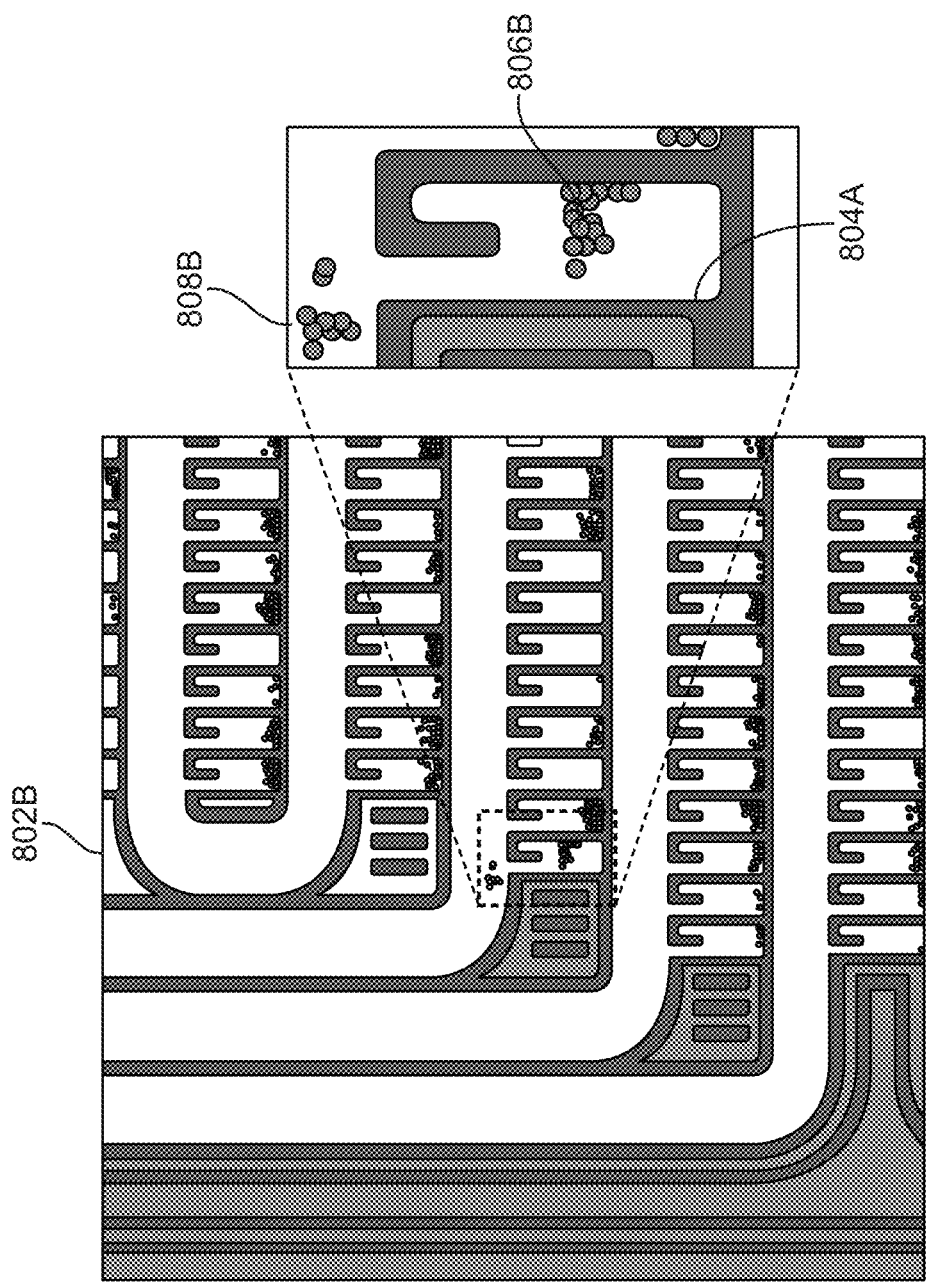
FIG. 8B illustrates another example image captured for the same multiple chambers at a next timepoint as those captured at a previous timepoint illustrated in FIG. 8A in some embodiments.

FIG. 8B illustrates another example image 802B captured for the same multiple chambers at a next timepoint as those captured at a previous timepoint illustrated in FIG. 8A in some embodiments. More specifically, FIG. 8B illustrates another example image 802B captured by the same image capturing device for the same multiple chambers at a next timepoint as those captured at a previous timepoint illustrated in FIG. 8A. In this example, the next individual image of the same chamber 804A is obtained during a process of unpenning and exporting biological samples. As illustrated in FIG. 8B, a portion of the biological samples 808B in FIG. 8B have been unpenned and thus exist in the flow channel region (808A in FIG. 8A) so that fewer biological samples 806B remain in the chamber 804A. This example illustrated in FIG. 8B further illustrates the dynamic slicing or cropping in constructing the individual image on the fly to show the flow channel so as to accommodate the presence of the biological samples 806B.

FIG. 8C illustrates another example image captured at a next timepoint for the same multiple chambers as those captured at previous timepoints in FIGS. 8A-8B in some embodiments. More specifically, FIG. 8C illustrates another example image 802C captured by the same image capturing device of the same multiple chambers as those captured at the previous timepoints in FIGS. 8A-8B in some embodiments. In this example, the next individual image of the same chamber 804C for exporting biological samples is shown. As illustrated in FIG. 8C, the biological samples that have been exported as shown in 808B in FIG. 8B have been moved or flushed out of the flow channel region (808A in FIG. 8A) at this next timepoint when the image 802C is captured, while the fewer biological samples 806B (e.g., the same biological samples as those 806B in FIG. 8B) remain in the chamber 804C (which is the same chamber as 804A in FIGS. 8A-8B). This example illustrated in FIG. 8C also illustrates the dynamic slicing or cropping in constructing the individual image on the fly to show the flow channel to serve as a visual validation of the export of the biological samples 808B from the chamber 804A in FIGS. 8A-8B.

Figure 8E:
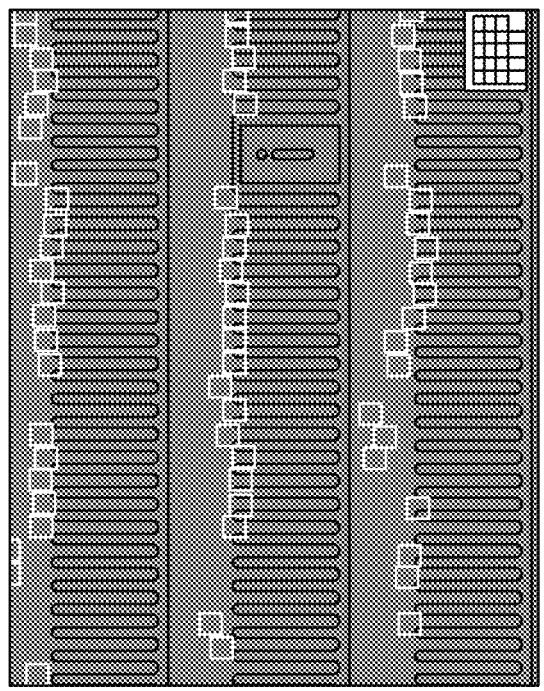
FIG. 8E illustrates the same micro-objects in FIG. 8D at a later time point in which the light cages have been moved along their selected trajectories in one or more embodiments.
Figure 8D:
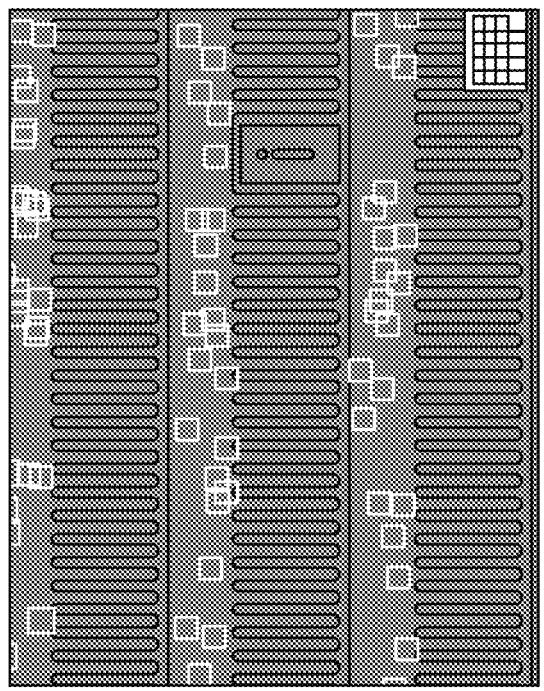
FIG. 8D illustrates micro-objects within the channel of a microfluidic circuit immediately following an identification of the micro-objects and the assignment of micro-objects to chambers in one or more embodiments.
Figure 8F:
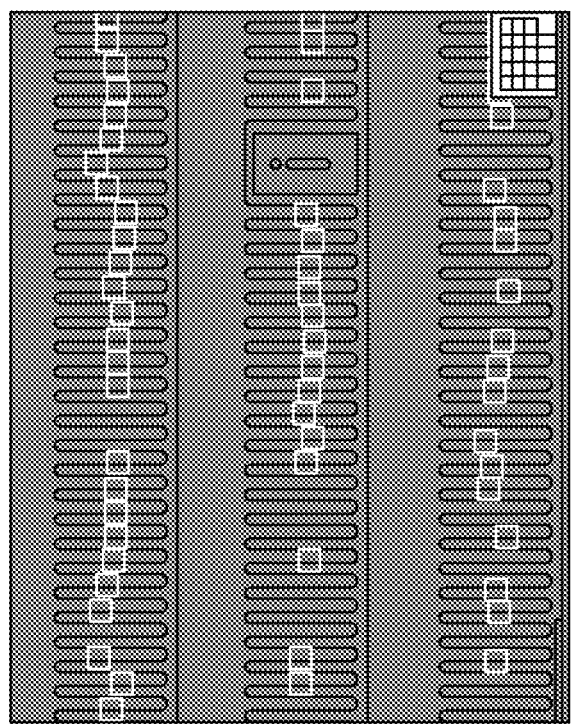
FIG. 8F illustrates the same cells at a third time point where the light cages have been almost fully moved along their selected trajectories to position the cells in the sequestration chambers in one or more embodiments.

FIG. 8D illustrates micro-objects within the channel of a microfluidic circuit immediately following an identification of a portion of the micro-objects and the assignment of the portion of identified micro-objects to chambers in one or more embodiments. Identification may be made on any desired criteria and may be the result of an assay or labeling operation performed on the cells prior to penning. FIG. 8E illustrates the same micro-objects in FIG. 8D at a later time point in which the light cages have been moved along their selected trajectories in one or more embodiments. FIG. 8F illustrates the same cells at a third time point where the light cages have been almost fully moved along their selected trajectories to position the cells in the sequestration chambers in one or more embodiments.

More specifically, FIGS. 8D-8F illustrate micro-object penning using light boxes. In FIG. 8D, biological cells within the channel of a microfluidic circuit are shown immediately following the identification of the cells and the assignment of cells to pens. The black boxes surrounding the biological samples illustrate the output of the biological sample identification algorithm—that is, an identification of biological sample(s) indicated by a box around the biological sample(s) in some embodiments. In these embodiments, the aforementioned black box representing the output of the biological sample identification algorithm may be visible in a user interface in an enlarged view based at least in part upon, for example, one or more configurations or settings of the user interface (e.g., background color, contrast setting, etc.) and/or the input data (e.g., the color depth or bit depth of an input image, etc.) The white boxes surrounding the black boxes are the light cages of OET force used to reposition the cells. Lastly, the black lines that connect the boxes surrounding the cells to the sequestration pens illustrate the optimal trajectory computed in assigning the cells to sequestration pens. FIG. 8E shows the same cells at a later time point in which the light cages have been moved along their selected trajectories. FIG. 8F shows the same cells at a third time point where the light cages have been almost fully moved along their selected trajectories to position the cells in the sequestration pens.

In moving the micro-objects, the speed at which OET and/or DEP is used to move the cells may be gradually accelerated in order to "ramp up" motion of the micro-objects and ensure that the micro-objects are not lost from their light cages. For example, in a specific embodiment, the initial velocity of the micro-objects may be gradually accelerated from a low initial velocity to a higher travelling velocity. This gradual acceleration may be applied both in instances where the micro-objects are automatically repositioned (e.g., penning, re-penning and export) and in instances where the micro-objects are manually repositioned (e.g., manually selecting and moving a cell). Similarly, the high travelling velocity may be "ramped down" to a final velocity of zero when the micro-objects reach the end of their trajectory and are at their final position.

The methods of the invention are useful for the automated detection and/or counting of micro-objects in all types of microfluidic devices. In certain embodiments, the microfluidic device may include a flow region (or flow channel) and one or more chambers (or sequestration pens). Alternatively, or in addition, the microfluidic device may be an electrokinetic device, such as an optically actuated electrokinetic device, or may include a region configured for electrokinesis. Electrokinetic devices, particularly electrokinetic devices having an array of transistors (e.g., phototransistors), may provide a particularly complicated background if the transistors in the array have an area that is similar to the cross-sectional area of a micro-object that is being detected. The methods described herein may be particularly effective at detecting micro-objects disposed in such a device.

Figure 9A:
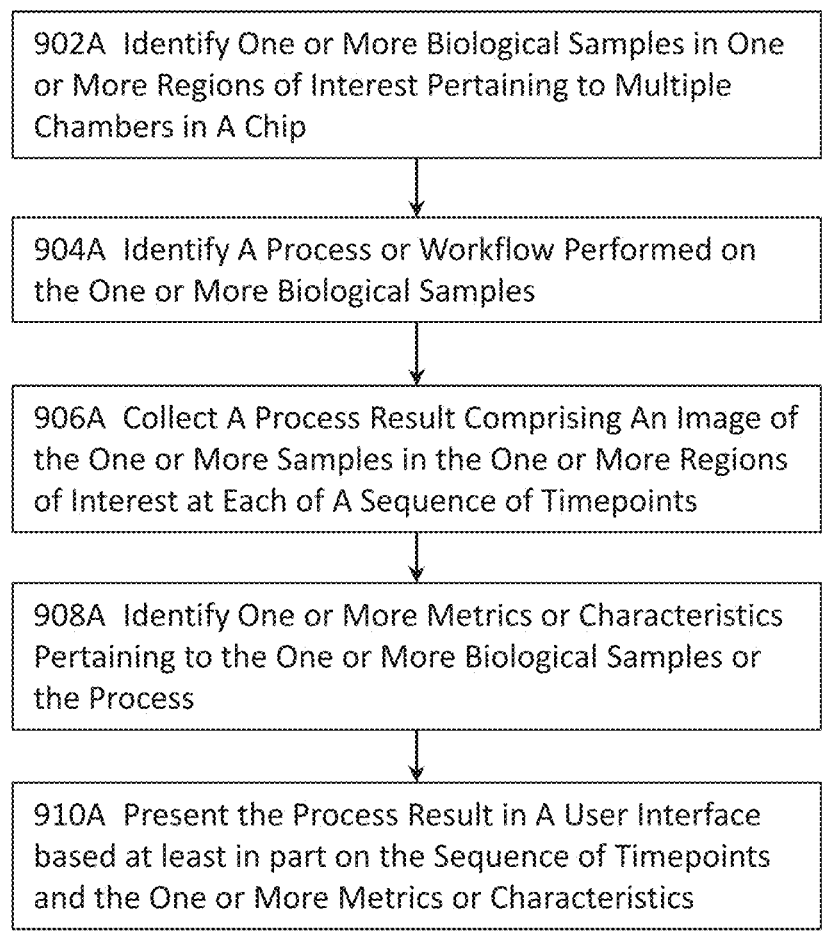
FIG. 9A illustrates a high-level flow diagram of a method and/or system for analyzing biological samples using a microfluidic device having multiple chambers in one or more embodiments.

FIG. 9A illustrates a high-level flow diagram of a method and/or system for analyzing biological samples using a microfluidic device having multiple chambers in one or more embodiments. More specifically, FIG. 9A illustrates a high-level flow diagram of a method or system for analyzing biological samples using a microfluidic device having multiple chambers in one or more embodiments. In these one or more embodiments, one or more biological samples in one or more regions of interest correlated with a plurality of chambers in a microfluidic device may be identified at 902A. The total number of chambers in a microfluidic device may range from a single-digit number of chambers to tens of thousands of chambers per microfluidic device. In addition, the biological samples that may constitute the target (or the "measured") of the process of interest may include, for example but not limited to, micro-object, a cell, a tissue, a protein, a gene, a virus, or an intracellular molecule such as DNA (deoxyribonucleic acid), RNA (ribonucleic acid), etc.

With the one or more biological samples loaded into the one or more chambers, a process or workflow that is to be performed or executed or that has been performed or executed on the one or more biological samples may be identified at 904A. The process referred to herein may include an assay, a sequencing process, etc. An assay includes an analytic or investigative procedure in laboratory medicine, pharmacology, biology (e.g., environmental biology, molecular biology, etc.) for qualitatively assessing or quantitatively measuring the presence, amount, and/or functional activity of a target of any of the aforementioned types of biological samples. A sequencing process may include a process for determining, for example, the nucleic acid sequence (e.g., the order of nucleotides in DNA) and may include any methods or technologies that may be used to determine the order of the one or more bases such as adenine, guanine, cytosine, and/or thymine to accelerate biological and/or medical research and discovery.

Some example workflows include, but not limited to, a CLD (cell line development) workflow, a T-cells workflow, an AbD (antibody discovery) workflow, a multiplex cytokine workflow, etc. A CLD workflow may use a quantitative diffusion assay as a part of the workflow to rank clones on a microfluidic device based at least in part upon, for example, secretion as measured by a score that measure the concentration of antibody in a chamber of the microfluidic device. A CLD workflow may also be used to assess or analyze cell productivity based at least in part upon, for example, a QP (product production) score or a relative QP score that normalizes the QP score by cell count.

An example CLD workflow may include importing an assay reagent onto a microfluidic device. The assay reagent equilibrates from one or more flow channels into multiple chambers where the assay reagent may bind with Immunoglobulin G (IgG) that is produced by clones. The one or more flow channels may then be flushed to remove the assay reagent. Unbound reagent and the reagent/IgG complex remaining in the chamber(s) may begin diffusing into the flow channel. Therefore, chambers with clones yielding high antibody titers will have a large fraction of the slowly diffusing reagent/IgG complex, thus appearing bright in fluorescence images. In addition, a chamber with clones producing little or no antibody may have mostly free reagent molecules that diffuse rapidly into the flow channel and thus appearing dark in the fluorescence image. The process or workflow then records and analyzes the fluorescence images after flushing the flow channel and to rank the relative titer from clones on the microfluidic device, allowing for the selection of top producing clones.

In some embodiments, multiple repeat assays may be performed during the culture stage during which secretion and biological growth of biological samples. Grown biological samples may then be exported. With the periodic or continuous monitoring of the microfluidic device and recording of data at a sequence of timepoints or time periods, export may be automatically triggered based at least in part upon, for example, a structure feature of one or more chambers. For example, when biological samples begin to come near the neck of a chamber (e.g., near the proximal opening of the chamber to a flow region), the risk of clonal contamination may increase. In some embodiments, the export stage in the workflow may be automatically triggered before biological samples begin to grow near or past the neck region of one or more chambers.

Another example workflow is a multiplex cytokine assay workflow analysis that provides the ability to sub-clone T cells, co-culture each T cell with antigen-presenting cells (APCs) or tumor cells, and screen for T cell activation by detecting a plurality of secreted cytokines (e.g., three secreted cytokines) and multiple cell-surface markers (e.g., two cell-surface markers) within a time period. In a multiplex cytokine assay workflow, cells may be loaded onto a microfluidic device. A chip timeline view may be presented, and an analysis of the image sequence(s) may be performed. In some embodiments, the techniques described herein may provide control (e.g., by automatically generating or custom generation of one or more chamber lists) over the APCs into one or more user-specified or automatically determined fields-of-view to serve as a negative control where data from the negative control population may be used to determine thresholds for selecting assay positives.

These loaded cells may be cultured for a desired or required time period, and imaged to screen for one or more phenotypic and functional characteristics (e.g., the presence of activation markers, the release of cytokines, etc.) During or after the culture stage, one or more screened regions of interest (e.g., chambers) may be automatically determined. A screened region of interest includes a region that comprises one or more T cells, at least one antigen-presenting cell (APC), and one or more cytokine capture beads.

In some embodiments where a screened chamber includes a single T cell, the system may automatically apply a single T cell filter to the plurality of chambers in the microfluidic device. In these embodiments, the system may further apply a target-based one-dimensional filter to the resulting chambers of the single T cell filter to further reduce the chambers to those that satisfy both the single T cell requirement and at least one APC requirement. Moreover, a one-dimensional target-based cytokine capture bead filter may be applied to the resulting chambers from the at least one APC filter to determine the screened chambers that further satisfy the cytokine capture bead requirement. In some other embodiments, a multiple-dimensional, nested, or hierarchically-arranged filter may be applied to the chambers in the microfluidic device where the multi-dimensional filter applies the single T cell filter, the at least one APC filter, and the cytokine capture bead filter in a nested or hierarchically-arranged manner. Other variations such as applying a one-dimensional filter and a two-dimensional filter may also be applied in some other embodiments. A multiple-dimensional, nested, or hierarchically-arranged filter may comprise a plurality lower-dimensional filters that are logically combined (e.g., through logical AND, OR, XOR, etc.) and applied in accordance with the logical combination.

To identify positives, one or more target-based filters (e.g., a median brightness filter, etc.) may be used to determine whether an object or a region of interest is positive or negative for a specific cytokine or surface marker based at least in part upon one or more thresholds that may be determined based at least in part upon, for example, the negative control population described above. Events above these one or more thresholds may be considered positive for the specified cytokine or cell surface marker. For example, some or all of the negative control population (e.g., negative control region(s) of interest) of may be excluded from the selection for cytokine secretion. One or more regions of interest may then be identified from the screened regions of interest described above.

The result of the process or workflow for the one or more biological samples may be collected at 906A at a sequence of timepoints. In some embodiments, the process result may include an image of at least one biological sample of the one or more biological samples in the one or more regions of interest at each of the sequence of timepoints. In some of these embodiments, an image is captured for multiple regions of interest at a specific timepoint. In some other embodiments, an image may be captured for each individual region of interest of the plurality of regions of interest in the microfluidic device, without showing another region of interest (e.g., a neighboring chamber). The process result may include the final result at the end of the process in some embodiments. In some of these embodiments, the process result may further include intermediate results that are captured, prior to the completion of the process, at one or more timepoints in the sequence of timepoints to demonstrate time progression of the process.

One or more metrics or one or more characteristics correlated with the one or more biological samples, any region of interest, the microfluidic device, and/or the process may be identified or determined at 908A. These one or more metrics or characteristics may include any responses or absence thereof of the one or more biological samples to the process or a portion of the process, the process or a portion thereof, any performance metrics of the process or the system on which the microfluidic device is loaded for the performance of the process, any statistical measures correlated with the one or more biological samples on which the process is performed, or any other suitable, desired, or required metrics or characteristics, etc.

The process results may then be presented at 910A in a user interface based at least in part upon the sequence of timepoints or a corresponding set of timecodes and the one or more metrics or characteristics. As described above, various functionalities, modules, user interfaces, elements of user interfaces, widgets, logic code, etc. are seamlessly integrated together to enable a user to efficiently and effectively identify an extremely fine-grained piece of analysis result (e.g., a specific characteristic correlated with a biological sample, a specific region of interest in a microfluidic device having thousands of regions of interest, a specific biological sample, and/or any other desired or required characteristics therefor) from a vast amount of data or results by using various techniques, modules, and/or functionalities described herein.

For example, a simply bioinformatics pipeline data may easily surpass many hundreds of gigabytes in size. Even with the current, state-of-the-art computing system and optimized software applications, such an enormous amount of data may easily bury useful information deeply within the data and overwhelms any experienced scientists. Various embodiments described herein provides flexibility, customizability, expedient speed, and extraordinary accuracy via, for example, various one- or multi-dimensional filters, custom creation of chamber lists, flexible configurations to pinpoint a specific characteristic, etc. described herein to enable any users to effectively and efficiently navigate through the vast amount of data of biological samples in thousands or even tens of thousands of regions of interest (e.g., chambers) in a single microfluidic device (e.g., a microfluidic device) and to provide accurate and expedient computational analytics. Compare the current, state-of-the-art approaches that typically process tens of chambers of biological samples and rely heavily on manual effort hoping to find some useful information from the data of the tens of chambers by mostly manually using a restrictive tool having a limited functionality, various techniques described herein solves the problems with and shortcomings of conventional approaches and vastly improve the accuracy and runtime of computational biology.

FIG. 10A illustrates a simplified example of a block diagram of a process and/or system for analyzing biological samples with an enhanced user interface in one or more embodiments. More specifically, FIG. 10A illustrates another high-level flow diagram of a method or system for analyzing biological samples using a microfluidic device having multiple chambers in one or more embodiments. In some embodiments, a method for analyzing biological samples may include identifying an analysis of biological samples in multiple regions of interest in a microfluidic device and a timeline correlated with the analysis at 1002A. An analysis may include an assay analysis, a sequencing analysis, etc. for a plurality of biological samples using a microfluidic device in some embodiments. The analysis identified at 1002A may have been performed on or for the biological samples of interest in some embodiments or may be awaiting to be performed or completed in some other embodiments. In some embodiments where an analysis has been performed and completed on biological samples of interest or is currently being performed but is not yet completed, identifying an analysis of biological samples may include, for example, gathering and storing data from one or more sources of data or information (e.g., image or video capturing device(s), data collection modules, data repositories, table(s), database(s), or any other suitable sources of data, etc.), retrieving data or one or more files correlated with the analysis, the apparatus(es) correlated with the analysis, the biological samples analyzed or being analyzed, etc. from any of the aforementioned one or more sources of data. In some embodiments, identifying an analysis of biological samples at 1002A may include identifying (e.g., via user selection) one or more target-based regions of interest, one or more structure-based regions of interest, and/or one or more chambers of a microfluidic device within which the biological samples are analyzed.

A timeline may comprise information that is temporally aligned with a workflow or pipeline of the analysis of the biological samples. In some embodiments, each region of interest or chamber comprises a unique identifier. In addition or in the alternative, the multiple identifiers correspond to one or more characteristics that further comprise at least one of an identifier of a region of interest in the microfluidic device, a size attribute of the plurality of biological samples, a maximum brightness attribute for the plurality of biological samples, a minimum brightness attribute for the plurality of biological samples, a first pixel count attribute in a first direction for a centroid of a biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of regions of interest, a gate path index, an area pixel attribute, a background pixel attribute, or a median brightness attribute for the plurality of biological samples.

One or more region-of-interest types may be determined at 1004A for the multiple regions of interest, wherein the one or more region-of-interest types comprise a target-based type correlated with at least one biological sample of the biological samples or a structure-based type correlated with the microfluidic device.

As described herein, a region of interest may include a target-based region that pertains to one or more attributes, characteristics, properties, and/or quantifiable metrics, etc. (e.g., a measured or derived diameter or a statistical measure correlated with a diameter of a cell in a region of interest, a count of genes in a region of interest, a number of cells cultured for a region of interest, a number or percentage of cells exported from a region of interest, etc.) of a biological sample of interest in some embodiments. A region of interest may also include a structure-based region of interest that pertains to one or more attributes, characteristics, properties, and/or quantifiable metrics, etc. (e.g., a characteristic to a structural aspect of a microfluidic device or a portion thereof, etc.) of a microfluidic device or any portion thereof in some embodiments.

With the one or more region-of-interest types determined, an attribute, a characteristic, a property, or a quantifiable metric may be determined at 1006A based at least in part upon the one or more region-of-interest types. In the aforementioned embodiments, a target-based characteristic, other type(s) of characteristic(s), property, or quantifiable metric may be determined for a target-based region of interest. In addition or in the alternative, a structure-based characteristic, characteristic, property, or quantifiable metric may be determined for a structure-based region of interest.

Associated data that respectively correspond to the multiple regions of interest may be arranged and rendered at 1008A in a user interface for at least a portion of the biological samples based at least in part upon the timeline and the attribute, characteristic, property, or quantifiable metric. An example of such an arrangement and display of associated data may include a gallery view in, for example, FIG. 6C, a miniaturized gallery view in, for example, FIG. 5A, a chip timeline view in, for example, FIG. 4A, a sequencing graph in, for example, FIG. 7H, or any other views or graphs. Rendering associated data for a region of interest in a user interface may comprise, for example, copping the associated data (e.g., binary data captured by an image or video capturing device or sensor and/or stored in a file or data structure, etc.) into cropped data in accordance with the region of interest (e.g., cropping a base image showing multiple regions of interest to a smaller subset of data corresponding to a specific region of interest), transmitting the associated data or the cropped data to a computer graphics program and/or a graphics processing unit (GPU) that transforms the binary data into photorealistic or non-photorealistic 2D or 3D image (e.g., a raster graphics representation) that represents the region of interest.

In some embodiments, associated data pertains to and is associated with an analysis of biological samples and may comprise, for example, one or more attributes, properties, or characteristics, etc. of an analysis of biological samples and/or of the biological samples, one or more systems that are correlated with the analysis, one or more workflows and/or one or more sequencing pipelines correlated with the analysis and/or the biological samples, one or more settings and/or configurations/input data/intermediate output data/ final output data of the analysis, one or more settings and/or configurations correlated with the one or more systems correlated with the analysis, metadata describing any of the associated data, and/or any combinations thereof, etc. In some embodiments, associated data may include static information or data (e.g., processed information), dynamic information or data (e.g., information or data that may varies over time), interactive information or data (e.g., information or data upon which a user may interact by, for example, issuing instructions or commands through a menu or a user interface manipulation, etc.), or any combination thereof. In addition or in the alternative, associated data correlated with an analysis of biological samples may include, for example, binary, textual, ASCII, graphical, image, video, and/or video sequence data. In some embodiments, associated data may include any of the aforementioned data or information, its equivalents, or its variants for one, some, or all regions of interest or all chambers in a microfluidic device and may be collected from various data sources (e.g., inputs from the user through a user interface, intermediate and final outputs of an analysis engine, images from one or more image capturing devices, data generated by one or more software application(s) correlated with the analysis, biological samples, and/or one or more systems associated with the analysis, etc.) and stored in a data structure (e.g., a microfluidic device data structure, a gallery structure, etc.) in a structured manner as described in greater details herein with reference to, for example, FIGS. 5B, 5G-5J, 7D, 10F, etc. Moreover, such a data structure may be indexed with one or more keys to facilitate more efficient access, queries, and manipulation of the associated data as described herein with reference to, for example, FIGS. 5B, 5G-5J, 7D, 10F, etc.

FIGS. 10B-10C illustrate more details about a portion of the simplified example of a block diagram illustrated in FIG. 10A in one or more embodiments. In these one or more embodiments, arranging and rendering the associated data comprises determining a gallery structure having a plurality of gallery sub-structures for the associated data based at least in part upon an allocable space in the user interface for rendering the associated data at 1002B. In some of these one or more embodiments, a gallery sub-structure of the plurality of gallery sub-structures corresponds to a characteristic correlated with the analysis of the biological samples or the biological samples, the gallery sub-structure comprises one or more gallery fields, and the characteristic comprises at least one target-based characteristic, at least one structure-based characteristic, or a combination of the at least one target-based characteristic and the at least one structure-based characteristic.

In these one or more embodiments, arranging and rendering the associated data comprises populating, at 1004B, the associated data into the plurality of gallery sub-structures in the gallery structure based at least in part upon the characteristic. In some of these embodiments, a gallery field of the gallery sub-structure corresponds to an image of an image sequence captured for a structured-based region of interest or a target-based region of interest of at least one of the biological samples, and the image or the image sequence is determined from one or more base images. In addition or in the alternative, the plurality of graphic representations in the timeline portion respectively corresponds to the plurality of gallery sub-structures.

In some embodiments, determining the gallery structure may comprise determining, at 1008B, a first sequence of data correlated with a set of time points or time periods for a first biological sample obtained from a first region of interest of the multiple regions of interest from the gallery structure stored in an addressable space in the non-transitory computer accessible storage medium, wherein the first sequence of data corresponds to at least a first identifier of the multiple identifiers. Optionally, determining the gallery structure may comprise determining, at 1006B, an attribute, characteristic, property, or quantifiable metric based at least in part upon one or more types of regions of interest.

In some of these embodiments, determining the gallery structure may further comprise determining, at 1010B, a second sequence of data correlated with the set of time points or time periods for a second biological sample obtained from a second region of interest of the multiple regions of interest from the gallery structure, wherein the second sequence of data corresponds to at least a second identifier of the multiple identifiers. In some of these embodiments, arranging and rendering associated data may comprise rendering, in a first window portion of the user interface and with a graphics processing unit at 1012B, the first and the second sequences of data in a gallery view.

In some embodiments, rendering the first and the second sequences of data in the first view may further comprise 1014B in response to a selection of a first characteristic from the multiple characteristics with a first selection widget in the user interface, extracting a first value of the first characteristic from a plurality of values for the first biological sample or for the analysis; and extracting a second value of the first characteristic from the plurality of for the second biological sample or for the analysis.

Referring to FIG. 10C, arranging and rendering associated data may comprise rendering, at 1016B, a first interactive object and a second interactive object respectively corresponding to the first and the second sequences of data into the gallery view in some embodiments. In some of these embodiments, the first interactive object is representative of the first value for the first biological sample or for the analysis, and the second interactive object is representative of the second value for the second biological sample or for the analysis. Moreover, the user interface is coupled to a processor for processing data for one or more characteristics of inputs and comprises a set of images captured from the biological samples and obtained at the set of time points or time periods. In addition, an image in the set of images is obtained from a respective biological sample disposed within a region of interest in the microfluidic device comprising a plurality of chambers.

In some embodiments, arranging and rendering associated data may comprise rendering, at 1018B, the first selection widget for selecting the first characteristic for the biological samples, a first set of data for a first set of images captured for the first region of interest in the microfluidic device is represented in a first gallery substructure of the gallery structure; and a second set of data for a second set of images captured for the second region of interest in the microfluidic device is represented in a second gallery substructure of the gallery structure.

In some of these embodiments, the first interactive object is associated with a first rank at a first time point or time period of a set of time points or time periods, the first rank indicating a first place of the first region of interest correlated with the plurality of chambers in the microfluidic device based at least in part upon the first value of the first characteristic for the first region of interest. In addition or in the alternative, the second interactive object is associated with a second rank at the first time point or time period of the set of time points or time periods, the second rank indicating a second place of the second region of interest correlated with the plurality of chambers in the microfluidic device based at least in part upon the first value of the first characteristic for the second region of interest.

Moreover, the first and second ranks are respectively displayed together with the first and the second interactive objects in the first view to respective indicate a first status of the first biological sample in the first region of interest and a second status of the second biological sample in the second region of interest at the first time point or time period in some embodiments. Additionally or alternatively, first gallery substructure of data and the second gallery substructure of data are arranged to comprise a third gallery substructure having an interactive identifier that corresponds to the first identifier.

In some of these embodiments, the interactive identifier of the third gallery substructure, when invoked in the user interface, triggers a ranking operation that arranges the first gallery substructure and the second gallery substructure based at least in part upon the first rank and the second rank; and a height or a width of a gallery sub-structure of the plurality of gallery sub-structures is configurable into a modified height or a modified width, or a width of a field in the third linear structure is configurable into a modified width in the first view.

In addition or in the alternative, the gallery structure includes a column structure and a row structure, the column structure comprises multiple columns, the row structure comprises multiple rows, and biological sample data that is specific to the analysis performed on one or more biological samples in a single chamber of the microfluidic device in some embodiments. In an example column structure, a column in the column structure corresponds to the biological sample data that is specific to the analysis performed on the single chamber, and each row corresponding to the column respectively corresponds to the biological sample data that is captured or generated for the single chamber at a specific time point or for a specific time period. In some of these embodiments, a row in the row structure corresponds to the biological sample data that is specific to the analysis performed on a chamber in the microfluidic device, and each column corresponding to the row respectively corresponds to the biological sample data that is captured or generated for the chamber at a specific time point or for a specific time period.

In some embodiments, an identifier of the multiple identifiers pertains to at least one aspect of an assay analysis or a result of the assay analysis that is performed on the at least one biological sample of the biological samples in the microfluidic device. In addition or in the alternative, the set of images, the first sequence of data, or the second sequence of data is time stamped with a unique time stamp at the time the set of images, the first sequence of data, or the second sequence of data is captured or generated.

In some embodiments, the multiple identifiers comprise at least one of an identifier of a chamber in the microfluidic device, a size attribute of the biological samples, a maximum brightness attribute for the biological samples, a minimum brightness attribute for the biological samples, a first pixel count attribute in a first direction for a centroid of a biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of chambers or the multiple regions of interest, a gate path index, an area pixel attribute, a background pixel attribute, or a median brightness attribute for the biological samples.

In some embodiments, rendering the first interactive object and the second interactive object may comprise determining, by the processor at 1020B, a dynamic width or length for a first gallery sub-structure of the gallery structure in the user interface based at least in part upon a first rank that is to be represented in the user interface. In some of these embodiments, rendering, at 1022B, the first interactive object and the second interactive object may further comprise rendering at least a portion of the first sequence of data comprising a first sequence of images into the first gallery sub-structure based at least in part upon the dynamic width or length for the first gallery sub-structure.

In some of the immediately preceding embodiments, a gallery field in a first plurality of gallery fields of the first gallery sub-structure corresponds to a region of interest of the multiple regions of interest, wherein the region of interest corresponds to a first unique identifier. In addition or in the alternative, the gallery field further corresponds to the region of interest correlated with the plurality of chambers and is further arranged to correspond to a plurality of gallery sub-structures. A gallery sub-structure of the plurality of gallery sub-structures may correspond to an identifier of the multiple identifiers in some of these embodiments.

FIGS. 10D-10E illustrate more details about a portion of the simplified example of a block diagram illustrated in FIG. 10A in one or more embodiments. Referring to FIG. 10D which illustrates more details about arranging and rendering associated data at 1008A in one or more embodiments, arranging and rendering associated data may comprise in response to an invocation of a timeline view through a timeline view activation interactive widget in the user interface based at least in part upon the timeline, rendering the timeline view and a matching grid portion in the user interface at 1002D. In some of these embodiments, the timeline view comprises respective progress of multiple workflow tasks or workflow stages in the analysis of the biological samples. Some examples of the multiple workflow tasks may include, for example, load, import, culture, profusion, assay, export, and/or flush, etc. A workflow stage may comprise one or more workflow tasks. For example, an assay analysis workflow stage may include a cell culture workflow task that further includes one or more workflow tasks. More specifically, the cell culture task may be performed over a time period during which a system described herein may measure, capture, or otherwise acquire various data or information (e.g., image(s), cell count(s), etc. at a plurality of time points or time periods, time sequencing data such as timestamps corresponding to the plurality of time points at which the aforementioned data or information was captured, etc.) A cell culture task may expend a longer time period than one or more other tasks. In some embodiments, a system described herein may programmatically segment a workflow stage into multiple uniform and/or non-uniform workflow tasks (e.g., by temporally partitioning the workflow stage), and the data or information acquired for the workflow stage may also be partitioned in accordance with the multiple workflow tasks such that a user may select the workflow stage to access all the information or data acquired therefor (e.g., presenting respective interactive image data for all workflow task(s) of a specific workflow stage in a gallery view) or select one or more workflow tasks of a workflow stage to access the corresponding one or more smaller portions of the information or data acquired therefor (e.g., presenting respective interactive image data for a workflow task of a specific workflow stage in a gallery view). For example, a user or a researcher may identify a workflow stage and/or a corresponding workflow task at a time point or in a time period from, for example, a chip timeline view (e.g., by clicking on a graphical representation corresponding to the time point or time period in the timeline view), and the techniques described herein may identify the corresponding associated data and direct the output to a gallery view to examine what actually occurred at that time point or during that time period.

In addition or in the alternative, the timeline view is rendered based at least in part upon a first sequence of data and a second sequence of data correlated with the analysis or to the biological samples. In some of the immediately preceding embodiments, the respective progress graphically indicates respective temporal durations of the multiple workflow tasks, however it should be noted herein that a workflow stage or workflow stages may be similarly depicted with the caveat that a workflow stage may be selected to reveal corresponding workflow tasks. Moreover, the respective progress may be optionally represented with an interactive progress widget which, when interacted upon in the timeline view, causes the processor at least to populate the matching grid portion with at least a portion of the first sequence of data or at least a portion of the first analysis result in some embodiments.

In some embodiments, arranging and rendering associated data may comprise in response to an identification of the microfluidic device, the first sequence of data, or the second sequence of data represented in the user interface, determining, at 1004D, whether the gallery structure exists for the microfluidic device. When it is determined that the gallery structure exists for the microfluidic device, arranging and rendering associated data may comprise populating, at 1006D, the matching grid portion with at least a portion of the first sequence of data or at least a portion of the associated data; and rendering, at 1006D, an identifier widget which, when receiving an identifier change input from the user interface, triggers an instruction that changes a first identifier of the first sequence of data in some embodiments.

In some of these embodiments, rendering, at 1008D, a delete widget which, when invoked in the user interface, causes at least the processor to remove the microfluidic device and data correlated with the microfluidic device from the timeline view. In some of these embodiments, the timeline view comprises a first adjustable size or shape in the user interface; the matching grid portion comprises a second adjustable size or shape in the user interface; and the timeline portion comprises multiple graphical representations or graphical elements respectively identifying corresponding experiment types of the multiple biological experiments.

In some embodiments, arranging and rendering associated data may comprise associating a first region of interest of the multiple regions of interest with one or more graphical elements illustrated in a timeline view at 1010D. In some of these embodiments, associating the first region of interest with the one or more graphical elements comprises rendering a first interactive object, which corresponds to a first sequence of data captured at a first time point or a first temporal period, for a first graphical element of the one or more graphical elements in a first column in a portion of the user interface.

In addition or in the alternative, associating the first region of interest with the one or more graphical elements may comprise rendering, at 1012D, a second interactive object, which corresponds to a first sequence of data captured at a second time point or a second temporal period, for a second graphical element of the one or more graphical elements, the second interactive object corresponding to a second column in the portion of the user interface. In some of these embodiments, a size of a graphical element of the one or more graphical elements corresponds to a temporal duration of a time period during which data is captured for the biological samples, and a larger graphical element indicates a longer temporal period.

Referring to FIG. 10E, arranging and rendering the associated data may comprise determining, at 1014D, the timeline based at least in part upon a pipeline or a workflow for the analysis of the biological samples in some embodiments; determining, at 1016D, a plurality of stages for the analysis based at least in part upon the timeline, wherein the plurality of stages respectively corresponds to a plurality of timepoints or time periods for the analysis of the biological samples; and respectively determining, at 1018D, a plurality of graphic representations for the plurality of stages based at least in part upon the plurality of timepoints or time periods. In some of these embodiments, arranging and rendering the associated data may further comprise arranging and rendering, at 1020D, the plurality of graphic representations in the timeline view in the user interface according to a temporal order correlated with the plurality of timepoints or time periods.

FIG. 10F illustrates more details about a portion of the simplified example of a block diagram illustrated in FIG. 10A in one or more embodiments. In these embodiments, arranging and display associated data may include rendering a data control view in the user interface at 1002F. In some of these embodiments, rendering the data control view comprises generating, at 1004F, a microfluidic device data structure having a plurality of fields for the microfluidic device having a plurality of chambers. In addition or in the alternative, rendering the data control view may comprise populating, at 1006F, first data of the microfluidic device into a first field in the microfluidic device data structure, wherein the first data comprises a first identifier of the microfluidic device; and rendering, at 1008F, a first interactive data control widget for the first field in the microfluidic device data structure, wherein the first interactive data control widget, when interacted upon, invokes one of multiple first candidate actions that are correlated to a timeline view or a gallery view, depending upon a first input received in the data control view for configuring a chamber list correlated with at least the first data and the gallery view.

In some embodiments, rendering the data control view may further comprise populating, at 1010F, second data of the microfluidic device into a second field in the microfluidic device data structure, wherein the second data comprises a tag correlated with a first biological processing (e.g., fluorescent labeling, magnetic labeling, radioactive labeling, enzymatic labeling, or any other biological processing performed on biological samples in an assay or sequencing, etc.) on the biological samples in the microfluidic device; and rendering, at 1012F, a second interactive data control widget for the second field, wherein the second interactive data control widget invokes at least one of multiple second candidate actions in response to a second user input in the data control view for configuring one or more visualization options of the associated data. A tag may comprise one or more labels (e.g., one or more fluorescent labels) that are used in, for example, a labeling process (e.g., a fluorescent labeling process) for biological samples. A digital object may be stored for a tag in, for example, a microfluidic device data structure, a gallery structure, etc. to represent the corresponding label. In some of these embodiments, rendering the data control view may further comprise populating, at 1014F, third data of the microfluidic device into one or more third fields in the microfluidic device data structure, wherein the third data comprises a time stamp for the microfluidic device; and rendering, at 1016F, a third interactive data control widget for the one or more third fields, wherein the third interactive data control widget, when interacted upon, invokes at least one of multiple third candidate actions in response to a third user input in the data control view for configuring dimensionality reduction or clustering for the analysis.

Biological processing as referred to herein, may include any of workflow stages (e.g., one or more workflow tasks) for operating upon one or more micro-objects, e.g., biological cells, as is generally known in the art, and in particular as is described herein. The biological processing may be performed within the environment of a device including the micro-objects or may include some portion of the processing that is performed external to the device, e.g., pre-processing or post-processing, including bulk selection and sequencing macromolecules captured from the micro-objects, respectively. Biological processing may include, but is not limited to: culturing; expanding a population of micro-objects (e.g., culturing the micro-objects over a period of time sufficient to permit the micro-objects to multiply, where in some embodiments, the expanded population is a clonal population of daughter cells); assaying the micro-object(s) for a particular attribute, feature, or functionality (e.g., biological or biophysical activity of the biological micro-object); assaying the secretions of the micro-objects for a particular attribute, feature, or functionality (e.g., binding to a target molecule or blocking binding between two or more molecules, such as a receptor-ligand pair, that would otherwise form a complex); assaying the media surrounding the micro-object(s) or adjacent to the region in which the micro-object(s) are disposed, for a particular attribute, feature, or functionality (e.g., concentration of nutrients, reactive species, or the like). Assaying the biological micro-object(s), secretions of the biological micro-object(s), or media surrounding or adjacent to the biological micro-object(s) may include providing a label or tag that produces a detectable signal, such as a colorimetric, fluorescent, luminescent, ultra-violet, infra-red signal, or is otherwise capable of being visually detected by an imaging system as described herein. Manipulation of the one or more micro-objects may further include, after assaying the one or more micro-objects for a particular attribute, feature or functionality, selection of all or a portion of the one or more micro-objects for unpenning. The unpenned micro-objects may be re-penned in another region of the microfluidic device, for retaining, grouping, or storage, or for additional processing, such as culturing or lysing (e.g., with subsequent capture of released macromolecules, such as proteins, nucleic acids, or products of the biological micro-objects, including gene expression products). The released macromolecules or products of the micro-objects may be detected in situ or may be exported for analysis external to the microfluidic device. The results of such analysis may be imported back to the system (e.g., in a pipeline or other data module), correlated with the source of one or more micro-objects, and optionally selected and viewed within a gallery view for analysis, for example, to determine which micro-objects express a desired biological product while also satisfying other biological activity criteria.

The tag, as referred to herein, may be an intrinsic property (e.g., fluorescence) or a reporter molecule or secretion, or may include any kind of detectable label and/or type of ligand that may recognize a portion of a micro-object, product of the micro-object (secreted or not secreted), or analyte associated with the micro-object or analyte to be measured within the media surrounding or adjacent to the micro-object. The detectable label may be, as mentioned above, a colorimetric, fluorescent, luminescent, ultra-violet, infra-red signal or other visually imageable moiety. The detectable label may itself be configured to associate (e.g., an intercalating dye) or may be connected to a ligand that is configured to bind (covalently or noncovalently) to the micro-object, product of the micro-object (secreted or not secreted), or analyte associated with the micro-object or analyte to be measured within the media surrounding or adjacent to the micro-object. Examples of such ligands include hybridizable polynucleotides, His tags, antibodies or fragments thereof. In some other embodiments, the tag may be a detectable label released from a biomolecule upon action by the micro-object, product of the micro-object (secreted or not secreted), or analyte associated with the micro-object or analyte to be measured within the media surrounding or adjacent to the micro-object. For example, a substrate for a protease may release a fluorescent tag upon being proteolyzed by a protease secreted by a micro-object or included within the micro-object. These examples are not limiting, as known in the art.

FIGS. 10G-1, 10G-2, 10G-3, and 10G-4 illustrate more details about a portion of the simplified example of a block diagram illustrated in FIG. 10A in one or more embodiments. In these embodiments, arranging and displaying associated data at 1008A may comprise rendering a filter view at 1002G. Rendering the filter view at 1002G may comprise determining, at 1004G, a first filter type for a first filter based at least in part upon an execution of one or more instructions triggered by an interaction with a first filter selector switch in a filter generation module. In some of these embodiments, rendering the filter view may further comprise in response to a determination of the first filter type, rendering, at 1006G, the first filter selector switch for the first filter type of one or more first filters in the filter view in the user interface, wherein the first attribute selector switch, when invoked, triggers a first presentation of a list of one or more first interactive filter attributes for the first filter type.

In some of the immediately preceding embodiments, rendering the filter view may further comprise in response to invocation of a first interactive filter attribute in the list of one or more first interactive filter attributes, rendering, at 1008G, a first filter configurator for filtering the plurality of chambers or the multiple regions of interest in the microfluidic device according to the first filter. In some of these embodiments, the first filter configurator imposes a first dynamic constraint on the plurality of chambers or the multiple regions of interest in response to a first interactive filter input for the first interactive filter attribute.

Moreover, the first dynamic constraint may constrain the plurality of chambers or the multiple regions of interest to generate a first set of filtered regions of interest from the plurality of chambers or the multiple regions of interest to be displayed in the user interface in some embodiments. The first filter configurator may further comprise a first configuration slider widget which, when manipulated with a dynamic manipulation in the filter view, confines a number of dynamically constrained regions of interest in the microfluidic device and further triggers a graphical representation of the number of dynamically constrained regions of interest in the filter view based at least in part upon the dynamic manipulation in some embodiments.

In some embodiments, rendering the filter view may further comprise dynamically determining and displaying, at 1010G in the filter view for the microfluidic device, a first total number of regions of interest for the first set of filtered regions of interest that satisfies the first dynamic constraint. In some of these embodiments, rendering the filter view may further comprise rendering, at 1012G, a first histogram that dynamically varies in response to a first dynamic change in the first dynamic constraint for the first filter, wherein the first histogram comprises a de-emphasized histogram of the plurality of chambers or a region of interest that is overlaid on top of the first histogram that dynamically varies in response to the first dynamic change in the first dynamic constraint. In some of these immediately preceding embodiments, the filter view further comprises information about a filtered region of interest of the first set of filtered regions of interest, the information comprising one or more region of interest identifiers, the first total number of regions of interest satisfying the first dynamic constraint, a histogram illustrating a first distribution of the plurality of chambers or the multiple regions of interest over the first interactive filter attribute, a highlighted portion of the histogram illustrating a second distribution of the first set of filtered regions of interest over the first interactive filter attribute, or any combination thereof.

In some embodiments, rendering the filter view may further comprise generating, at the filter generation module at 1014G, a logical combination of at least a second filter of a second filter type and a third filter of a third filter type; and rendering, at 1016G, the first filter selector switch for the second filter type, wherein the first filter selector switch, when invoked, is used to determine the second filter type, a second attribute selector for the second filter, or a third attribute selector for the third filter.

In addition or in the alternative, rendering the filter view may further comprise in response to a determination of a second filter attribute, rendering, at 1018G, a second filter configurator for filtering the plurality of chambers or the multiple regions of interest according to the second filter, wherein the second filter configurator imposes a second dynamic constraint in response to a second filter input, the second dynamic constraint constrains a second number of filtered regions of interest from the multiple regions of interest to be displayed in the user interface.

In some of these embodiments, rendering the filter view may further comprise dynamically determining and displaying, at 1020G in the filter view for the microfluidic device, a second total number of filtered regions of interest that satisfies the second dynamic constraint; rendering, at 1022G, a second histogram that dynamically varies in response to a second dynamic change in the second dynamic constraint from the second filter input; and rendering, at 1024G, the first filter selector switch for the second filter type, wherein the first filter selector switch, when invoked, is used to determine the second filter type and the second attribute selector corresponding to the second filter type.

In addition or in the alternative, rendering the filter view may further comprise in response to an invocation of the second filter type, rendering, at 1026G, the second attribute selector switch for the second filter type of one or more second filters in the filter view in the user interface, wherein the second attribute selector, when invoked, triggers a second presentation of a list of one or more second interactive filter attributes for the second filter type. In some of these embodiments, rendering the filter view may further comprise rendering, at 1028G, the first filter selector switch in the filter generation module for the third filter type, wherein the first filter selector switch, when invoked, is used to determine the third filter type and the third attribute selector corresponding to the third filter type.

Moreover, rendering the filter view may further comprise in response to an invocation of the third filter type, rendering, at 1030G, the third attribute selector for the third filter type of one or more third filters in the filter view in the user interface, wherein the third attribute selector, when invoked, triggers a third presentation of a list of one or more third interactive filter attributes for the third filter type; and in response to selection of a second interactive filter attribute, rendering, at 1032G, the second filter configurator for filtering the plurality of chambers or the multiple regions of interest in the microfluidic device according to the second filter, wherein the second filter configurator is used to impose the second dynamic constraint in response to a second interactive filter input.

In some of these embodiments, the second dynamic constraint constrains the plurality of chambers or the multiple regions of interest from the first filter into a second set of filtered regions of interest to be displayed in the user interface; and the second filter configurator comprises a second configuration slider widget which, when manipulated with a second dynamic manipulation, confines the plurality of chambers or the multiple regions of interest into a separate number of dynamically constrained regions of interest for the microfluidic device and further triggers rendering a graphical representation of the separate number of dynamically constrained regions of interest in the filter view based at least in part upon the second dynamic manipulation.

In some embodiments, rendering the filter view may further comprise in response to selection or determination of a third interactive filter attribute, rendering, at 1034G, a third filter configurator for filtering the second set of filtered regions of interest in the microfluidic device according to the third filter, wherein the third filter configurator imposes a third dynamic constraint in response to a third interactive filter input, and the third dynamic constraint constrains the second set of filtered regions of interest from the second filter into a third set of filtered regions of interest to be displayed in the user interface.

In some of these embodiments, rendering the filter view may further comprise dynamically determining and displaying, at 1036G, in the filter view for the microfluidic device, a second total number of regions of interest for the second set of filtered regions of interest that satisfies the second dynamic constraint. In some of these immediately preceding embodiments, rendering the filter view may further comprise dynamically determining and displaying, at 1038G in the filter view for the microfluidic device, a third total number of regions of interest for the third set of filtered regions of interest that satisfies the third dynamic constraint, wherein the filter view further comprises second information about a filtered region of interest of the second or the third set of filtered regions of interest, the second information comprising one or more region of interest identifiers, the second or the third total number of regions of interest respectively satisfying the second or the third dynamic constraint, a separate histogram illustrating a separate distribution of the plurality of regions of interest over the second and the third interactive filter attributes, a separate highlighted portion of the separate histogram illustrating a third distribution of the second or the third set of filtered regions of interest over the first interactive filter attribute, or any combination thereof.

In some embodiments, rendering the filter view may further comprise rendering, at 1040G, a third histogram or scatter plot that dynamically varies in response to the second dynamic change in the second dynamic constraint from the second interactive filter input; rendering, at 1042G, a fourth histogram or scatter plot that dynamically varies in response to a third dynamic change in the third dynamic constraint from the third interactive filter input; generating, at a list generation module, a first region of interest list. In some embodiments, generating the first region of interest list may comprise at least one of receiving, at 1044G, a first instruction from the user interface for generating the first region of interest list based at least in part upon a first interaction with the user interface, wherein the first interaction corresponds to toggling a multi-state selector in the user interface to set a selected state for a selected region of interest in a set of filtered regions of interest or in the plurality of chambers or the multiple regions of interest in the filter view; rendering, at 1046G, a list generation switch in the filter view, wherein the list generation switch, when invoked, is used to generate the first region of interest list to include one or more first selected regions of interest that are selected by at least the first interaction from the set of filtered regions of interest or the plurality of chambers or the multiple regions of interest; or generating, at 1048G, the first region of interest list for the one or more first selected regions of interest in response to an interaction with the list generation switch.

In some embodiments, rendering the filter view may further comprise generating, at the list generation module, a second region of interest list at 1050G; and presenting, at 1050G, a number of presented regions of interest in a graphical plot in the filter view based at least in part upon one or more filters, wherein the graphical plot illustrates how one or more properties of the number of presented regions of interest distribute with respect to the one or more filters. In some of these embodiments, rendering the filter view may further comprise receiving, at 1052G, a second instruction based at least in part upon a second interaction from the user interface, wherein the second interaction comprises a selection of a subset of regions of interest from the number of presented regions of interest with a user-defined curvilinear or rectilinear boundary that encloses one or more display areas displaying data correlated with the associated data in the user interface. In some of these immediately preceding embodiments, rendering the filter view may further comprise generating, at 1054G, the second region of interest list for the one or more display areas in response to activation of the list generation switch, wherein the user-defined curvilinear or rectilinear boundary in the filter view is determined based at least in part upon one or more selection criteria that comprise one or more characteristics of one or more regions of interest in the number of presented regions of interest, and the number of presented regions of interest is displayed in the filter view with a heat map having multiple colors or a uniform color scheme based at least in part upon a first property of the number of presented regions of interest.

In some embodiments, rendering the filter view may further comprise in response to a cursor of a pointing device hovering at or around the region of interest in the filter view, triggering, at 1056G, a generation of a pop-up display region to display information about the region of interest, wherein the information is configurable by a user based at least in part upon a selection of one or more characteristics of the region of interest. In some of these embodiments, rendering the filter view may further comprise modifying, at 1058G, the use-defined curvilinear or rectilinear boundary at least by adding one or more nodes to the use-defined curvilinear or a rectilinear bound and by modifying the use-defined curvilinear or a rectilinear bound based at least in part upon the one or more nodes.

FIGS. 10H-1 and 10H-2 illustrate more details about a portion of the simplified example of a block diagram illustrated in FIG. 10A in one or more embodiments. In these one or more embodiments, arranging and displaying the associated data may comprise generating a bioinformatics pipeline view, wherein generating the bioinformatics pipeline view comprises determining, at 1002H, a sequencing dataset for the biological samples in the plurality of chambers or the multiple regions of interest of the microfluidic device, wherein a biological sample comprises a sequence of nucleotides or amino acids. In some of these embodiments, generating the bioinformatics pipeline view may further comprise receiving, at 1004H, the sequencing dataset in the user interface; and identifying, in the user interface, a characteristic correlated with a sequence of nucleotides or amino acids at 1004H.

In some embodiments, generating the bioinformatics pipeline view may further comprise in response to a first interaction with a first sequencing view widget in the user interface, rendering, at 1006H, a first sequencing view in the bioinformatics pipeline view that illustrates a distribution of the characteristic of the sequence of nucleotides or amino acids in the plurality of chambers or the multiple regions of interest. In some of these embodiments, generating the bioinformatics pipeline view may further comprise overlaying, at 1008H, the first sequencing view with first information that comprises one or more statistical measures of the distribution of the characteristic of the sequences of nucleotides or amino acids, wherein the user interface comprises a total number of multiple sequences of nucleotides or amino acids, a total number of regions of interest having the sequences of nucleotides or amino acids, and a respective total number of one or more sequences of nucleotides or amino acids in a respective region of interest of the array of regions of interest.

In addition or in the alternative, generating the bioinformatics pipeline view may further comprise in response to a second interaction on a portion of the distribution in the first sequencing view, overlaying the first sequencing view with second information that comprises one or more quantifiable measures correlated with one or more sequences of multiple sequences of nucleotides or amino acids with respect to the portion of the distribution in the first sequencing view at 1010H; and receiving, at 1012H, the second interaction with a first curvilinear or rectilinear selection widget in the bioinformatics pipeline view of the user interface, the second interaction triggers a first instruction to eliminate a portion of the first sequencing view in the bioinformatics pipeline view based at least in part upon an extent of the second interaction.

In some of these embodiments, generating the bioinformatics pipeline view may further comprise in response to a third interaction with a second sequencing view widget in the user interface, rendering, at 1014H, a second sequencing view in the bioinformatics pipeline view that illustrates a second distribution of the characteristic of the sequence of nucleotides or amino acids in the plurality of chambers or the multiple regions of interest, wherein the second distribution comprises respective intensities of the plurality of biological samples in the plurality of chambers or the multiple regions of interest in response to a fluorescent dye, and the respective intensities are associated with respective coloring tones that are customizable by users.

In some of these embodiments, generating the bioinformatics pipeline view may further comprise receiving, at 1016H, a fourth interaction with the curvilinear or rectilinear selection widget or a different curvilinear or rectilinear selection widget in the bioinformatics pipeline view, the fourth interaction causes execution of a second instruction to select one or more regions of interest from the second sequencing view in the bioinformatics pipeline view based at least in part upon an extent of the fourth interaction; and receiving, at 1016H, a fifth instruction from the user interface for generating a first region of interest list.

In some embodiments, receiving the fifth instruction for generating the first region of interest list may comprise generating, at 1018H, the first region of interest list for the one or more regions of interest selected from the second sequencing view based at least in part upon the curvilinear or rectilinear selection widget or the different curvilinear or rectilinear selection widget in the bioinformatics pipeline view; and in response to generation of the first region of interest list comprising the one or more regions of interest selected from the second sequencing view, triggering, at 1020H, a sixth instruction that invokes an operation for rendering a second sequence of data into multiple gallery fields in the gallery structure or a separate gallery structure.

In some of these embodiments, receiving the fifth instruction for generating the first region of interest list may comprise determining, at 1022H, the dynamic width or a different dynamic width for a respective gallery field of the multiple gallery fields for display in the user interface; and rendering, at 1024H, a respective interactive object with a corresponding display property for a respective region of interest of the one or more regions of interest selected from the second sequencing view. A multi-direction placement widget may be rendered in the user interface for a user to identify an additional instruction for adding a separate object into the user interface at 1026H. A candidate placement position may be determined at 1028H for the separate object to be added to the user interface. A ghosting object may be rendered at 1030H at the candidate placement position prior to placement of the separate object in the user interface. The separate object may be snapped to the candidate placement position at 1032H.

FIG. 10H-3 illustrates more details about a portion of the simplified example of a block diagram illustrated in FIG. 10A in one or more embodiments. In these one or more embodiments, arranging and displaying the associated data may comprise rendering, at 1034H, a multi-directional placement widget in the user interface that includes at least one view; and identifying an addition instruction for adding a separate object into the user interface based at least in part upon a first input from a user at 1034H.

In some of these embodiments, arranging and displaying the associated data may comprise determining, at 1036H, a candidate placement position from multiple candidate placement positions for the separate object based at least in part upon the first input. A ghosting object may be rendered at the candidate position in the user interface at 1038H to graphically present where the separate object is to be placed in relation to the at least one view prior to placement of the separate object in the user interface in some embodiments. The separate object may be snapped to the candidate placement position at 1040H upon a separate input from the user input device, wherein the multi-directional placement widget provides multiple candidate placement positions in at least two orthogonal directions for placing the separate object in the user interface, and one or more boundaries of the separate object are individually adjustable after the placement of the separate object in the user interface.

In some embodiments, the first input comprises information correlated with a relative position of the cursor of the user input device in relation to the multi-directional placement widget rendered in the user interface, or the at least one view and the separate object are both presented in a non-overlapping manner in the user interface at least by resizing the at least one view to accommodate the placement of the separate object at the candidate placement position in the user interface.

FIG. 10I illustrates more details about a portion of the simplified example of a block diagram illustrated in FIG. 10A in one or more embodiments. In these one or more embodiments, arranging and displaying the associated data may comprise determining a first count of the biological samples at a first time point in a region of interest in the microfluidic device, determining the first count comprising receiving, at 1002I, first image data captured at a first time point for a region of interest in the microfluidic device. The first image data may be pre-processed at 1004I, into first pre-processed image data at least by arranging the first image data into an array of first pixel information by second pixel information by a pixel depth information.

In some of these embodiments, determining the first count may further comprise determining, at 1006I, a first count of the biological samples in the region of interest at least by recognizing the biological samples with the convolutional neural network (CNN) having multiple processing blocks; and determining, at 1008I, a first class or type of the first image data at least by classifying the first image data or the first pre-processed image data into the first class or type with at least a machine learning model. In some of these immediately preceding embodiments, a first class or type of the first image data may be determined at 1008I at least by classifying the first image data or the first pre-processed image data into the first class or type with at least a machine learning model.

The first count of the biological samples in the region of interest may be determined at 1010I based at least in part upon the first class or type using the convolutional neural network (CNN). Textual or graphical information correlated with the first count may be displayed at 1012I for the region of interest in a gallery view of a graphical user interface (GUI).

In some embodiments, convolutional layers in the convolutional neural network have filter sizes greater than one-by-one so that no convolutional layers in the convolutional neural network have a one-by-one filter. In addition or in the alternative, the convolutional neural network comprises no pooling layers.

In some embodiments, the multiple processing blocks in the CNN may comprise a first processing block, a second processing block, and a third processing block, the first processing block comprising a first down-sampling block that down-samples a first input to the second down-sampling block into first down-sampled image data. In some of these embodiments, the first processing block may comprise a first residual network, wherein the first residual network follows the first down-sampling block, wherein each of the first down-sampling block and the first residual network in the first processing block comprises at least one first convolutional layer.

In addition or in the alternative, the first residual network comprises a first parallel path and a second parallel path, both of which receive a first down-sampling block output from the first down-sampling block, the first parallel path comprises a first filter size, and the second parallel path comprises a second filter size that is smaller than the first filter size of the first parallel path.

In some embodiments, the multiple processing blocks further comprise a fourth processing block that further comprises a number of transpose convolutional layers each of which is followed by a respective normalization layer. In some of these embodiments, a transpose convolutional layer of the number of transpose convolutional layers has a same stride number as the at least one first convolutional layer in the first processing block or the at least one second convolutional layer in the second processing block.

FIG. 10J illustrates more details about a portion of the simplified example of a block diagram illustrated in FIG. 10A in one or more embodiments. In these one or more embodiments, arranging and displaying the associated data may comprise generating a differential gene expression view that may comprise receiving, at a differential gene expression module, a first dataset correlated with the biological samples in the multiple regions of interest in the microfluidic device at a first time point or time period at 1002J; and receiving, at the differential gene expression module, a second dataset correlated with the biological samples in the multiple regions of interest at a second time point or time period at 1002J.

Moreover, generating the differential gene expression view may further comprise determining, at 1004J a first list of regions of interest for first dataset of the biological samples; and determining, at 1004J, a second list of regions for the second dataset of the biological samples. In some of these embodiments, generating the differential gene expression view may further comprise determining, at 1006J, at least one statistic measure correlated with a change in a first quantifiable metric between the first and the second time points or time periods. In some of these embodiments, the at least one statistic measure comprises a fold change, and the change comprises a first ratio between the first quantifiable metric at the first time point or time period and the first quantifiable metric at the second time point or time period. Moreover, the at least one statistic measure comprises a logarithm of a second ratio between the first quantifiable metric at the first time point or time period and the first quantifiable metric at the second time point or time period.

In some embodiments, generating the differential gene expression view may further comprise receiving, at 1008J, a first configurable constraint value from a first user interaction with a fold change slider widget, wherein the first configurable constraint value suppresses first data correlated with the biological samples that exhibits the change in the first quantifiable metric below the first configurable constraint value. In some of these embodiments, at least a portion of the first and the second datasets may be dynamically filtered at 1010J based at least in part upon the first user interaction. In addition or in the alternative, first differential gene expression data may be displayed, at 1012J, in a differential gene expression view from the first dataset and the second dataset based at least in part upon the first configurable constraint value, wherein the first data correlated with the first and the second datasets that exhibit the change below the first configurable constraint value is suppressed in the differential gene expression view.

FIGS. 10K-1 and 10K-2 illustrate more details about a portion of the simplified example of a block diagram illustrated in FIG. 10A in one or more embodiments. In these one or more embodiments, arranging and displaying the associated data may comprise configuring a bioinformatics pipeline view for a first dataset correlated with the biological samples in the microfluidic device with a set of configuration widgets at 1002K, wherein the plurality of configuration widgets comprises at least one of a dimensionality reduction widget, a clustering widget, a coordinate configuration widget, a color scale configuration widget, a number of color scales configuration widget, a scatter plot configuration widget, a list of regions of interest manipulation module, or a dynamic filtering slider widget.

In some of these embodiments, configuring the bioinformatics pipeline view may comprise receiving, from a first interaction with the dimensional reduction widget, a number of principal component analysis (PCA) components for the first dataset of the biological samples at 1004K. In some of these immediately preceding embodiments, dimensionality of the first dataset correlated with the biological samples may be reduced at 1006K based at least in part upon the number of principal component analysis components.

In addition or in the alternative, configuring the bioinformatics pipeline view may comprise receiving, from a second interaction with the clustering widget, a Louvain clustering parameter value for the first dataset of the biological samples at 1008K. At least a portion of the biological samples may be clustered at 1010K into one or more clusters at least by processing the first dataset based at least in part upon the Louvain clustering parameter value in some embodiments.

In some embodiments, configuring the bioinformatics pipeline view may comprise determining, from a third interaction with the coordinate configuration widget, a coordinate system at 1012K for presenting at least a portion of the first dataset in the bioinformatics pipeline view, wherein the third interaction selects the coordinate system from a plurality of options that comprises Uniform Manifold Approximation and Projection (UMAP) or a principal component analysis (PCA).

In some embodiments, configuring the bioinformatics pipeline view may comprise determining, from a fourth interaction with the color scale configuration widget, a color scale at 1014K for presenting at least a portion of the first dataset in the bioinformatics pipeline view, wherein the fourth interaction selects the color scale from a plurality of options that comprises a linear color scale or a logarithmic color scale.

In some embodiments, configuring the bioinformatics pipeline view may comprise determining, from a fifth interaction with the number of color scales configuration widget, a number of color scales at 1016K for presenting at least a portion of the first dataset in the bioinformatics pipeline view, wherein the fifth interaction selects the number of color scales from a plurality of options that comprises a single color-bar or multiple color-bars.

In some embodiments, configuring the bioinformatics pipeline view may comprise determining, from a sixth interaction with the scatter plot configuration widget, one or more scatter plot options at 1018K for presenting at least a portion of the first dataset in the bioinformatics pipeline view, wherein the six interaction selects the one or more scatter plot options from a plurality of scatter plot options.

In some embodiments, configuring the bioinformatics pipeline view may comprise determining, from a seventh interaction with the list of regions of interest manipulation module, one or more options at 1020K for one or more lists of regions of interest for the first dataset, wherein the seventh interaction selects the one or more options from a plurality of options that comprises a first list selection mode option, a second list selection mode option, or a identifier option for the one or more lists of regions of interest.

In some embodiments, configuring the bioinformatics pipeline view may comprise identifying, at 1022K, a graphic representation for at least a portion of the first dataset for the biological samples in the bioinformatics pipeline view; and dynamically generating, at 1024K, the dynamic filtering slider widget associated with a dynamically generated range for the graphic representation of the at least a portion of the first data set for the biological samples. In some of these embodiments, configuring the bioinformatics pipeline view may comprise determining, from an eighth interaction with the dynamic filtering slider widget, a dynamic value based at least in part upon the eighth interaction with the dynamically generated range of the dynamic filtering slider widget at 1026K. In these embodiments, the graphic representation for the at least a portion of the first dataset for the biological samples may be dynamically refreshed at 1028K in response to the dynamic value that is determined based at least in part upon the eighth interaction with the dynamically generated range.

FIG. 11A-1 illustrates another high-level flow diagram of a method and/or system for analyzing biological samples using a microfluidic device having multiple chambers in one or more embodiments. In these one or more embodiments, arranging and displaying the associated data may comprise determining a first count of the biological samples at a first time point in a region of interest in the microfluidic device, determining the first count comprising receiving, at 1102A, first image data captured at a first time point for a region of interest in the microfluidic device. The first image data may be pre-processed at 1104A, into first pre-processed image data at least by arranging the first image data into an array of first pixel information by second pixel information by a pixel depth information.

In some of these embodiments, determining the first count may further comprise determining, at 1106A, a first class or type of the first image data at least by classifying the first image data or the first pre-processed image data into the first class or type with at least a machine learning model. In some of these immediately preceding embodiments, a first class or type of the first image data may be determined at 1106A at least by classifying the first image data or the first pre-processed image data into the first class or type with at least a machine learning model.

In some embodiments, determining the first class or type may comprise processing a plurality of low-level features by using at least the first processing block of the convolutional neural network. In some of these embodiments, determining the first class or type may further comprise determining the first class or type or a first statistic corresponding to the first class or type, wherein the first statistic comprises a first probability that one or more pixels in the first image data represent a corresponding biological sample characteristic.

The first count of the biological samples in the region of interest may be determined at 1108A based at least in part upon the first class or type using the convolutional neural network (CNN). Textual or graphical information correlated with the first count may be displayed at 1110A for the region of interest in a gallery view of a graphical user interface (GUI).

In some embodiments, convolutional layers in the convolutional neural network have filter sizes greater than one-by-one so that no convolutional layers in the convolutional neural network have a one-by-one filter. In addition or in the alternative, the convolutional neural network comprises no pooling layers.

In some embodiments, the multiple processing blocks in the CNN may comprise a first processing block, a second processing block, and a third processing block, the first processing block comprising a first down-sampling block that down-samples a first input to the second down-sampling block into first down-sampled image data. In some of these embodiments, the first processing block may comprise a first residual network, wherein the first residual network follows the first down-sampling block, wherein each of the first down-sampling block and the first residual network in the first processing block comprises at least one first convolutional layer.

In addition or in the alternative, the first residual network comprises a first parallel path and a second parallel path, both of which receive a first down-sampling block output from the first down-sampling block, the first parallel path comprises a first filter size, and the second parallel path comprises a second filter size that is smaller than the first filter size of the first parallel path.

In some embodiments, the multiple processing blocks further comprise a fourth processing block that further comprises a number of transpose convolutional layers each of which is followed by a respective normalization layer. In some of these embodiments, a transpose convolutional layer of the number of transpose convolutional layers has a same stride number as the at least one first convolutional layer in the first processing block or the at least one second convolutional layer in the second processing block.

In some embodiments, a method for analyzing biological samples may first identify an analysis of biological samples in multiple regions of interest in a microfluidic device. In addition, a timeline correlated with the analysis may be identified. Some examples of the analysis may include, without limitation, an assay analysis, a sequencing analysis, etc. for a plurality of biological samples using a microfluidic device in some embodiments.

A timeline may comprise information that is temporally aligned with a workflow or pipeline of the analysis of the biological samples. One or more region-of-interest types may be determined for the multiple regions of interest, wherein the one or more region-of-interest types comprise a target-based type correlated with at least one biological sample of the biological samples or a structure-based type correlated with the microfluidic device.

As described herein, a region of interest may include a target-based region that pertains to one or more attributes, characteristics, properties, and/or quantifiable metrics, etc. (e.g., a measured or derived diameter or a statistical measure correlated with a diameter of a cell in a region of interest, a count of genes in a region of interest, a number of cells cultured for a region of interest, a number or percentage of cells exported from a region of interest, etc.) of a biological sample of interest in some embodiments. A region of interest may also include a structure-based region of interest that pertains to one or more attributes, characteristics, properties, and/or quantifiable metrics, etc. (e.g., a characteristic to a structural aspect of a microfluidic device or a portion thereof, etc.) of a microfluidic device or any portion thereof in some embodiments.

With the one or more region-of-interest types determined, an attribute, a characteristic, a property, or a quantifiable metric may be determined at 1108A based at least in part upon the one or more region-of-interest types. In the aforementioned embodiments, a target-based attribute, characteristic, property, or quantifiable metric may be determined for a target-based region of interest. In addition or in the alternative, a structure-based attribute, characteristic, property, or quantifiable metric may be determined for a structure-based region of interest.

Associated data that respectively correspond to the multiple regions of interest may be arranged and displayed at 1110A in a user interface for at least a portion of the biological samples based at least in part upon the timeline and the attribute, characteristic, property, or quantifiable metric. An example of such an arrangement and display of associated data may include a gallery view in, for example, FIG. 6C, a miniaturized gallery view in, for example, FIG. 5A, a chip timeline view in, for example, FIG. 4A, a sequencing graph in, for example, FIG. 7H, or any other views or graphs.

FIG. 11A-2 illustrates more details about a portion of the high-level flow diagram illustrated in FIG. 11A-1 in one or more embodiments. More specifically, FIGS. 11A-2 illustrates more details about determining the first count at 1108A of FIG. 11A-1. In these one or more embodiments, determining the first count may comprise reducing, at 1112A, first loss of spatial information in processing the first image data at least by processing a first down-sampling block output with a third convolution kernel having a third dimension with a third stride along the second parallel path, wherein the third dimension is smaller than the first dimension and the second dimension, and the third stride is smaller than the first stride.

In some of these embodiments, the first processing block may further comprise a first recombination layer that is followed by a second activation layer, wherein the first recombination layer is operatively coupled to both the first parallel path and the second parallel path. In some embodiments, the multiple blocks further comprise a second processing block that further comprises a second down-sampling block that down-samples a second input to the second down-sampling block into second down-sampled image data; and a second residual network that follows the second down-sampling block, wherein each of the second down-sampling block and the second residual network in the second processing block comprises at least one second convolutional layer.

In some of these embodiments, the second down-sampling block comprises a fourth convolution kernel having a fourth dimension and a fourth stride for a fourth depth, and the fourth dimension is greater than one-by-one, and the fourth stride is greater than one. In some of the immediately preceding embodiments, the second convolution kernel is followed by a second batch normalization layer that is further followed by a third activation layer in the second down-sampling block. In addition or in the alternative, the second residual network comprises a third parallel path and a fourth parallel path, both of which receiving a second down-sampling block output from the second down-sampling layer, and the fourth parallel path comprises a second smaller filter size that is smaller than a second larger filter size of the third parallel path. Moreover, the third parallel path comprises a plurality of third convolution kernels having at least a fifth dimension and a fifth stride for a fifth depth, the fifth dimension is lower than the fourth dimension and greater than one-by-one, and the fifth stride is smaller than the fourth stride in some of these embodiments.

In some embodiments, determining the first count may further comprise reducing, at 1114A, second loss of the spatial information at least by processing the second down-sampling block output with a sixth convolution kernel having a sixth dimension with a sixth stride along the fourth parallel path, wherein the sixth dimension is smaller than the fourth dimension and the fifth dimension, and the sixth stride is smaller than the fourth stride. In these embodiments, the second processing block further comprising a second recombination layer that is followed by a fourth activation layer, wherein the second recombination layer is operatively coupled to both the third parallel path and the fourth parallel path.

In some of these embodiments, the multiple blocks further comprise a third processing block that further comprises a third down-sampling block that down-samples a third input to the third down-sampling block into third down-sampled image data; and a third residual network that follows the third down-sampling block, wherein each of the third down-sampling block and the third residual network in the third processing block comprises at least one third convolutional layer.

In some of the immediately preceding embodiments, the third down-sampling block comprises a seventh convolution kernel having a seventh dimension and a seventh stride for a seventh depth, and the seventh dimension is greater than one-by-one, and the seventh stride is greater than one. In addition or in the alternative, the seventh convolution kernel is followed by a third batch normalization layer that is further followed by a fifth activation layer in the third down-sampling block.

Moreover, the third residual network may comprise a fifth parallel path and a sixth parallel path, both of which receiving a third down-sampling block output from the third down-sampling layer, and the sixth parallel path comprises a third smaller filter size that is smaller than a third larger filter size of the fifth parallel path in some embodiments, and the fifth parallel path comprises a plurality of eighth convolution kernels having at least an eighth dimension and an eighth stride for a depth value, the eighth dimension is lower than the seventh dimension and greater than one-by-one, and the eighth stride is smaller than the seventh stride.

In some embodiments, determining the first count may further comprise reducing, at 1116A, third loss of the spatial information at least by processing the third down-sampling block output with a ninth convolution kernel having a ninth dimension with a ninth stride along the sixth parallel path, wherein the ninth dimension is smaller than the seventh dimension and the eighth dimension, and the ninth stride is smaller than the seventh stride, wherein the third processing block further comprises a third recombination layer that is followed by a sixth activation layer, wherein the third recombination layer is operatively coupled to both the fifth parallel path and the sixth parallel path.

In some of these embodiments, the multiple blocks further comprise a fourth processing block that may further comprise a number of transpose convolutional layers each of which is followed by a respective normalization layer, wherein a transpose convolutional layer of the number of transpose convolutional layers has a same stride number as the at least one first convolutional layer in the first processing block or the at least one second convolutional layer in the second processing block. In some these immediately preceding embodiments, the number of transpose convolutional layers corresponds to a value that is at least one less than a total number of convolutional layers in the first and the second processing blocks.

In some embodiments, convolutional layers in the convolutional neural network have filter sizes greater than one-by-one so that no convolutional layers in the convolutional neural network have a one-by-one filter. In addition or in the alternative, the convolutional neural network comprises no pooling layers; and pre-processing the first image data into the first pre-processed image data comprises at least reducing the first image data into the first pre-processed image data based at least in part upon the region of interest or a type of the first image data, wherein a type of the first image data corresponds an operation during which the first image data is captured for analyzing the biological samples, and the operation comprises an export operation or an import operation.

In some embodiments, determining the first count may further comprise determining, at 1118A, a pixel size for the first image data based at least in part upon a first geometric characteristic of the biological samples and a second geometric characteristic of the region of interest, wherein the first geometric characteristic of the biological samples comprises a diameter, a major diameter, a minor diameter, or an area of the biological samples, and the second geometric characteristic of the region of interest comprises a width or a length of the region of interest or a portion thereof.

In some of these embodiments, the determination of the first count may further comprise determining the first class or type at least by processing, at 1120A, a plurality of low-level features by using at least the first processing block of the convolutional neural network; processing, at 1122A, a plurality of abstract features by using at least the third processing block of the convolutional neural network; and determining, at 1124A, the first class or type or a first statistic corresponding to the first class or type, wherein the first statistic comprises a first probability that one or more pixels in the first image data represent a corresponding biological sample characteristic.

FIGS. 11B-1 and 11B-2 illustrate more details about a portion of the high-level flow diagram illustrated in FIG. 11A-1 in one or more embodiments. More specifically, FIGS. 11B-1 and 11B-2 illustrate more details about determining the first count of the biological samples (1108A) illustrated in FIG. 11A-1. In these one or more embodiments, determining the first count may comprise determining, at 1102B, a second count of the biological samples from second image data captured at a second time point or time period for the region of interest using at least the convolutional neural network (CNN) having the multiple processing blocks. A video or image sequence of the region of interest may be replayed at 1104B at least by sequentially rendering a portion of the first image data and a portion of the second image data in the gallery view of the graphical user interface (GUI).

In addition or in the alternative, determining the second count of the biological samples may comprise receiving, at 1106B, the second image data captured at the first time point for the region of interest in the microfluidic device; and pre-processing, at 1108B, the second image data into second pre-processed image data at least by arranging the second image data into the array of the first pixel information by the second pixel information by the pixel depth information. In these embodiments, pre-processing the second image data into the second pre-processed image data comprises at least reducing the second image data into the second pre-processed image data based at least in part upon the region of interest or the type of the second image data, wherein the type of the second image data corresponds a separate operation during which the second image data is captured for analyzing the biological samples, and the separate operation comprises the export operation, the import operation, a separate export operation, or a separate import operation.

In some embodiments, determining the second count may further comprise classifying, at 1110B, the second image data into the first class or type with at least a machine learning model; and determining, at 1112B, the second count of the biological samples at the second time point in the region of interest based at least in part upon the first class or type at least by recognizing the biological samples with a convolutional neural network having the multiple processing blocks. In some of these embodiments, determining the second count may further include determining, at 1114B, one or more first images from the first images data, the one or more first images comprising first information correlated with the first count and temporally corresponding to the first time point or time period. In addition, one or more second images may be determined at 1116B from the second images data, the one or more second images comprising second information correlated with the second count and temporally corresponding to the second time point or time period; and a temporal progression of at least a portion of the biological samples may be presented at 1118B at least by dynamically rendering the one or more first images and the one or more second images in a temporal sequence in the graphical user interface.

Figure 12A:
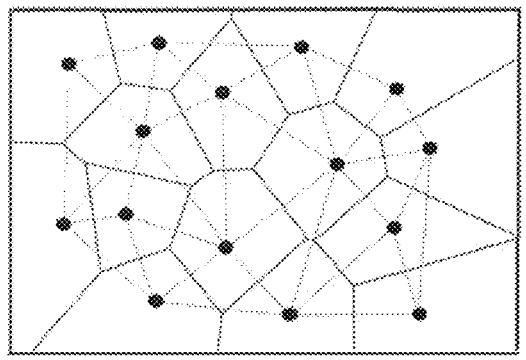
Figure 12B:
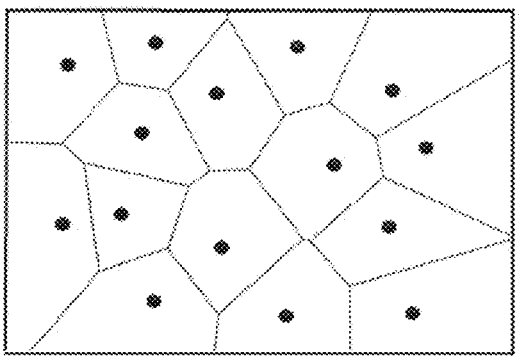
Figure 12C:
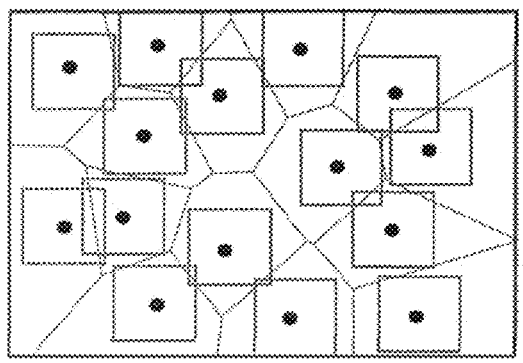
Figure 12D:
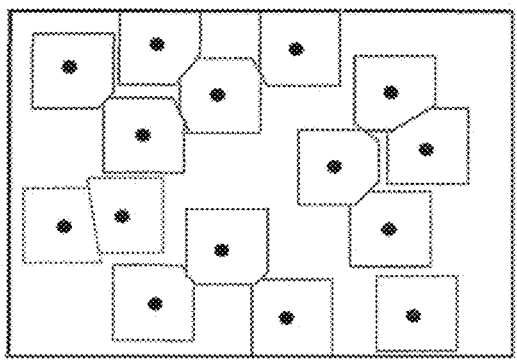
Figure 12E:
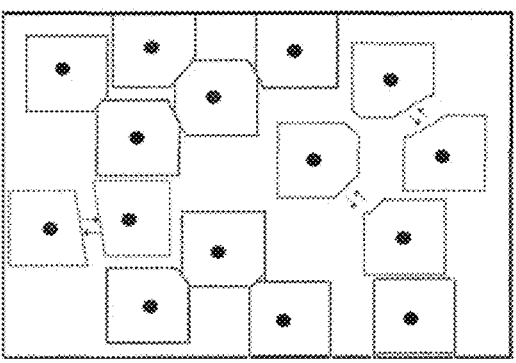
Figure 12F:
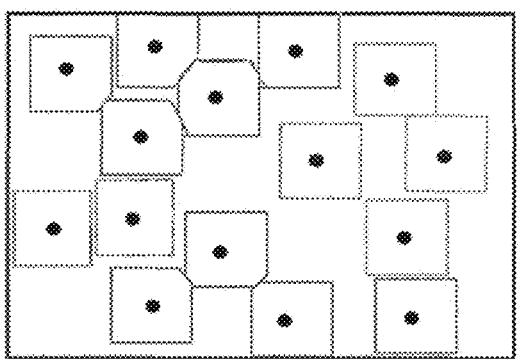

FIGS. 12A-12F illustrate some example micro-object separation examples according to one or more embodiments. More specifically, once a set of vertices has been computed, the set of vertices may be used in combination with OET and/or DEP forces to move the micro-objects. FIGS. 12A-12F illustrate micro-object separation according to various embodiments of the present invention. FIG. 12A illustrates the Delauney triangulation of a set of micro-objects within a specified spatial region and the corresponding Voronoi diagram. FIG. 12B illustrates the corresponding Voronoi diagram without the Delauney triangulation. FIG. 12C illustrates light cages typically used to move micro-objects overlaid upon the Voronoi diagram. FIG. 12D illustrates modified light cages generated by computing the intersection between the typical light cages of FIG. 12C and the Voronoi diagram. FIG. 12E illustrates the separation of the micro-objects that are in close proximity with each other using the modified light cages. FIG. 12F illustrates the separated micro-objects.

In one embodiment, one or more light cages are generated by generating a plurality of light bars that link a subset of vertices of the set of vertices, wherein the sub-set of vertices comprises (or consists of) vertices which are most proximal to and surround each micro-object to be moved. For example, any of the polygon shapes shown in FIG. 12B may be used to define a light cage that surrounds a micro-object. In certain embodiments, a light cage formed in this manner may be shrunk to thereby separate the micro-object within the light cage from other micro-objects and/or light cages in the specified spatial region. In other embodiments, a light cage may be defined by superimposing a "standard" light cage design (e.g., a square or circle) upon the polygon shapes (see FIG. 12C) and generating a light cage that results from the intersection of the standard light cage design and the polygon shapes, as illustrated in FIG. 12D. In this example, the intersection of the vertices and the light cages is defined as an area where the light cages do not intersect or overlap, allowing the "standard" light cage to be re-drawn such that it does not interfere with other micro-objects. Regardless of the method of formation, once formed the light cages may be used to separate micro-objects by repositioning the micro-object by moving the micro-objects away from each other. In some instances, modified light cage may be re-drawn as the micro-objects are repositioned such that the original light cages are drawn when the micro-objects are in the final position.

Non-standard (or "modified") light cages may be used to reposition the micro-objects in a variety of embodiments. Depending on the embodiment, the modified light cages for two proximate micro-objects are used to reposition the micro-objects prior to, or after, computing and selecting the trajectory and assignment to a sequestration pen for each micro-object. In some embodiments, modified light cages are used to reposition micro-objects iteratively or sequentially. In addition, modified light cages may be used to pen micro-objects in their assigned sequestration pens. In some embodiments, micro-objects that are closest to the perimeter of the spatial area or closest together in space may be re-positioned or penned prior to repositioning or penning other micro-objects.

FIG. 13A illustrates a simplified schematic diagram of a convolutional neural network in accordance with one or more embodiments. FIGS. 14A-14C illustrate schematic diagrams of a residual network, down-sampling block, and up-sampling block in accordance with one or more embodiments. FIGS. 14D-14G illustrate more details about a convolutional neural network in one or more embodiments. In various embodiments, a convolutional neural network (or CNN) is provided, as illustrated, for example, by a neural network 1300A of FIG. 13A. Additional detail related to example neural networks are illustrated in FIG. 14A-14G and may be used for reference purposes only in describing this embodiment, as the CNN features captured by FIG. 14A-14G may be used in conjunction with the illustrated network of FIG. 13A or with various other embodiments herein.

When programming a CNN, the input is a tensor with shape (number of images)×(image height)×(image width)×(image depth). Then after passing through a convolutional layer, the image becomes abstracted to a feature map, with shape (number of images)×(feature map height)×(feature map width)×(feature map channels). Convolutional layers convolve the input and pass its result to the next layer in a way that is similar to the response of a neuron in the visual cortex to a specific stimulus. Although fully connected feedforward neural networks may be used to learn features as well as classify data, it is impractical and prohibitively expensive to apply this fully-connected feedforward neural network architecture to images.

More specifically, a very high number of neurons may be necessary, even in a shallow (opposite of deep) network architecture, due to the very large input sizes associated with images, where each pixel is a relevant variable. For example, a fully connected layer for a (small) image of size 100 (pixels)×100 (pixels) has 10,000 weights for each neuron in the second layer. The convolution operation brings a solution to address this very problem as convolution reduces the number of free parameters and thus allows the network to be deeper with fewer parameters. For example, regardless of image size, tiling regions of size 5×5, each with the same shared weights, requires only 25 learnable parameters. By using regularized weights over fewer parameters, the vanishing gradient and exploding gradient problems seen during backpropagation in traditional neural networks may be avoided.

Moreover, in a convolutional layer, neurons receive input from only a restricted subarea of the previous layer. Conventionally, the subarea is of a square shape (e.g., size 5 by 5). In some embodiments, the subarea is of a rectangular shape, not a square shape as conventional convolutions. The input area of a neuron may be referred to as the receptive field of the neuron. In a fully connected layer, the receptive field is thus the entire previous layer. In convolutional layers described herein, the receptive area is smaller than the entire previous layer. In a deeper convolutional neural network as described herein in some embodiments, a subarea of the original input image in the receptive field is increasingly growing as getting deeper in the convolutional neural network architecture because of the repeated application of a convolution that takes into account the value of a specific pixel, but also some surrounding pixels.

In some embodiments, it may be impractical to connect neurons to all neurons in the previous volume because such a network architecture does not take the spatial structure of the data into account when dealing with high-dimensional inputs such as images. In these embodiments, convolutional neural networks may exploit spatially local correlation by enforcing a sparse local connectivity pattern between neurons of adjacent layers: each neuron is connected to only a small region of the input volume. The extent of this connectivity corresponds to a hyperparameter (e.g., the receptive field) of the neuron. The connections are local in space (along width and height) and extend along the entire depth of the input volume. Such a convolutional neural network architecture ensures that the learnt filters produce the strongest response to a spatially local input pattern in these embodiments.

A convolution layer's parameters include a set of learnable filters (or kernels), which have a small receptive field, but extend through the full depth of the input volume. During a forward pass, each filter may be convolved across the width and height of the input volume, computing the dot product between the entries of the filter and the input and producing a two-dimensional activation map of that filter in some embodiments. In these embodiments, the convolutional neural network learns the set of learnable filters that activates when it detects some specific type of feature at some spatial position in the input.

Moreover, stacking the activation maps for all filters along the depth dimension forms the full output volume of the convolution layer. Every entry in the output volume may thus also be interpreted as an output of a neuron that looks at a small region in the input and shares parameters with neurons in the same activation map.

In FIG. 13A, neural network 1300A includes a first down-sampling block 1310A, a second down-sampling block 1330A, and a third down-sampling block 1350A, with associated first 1320A, second 1340A, and third 1360A processing blocks (or residual network block). First down-sampling block 1310A receives an input image 1301A. As illustrated, each down-sampling block may be followed by its associated processing (or residual) block. The processing (or residual) block may be single or multi branched as discussed in detail below.

The CNN may comprise a plurality of down-sampling blocks (such as, for example, three as in FIG. 13A), wherein each down-sampling block may comprise a down-sampling convolutional layer (Cony), a batch normalization (norm) layer, and an activation layer comprising a gating function.

FIG. 143 illustrates an example of a down-sampling block 1470B that accepts input 1471B and provides an output 1479B, and that includes a Cony 1474B having kernel size D×D, a batch norm layer 1476B and an activation layer 1478B. The activation layer may be, for example, an FLU (exponential linear unit) layer or a ReLU (rectified linear unit) layer. In various embodiments, the activation layer receives image data directly from the batch norm layer, which receives image data directly from the down-sampling convolutional layer. The down-sampling convolutional layers may function to reduce the spatial resolution of image data that it receives. This will be discussed in more detail with reference to FIGS. 14D-14G.

Processing blocks (or residual network block) may be a single branch processing block or a multi-branch processing block where each branch processes outputs from a preceding down-sampling block, and then combines the output of both branches to produce a down-sampled activation map for further down-sampling, or up-sampling to a final output.

Figure 14D:
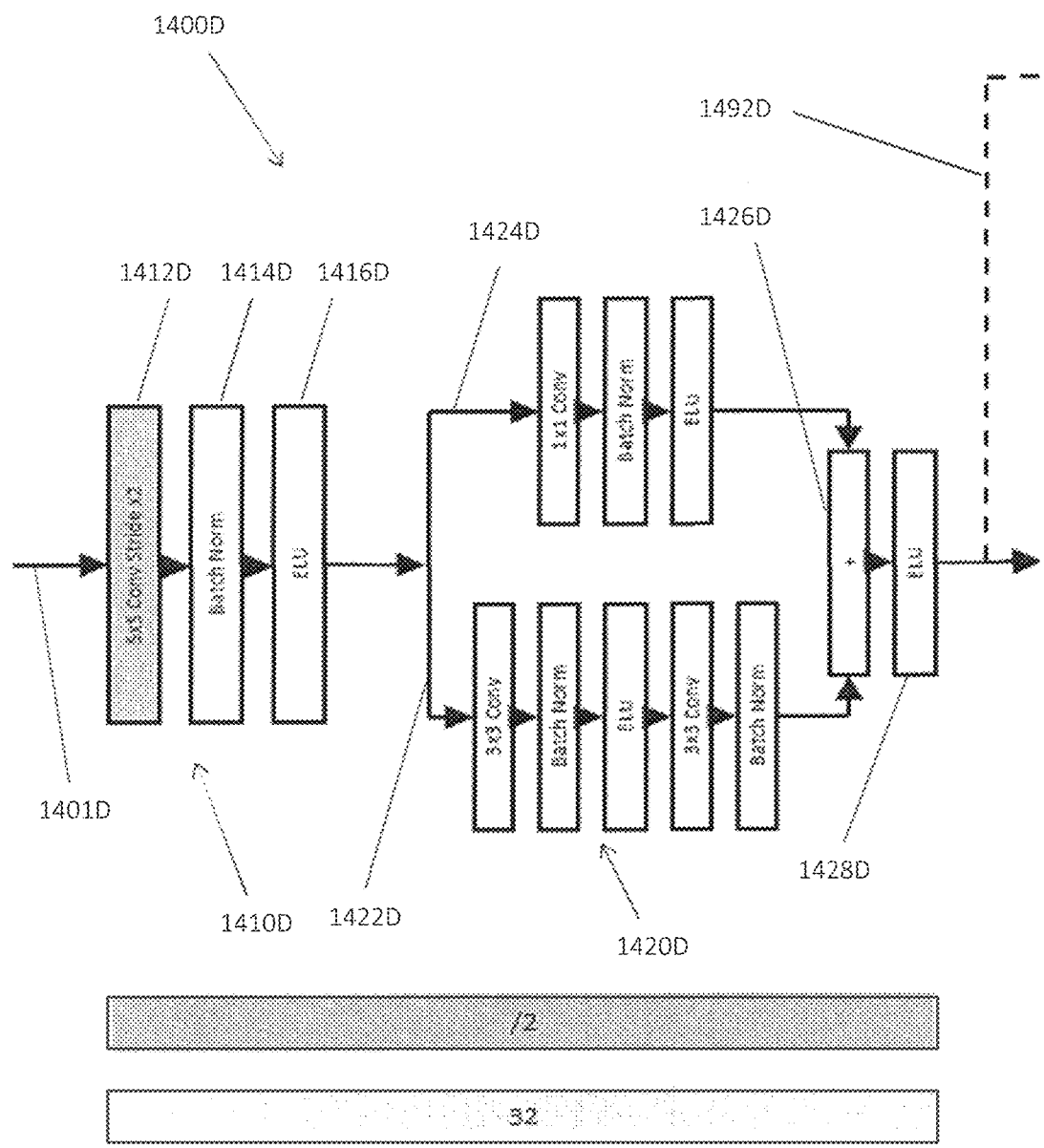
Figure 14E:
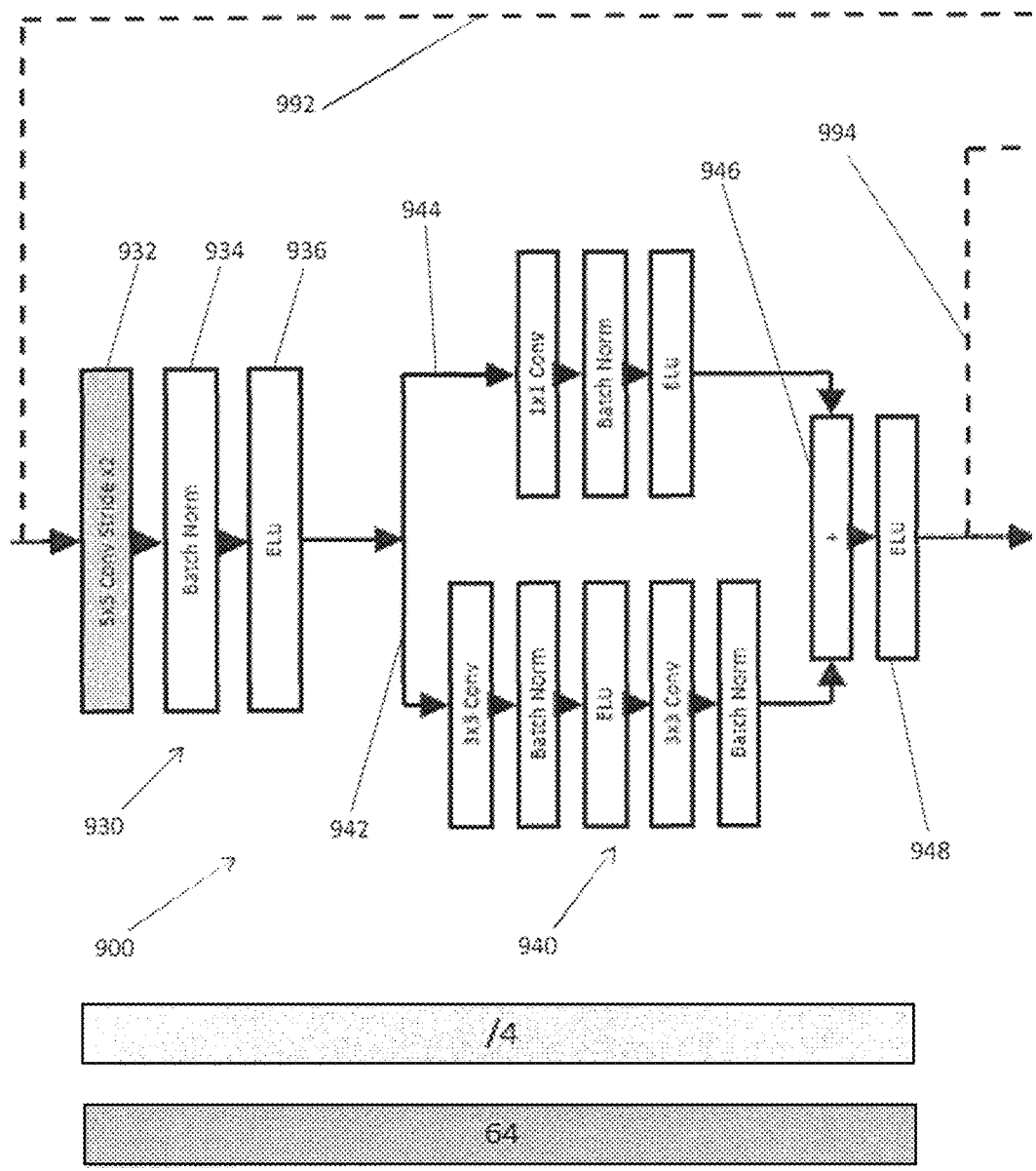
Figure 14F:
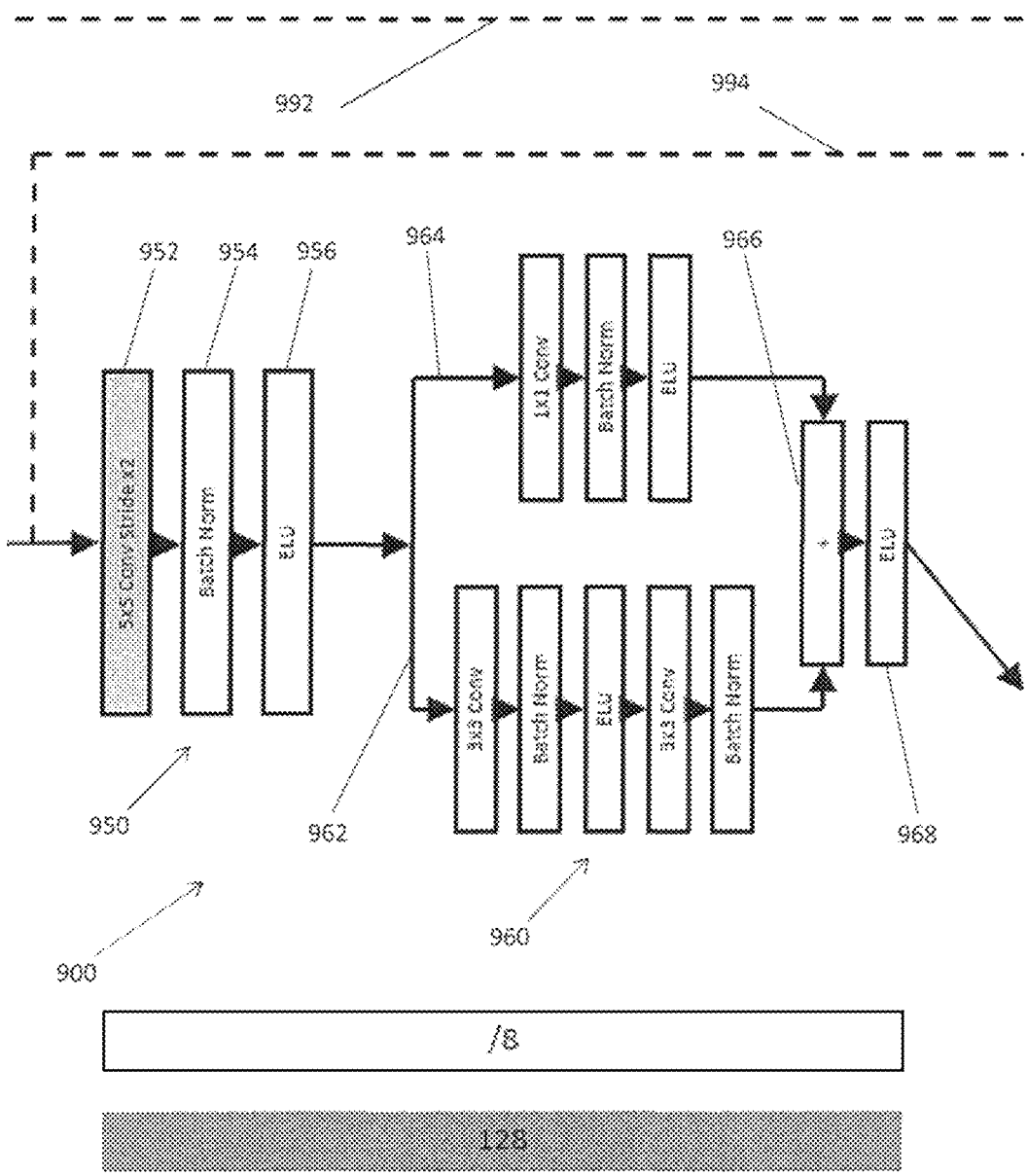

FIG. 14A illustrates an example of a multi-branched processing block 1400A (or residual network block) configured to accept input 1405A (e.g., in the form of an activation map) from an upstream down-sampling block (not pictured, see discussion related to FIG. 19). Block 1400A includes a first branch 1410A and a second branch 1440A. First branch 1410A includes a first convolutional layer 1415A (Cony) having a kernel of N×N, a first batch normalization (norm) layer 1420A that receives data from first Cony 1415A, a first activation layer 1425A (which may include or act as a gating function) that receives data from first batch norm layer 1420a, a second Cony 1430a, having a kernel of M×M, that receives data passing through first activation layer 1425A, and a second batch norm layer 1435A that receives data from second Cony 1430A. Note that the kernels of Cony 1415A (N×N) and 1430A (M×M) may have the same size or may differ. As illustrated in FIG. 14D-14F (discussed below), the kernels from serial Convs (convolutions) in the illustrated residual networks are the same (3×3). Regardless, it is generally preferable for the Convs 1415A/1430A to have a kernel greater than 1×1.

Second branch 1440A includes a third Cony 1445A, a third batch norm layer 1450A that receives data from third Cony 1445A, and a second activation layer 1455A (which may include or act as a gating function) that receives data from third batch norm layer 1450A. Block 1400A further includes a recombination layer 1460A that receives data from both second batch norm layer 1435A and data passing through second activation layer 1455A. Finally, block 1400A includes a block activation layer 1462A that may serve as a gating function, for data received from recombination layer 1460A, before an output 1464A is produced from block 1400A for further processing. As noted above, the activation layer may be, for example, an ELU or a ReLU. In various embodiments, the activation layer(s) is an ELU.

In FIGS. 14A-14C, second branch 1440A processes image data received from a preceding down-sampling block to a lesser extent that first branch 1410A. In particular, the third Cony 1445A of second branch 1440A uses a filter window (or dimensions or kernel) of 1×1, whereas first and second Cony 1415A/1430A of first branch 1410A uses a filter window (or dimensions or kernel) of N×N and M×M respectively, which, as discussed above, will generally be greater than 1×1. These filter windows may be adjusted as needed depending on need, considering factors such as, for example, image type, image quality, object type, object size, object shape, output requirements, time constraints, stride length (discussed below), and power/processing resources. For example, first and second Cony 1415A/1430A could use a filter window (or dimensions) of 3×3 (see FIGS. 14D-14G below illustrating this filter window size).

While both branches in FIGS. 14A-14C have Convs with stride of one, strides may differ as wed. However, to allow for recombination layer 1460A to be effective, the product of multiplying the strides of Convs 1415A/1430A on the first branch 1410A may be equal to the stride of Cony 1445A of second branch 1440A.

The insertion of batch normalization layers before activation steps provides the advantage of helping to minimize internal covariate shift. By inserting batch norm layers as such, and by extension, after a Cony, the batch norm may normalize the output of the Cony, thus providing normalized data to the activation step, allowing for a more stable distribution of activations, By minimizing internal covariate shift during the backpropagation process, training the neural network may be done more aggressively via higher learning rates (extent of weight update), leading to faster CNN learning without the loss of efficiency and accuracy as the CNN works towards optimal parameters for the given filters in the network.

Moreover, addition of residual networks with a branch of minimally processed information (e.g., 1×1 Cony branch), allows for easier learning during training. This minimally processed branch provides a more direct pathway to trace influence of earlier parameters on a final result. In effect, this branch serves much the same purpose as a skip connection (discussed in greater detail below) within a given residual network, allowing some information to pass through the network unchanged so as not to lose spatial info that may be lost during down-sampling.

In summary, therefore, the use of residual networks alone and in combination with batch normalization layers, allows for easier and more efficient learning during training versus neural networks known in the art. This advantage is accomplished by, for example, retaining more spatial info during down-sampling and minimizing internal covariate shift. Minimizing loss of spatial info is also accomplished using striding (discussed in more detail below), which allows for more overlap during down-sampling versus known methods such as pooling, as well as skip connections, which allow for less processed information to be fed forward during the neural network process (within down-sampling steps as discussed above, and forward to up-sampling steps as will be discussed below). A pooling layer reduces the dimensions of the data by combining the outputs of neuron dusters at one layer into a single neuron in the next layer. Local pooling combines small dusters (e.g., 2×2). Global pooling acts on all the neurons of the convolutional layer. pooling may compute a max or an average. Max pooling uses the maximum value from each of a cluster of neurons at the prior layer. Average pooling uses the average value from each of a cluster of neurons at the prior layer. Various embodiments may employ one or more local pooling layers, one or more global pooling layers, one or more average pooling layers, one or more max pooling layers, or any combinations thereof.

By using multi-branch residual networks, particularly with one of the branches using a 1×1 filter window (La, not down-sampled), the neural network is allowed to further convolve the output data from the preceding Cony while maintaining the same resolution to ensure that analysis of every pixel as a single window is combined, at recombination layer 860, with data from the other branch (which may undergo multiple convolutions at a greater kernel or filter size) to output quality image data (not down-sampled from preceding Cony) that is prepared for further down-sampling.

Returning to FIG. 13A, neural network 1300A further includes a first up-sampling block 1370A, a second up-sampling block 1380A, and a third up-sampling block 1390A, with an output 1399A following third up-sampling block 1390A. Each up-sampling block may comprise a transpose convolutional (or deconvolutional) layer, an up-sampling batch norm layer, and an up-sampling activation layer comprising a gating function.

FIG. 14C illustrates an example of an up-sampling block 1480C that accepts input 1481C and provides an output 1489C, and that includes a transpose Cony 1484C having kernel size Z×Z, a batch normalization (batch norm) layer 1486C and an activation layer 1488C. These subcomponents will be discussed in more detail with respect to FIGS. 14D-14G. The transpose convolutional layer of each up-sampling block may be configured to increase the spatial resolution of image data that it receives, and thereby reconstruct the down-sampled output. Additionally, one or more of the up-sampling blocks may also include a recombination layer, whereby image data from the up-sampling batch normalization layer is merged with image data from a preceding residual network block (via skip connection, discussed below).

Regarding architecture of a neural network, the number of up-sampling blocks may be configured to be equal to the number of down-sampling blocks. In various embodiments, the neural network has n down-sampling blocks, n residual network (or processing) blocks, n up-sampling blocks, and n−1 up-sampling blocks that include a recombination layer (see discussion of FIG. 14G). As will be discussed in greater detail below, as spatial resolution is reduced fractionally during the down-sampling process, one may desire to increase spatial resolution at the same fractional rates. For example, if spatial resolution is halved (factor of 2) each time through a down-sampling block (or combined down-sampling and residual network block), it may be most efficient to, in turn, double (factor of 2) the spatial resolution back up to original image dimensions. This may lead to an equal number of down-sampling and up-sampling blocks.

For example, in FIG. 13A, each Cony decreases spatial resolution of image data by a factor of 2 and each transpose Cony increases spatial resolution of image data by a factor of 2. The reduction in spatial resolution may be accomplished, for example, by sliding a convolutional filter (or kernel) two pixels at a time. This two-pixel slide is referred to as the stride length. In the case of sliding two pixels at a time, the stride would be two. By using a stride length of 2, the Cony may down-sample by halving the dimensions of the activation map that is output from the Cony.

However, by striding, and not pooling as taught above, one may avoid loss of spatial information that may be inherent in pooling. A filter size determines how much local information gets pulled in to a single pixel analysis to affect each pixel of the next layer in the network. Generally, the filter size is odd so as to be centered on the pixel of interest. For example, a 5×5 filter will examine the surrounding 24 pixels to analyze the one center pixel of a given area. With pooling, a first area is examined to effectively determine a single value that corresponds to the pixels in that first area. Once the filter moves on to a second area, the pixels in the first area are no longer analyzed during that filter sweep. That may lead to very misleading, coarse, or inaccurate results depending on the type of image analysis conducted (e.g., object type being detected).

On the other hand, using the stride theory, once a first area is examined (a 5×5 area for example), and the two-pixel stride occurs to a second area (also at 5×5), there will clearly by overlap such that pixel points will be looked at more than once and are factored into decisions for multiple pixels, all the while still allowing for down-sampling, since the end result of a two-pixel stride sampling will result in an image output (activation map output) half the size of previous. Therefore, with striding, down-sampling would occur with much less loss of spatial info compared to pooling. Factors for determining appropriate stride length include, for example, image type, image quality, object type, object size, object shape, output requirements, time constraints, and power/processing resources.

As illustrated, if the spatial resolution of input image 1301A is X, down-sampling block 1310A may reduce spatial resolution by half to X/2, then X/4 by down-sampling block 1330A, then X/8 by down-sampling block 1350A. Up-sampling block 1370A may then double the X/8 input to X/4, block 1380A to X/2 and block 1390A to X, or original size at output 1399A. FIG. 13A visually represents this with the decreasing height of each down-sampling block and increasing height of each up-sampling block.

As down-sampling progresses, a CNN may be designed to increase its feature complexity of processing, going from lower level feature analysis to higher level feature analysis. As discussed earlier, to further enable a CNN to detect more complex features, additional Convs may be added to analyze what outputs from the previous Conv (i.e., activation maps). For example, if a first Convs looks for a basic feature such as a curve or an edge, a second Conv may look for a more complex feature such as shapes, which may be a combination of individual features detected in an earlier Conv. By providing a series of Convs, the CNN may detect increasingly higher-level features to eventually arrive at the specific desired object detection. Moreover, as the Convs stack on top of each other, analyzing the previous activation map output, each Conv in the stack is naturally going to analyze a larger and larger receptive field by virtue of the scaling down that occurs at each Conv level, thereby allowing the CNN to respond to a growing region of pixel space in detecting the object of interest.

In FIG. 13A, each Conv and processing block increases channel depth by a factor of 2 and each up-sampling block decreases channel depth by a factor of 2 until the third up-sampling block 1390A. As illustrated, at down-sampling block 1310A and processing block 1320A, 32 channels or filters are used. At down-sampling block 1330A and processing block 1340A, the number of channels is 64. Finally, down-sampling block 1350A and processing block 1360A uses 128 channels. In reverse, up-sampling block 1370A halves the channels back up to 64, up-sampling block 1380A to 32 and up-sampling block 1390A to three (the significance of which will be discussed in more detail below). FIG. 13A visually generally represents this increase and decrease in channel use with the increasing width of each down-sampling block and decreasing width of each up-sampling block (except final block 1390A).

While the rate of change in spatial resolution (original, X/2, X/4, X/8, X/4, X/2, original) is nearly the opposite that of channel depth rate (0, 32, 64, 128, 64, 32, 3, 0), this is not necessary for a CNN architecture. However, the coinciding changes in spatial resolution versus channel number advantageously allow the CNN to maximize time, processing power, and quality of output 1399A by offsetting a sequential increase in filter depth with a sequential decrease in input data (activation map dimension). In effect, as the processing demands on the CNN increase with the depth of filter through each successive down-sampling block, the CNN offsets this by decreasing the image array input (activation map dimension) through each successive down-sampling block to allow the CNN to analyze smaller inputs across greater depth. Correspondingly, the reverse occurs back up the up-sampling blocks to output 1399A.

Reconstruction of an image volume may also be aided by a form of skip architecture. For example, skip connections inserted within a neural network may project information from an earlier down-sampling layer to a later up-sampling layer so that this earlier, minimally processed, information becomes part of the reconstruction process. Without the use of skip architecture, some information that was captured in the initial Conv layers, which may greatly assist in reconstruction during up-sampling, would have been lost during the down-sampling process. In other words, such valuable information would have been down-sampled to the point that it could become too abstract for the information to be used further. Feeding this information from the primary layers to the later up-sampling layers using the skip architecture allows the earlier information to be retained and used for efficient up-sampling.

In various embodiments, the neural network may include a first up-sampling block having a recombination layer that receives image data from a second residual network block (e.g., via a skip connection), a second up-sampling block having a recombination layer that receives image data from a first residual network block (e.g., via a skip connection), and a third up-sampling block that does not include a recombination layer.

In FIG. 13A, for example, a first skip connection 1392A and a second skip connection 1394A are provided. First skip connection 1392A forward feeds output information from processing block 1320A at X/2 resolution to a recombination layer, post-batch norm processing (discussed below), of up-sampling block 1380A, also at X/2 resolution. Via this skip connection, the neural network provides earlier and minimally processed information, at the same resolution as the corresponding up-sampling block, to allow for more accurate and efficient up-sampling. Second skip connection 1394A functions similarly by forward feeding output information from processing block 1340A at X/4 resolution to a recombination layer, for post-batch norm processing (discussed below), of up-sampling block 1370A, also at X/4 resolution.

As noted above, CNN's may be used for many purposes, including image classification and image detection (also object detection within an image). As such, depending on the target of the CNN, the output must answer the main question posed to the CNN. In various embodiments herein, the CNN is used in image detection. In various embodiments, the image detection may be used detection objects of interest. In various embodiments, the objects of interest may be micro-objects. In various embodiments, the image detection may be used for classifying the micro-objects into at least one of a plurality of micro-object types. In various embodiments, the micro-objects are biological cells. In various embodiments, the biological cells are immunological cells such as, for example, T cells, B cells, NK cells, macrophages, or combinations thereof. In various embodiments, the biological cells are cells from a cell line (e.g., CHO cells) or cancer cells. In various embodiments, the biological cells are oocytes, sperm, or embryos.

Regarding the illustrated use of three channels in up-sampling block 1390A of FIG. 13A, in various embodiments, a system utilizing a CNN obtains a micro-object count from an image input. The system may do this by annotating a plurality of pixels of the input image, each pixel annotation of the set representing a probability that a corresponding pixel in the image represents the corresponding micro-object characteristic. From this analysis, a micro-object count may be obtained. In various embodiments, the plurality of micro-object characteristics comprises at least three micro-object characteristics. In various embodiments, the plurality of micro-object characteristics comprises at least a micro-object center, a micro-object edge, and a non-micro-object (or cell center, cell edge, and non-cell). Up-sampling block 1390A of FIG. 13A illustrates this three-micro-object characterization by its three-channel depth. As such, the last up-sampling block 1390A of FIG. 13A provides the object characterization necessary for neural network 1300A to determine an accurate micro-object (e.g., cell) count.

FIGS. 14D-14G illustrate a schematic diagram of a more detailed convolutional neural network (CNN) 1400D in accordance with various embodiments. The schematic diagram incorporates many of the neural network principles discussed above and, for that reason, these principles will not be repeated in detail. Note, however, that while the principles may be similar, the parameters used in the various embodiments herein all may vary based on specific reasons as discussed above, which include, for example, image type, image quality, object type, object size, object shape, output requirements, time constraints, and power/processing resources. As such, the parameters used in the schematic diagram of FIGS. 14D-14G are examples only.

Figure 14G:
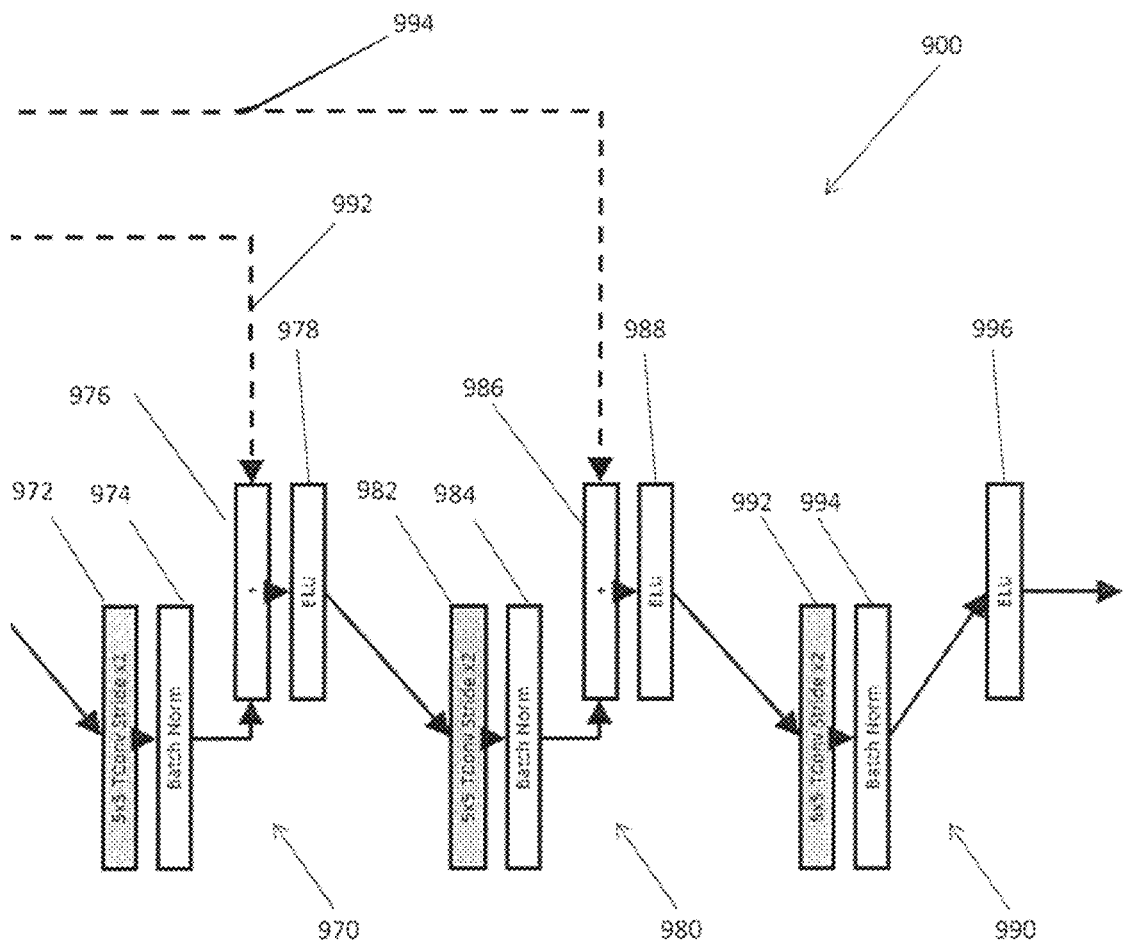

For orientation purposes, FIG. 14D, from left to right, illustrates a first down-sampling block 1410D followed by a first residual network block 1420D, according to various embodiments. FIG. 14E shows, from left to right, a second down-sampling block 1430E which receives data from first residual network block 1420D (of FIG. 14D), followed by a second residual network block 1440E, according to various embodiments. FIG. 14F shows, from left to right, a third down-sampling block 1450F, which receives data from second residual network block 1440E (of FIG. 14E), followed by a third residual network block 1460F, according to various embodiments. FIG. 14G shows, from left to right, a first up-sampling block 1470G, a second up-sampling block 1480G, and a third up-sampling block 1490G. First up-sampling block 1470G receives data from third residual network block 960 (FIG. 14F), and includes a first up-sampling recombination layer 1476G whereby data from a batch normalization layer of first up-sampling block 1470G is recombined with data from a final ELU layer 1448E of second residual network block 1440E fed forward via a second skip connection 1494E. Similarly, second up-sampling block 1480G includes a second up-sampling recombination layer 1486G whereby data from a batch normalization layer of second up-sampling block 1480G is recombined with data from a final ELU layer 1428D of first residual network block 1420D fed forward via a first skip connection 1492D.

Referring back to FIG. 14D, CNN 1400D includes first down-sampling block 1410D that is configured to receive an image input 1401D. First down-sampling block 1410D includes a first Conv 1412D, a first batch norm layer 1414D, and a first activation layer 1416D (e.g., an ELU in FIG. 14D). First Conv 1412D may have differing parameters for kernel size and stride. Here, the kernel is 5×5 and the stride is two pixels. Output from layer 1416D feeds first residual network block 1420D, which includes a first branch 1422D and a second branch 1424D. See FIGS. 14A-14C for a general discussion of layout of residual networks. In first branch 1422A, the two Convs have kernel size of 3×3. FIG. 14D also illustrates the beginning of first skip connection 1492D that feeds forward data that outputs post a first recombination layer 1426D and first ELU 1428D, as discussed above. Note also that the scale down for this stage of CNN 1400D is by a factor of 2 (down-sampled to ½ spatial resolution) and that 32 channels of features are used at this stage.

Referring to FIG. 14E, CNN 1400E further includes second down-sampling block 1430E, which includes a second Conv 1432E, second batch norm layer 1434E and second activation layer 1436E (e.g., an ELU in FIG. 14E). Second down-sampling block 1430E is configured to receive output from first ELU 1428D. Second Conv 1432E may have differing parameters for kernel size and stride. Here, the kernel is again 5×5 and the stride is again two pixels. Output from layer 1436E feeds second residual network block 1440E, which includes a third branch 1442E and a fourth branch 1444E. See FIGS. 14A-14C for a general discussion of layout of residual networks. In the third branch 1442E, the two Convs have kernel size of 3×3. FIG. 14E also illustrates the beginning of second skip connection 1494E that feeds forward data that outputs post a second recombination layer 1496E and second ELU 1448E, as discussed above. Note also that the scale down for this stage of CNN 1400E is by a factor of 2 versus the previous stage of FIG. 14D (down-sampled to ¼ spatial resolution versus original) and that 64 channels of features are used at this stage.

Referring to FIG. 14F, the portion of the CNN 1400F includes third down-sampling block 1450F, which includes a third Conv 1452F, a third batch norm layer 1454F, and a third activation layer 1456F (e.g., an ELU in FIG. 14F). Third down-sampling block 1450F is configured to receive output from second ELU 1448E. Third Conv 1452F may have differing parameters for kernel size and stride. Here, the kernel is again 5×5 and the stride is again two pixels. Output from layer 1456F feeds third residual network block 1460F, which includes a fifth branch 1462F and a sixth branch 1464F. See FIGS. 14A-14C for a general discussion of layout of residual networks. In fifth branch 1462F, the two Convs have kernel size of 3×3. Note also that the scale down for this stage of CNN 1400F is by a factor of 2 (down-sampled to ⅛ spatial resolution) and that 128 channels of features are used at this stage. The outputs of the fifth branch 1462F and the sixth branch 1464F may be combined in a combination layer 1466F before the combined output is transmitted to a linear unit 1468F (e.g., an exponential linear unit, a rectified linear unit (ReLU), etc.)

Referring to FIG. 14G, this portion of the CNN 1400G includes first up-sampling block 1470G, second up-sampling block 1480G, and third up-sampling block 1490G. First up-sampling block 1470G includes a first up-sampling Conv 1472G, a first up-sampling batch norm layer 1474G, first up-sampling recombination layer 1476G and a first up-sampling activation layer 1478G (e.g., ELU). First up-sampling recombination layer 1476G is configured to receive input from first skip connection 1492D, combine that input with the output from first up-sampling batch norm layer 1474G, and feed that combined output to first up-sampling activation layer 1478G. As discussed above with reference to down-sampling Conv 1412D/1432E/1452F, up-sampling Conv layers may have differing parameters for kernel size and stride. Here, the kernel is 5×5 and the stride is two pixels for first up-sampling Conv 1472G. Note also that the scale up for this stage of CNN 1400G is by a factor of 2 versus the output from third residual network 1460F (up-sampled to ¼ spatial resolution) and that 64 channels of features are used at this stage.

Second up-sampling block 1480G includes a second up-sampling Cony 1482G, a second up-sampling batch norm layer 1484G, second up-sampling recombination layer 1486G and a second up-sampling activation layer 1488G (e.g., ELU). Second up-sampling recombination layer 1486G is configured to receive input from second skip connection 1494E, combine that input with the output from second up-sampling batch norm layer 1484G, and feed that combined output to second up-sampling activation layer 1488G. As discussed above with reference to down-sampling Cony 1412D/1432E/1452F, up-sampling Cony layers may have differing parameters for kernel size and stride. Here, the kernel is 5×5 and the stride is two pixels for second up-sampling Cony 1482G. Note also that the scale up for this stage of CNN 1400G is by a factor of 2 versus the output from first up-sampling block 1470G (up-sampled to ½ spatial resolution) and that 32 channels of features are used at this stage.

Third up-sampling block 1490G includes a third up-sampling Cony 1492G, a third up-sampling batch norm layer 1494G, and a third up-sampling activation layer 1496G (e.g., ELU). Layer 1496G produces an output 1499G for CNN 1400G. As discussed above with reference to down-sampling Cony 1412D/1432E/1452F, up-sampling Cony layers may have differing parameters for kernel size and stride. Here, the kernel is 5×5 and the stride is two pixels for third up-sampling Cony 1492G. Note also that the scale up for this stage of CNN 1400G is by a factor of 2 versus the output from second up-sampling block 1480G (up-sampled to original spatial resolution) and that three channels of features are used at this stage.

As discussed above in relation to FIG. 13A, in various embodiments, a system utilizing a CNN obtains a micro-object count from an image input. The system may do this by annotating a plurality of pixels of the input image, each pixel annotation of the set representing a probability that a corresponding pixel in the image represents the corresponding micro-object characteristic. From this analysis, a micro-object count may be obtained, hi various embodiments, the plurality of micro-object characteristics comprises at least three micro-object characteristics. In various embodiments, the plurality of micro-object characteristics comprises at least a micro-object center, a micro-object edge, and a non-micro-object (or cell center, cell edge, and non-cell). Up-sampling block 1490G of FIG. 14G illustrates this three-micro-object characterization by its three-channel depth. As such, the last up-sampling block 1490G of FIG. 14G provides the object characterization necessary for neural network 1400G to determine an accurate micro-object (e.g., cell) count.

In accordance with various embodiments, systems and methods for automatically detecting micro-objects in an image are disclosed. In various embodiments, the micro-objects are biological cells. In various embodiments, the biological cells are immunological cells such as, for example, T cells, B cells, NK cells, macrophages, or combinations thereof. In various embodiments, the biological cells are cells from a cell line (e.g., CHO cells) or cancer cells. In various embodiments, the biological cells are oocytes, sperm, or embryos.

FIG. 15 illustrates a simplified example flow chart of a method for automatically detecting micro-objects in an image in accordance with one or more embodiments. More specifically, FIG. 15 is an example flow chart illustrating a method for automatically detecting micro-objects in an image, in accordance with various embodiments. The example flow chart may be carried out on, for example, a system 1600 of FIG. 16, as will be described in detail below. As depicted herein, step 1510, which may be carried out by imaging element 1606 of image acquisition unit 1602 of system 1600, includes receiving imaging data of a microfluidic device.

As depicted herein, step 1520 details an example workflow step that may be implemented by image pre-processing engine 1608 of image acquisition unit 1602 of system 1600. At step 1520, the method includes pre-processing the image data to reduce anomalies in the image data.

As depicted herein, step 1530 details an example workflow step that may be implemented by neural network 1610 of micro-object detection unit 1604 of system 1600. At step 1530, the method processes pixel data in the imaging data using a neural network to annotate the pixel data according to a plurality of micro-object characteristics and output probability values for each pixel in the pixel data. The output probability values may be in the form of a plurality of pixel masks, each mask corresponding to a micro-object characteristic from a plurality of micro-object characteristics. Each mask may comprise a set of pixel annotations (or set of probability values) for the image in relation to the specific micro-object characteristic associated with that mask.

As depicted herein, steps 1540-1550 detail some example workflow steps that may be implemented by threshold engine 1612 of micro-object detection unit 1604 of system 1600. At step 1540, the method includes applying a threshold to determine which pixel probabilities at least meet a defined threshold.

As depicted herein, step 1540 details an example workflow step that may be implemented by detection engine 1614 of micro-object detection unit 1604 of system 1600. At step 1550, the method includes determining a micro-object count based on number of micro-objects identifiable after threshold application.

FIG. 16 illustrates a simplified example system for automatically detecting micro-objects in an image in accordance with one or more embodiments. More specifically, FIG. 16 illustrates an example schematic diagram of a system for automatically detecting micro-objects in an image, in accordance with various embodiments. As depicted herein, the system 1600 may include an image acquisition unit 1602, an image pre-processing engine 1608, a micro-object detection unit 1604, and an input/output device (I/O device) 1616 for outputting a final micro-object.

I/O device 1616 may be configured to include, for example, an associated display device and/or input device 512O of the system illustrated in, for example, FIG. 5O, which may be in the form of data (for example, parameters, user requirements, etc.) that may be transferred to, for example, image acquisition unit 1602, image pre-processing engine 1608, micro-object detection unit 1604, or combinations thereof. I/O device 1616 may also be configured to receive user input via an associated display device and/or input device 512O of the system illustrated in, for example, FIG. 5O, which may be in the form of data (for example, parameters, user requirements, etc.) that may be transferred to, for example, image acquisition unit 1602, image pre-processing engine 1608, micro-object detection unit 1604, or combinations thereof. Alternatively, or in combination, input device 512O of the computer system (e.g., FIG. 5O) may also be used to directly transfer user input, parameters, and/or the like, to; for example, image acquisition unit 1602, image pre-processing engine 1608, micro-object detection unit 1604, or combinations thereof. Moreover, I/O device 1616 may be configured to display data or images received from, for example, detection engine 1614, on an embedded display device. Device 1616 may also be configured to transfer data or images to a separate display for data or image display.

Image acquisition unit 1602 may include an imaging element 1606 (such as, but not limited to, one or more cameras, one or more image sensors, etc.). Alternatively, unit 1602 may also be configured to include (or house) image pre-processing engine 1608.

Imaging element 1606 may be configured to capture one or more images (or image data). The images may be of, for example, the plurality of chambers (e.g., sequestration pens) and/or surrounding structures (e.g., channels) of a microfluidic device. The microfluidic device may include any of the various examples described herein (such as, but not limited to, microfluidic device 100, 200, 230, etc. depicted in FIGS. 3A-3E above). The microfluidic device may include a flow region and a chamber, or plurality of chambers, which may be fluidically connected to the flow region, wherein each of the chambers may hold one or more micro-objects. As previously noted, the chambers may be, for example, sequestration pens. It should be appreciated that the chambers may be of on any shape, size or orientation as required by the particular application that they are used for. The flow region may be a single microfluidic channel, or a plurality of microfluidic flow channels (such as, but not limited to, channel 122A as depicted in FIG. 3A, and flow channels 264 as depicted in FIG. 3G above), which provide a single flow path or a plurality of flow paths (such as, but not limited to, flow path 106A depicted in FIG. 3A above). The flow region may be in fluid communication with a single, or a plurality of chambers. Alternatively, the flow region may be in fluid communication with the single chamber, or a plurality of chambers, via a reversible closure such as, for example, a valve. The flow region may be configured to receive a flow of material via an inlet as previously described. The flow of material may include, for example, a flow of micro-objects, binding agent or reagents, or a flow of medium including the material.

In various embodiments, imaging element 1606 may also be configured to resize the captured image prior to sending forward for further processing. Resizing may be accomplished, for example, by binning (e.g., four pixels to one). Image pre-processing engine 1608 may be configured to prepare an image for further analysis in accordance with various embodiments. For example, if the capture image was binned prior to being received by engine 1608, engine 1608 may resize the image to full size to compensate for binning. Engine 1608 may resize using, for example, linear interpolation between pixel values. Engine 1608 may flip and/or rotate the image as necessary to a desired orientation. Engine 1608 may apply a distortion correction step to the image using, for example, a lookup table computed by examining a dot array having known spacings between the dots.

In various embodiments, engine 1608 may execute a level brightness procedure across the image. For example, engine 1608 may use a polynomial best-fit correction, such as a quadratic or higher order polynomial best-fit correction. Optionally, a sine wave or exponential function could be used in lieu of polynomial function. Leveling may be achieved by multiplying the image brightness by a scaling image, with the desired multipliers of the best-fit function being determined during system calibration. Engine 1608 may also execute a radiometric correction, to subtract background brightness stemming from, for example, auto-fluorescence.

In various embodiments, the image pre-processing engine 1608 may be configured to obtain a field of view image comprising a plurality of features of the microfluidic device (e.g., channel(s), pens(s), traps(s), frames, flow regions, phototransistor arrays, etc.), wherein the image pre-processing engine 1608 may crop a field of view image into at least two cropped images. The image pre-processing engine may be configured to crop the image. Cropping may be performed according to information obtained from a calibrated image. In some instances, calibration of an image may comprises identifying one or more features of a microfluidic device and establishing those features as a benchmark or baseline from which images may be referenced. Cropping may also be performed based on any of the methods disclosed herein to identify features of each field of view image. Cropped images may be generated based on one or more features of the microfluidic device (e.g., channel(s), chamber(s) pen(s), trap(s), micro-object(s) position, brightness, etc.). In some embodiments the pre-processing engine may perform cropping on a single field of view at a time. In alternate embodiments the pre-processing engine may perform cropping on multiple fields of view in parallel.

The image pre-processing engine 1608 may be configured to crop one or more field of view images into cropped images with features or characteristics. For example, a pre-processing engine 1608 may receive a field of view image comprising multiple chambers, pens, traps, or micro-objects. The image pre-processing engine 1608 may receive a field of view image and then convert the field of view image into a series of cropped images. In some instances, the image pre-processing engine 1608 may be configured to crop a field of view image into a plurality of cropped images, wherein each cropped image comprises a single feature (e.g., a single chamber, pen, trap, or micro-object of said plurality of chambers, pens, traps, or micro-objects), In further instances, the pre-processing engine may generate a plurality of cropped images, wherein at least one of said plurality of cropped images comprises a micro-object.

Cropped images generated by the pre-processing engine may have different pixel size. Pixel size may be calculated by multiplying the number of pixels in the image width by the number of pixels in the image height. Differences in pixel size of cropped images may result from the cropping process performed by the pre-processing engine. In additional or alternative embodiments, differences in pixel size of cropped images may result from differences resulting from the field of view—for example, differences in the magnification of the field of view, and/or field of views images taken with different regions of interest (e.g., with regions of interest according to features of the microfluidic device that differ between a first field of view and a second field of view).

In various embodiments, cropped images of different pixel size may be input into a neural network for example a convoluted neural network (CNN). As mentioned previously, CNN architecture may generally consist of a group of processing blocks, including at least one processing block for convoluting an input volume (image). In embodiments applied to micro-object counting, the CNN may omit any previously disclosed steps for deconvolution (or transpose convolution). Neural networks for performing micro-object counting without deconvolution on the devices and systems disclosed herein. One of the challenges of the systems disclosed herein is that cropping of images is done to isolate regions from a field of view before counting is to be performed. The cropping of the images may yield images of different size, so the CNN needs to be able to accommodate cropped images of different size.

The CNN may take an input image, which may comprise a field of view image and/or cropped segments of the field of view image. The input image may be in color or it may be black/white. In some instances, the input image may have a plurality of repeating features, including but not limited to transistor array grids, pens, wells, channels, walls, chambers, etc. The image may comprise features of texture, shading, differences in focus and differences in magnifications.

FIG. 17 illustrates example processes for performing global average pooling, and example regions of a microfluidic device for which counts may be determined by any one of the methods disclosed herein. FIG. 18 illustrates some example regions of a microfluidic device for which counts may be determined by any one of the processes disclosed herein. These two FIGS. 17-18 will be described together.

More specifically, automated detection and/or counting of a micro-object of interest. In one aspect, methods are provided for the automated detection of a micro-object of interest in an image, particularly a digital image (or an image that has been digitized). The micro-object of interest may be disposed within a microfluidic device. The micro-object of interest may be a cell, such as a mammalian cell (e.g., a blood cell, a hybridoma, a cancer cell, a transformed cell, a gamete, an embryo, or the like). Alternatively, the micro-object of interest may be a bead, such as might be used in an assay (e.g., a microbead, a magnetic bead, or the like). The methods may involve the use of a machine learning algorithm to process image data (i.e., data relating to pixels in the image). The machine learning algorithm may include a neural network, such as a convolutional neural network.

Image classification requires accepting an input image and outputting a class or a probability of classes that best describes the image. This may be done using a computer system equipped with a processing engine, which utilizes algorithms, to process the input image and output a result. Image detection may also utilize a similar processing engine, whereby the system accepts an input image and identifies objects of interest within that image with a high level of accuracy using the algorithms pre-programmed into the processing engine.

Regarding the input image, the system will generally orient the input image as an array of pixel values. These pixel values, depending on the image resolution and size, will be an array of numbers corresponding to (length)× (width)×(# of channels). The number of channels may also be referred to as the depth. For example, the array could be L×W×Red Green Blue color model (RGB values). The RGB would be considered three channels, each channel representing one of the three colors in the RGB color model. For example, the system may generally characterize a 20×20 image with a representative array of 20×20×3 (for RGB), with each point in the array assigned a value (e.g., 0 to 255) representing pixel intensity. Given this array of values, the processing engine may process these values, using its algorithms, to output the number of micro-objects that are in the image. In alternate embodiments, images may be depicted based on intensity without consideration for pixel color. For example, instead of 20×20×3 with 3 representing RGB, the array may be represented as 20×30×1 with the value of 1 representing brightness (e.g., black or white). The use of RGB or black/white brightness may be interpreted as interchangeable concepts throughout this application and may be selected based on preference or clear objective performance metrics. Examples of performance metrics that may impact whether RGB or black/white methods are incorporated into the analysis may comprise: computational intensity, image configuration during other aspects of the method (e.g., during the assay being performed), and/or the amount of time it takes to perform an analysis.

Counting of a micro-object of interest may comprise obtaining an image (e.g., cropped image, field of view image, etc.) of said micro-object disposed in a microfluidic device (e.g., in a channel, well, chamber, sub-region of any of the aforementioned, flow region, isolation region, connection region, etc.) for performing a cell count may comprise receiving an image or a portion of an image (e.g., 1305 of FIGS. 17-18), and performing a series of operations on said image to compute a number that represents the amount of cells 1308 in a particular region of a microfluidic device—for example, in the representation depicted in FIGS. 17-18, the number of cells may be computed according to the methods disclosed herein to generate a number corresponding to the cells 1308 in the areas of a particular defined area (1355) of the microfluidic device—in this case pen number "957" and pen number "958" of the illustrated device in FIG. 17 and pen number 820 through pen number 824 of FIG. 18. In some embodiments, although the example illustrated in 1312 of FIG. 17 shows thirty-one (31) cells in chamber 957 and one (1) cell in chamber 958, the method may be configured to perform counting on hundreds, thousands, or tens of thousands of defined regions (e.g., channel, pen, chamber, well, etc.) of the micro-fluidic device, for example a microfluidic device that may comprise a plurality of defined regions (e.g., thousands of pens, wells, channels, etc.)

The number or count for each defined region of the microfluidic device may be displayed on a GUI, integrated into additional computations for further data analysis, and/or shown in a table according to one or more features of the image or microfluidic device from which it was derived. In further instances, the count obtained for the micro-object may be integrated into a workflow, wherein the count is taken at discrete time points in a method for performing an analysis on the micro-object.

A convolutional neural network (CNN) generally accomplishes an advanced form of image processing and classification/detection by first looking for low level features such as, for example, edges and curves, and then advancing to more abstract (e.g., unique to the type of images being classified) concepts through a series of convolutional layers. A CNN may do this by passing an image through a series of convolutional, nonlinear, pooling (or down-sampling, as will be discussed in more detail below), and fully connected layers, and get an output. Again, the output may be a single class or a probability of classes that best describes the image or detects objects on the image.

Regarding layers in a CNN, the first layer is generally a convolutional layer (Cony). This first layer will process the image's representative array using a series of parameters. Rather than processing the image as a whole, a CNN will analyze a collection of image sub-sets using a filter (or neuron or kernel). The sub-sets will include a focal point in the array as well as surrounding points. For example, a filter may examine a series of 5×5 areas (or regions) in a 32×32 image. These regions may be referred to as receptive fields. Since the filter generally will possess the same depth as the input, an image with dimensions of 32×32×3 would have a filter of the same depth (e.g., 5×5×3). The actual step of convolving, using the example dimensions above, would involve sliding the filter along the input image, multiplying filter values with the original pixel values of the image to compute element wise multiplications, and summing these values to arrive at a single number for that examined region of the image.

After completion of this convolving step, using a 5×5×3 filter, an activation map (or filter map) having dimensions of 28×28×1 will result. For each additional layer used, spatial dimensions are better preserved such that using two filters will result in an activation map of 28×28×2. Each filter will generally have a unique feature it represents (e.g., colors, edges, and/or curves, etc.) that, together, represent the feature identifiers required for the final image output. These filters, when used in combination, allow the CNN to process an image input to detect those features present at each pixel. Therefore, if a filter serves as a curve detector, the convolving of the filter along the image input will produce an array of numbers in the activation map that correspond to high likelihood of a curve (high summed element wise multiplications), low likelihood of a curve (low summed element wise multiplications) or a zero value where the input volume at certain points provided nothing that would activate the curve detector filter. As such, the greater number of filters (also referred to as channels) in the Cony, the more depth (or data) that is provided on the activation map, and therefore more information about the input that will lead to a more accurate output.

Balanced with accuracy of the CNN is the processing time and power needed to produce a result. In other words, the more filters (or channels) used, the more time and processing power needed to execute the Cony. Therefore, the choice and number of filters (or channels) to meet the needs of the CNN method should be specifically chosen to produce as accurate an output as possible while considering the time and power available.

To further enable a CNN to detect more complex features, additional Convs may be added to analyze what outputs from the previous Cony (i.e., activation maps). For example, if a first Cony looks for a basic feature such as a curve or an edge, a second Cony may look for a more complex feature such as shapes, which may be a combination of individual features detected in an earlier Cony layer. By providing a series of Convs, the CNN may detect increasingly higher-level features to eventually arrive at a probability of detecting the specific desired object. Moreover, as the Convs stack on top of each other, analyzing the previous activation map output, each Cony in the stack is naturally going to analyze a larger and larger receptive field by virtue of the scaling down that occurs at each Cony level, thereby allowing the CNN to respond to a growing region of pixel space in detecting the object of interest.

A CNN architecture generally consists of a group of processing blocks, including at least one processing block for convoluting an input volume (e.g., image) and at least one for deconvolution (or transpose convolution). Additionally, the processing blocks may include at least one pooling block and un-pooling block. Pooling blocks may be used to scale down an image in resolution to produce an output available for Cony. This may provide computational efficiency (efficient time and power), which may in turn improve actual performance of the CNN. Those pooling, or subsampling, blocks keep filters small and computational requirements reasonable, these blocks may coarsen the output (may result in lost spatial information within a receptive field), reducing it from the size of the input by a specific factor.

Un-pooling blocks may be used to reconstruct these coarse outputs to produce an output volume with the same dimensions as the input volume. An un-pooling block may be considered a reverse operation of a convoluting block to return an activation output to the original input volume dimension. However, the un-pooling process generally just simply enlarges the coarse outputs into a sparse activation map. To avoid this result, the deconvolution block densifies this sparse activation map to produce both and enlarged and dense activation map that eventually, after any further necessary processing, a final output volume with size and density much closer to the input volume. As a reverse operation of the convolution block, rather than reducing multiple array points in the receptive field to a single number, the deconvolution block associates a single activation output point with one or more outputs to enlarge and densify the resulting activation output.

It should be noted that while pooling blocks may be used to scale down an image and un-pooling blocks may be used to enlarge these scaled down activation maps, convolution and deconvolution blocks may be structured to both convolve/deconvolve and scale down/enlarge without the need for separate pooling and un-pooling blocks. The pooling and un-pooling process may have drawbacks depending on the objects of interest being detected in an image input. Since pooling generally scales down an image by looking at sub-image windows without overlap of windows, there is a clear loss of spatial info as scale down occurs.

In some embodiments methods for pooling may comprise integrating a global average pooling layer, as illustrated in FIG. 17. In a global average pooling layer, the input may comprise a set of images (e.g., N images, 1320). A global average pooling layer may compute averages of every image (1322) and pool the averages to generate a 1-dimensional vector of size M (1324) comprising the average of each input image (1322). Additionally, or alternatively, pooling methods may comprise global max pooling and/or global average pooling. Global pooling comprises pooling performed across the full image or tensor. Global pooling methods differ from down sampling pooling methods. In down sampling pooling (e.g., max pooling or mean pooling) may be used across parts of an image. Down sampling may be useful after a convolution layer has processed the tensor in preparation for additional convolutional layers. Global pooling methods, in the disclosed embodiments for micro-object counting may comprise methods for compiling tensors resulting from convolutional layers to prepare data derived from cropped or field of view images of different sizes so that they may be further analyzed by fully connected layers and corresponding activation layers—without this improvement, the data derived from the systems and methods disclosed herein could not be processed by the disclosed fully connected layers and could not yield a positive integer correlated with the micro-object count.

A processing block may include other layers that are packaged with a convolutional or deconvolutional layer. These may include, for example, a rectified linear unit layer (ReLU) or exponential linear unit layer (ELU), which are activation functions that examine the output from a Cony in its processing block. The ReLU or ELU layer acts as a gating function to advance only those values corresponding to positive detection of the feature of interest unique to the Cony.

Given a basic architecture, the CNN is then prepared for a training process to hone its accuracy in image classification/detection (of objects of interest). This involves a process called backpropagation (backprop), which uses training data sets, or sample images used to train the CNN so that it updates its parameters in reaching an optimal, or threshold, accuracy. Backpropagation involves a series of repeated steps (training iterations) that, depending on the parameters of the backprop, will either slowly or quickly train the CNN. Backprop steps generally include a forward pass, loss function, backward pass, and parameter (weight) update according to a given learning rate. The forward pass involves passing a training image through the CNN. The loss function is a measure of error in the output. The backward pass determines the contributing factors to the loss function. The weight update involves updating the parameters of the filters to move the CNN towards optimal. The learning rate determines the extent of weight update per iteration to arrive at optimal. If the learning rate is too low, the training may take too long and involve too much processing capacity. If the learning rate is too fast, each weight update may be too large to allow for precise achievement of a given optimum or threshold.

The backprop process may cause complications in training, thus leading to the need for lower learning rates and more specific and carefully determined initial parameters upon start of training. One such complication is that, as weight updates occur at the conclusion of each iteration, the changes to the parameters of the Convs amplify the deeper the network goes. For example, if a CNN has a plurality of Convs that, as discussed above, allows for higher level feature analysis, the parameter update to the first Conv is multiplied at each subsequent Conv. The net effect is that the smallest changes to parameters may have large impact depending on the depth of a given CNN. This phenomenon is referred to as internal covariate shift.

The embodiments disclosed herein have several advantages versus known CNNs. These advantages include, for example, providing a CNN that avoids the lost spatial information inherent in pooling layers, reduces/minimizes the internal covariate shift inherent in the backprop process, and reduces the processing time and speed generally needed in deep neural networks to achieve more complex feature detection.

As described above, CNNs include multiple layers of receptive fields. These are "neuron" (or kernel) collections which process portions of the input image. The outputs of these collections are then tiled so that their input regions overlap, to obtain a better representation of the original image; this is repeated for every such layer. Tiling allows CNNs to tolerate translation of the input image. CNNs have been described, for example, in Long et al., "Fully Convolutional Networks for Semantic Segmentation," CVPR 2015, and Noh et al., "Learning Deconvolution Network for Semantic Segmentation," ICCV 2015, the contents of each of which are incorporated herein by reference.

A CNN may comprise combinations of convolutional and fully connected layers, with pointwise nonlinearity applied at the end of or after each layer. Convolution operation on small regions of input is introduced to reduce the number of free parameters and improve generalization. One major advantage of convolutional networks is the use of shared weight in convolutional layers, which means that the same filter (weights bank) is used for each pixel in the layer; this both reduces memory footprint and improves performance. In one embodiment, the CNN is formed by a stack of distinct layers that transform the input volume into an output volume (e.g., holding the class scores) through a differentiable function.

In this embodiment, the convolutional layers are defined for this embodiment as empty, monoclonal, and polyclonal. The layer's parameters may include a set of learnable filters, which have a small receptive field, but extend through the full depth of the input volume. During the forward pass, each filter is convolved across the width and height of the input volume; computing the dot product between the entries of the filter and the input and producing a 2-dimensional activation map of that filter. As a result, the network learns filters that activate when they see some specific type of feature at some spatial position in the input.

Stacking the activation maps for all filters along the depth dimension forms the full output volume of the convolution layer. Every entry in the output volume may thus also be interpreted as an output of a neuron that looks at a small region in the input and shares parameters with neurons in the same activation map. In one embodiment, the spatial arrangement is based on hyperparameters that control the size of the output volume of the convolutional layer: such as, the depth, stride, and zero-padding.

In one embodiment, the depth of the output volume controls the number of neurons in the layer that connect to the same region of the input volume. All of these neurons will learn to activate for different features in the input. For example, if the first convolutional layer takes the raw image as input, then different neurons along the depth dimension may activate in the presence of various oriented edges, or blobs of color.

In one embodiment, stride controls how depth columns around the spatial dimensions (width and height) are allocated. When the stride is 1, a new depth column of neurons is allocated to spatial positions only 1 spatial unit apart. This leads to heavily overlapping receptive fields between the columns, and also to large output volumes. Conversely, if higher strides are used then the receptive fields will overlap less and the resulting output volume will have smaller dimensions spatially. In some embodiments, it may be convenient to pad the input with zeros on the border of the input volume. The size of this zero-padding is a third hyperparameter. Zero padding provides control of the output volume spatial size. In particular, sometimes it is desirable to exactly preserve the spatial size of the input volume.

In this embodiment, parameter sharing scheme is used in convolutional layers to control the number of free parameters. It relies on one reasonable assumption: That if one patch feature is useful to compute at some spatial position, then it should also be useful to compute at a different position. In other words, denoting a single 2-dimensional slice of depth as a depth slice, we constrain the neurons in each depth slice to use the same weights and bias. Because all neurons in a single depth slice are sharing the same parametrization, then the forward pass in each depth slice of the CONV layer may be computed as a convolution of the neuron's weights with the input volume (hence the name: convolutional layer) in some embodiments. In these embodiments, it may be permissible to refer to the sets of weights as a filter which is convolved with the input. The result of this convolution is an activation map, and the set of activation maps for each different filter are stacked together along the depth dimension to produce the output volume. Parameter Sharing contributes to the translation invariance of the CNN architecture.

FIG. 19 illustrates a schematic diagram of a neural network in accordance with one or more embodiments. More specifically, In FIG. 19, neural network 1900, takes an input image 1905 that comprise a pixel size. The neural network includes a first processing block 1910, a first down-sampling block 1915, a second processing block 1920, a second down-sampling block 1925, and a final processing block 1930. The first processing block 1910 may receive the image. Example numbers of filters have been shown in the figures (e.g., the first processing block 1910 and the first down-sampling block 1915 have a filter size of 64, the second processing block 1920 and the second down-sampling block 1925 have a filter size (or depth) of 128, and the final processing block has a filter size (or depth) of 256).

In some embodiments, padding may be performed before the convolution processing block. In this embodiment, each processing block, with the exception of the final processing block, is followed by a down sampling block; however, alternative embodiments may have a processing block without a down sampling block. Other alternative embodiments may use different numbers of processing blocks, different down sampling blocks functions (average pooling for example). Furthermore, FIG. 19 illustrates two sets of processing blocks and down sampling blocks, however a single processing block, two or more processing blocks, or a plurality of processing blocks may be incorporated into the neural net. Additionally, or alternatively, FIG. 19 illustrates two down sampling blocks, however a single down sampling block, two or more down sampling blocks, or a plurality of down sampling blocks may be incorporated into the neural net.

Also shown in FIG. 19, the convoluted data resulting from the final processing block 1930 is averaged 1935 to produce a matrix of size (1, number of filters of the last processing block) and then fed into a fully connected layer 1940 yielding a fully connected layer which yields a matrix of size [1, number of units of the fully connected layer]. The matrix of size [1, number of units of the fully connected layer] may be fed into a first activation layer 1945. The first activation layer may be, for example, an ELU or ReLU.

In various embodiments, the first activation layer receives image data and performs a regression analysis on the matrix of size [1, the number of units of the fully connected layer]. The result of the first activation layer may then be fed to a second fully connected layer 1950 to yield a matrix of size [1, the number of units of the fully connected layer], which may be fed to a second activation layer (ELU, ReLU, or other model) to perform regression. In instances where the regression model is an ReLU the regression has 1 unit and results in only positive numbers. The resulting positive numbers may comprise the linear output or count 1960 for the micro-objects in the input image 1905. In other embodiments, the number of units of each fully connected layer as well as the activation functions of the fully connected layer may be changed.

FIG. 20 illustrates a schematic diagram of a processing block in accordance with one or more embodiments. More specifically, FIG. 20 represents an example illustration of a processing block 2002, for example the processing blocks disclosed in FIG. 19. In this processing block example, an input tensor 2005 (e.g., a greater than or equal to 3-dimensional matrix of defined [height, width, filter size]) is fed into a first pair of convolution and activation layers (2010, 2015), and then into a second pair of convolution and activation layers (2020, 2025). Unlike conventional convolutional square layers. The two convolution layers are [M×N] in this model, and the output of the processing layer is an output tensor 2030 that may be fed into subsequent layers of the neural network (e.g., as shown in FIG. 19).

FIG. 21 illustrates a schematic diagram of a final processing block in accordance with one or more embodiments. More specifically, FIG. 21 represents an example illustration of the final processing block. A final processing block may in some instances, not be followed by a down sampling block, as shown in FIG. 19. In other instances, a final processing block may have a different number of convolution layers, the size of the convolution kernels could be changed or the activation functions of the convolution layer could be modified. In this processing block example, an input tensor 2105 (e.g., a greater than or equal to 3-dimensional matrix of defined [height, width, filter size]) is fed into a first pair of convolution and activation layers (2110, 2115), and then into a second pair of convolution and activation layers (2120, 2125). The two convolution layers are [M×N] in this model, and make up a processing block 2102, however following the processing block is another third pair of convolution and activation layers (2130, 2135) which receive an input tensor and generate the output tensor 2140. The output of the processing layer is an output tensor 2140 that may be fed into subsequent layers of the neural network (e.g., as shown in FIG. 19).

Output tensors may be averaged using an averaging function, including for example a layer that performs global average pooling. Global average pooling is necessary to overcome the technical challenges of applying a convoluted neural network as disclosed herein, to images (e.g., cropped images or field of view images, that differ in pixel size), and more specifically to the challenges of processing the varied pixel size data using fully connected layers. For example, the output tensor of any of the disclosed processing layers comprising convolutional layers (e.g., FIG. 19 or FIG. 20) may be averaged as disclosed herein. In other embodiments, one could use other global pooling functions such as global max pooling.

The output tensor (2140) of a final processing block, for example the final processing block illustrated in FIG. 21, may be fed into an averaging filter, for example the global average pooling filter. Additionally, or alternatively some other means of averaging as shown in the averaging layer of FIG. 19 (1935) may be used to average a final processing block. In instances where Global Average Pooling is applied, the result is a matrix of size [1, N] where N is the number of filters in the last processing block. For example, in the specific embodiment illustrated in FIG. 19, the [1×N] matrix is fed into the fully connected block (1940) which produces for example a [1, 256] matrix where the fully connected layer has 256 units, which is then fed into subsequent fully connected layer (1950) which produces another [1, N] matrix which may be a [1,256] matrix where the fully connected layer has 256 units. The resulting [1, N] matrix, or [1, 256] matrix in this example may be input into a final fully connected (linear output or count, 1960) layer, which compresses the [1×N] or this example [1, 256] matrix to regression output of [1] comprising a single integer. Although only two fully connected layers are illustrated in FIG. 19, there may be a single fully connected layer, two or more fully connected layers, or a plurality of fully connected layers. The illustration of FIG. 14 is not meant to indicate a limitation on the number of fully connected or activation layers that may be used to generate the linear output.

In various embodiments, sometimes fluorescent images are needed to visualize cells that may otherwise appear translucent (e.g., DAPI may be used to stain nuclei as a means of better detecting/counting certain cells). In those cases, engine 1208 may scale, shift, and/or rotate fluorescent images to align with bright-field images, with calibration being accomplished using dot array.

In various embodiments, a Fourier transform may be used to reduce interference from a conductive silicon substrate on the microfluidic device. The Fourier transform allows for a frequency representation of the image that facilitates identification of artifacts and interference associated with the conductive silicon substrate, such as a photo-transistor array. The Fourier transform of a function of time itself is a complex-valued function of frequency, whose absolute value represents the amount of that frequency present in the original function, and whose complex argument is the phase offset of the basic sinusoid in that frequency. The Fourier transform is called the frequency domain representation of the original signal. The term Fourier transform refers to both the frequency domain representation and the mathematical operation that associates the frequency domain representation to a function of time. The Fourier transform is not limited to functions of time, but in order to have a unified language, the domain of the original function is commonly referred to as the time domain.

As described in greater detail above, micro-objects of interest may have similar, confounding morphology compared to features of the microfluidic device, such as, for example, a phototransistor array. In addition, micro-objects such as cells may be relatively translucent compared to various features of the microfluidic device. Accordingly, it may be helpful to identify and remove unwanted features of the microfluidic device (e.g., photo transistor arrays, wads or circuit elements of the microfluidic device) prior to identifying micro-objects of interest. Fourier analysis may be used to remove, for example, a transistor pattern prior to micro-object detection. This step may occur within a pre-processing engine 1608 or, alternatively, in a post-processing step in a detection engine 1614 of micro-object detection unit 1604 (described in more detail below).

In various embodiments, the pre-processing the image may include utilizing a brightness normalization or a contrast enhancement to reduce interference from the conductive silicon substrate on the microfluidic device. In various embodiments, an image pre-processing engine 1608 may make a copy of the image pre-processed as described above and transfer to various 'clients' 1620 (e.g., GUI, image processing, movie creation, image capture, memory/storage/server, etc.). In various embodiments, micro-object detection unit 1604 may be implemented as an integrated instrument system assembly with the image acquisition unit 1602. That is, micro-object counting or detection unit 1604 and image acquisition unit 1602 may be housed in the same housing assembly and communicate via conventional device/component connection means (e.g., serial bus, optical cabling, electrical cabling, etc.).

In various embodiments, micro-object counting unit 1604 may be implemented as a standalone computing device (as shown in FIG. 16) that is communicatively connected to the image acquisition unit 1602 via an optical, serial port, network or modem connection. For example, the image processing unit may be connected via a LAN or WAN connection that allows for the transmission of imaging data acquired by the image acquisition unit 1602 to micro-object detection unit 1604 for analysis. In various embodiments, the functions of micro-object counting unit 1604 may be implemented on a distributed network of shared computer processing resources (such as a cloud computing network) that is communicatively connected to the image acquisition unit 1602 via a WAN (or equivalent) connection. For example, the functionalities of micro-object counting unit 1604 may be divided up to be implemented in one or more computing nodes on a cloud processing service such as AMAZON WEB SERVICES™.

Numerous post-processing techniques are contemplated with some examples provided as follows. A detection engine 1614 may be configured to align CAD (computer-aided design) model of sequestration pens (in the microfluidic device) to the actual image output to find precisely where pens are located. In the case of fluorescent images (depending on cell type being detected), detection engine 1614 may be configured to remove background by subtraction, for example, by subtracting a corresponding image obtained from a blur (image) routine. Detection engine 1614 may also be configured to chop an image output into individual pens for micro-object count. That count and output image from detection engine 1614 may be transferred to I/O device 1616, where it may be, for example, stored, transferred to a memory storage, further analyzed, and/or transferred to clients 1620.

In accordance with various embodiments, image acquisition unit 1602 and micro-object detection unit 1604 may be integrated into a single physical unit. Alternatively, image acquisition unit 1602 and micro-object detection unit 1604 may be separably oriented, provided in independent units such that units are still communicatively connected to exchange information. Each component of micro-object detection unit 1604 described above may be hardware or may partially or entirely be a software module.

Automated Detection and/or Counting of Micro-Objects. Methods are provided for automatically detecting a micro-object of interest in an image. The micro-object of interest may have similar, confounding morphology compared to one or more other features in the image. For example, in some instances detection of micro-objects disposed within a microfluidic device may be complicated by features of the microfluidic device that have similar morphology to the micro-object of interest. For example, in instances where cells have a diameter of 10 microns, it may be difficult to distinguish the cells from a phototransistor array that has a 10-micron pitch in both dimensions (i.e., each phototransistor has a 10-micron×10-micron size). In addition, micro-objects such as cells may be relatively translucent compared to various features of the microfluidic device. Accordingly, it may be helpful to identify and remove unwanted features of the microfluidic device (e.g., photo transistor arrays, walls or circuit elements of the microfluidic device) prior to identifying micro-objects of interest.

In various embodiments, it is desirable for images obtained from the image pre-processing engine 1608 to comprise a count associated with a structure of a microfluidic device and/or the properties of one or more features of the microfluidic device. In more specific embodiments, the associated count may be used to associate a count obtained for a region of a microfluidic device (e.g., for the number of micro-objects in a particular region of a microfluidic device). In some embodiments, a micro-object is a cell and the micro-fluidic device may be used to perform an assay on the cell. In further instances, the microfluidic device as described herein may be configured to flow micro-objects into chambers or pens of the micro-fluidic device in order to perform the steps of the assay. A micro-object count may be a critical piece of information for performing the assay, and in some instances micro-object counts must be performed quickly with minimal computational load, and in an automated way in order for the assay to be performed in a massively parallel way.

In some embodiments, a single pixel may correspond to an area in the microfluidic device that is substantially smaller than the cross-sectional area of a micro-object of interest. For example, the micro-object may have a cross-sectional area of about 80 microns$^2$, whereas a pixel may correspond to an area of about 2 microns$^2$. In such embodiments, one or more clusters of pixels will be required to cover the cross-sectional area of the micro-object (e.g., in the foregoing example, it would take substantially 40 pixels to cover the cross-section area of the micro-object, or 24 pixels to cover the cross-sectional area of the circumference of the micro-object). For a given image, a pixel size may be calculated as the mathematical product of a pixel width and a pixel height for the given image.

Generating a micro-object count for a microfluidic device may comprise receiving image data comprising an image, a series of obtained images (e.g., a series of images taken over time), and/or a set of images (e.g., a set of images taken from different "nests" or structures of a system 300). The image data may comprise a field of view image, wherein the field of view image comprises a plurality of features of the microfluidic device (e.g., channel(s), pens(s), traps(s), frames, flow regions, phototransistor arrays, etc.). The image data may be received by the image pre-processing engine 1208, which may crop the image data (e.g., the field of view image) into at least two cropped images. The image pre-processing engine may be configured to crop the image (e.g., features of the image, components of the microfluidic device represented in the image, etc.). Cropping may be performed according to information obtained from a calibration procedure. Calibration may comprise a system wide calibration step performed prior to capture of the field of view image and/or image data. Cropping may be performed according to information obtained from a calibrated image. In some instances, calibration of an image may comprises identifying one or more features of a microfluidic device and establishing those features as a benchmark or baseline from which images may be referenced. Cropping may also be performed based on any of the methods disclosed herein to identify features of each field of view image. Cropping may also be performed based on any of the methods disclosed herein to identify features of each field of view image. Cropped images may be generated based on one or more features of the microfluidic device (e.g., channel(s), chamber(s) pen(s), trap(s), micro-object(s) position, brightness, etc.). In some embodiments the pre-processing engine may perform cropping on a single field of view at a time. In alternate embodiments the pre-processing engine may perform cropping on multiple fields of view in parallel.

An image pre-processing engine 1608 may be configured to crop one or more field of view images into cropped images with particular features or characteristics. For example, a pre-processing engine 1608 may receive a field of view image comprising multiple chambers, pens, traps, or micro-objects. The image pre-processing engine 1608 may receive a field of view image and then convert the field of view image into a series of cropped images. In some instances, the image pre-processing engine 1608 may be configured to crop a field of view images into a plurality of cropped images, wherein each cropped image comprises a single feature (e.g., a single chamber, pen, trap, or micro-object of said plurality of chambers, pens, traps, or micro-objects). In further instances, the pre-processing engine may generate a plurality of cropped images, wherein at least one of said plurality of cropped images comprises a micro-object.

Cropped images generated by the pre-processing engine may have different pixel size. Pixel size may be calculated by multiplying the number of pixels in the image width by the number of pixels in the image height. Differences in pixel size of cropped images may result from the cropping process performed by the pre-processing engine. In additional or alternative embodiments, differences in pixel size of cropped images may result from differences in the field of view—for example, differences in the magnification of the field of view, and/or field of views images taken with different regions of interest (e.g., with regions of interest according to features of the microfluidic device that differ between a first field of view and a second field of view).

Micro-object identification (discussed in greater detail below) or counting may also be used in conjunction with manipulating or repositioning the micro-objects using force, such as OET or DEP force. In some embodiments, micro-objects that are identified in a specific circuit element (e.g., channel or sequestration pen) or location of the microfluidic circuit may be moved to (i.e., repositioned in) another type of circuit element or location of the microfluidic circuit. For example, micro-objects may be identified in a channel in the microfluidic circuit and repositioned in sequestration pens in the microfluidic circuit (referred to herein as "penning" a micro-object). Conversely, micro-objects identified in sequestration pens in the microfluidic circuit may be moved to in channels in the microfluidic circuit. Alternately, one or more micro-objects may be identified in one sequestration pen and repositioned in an empty sequestration pen (referred to herein as "re-penning" a micro-object). According to the embodiment, the micro-objects may be moved using various mechanisms, including OET and DEP force. Similarly, micro-objects may be repositioned sequentially (i.e., one micro-object at a time), in parallel, or any combination thereof (e.g., sequentially repositioning groups of multiple cells in parallel).

In instances where micro-objects are repositioned from the channel to individual sequestration pens (or re-penning from an individual sequestration pen to another sequestration pen), different algorithms may be used to assign micro-objects to empty sequestration pens and/or to determine the number of micro-objects in the particular sequestration pen. In some embodiments, an algorithm will be used to assign micro-objects to empty sequestration pens such that distance between the micro-objects and the pens (i.e., the trajectory or path that the micro-objects have to travel during repositioning) is minimized, and counting may be used to confirm the number of micro-objects in the pens. In these embodiments, the use of force (e.g., OET or DEP force) to move the micro-objects is also minimized because the micro-objects are only required to travel a minimum distance to be repositioned in an empty sequestration pen.

In these embodiments, a local micro-object density in a channel (i.e., number of micro-objects within a specific spatial area of the channel) may be used to determine a suitable algorithm to assign specific micro-objects in the channel to empty sequestration pens. Local micro-object density may be computed in a number of ways. In some embodiments, local micro-object density may be computed based on a fixed size area (e.g., 200 microns$^2$, or an area of the channel 100 microns long and extending the width of the channel) or using approaches that use various sizes of areas. In other embodiments, local micro-object density may be calculated based on clusters of identified micro-objects or the distance between identified micro-objects. Local micro-object density also may be computed by subdividing the channel into a grid or using a "sliding window" approach to compute density for overlapping areas of the channel.

If the local micro-object density is above a threshold value $T1_{density}$, then micro-objects may be assigned to the nearest empty sequestration pens such that the distance between the micro-objects and sequestration pens is minimized. If the local micro-object density is below a specific threshold value $T1_{density}$, then the empty sequestration pens may be assigned to the micro-objects that are closest to the empty sequestration pens, such that the distance between the micro-objects and the sequestration pens is minimized. In some instances, local $T1_{density}$, may be computed based on the number of empty pens as well as the density of micro-objects within the channel in a predefined neighborhood area.

Different methods of computing the distance between a micro-object and an empty sequestration pen (i.e., the trajectory the micro-object or path needs to be moved during penning) may be used to assign specific micro-objects to empty sequestration pens. In some embodiments, the distance between the micro-object and a potential sequestration pen may be computed based only on the optimal trajectory using OET and/or DEP force. In some instances, the optimal trajectory using OET or DEP force involves a combination of orthogonal motion paths (e.g., combination of distinct movement only along a y-axis and an x-axis) to move the micro-objects. In other instances, the distance may be based on the shortest possible path between the micro-object and the sequestration pen, without constraint (i.e., the micro-objects may travel along any path to reach the sequestration pens). In most embodiments, the micro-objects will be re-positioned (i.e., "penned" or "re-penned") using the same trajectory as determined by the algorithm used to calculate the distance (trajectory).

Similarly, in instances where a large number of micro-objects are assigned to sequestration pens (or vice versa), different algorithms may be used to compute the optimal assignment of micro-objects to pens (or vice versa). These algorithms may use different computational methods of determining a micro-object-to-sequestration pen assignment that minimizes the overall distance (i.e., length of the trajectory) that the micro-objects need to be moved in order to reposition the micro-objects into sequestration pens. For example, the algorithms may use the sum of the lengths of all the trajectories as a heuristic to minimize the distance that the micro-objects need to travel. In some embodiments, constraints such as a maximum distance that a micro-object may be moved during repositioning may be introduced into the computation of the optimal assignment. Various combinatorial algorithms may be used to compute the optimal assignment between micro-objects and sequestration pens. Suitable algorithms include: greedy algorithms, nonlinear optimization, heuristic-based algorithms and constrained search. Other similar algorithms are known in the art.

Once the optimal assignment and trajectory has been computed for the micro-objects, a force, such as OET and/or DEP, may be used to move the micro-objects to their assigned pens. The micro-objects may be repositioned using patterns of light, such as a "light cage", that surround the micro-objects and subject the micro-objects to OET and/or DEP force or by using bars or similar structures to apply OET and/or DEP force to the micro-objects. Typically, a light cage will be a structure that substantially encloses the micro-object (e.g., a square, a circle or a polygon). However, in some instances, a light cage may include a break or an opening such that the micro-object is not fully enclosed.

As discussed above, in most embodiments, the micro-objects will be moved according to the distance (trajectory) used to compute the optimal assignment of micro-objects to pens. According to the embodiment, micro-objects may be moved sequentially or in parallel or any combination thereof (e.g., sequentially moving groups of cells in parallel). In embodiments where the micro-objects are moved in parallel, the algorithm used to compute the optimal assignment or trajectory may compare the trajectories and ensure that the micro-objects do not collide when they are moved in parallel by modifying the trajectory and assignments of the micro-objects to pens. In a specific embodiment, the algorithm may "swap" micro-object assignments to pens when a potential collision is identified. In this embodiment, when the optimal trajectory for a first micro-object intersects with the optimal trajectory for a second micro-object, the optimal trajectory for the first micro-object is assigned to the second micro-object and the optimal trajectory for the second micro-object is assigned to the first micro-object. In another specific embodiment, the algorithm delays the repositioning of the first micro-object until such a time that the first and second micro-objects may move along their respective trajectories without colliding.

In some instances, the micro-object density may be so high that the micro-objects need to be separated from one another prior to assigning the micro-objects to sequestration pens and repositioning (i.e., "penning" or "re-penning") the micro-objects. For example, the micro-object density may be so high that the micro-objects cannot be penned using OET and/or DEP force because the light cage used to reposition objects using OET and/or DEP force cannot be used on a single micro-object without interfering with other micro-objects. This interference is of particular concern in instances where it is important to minimize the amount of OET and/or DEP force applied to the micro-object. For examples, instances where the micro-objects could be harmed by OET and/or DEP force or by-products of OET force (e.g., electrolysis associated with OET and/or DEP force). In these instances, information produced during micro-object identification (e.g., the radius, the centroid, the perimeter and the location of a micro-object) may be used to move the micro-objects such the micro-objects may be penned or re-penned without interfering with other cells (herein referred to as "separating" the micro-objects).

In order to identify instances where the micro-objects need to be separated prior to penning, a local micro-object density may be computed based on a defined spatial region and compared to a second threshold value $T2_{density}$. Alternately, the distance between the micro-objects may be computed (e.g., the distance between centroids of micro-objects, the distance between the perimeters of the micro-objects) and used to determine whether the micro-objects need to be separated. However, as may appreciated, in some instances, the distance between micro-objects may be too small to identify the micro-objects as separate micro-objects. In these instances, the micro-objects may be re-identified after repositioning (i.e., "penning") the micro-objects to ensure that each sequestration pen includes a single micro-object.

In some embodiments, a light box is used to separate the micro-objects prior to, or during, penning (or re-penning). When forming the light boxes (or light cages), a division algorithm may be used to compute a set of vertices that partition each identified micro-object in the spatial region of the microfluidic device (e.g., the portion of the channel or the sequestration pen) from the other micro-objects in the same spatial region. However, as may be appreciated by those skilled in the art, the set of vertices may be drawn such that only a subset of the micro-objects in the spatial region of the microfluidic device are separated from the other micro-objects. For example, the set of vertices may only separate the subset of micro-objects in the spatial region that need to be repositioned due to their close proximity to other micro-objects.

In a specific embodiment, a Delaunay triangulation is computed using the centroids of each micro-object. The Delaunay triangulation produces a set of triangles that connect the centroids of the micro-objects. A Voronoi diagram is then computed based on the circumcircles of the triangles computed using the Delaunay Triangulation. The Voronoi diagram is a set of vertices that divide the spatial area into a set of sub-areas such that the distance between the set of vertices and the centroid of the micro-object is maximized. Other methods of computing a set of vertices that partition each cell from the other cells in the spatial region are known in the art. Once the set of vertices has been computed, the set of vertices may be used in combination with OET and/or DEP forces to move the micro-objects such as the examples illustrated in FIGS. 12A-12F described above.

FIG. 22A illustrates a simplified high-level block diagram for a process or system for programmatically analyzing biological samples in a microfluidic device in one or more embodiments. In these one or more embodiments, the process or system may receive first image data that is captured at a first time point for a region of interest in a microfluidic device at 2102A. For example, an image or data thereof may be captured for a region of interest for one or more chambers in a microfluidic device may be received at 2102A for the process or the system illustrated in FIG. 22A to recognize and to determine a total count of biological samples in the region of interest.

The first image data received at 2102A may be pre-processed into first pre-processed image data at least by arranging the first image data into an array having dimensions of a first pixel information by a second pixel information by a pixel depth information at 2104A. For example, the first image data may be arranged into an array having dimensions of length by width by depth, wherein the length dimension may include, without limitations, a first number of pixels; the width dimension may include a second number of pixels; and the depth dimension may include a number of channels each representing a color (e.g., a color depth of three (3) for red, blue, and green), brightness (e.g., a depth of one (1) for black or white), intensity, of the data in the first image data.

In some embodiments, one or more characteristics of the size of an image sensor (e.g., a photodiode, a phototransistor, etc.), the pitch between two immediately adjacent phototransistors, the sizes of biological samples of interest, the size of a chamber, the dimensions of surrounding area near a chamber, etc. may be determined or configured based at least in part upon one or more other characteristics mentioned above. For instance, it may be difficult to process (e.g., recognize, classify, count, etc.) biological samples with a photo sensor diode or transistor having a size or pitch of about 10-microns where the size of biological samples is also about, for example, 10 microns. Similarly, a chamber having a width of about 10-microns may be used for biological samples having a size of about two-microns but not necessarily suitable for larger biological samples.

A first class or type of the first image data may be determined at 2106A for the first image data or the first pre-processed data at least by classifying the first image data into the first class or type with at least a machine learning model. In some embodiments, the determination or classification at 2106B may be performed by using additional data or metadata correlated with the targeted analysis of the biological samples in the microfluidic device. The class or type may include, for example, a class or type of the biological samples (e.g., immunological cells such as T cells, B cells, NK cells, macrophages, etc., other types of cells, proteins, viruses, etc.)

A first count of the biological samples in the region of interest may be determined at 2108A at least by recognizing the biological samples with the machine learning model that comprises a convolutional neural network having multiple processing blocks. In some of these embodiments, the first count may be determined based at least in part upon the first class or type determined at 2106A. It shall be noted that recognizing a biological sample at 2108A may or may not discern much details about the biological sample. For example, for the purpose of determining a total count of biological samples in a chamber of a microfluidic device, the process or system may recognize the boundary, morphology (e.g., size, shape, etc.), the nucleus, the nucleus size, the nucleus-to-cytoplasma ratio, etc. of the biological sample so that the process or system may estimate the size of the biological sample, without further discerning additional details about the biological sample if the primary purpose of the processing at 2108A is to determine a total count of biological samples.

A textual or graphical representation of information correlated with the first count for the region of interest may be displayed at 2110A. For example, a textual description or a graphical representation may be displayed in a gallery view of a graphical user interface at 2110A.

FIGS. 22B-22E illustrate more details about the high-level block diagram illustrated in FIG. 22A in one or more embodiments. More specifically, FIGS. 22B-22E illustrate more details about the machine learning model that is used in the process or system illustrated in FIG. 22A. In these one or more embodiments, the multiple process blocks 2102B of the convolutional neural network may include a first processing block 2104B, a second processing block 2106B, a third processing block 2108B, and a fourth processing block 2110B.

Figure 22C:
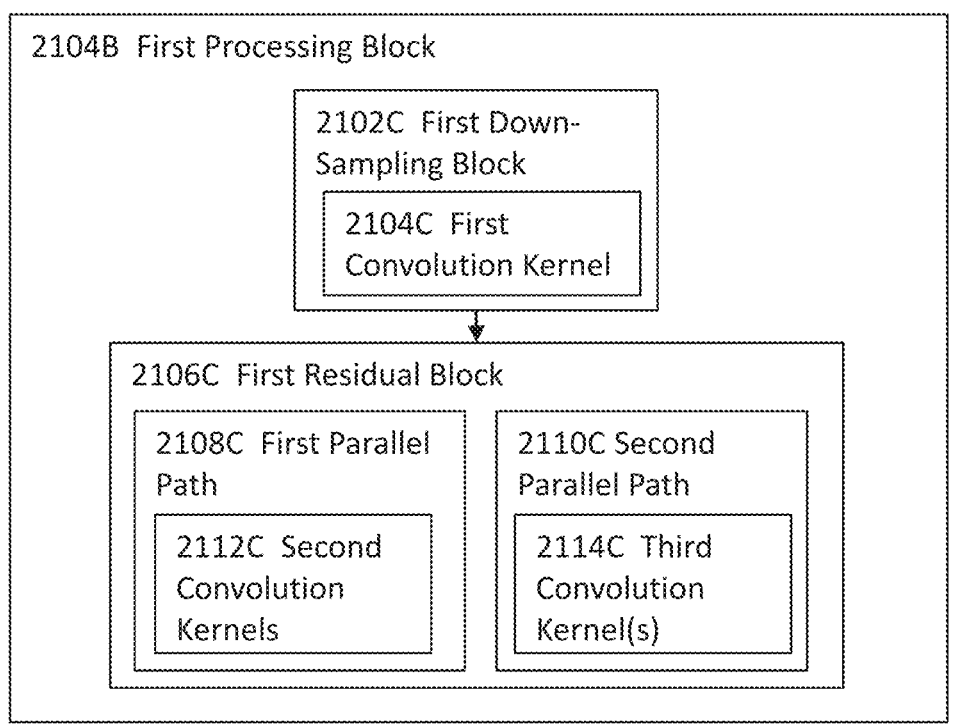

In some embodiments as illustrated in FIG. 22C, the first processing block 2104B may include a first down-sampling block 2102C and a first residual block 2106C that receives the input from the first down-sampling block 2102C. The first down-sampling block 2102C may include a first convolutional kernel 2104C. In some of these embodiments, the first convolutional kernel has a first dimension and a first stride for a first depth, the first dimension is greater than one-by-one, and the first stride is greater than one. In one embodiment, the first convolutional kernel 2104C has a dimension of three-by-three (3×3) and a first stride of two (2).

The first residual block 2106C comprises a first parallel path 2108C and a second parallel path 2110C, both of which receive a first down-sampling block output from the first down-sampling block 2102C. The first parallel path 2108C comprises multiple second convolutional kernels 2112C having a second dimension or filter size, and the second parallel path 2110C has a third convolution kernel 2114C having a third dimension or filter size that is smaller than the second dimension or filter size. In one embodiment, the second dimension or filter size is three-by-three (3×3), and the third dimension or filter size is one-by-one (1×1).

Figure 22D:
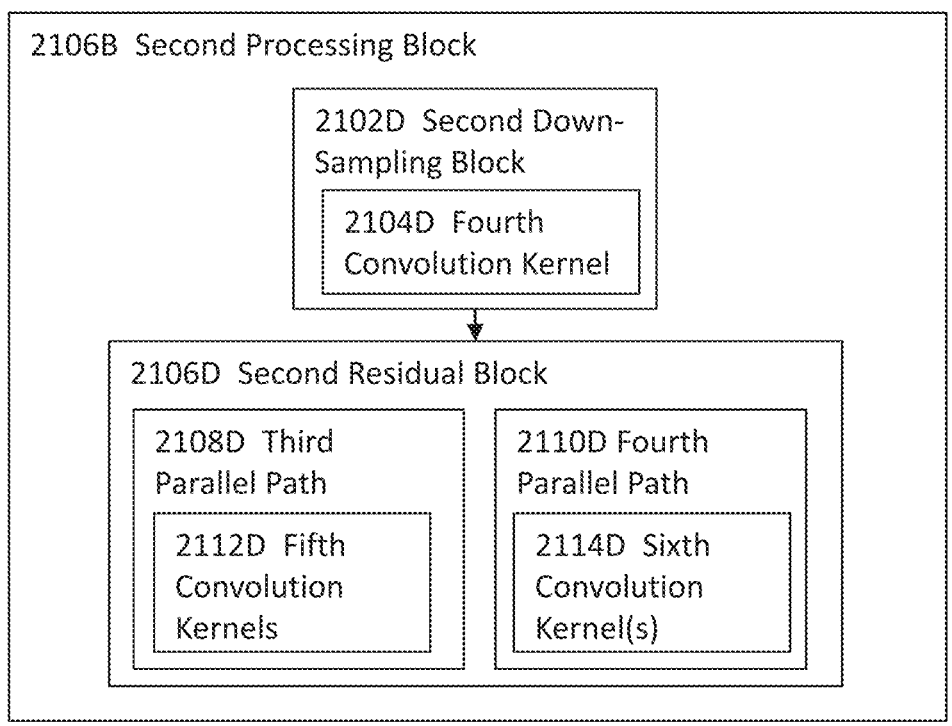

In some embodiments as illustrated in FIG. 22D, the second processing block 2106B may include a second down-sampling block 2102D and a second residual block 2106D that receives the input from the second down-sampling block 2102D. The second down-sampling block 2102D may include a fourth convolutional kernel 2104D. In some of these embodiments, the fourth convolutional kernel has a fourth dimension and a fourth stride for a fourth depth, the fourth dimension is greater than one-by-one, and the fourth stride is greater than one. In one embodiment, the fourth convolutional kernel 2104D has a dimension of three-by-three (3×3) and a fourth stride of two (2).

The second residual block 2106D comprises a third parallel path 2108D and a fourth parallel path 2110D, both of which receive a second down-sampling block output from the second down-sampling block 2102D. The third parallel path 2108D comprises multiple fifth convolutional kernels 2112D having a fifth dimension or filter size, and the fourth parallel path 2110D has a sixth convolution kernel 2114D having a sixth dimension or filter size that is smaller than the fifth dimension or filter size of the fifth convolution kernels 2112D. In one embodiment, the fifth dimension or filter size is three-by-three (3×3), and the sixth dimension or filter size is one-by-one (1×1).

Figure 22E:
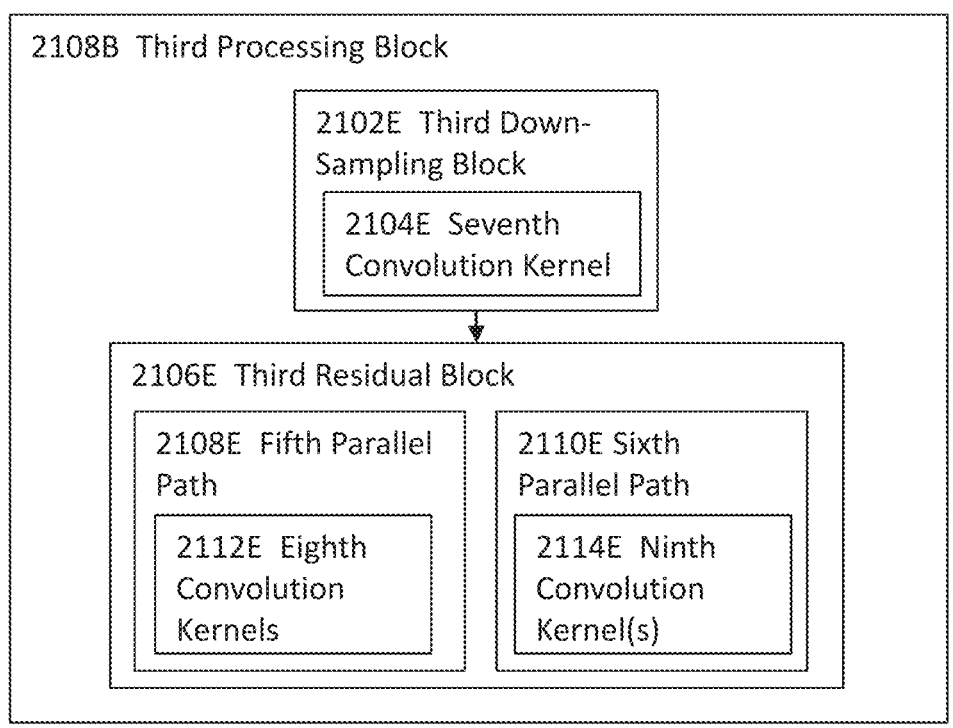

In some embodiments as illustrated in FIG. 22E, the third processing block 2106E may include a third down-sampling block 2102E and a third residual block 2106E that receives the input from the third down-sampling block 2102E. The third down-sampling block 2102E may include a seventh convolutional kernel 2104E. In some of these embodiments, the seventh convolutional kernel 2104E has a seventh dimension and a seventh stride for a seventh depth, the seventh dimension is greater than one-by-one, and the seventh stride is greater than one. In one embodiment, the seventh convolutional kernel 2104E has a dimension of three-by-three (3×3) and a seventh stride of two (2).

The third residual block 2106E comprises a fifth parallel path 2108E and a sixth parallel path 2110E, both of which receive a third down-sampling block output from the third down-sampling block 2102E. The fifth parallel path 2108E comprises multiple eighth convolutional kernels 2112E having an eighth dimension or filter size, and the sixth parallel path 2110E has a ninth convolution kernel 2114E having a ninth dimension or filter size that is smaller than the eighth dimension or filter size of the multiple eighth convolution kernels 2112E. In one embodiment, the eighth dimension or filter size is three-by-three (3×3), and the ninth dimension or filter size is one-by-one (1×1).

Figure 22F:
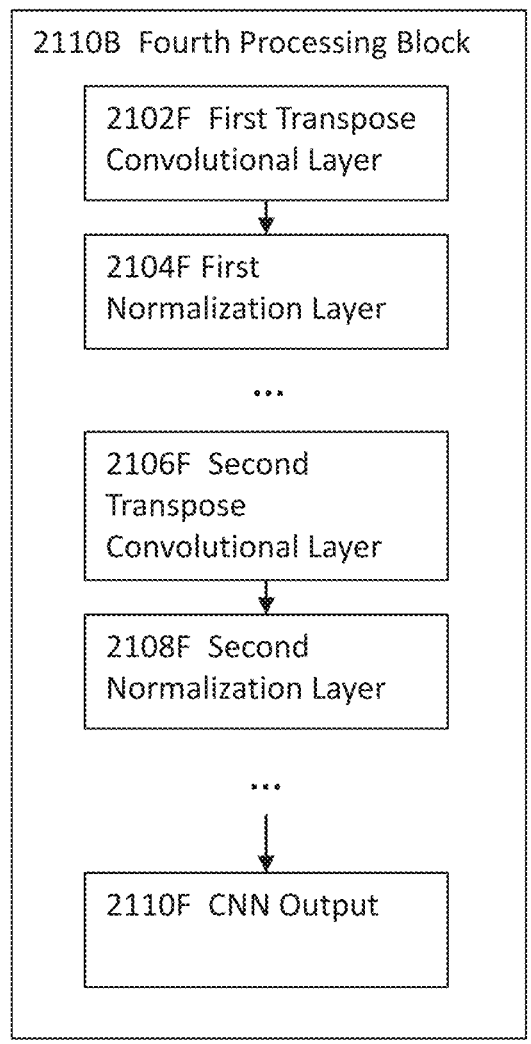

The fourth processing block 2110B comprises, as shown in FIG. 22F illustrating more details about the fourth processing block 2110B, a first transpose convolutional layer 2102F followed by a first normalization layer 2104F (e.g., a first batch normalization layer). The fourth processing block 2110B may further comprises a second transpose convolutional layer 2106F followed by a second normalization layer 2108F (e.g., a batch normalization layer). The execution of the first transpose convolutional layer 2102F and the first normalization layer 2104F precedes that of the second transpose convolutional layer 2106F and the second normalization layer 2184F. The fourth processing block 2110B generates the convolutional neural network (CNN) output 2110F. More details about the data flow among the first through the fourth process block are described above with reference to FIGS. 14D-14G.

In some embodiments, the total number of transpose convolutional layers in the fourth processing block corresponds to a value that is at least one less than the total number of convolutional layers in the first and the second processing blocks. In some embodiments, the convolutional neural network comprises no pooling layers. In addition or in the alternative, all of the convolutional layers in the convolutional neural network have filter sizes greater than one-by-one so that no convolutional layers in the convolutional neural network have a one-by-one filter.

In some embodiments, pre-processing the first image data into the first pre-processed image data comprises at least reducing the first image data into the first pre-processed image data based at least in part upon the region of interest or a type of the first image data, wherein a type of the first image data corresponds an operation during which the first image data is captured for analyzing the biological samples, and the operation comprises an export operation or an import operation. Additionally or alternatively, a pixel size for the first image data may be determined based at least in part upon a first geometric characteristic of the biological samples and a second geometric characteristic of the region of interest in some embodiments. In some of these immediately preceding embodiments, the first geometric characteristic of the biological samples comprises a diameter, a major diameter, a minor diameter, or an area of the biological samples, and the second geometric characteristic of the region of interest comprises a width or a length of the region of interest or a portion thereof.

In some embodiments, determining the first class or type of the first image data comprises processing a plurality of low-level features by using at least the first processing block of the convolutional neural network and processing a plurality of abstract features by using at least the third processing block of the convolutional neural network. In some of these embodiments, determining the first class or type may further comprise determining the first class or type or a first statistic corresponding to the first class or type, wherein the first statistic comprises a first probability that one or more pixels in the first image data represent a corresponding biological sample characteristic.

In some embodiments, a second count of the biological samples may be determined from second image data captured at a second time point for the region of interest based with the convolutional neural network (CNN) having the multiple processing blocks, and a video sequence of the region of interest may be replayed in the gallery view of the graphical user interface at least by sequentially rendering a portion of the first image data and a portion of the second image data.

In some of these embodiments, determining the second count may include receiving the second image data captured at the first time point for the region of interest in the microfluidic device; pre-processing the second image data into second pre-processed image data at least by arranging the second image data into an array of the first pixel information by the second pixel information by the pixel depth information; classifying the second image data into the first class or type with at least a machine learning model; and determining the second count of the biological samples at the second time point in the region of interest based at least in part upon the first class or type at least by recognizing the biological samples with the convolutional neural network having the multiple processing blocks.

In some embodiments, pre-processing the second image data into the second pre-processed image data comprises at least reducing the second image data into the second pre-processed image data based at least in part upon the region of interest or the type of the second image data, wherein the type of the second image data corresponds a separate operation during which the second image data is captured for analyzing the biological samples, and the separate operation comprises the export operation, the import operation, a separate export operation, or a separate import operation.

While the invention has been described in detail with reference to example embodiments thereof, it will be apparent to one skilled in the art that various changes may be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

Various example embodiments of the disclosure are described herein. Reference is made to these examples in a non-limiting sense. Examples are provided to illustrate more broadly applicable aspects of the invention. Various changes may be made to various embodiments described herein and equivalents may be substituted without departing from the true spirit and scope of the invention. In addition, many modifications may be made to adapt a particular situation, material, composition of matter, process, process act(s) or step(s) to the objective(s), spirit or scope of the present disclosure. Further, as will be appreciated by those with skill in the art that each of the individual variations described and illustrated herein has discrete components and features which may be readily separated from or combined with the features of any of the other several embodiments without departing from the scope or spirit of the present disclosures. All such modifications are intended to be within the scope of claims associated with this disclosure.

The disclosure includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Example aspects of the invention, together with details regarding material selection and manufacture have been set forth above. As for other details of the present disclosure, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure. The above description of illustrated embodiments is not intended to be exhaustive or to limit the embodiments to the precise forms disclosed. Although specific embodiments and examples are described herein for illustrative purposes, various equivalent modifications may be made without departing from the spirit and scope of the disclosure, as will be recognized by those skilled in the relevant art. The teachings provided herein of the various embodiments may be applied to other devices that implement virtual or AR or hybrid systems and/or which employ user interfaces, not necessarily the example AR systems generally described above.

For instance, the foregoing detailed description has set forth various embodiments of the devices and/or processes via the use of block diagrams, schematics, and examples. Insofar as such block diagrams, schematics, and examples include one or more functions and/or operations, it will be understood by those skilled in the art that each function and/or operation within such block diagrams, flowcharts, or examples may be implemented, individually and/or collectively, by a wide range of hardware, software, firmware, or virtually any combination thereof.

In one embodiment, the present subject matter may be implemented via Application Specific Integrated Circuits (ASICs), Field Programmable Gate Array (FPGA), etc. However, those skilled in the art will recognize that the embodiments disclosed herein, in whole or in part, may be equivalently implemented in standard integrated circuits, as one or more computer programs executed by one or more computers (e.g., as one or more programs running on one or more computer systems), as one or more programs executed by on one or more controllers (e.g., microcontrollers), as one or more programs executed by one or more processors (e.g., microprocessors), as firmware, or as virtually any combination thereof, and that designing the circuitry and/or writing the code for the software and/or firmware would be well within the skill of one of ordinary skill in the art in light of the teachings of this disclosure.

When logic is implemented as software and stored in memory, logic or information may be stored on any non-transitory computer-readable medium for use by or in connection with any processor-related system or method. In the context of this disclosure, a memory is a computer-readable medium that is an electronic, magnetic, optical, or other physical device or means that includes or stores a computer and/or processor program. Logic and/or the information may be embodied in any computer-readable medium for use by or in connection with an instruction execution system, apparatus, or device, such as a computer-based system, processor-including system, or other system that may fetch the instructions from the instruction execution system, apparatus, or device and execute the instructions associated with logic and/or information.

In the context of this specification, a "non-transitory computer-readable medium" may be any element that may store the program associated with logic and/or information for use by or in connection with the instruction execution system, apparatus, and/or device. The computer-readable medium may be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random-access memory (RAM), a read-only memory (ROM), an erasable programmable read-only memory (EPROM, EEPROM, or Flash memory), a portable compact disc read-only memory (CDROM), digital tape, and other non-transitory media.

Many of the methods described herein may be performed with variations. For example, many of the methods may include additional acts, omit some acts, and/or perform acts in a different order than as illustrated or described. Various embodiments described above may be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet. Aspects of the embodiments may be modified, if necessary, to employ systems, circuits and concepts of the various patents, applications and publications to provide yet further embodiments.

These and other changes may be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure. Moreover, the various embodiments described above may be combined to provide further embodiments. Aspects of the embodiments may be modified, if necessary, to employ concepts of the various patents, applications and publications to provide yet further embodiments.

These and other changes may be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

In the foregoing specification, the invention has been described with reference to specific embodiments thereof. It will, however, be evident that various modifications and changes may be made thereto without departing from the broader spirit and scope of the invention. For example, the above-described process flows are described with reference to a particular ordering of process actions. However, the ordering of many of the described process actions may be changed without affecting the scope or operation of the invention. The specification and drawings are, accordingly, to be regarded in an illustrative rather than restrictive sense.

Various example embodiments of the invention are described herein. Reference is made to these examples in a non-limiting sense. The examples described herein are provided to illustrate more broadly applicable aspects of the invention. Various changes may be made to any of the examples or embodiments described herein, and equivalents thereof may be substituted without departing from the true spirit and scope of these examples or embodiments described herein.

In addition, many modifications may be made to adapt a particular situation, material, composition of matter, system, module, process, and/or process act(s) or step(s) to the objective(s), spirit or scope of the present disclosure. Further, as will be appreciated by those with skill in the art, each of the individual variations, examples, and/or embodiments, etc. described and illustrated herein has discrete components and features which may be readily separated from or combined with the feature or features of any of the other several variations, examples, and/or embodiments, etc., without departing from the scope or spirit of various variations, examples, and/or embodiments, etc. described herein. All such modifications are intended to be within the scope of claims associated with this disclosure. Moreover, various embodiments or portion(s) thereof described herein may be combined to provide further embodiments. Any aspects of the embodiments may be modified, if necessary, to employ concepts of the various variations, examples, and/or embodiments, etc. described herein to provide yet further embodiments.

The invention claimed is:

1. A method for analyzing biological samples, comprising:
identifying an analysis of biological samples in multiple regions of interest in a microfluidic device and a timeline correlated with the analysis, wherein the timeline comprises information that is temporally aligned with at least one of a workflow or a pipeline of the analysis of the biological samples;
determining one or more region-of-interest types for the multiple regions of interest, wherein the one or more region-of-interest types comprise a target-based type correlated with at least one biological sample of the biological samples or a structure-based type correlated with the microfluidic device;
determining multiple characteristics for the biological samples based at least in part upon the one or more region-of-interest types, wherein the multiple characteristics respectively correspond to an attribute, a property, or a quantifiable metric for the biological samples or the analyses;
arranging and rendering associated data from the analysis that respectively correspond to the multiple regions of interest in a user interface for at least a portion of the biological samples based at least in part upon the multiple characteristics and the timeline; and
generating a bioinformatics pipeline view, generating the bioinformatics pipeline view comprising:
determining a sequencing dataset for the biological samples in a plurality of chambers or the multiple regions of interest of the microfluidic device, wherein a biological sample comprises a sequence of nucleotides or amino acids.

2. The method of claim 1, wherein arranging and rendering the associated data comprises:
determining a gallery structure having a plurality of gallery sub-structures for the analysis results based at least in part upon an allocable space in the user interface for rendering the analysis results.

3. The method of claim 2, wherein arranging and rendering the analysis results comprises:
populating the analysis results into the plurality of gallery sub-structures in a gallery structure based at least in part upon a characteristic of the multiple characteristics.

4. The method of claim 3, determining the gallery structure comprising:
determining a first sequence of data correlated with a set of time points or time periods for a first biological sample obtained from a first region of interest of the multiple regions of interest from the gallery structure stored in an addressable space in a non-transitory computer accessible storage medium, wherein the first sequence of data corresponds to at least a first characteristic of the multiple characteristics;
determining a second sequence of data correlated with the set of time points or time periods for a second biological sample obtained from a second region of interest of the multiple regions of interest from the gallery structure, wherein the second sequence of data corresponds to at least a second characteristic of the multiple characteristics; and
in response to a selection of the at least the first characteristic from the multiple characteristics with a first selection widget in the user interface, extracting a first value of at least the first characteristic from a plurality of values for the first biological sample or for the analysis; and
extracting a second value of at least the first characteristic from the plurality of values for the second biological sample or for the analysis.

5. The method of claim 4, arranging and rendering analysis results comprising:
rendering a first interactive object and a second interactive object respectively corresponding to the first sequence of data and the second sequence of data into the gallery view, wherein the first interactive object is representative of the first value for the first biological sample or for the analysis, and the second interactive object is representative of the second value for the second biological sample or for the analysis.

6. The method of claim 1, further comprising:
in response to an invocation of a timeline view through a timeline view activation interactive widget in the user interface based at least in part upon the timeline, rendering the timeline view and a matching grid portion in the user interface.

7. The method of claim 6, wherein
the timeline view comprises a respective progress of multiple workflow tasks in the analysis of the biological samples, and
the respective progress graphically indicates respective temporal durations of the multiple workflow tasks.

8. The method of claim 1, further comprising:
associating a first region of interest of the multiple regions of interest with one or more graphical elements illustrated in a timeline view.

9. The method of claim 8, wherein arranging and rendering the analysis results comprises:
determining the timeline based at least in part upon the pipeline or the workflow for the analysis of the biological samples.

10. The method of claim 9, wherein arranging and rendering the analysis results comprises:
determining a plurality of stages for the analysis based at least in part upon the timeline, wherein the plurality of stages respectively corresponds to a plurality of timepoints or time periods for the analysis of the biological samples.

11. The method of claim 10, wherein rendering the respective analysis results comprises:
respectively determining a plurality of graphic representations for the plurality of stages based at least in part upon the plurality of timepoints or time periods.

12. The method of claim 1, further comprising rendering a data control view in the user interface, rendering the data control view comprising:
generating a microfluidic device data structure having a plurality of fields for the microfluidic device having a plurality of chambers.

13. The method of claim 12, rendering the data control view comprising:
populating first data correlated with the microfluidic device into a first field in the microfluidic device data structure, wherein the first data comprises a first identifier of the microfluidic device.

14. The method of claim 1, further comprising rendering a filter view, wherein rendering the filter view comprises:
determining a first filter type for a first filter based at least in part upon an execution of one or more instructions triggered by an interaction with a first filter selector switch in a filter generation module.

15. The method of claim 14, rendering the filter view further comprising:
dynamically determining and displaying, in the filter view for the microfluidic device, a first total number of regions of interest for a first set of filtered regions of interest that satisfies a first dynamic constraint of the first filter applied to the multiple regions of interest.

16. The method of claim 14, rendering the filter view further comprising:
generating, at a filter generation module, a logical combination of at least a second filter of a second filter type and the first filter of the first filter type.

17. The method of claim 1, generating the bioinformatics pipeline view further comprising:
in response to a first interaction with a first sequencing view widget in the user interface, rendering a first sequencing view in the bioinformatics pipeline view that illustrates a distribution of an attribute of the sequence of first biological samples including at least one of a sequence of nucleotides, a sequence of amino acids, or a sequence of macromolecules in the plurality of chambers or the multiple regions of interest of the microfluidic device.

18. The method of claim 17, generating the bioinformatics pipeline view further comprising:
overlaying the first sequencing view with first information that comprises one or more statistical measures of the distribution of the attribute of multiple sequences of first biological samples including the sequence of first biological samples, wherein the user interface comprises a total number of the multiple sequences of first biological samples, a total number of regions of interest having the sequence of first biological samples, and a respective total number of one or more sequences of first biological samples in a respective region of interest of the array of regions of interest.

19. The method of claim 1, wherein the multiple characteristics correspond to one or more attributes that further comprise at least one of an identifier of a region of interest in the microfluidic device, a size attribute of the biological samples, a maximum brightness attribute for the biological samples, a minimum brightness attribute for the biological samples, a first pixel count attribute in a first direction for a centroid of a first biological sample, a second pixel count attribute in a second direction for the centroid of the biological sample, a size attribute for the centroid of the biological sample, a time lapse index attribute, a device identifier for the microfluidic device, a biological sample count attribute, a verified biological sample count attribute, a biological sample type attribute, a score attribute of the plurality of regions of interest, a gate path index, an area pixel attribute, a background pixel attribute, or a median brightness attribute for the plurality of biological samples.

20. An article of manufacture comprising a non-transitory machine accessible storage medium storing thereupon a sequence of instructions which, when executed by a processor, causes the process to perform the method of claim 1.

21. A system, comprising:
a processor;
a user interface coupled to the processor for processing a plurality of molecular-biological samples that comprise a first molecular-biological sample and a second molecular-biological sample in a first molecular-biological device;
a non-transitory computer accessible storage medium storing thereupon a sequence of instructions which, when executed by a processor, causes the processor to perform any of the method of claim 1.

\* \* \* \* \*